United States Patent
Hu et al.

(10) Patent No.: US 9,394,260 B2
(45) Date of Patent: Jul. 19, 2016

(54) PYRIMIDINONE CARBOXAMIDE INHIBITORS OF ENDOTHELIAL LIPASE

(71) Applicant: BRISTOL-MYERS SQUIBB COMPANY, Princeton, NJ (US)

(72) Inventors: Carol Hui Hu, New Hope, PA (US); Jennifer X. Qiao, Princeton, NJ (US); Tammy C. Wang, Lawrenceville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 15 days.

(21) Appl. No.: 14/390,152

(22) PCT Filed: Apr. 1, 2013

(86) PCT No.: PCT/US2013/034786
§ 371 (c)(1),
(2) Date: Oct. 2, 2014

(87) PCT Pub. No.: WO2013/151923
PCT Pub. Date: Oct. 10, 2013

(65) Prior Publication Data
US 2015/0361052 A1    Dec. 17, 2015

Related U.S. Application Data

(60) Provisional application No. 61/619,496, filed on Apr. 3, 2012.

(51) Int. Cl.
| | |
|---|---|
| *C07D 401/12* | (2006.01) |
| *A61K 31/513* | (2006.01) |
| *C07D 239/557* | (2006.01) |
| *A61K 31/5377* | (2006.01) |
| *C07D 403/12* | (2006.01) |
| *C07D 401/14* | (2006.01) |
| *C07D 403/14* | (2006.01) |
| *C07D 413/12* | (2006.01) |
| *C07D 417/12* | (2006.01) |
| *C07D 417/14* | (2006.01) |

(52) U.S. Cl.
CPC .......... *C07D 239/557* (2013.01); *A61K 31/513* (2013.01); *A61K 31/5377* (2013.01); *C07D 401/12* (2013.01); *C07D 401/14* (2013.01); *C07D 403/12* (2013.01); *C07D 403/14* (2013.01); *C07D 413/12* (2013.01); *C07D 417/12* (2013.01); *C07D 417/14* (2013.01)

(58) Field of Classification Search
CPC ............ C07D 239/557; C07D 401/12; C07D 401/14; C07D 403/12; C07D 403/14; A61K 31/513; A61K 31/5377
USPC .............. 544/122, 295, 310, 311; 514/235.8, 514/252.14, 274
See application file for complete search history.

(56) References Cited

U.S. PATENT DOCUMENTS

| | | | |
|---|---|---|---|
| 7,217,727 B2 | 5/2007 | Eacho et al. | |
| 7,595,403 B2 | 9/2009 | Eacho et al. | |
| 2005/0261322 A1 | 11/2005 | Naidu et al. | |
| 2006/0211755 A1 | 9/2006 | Eacho et al. | |
| 2008/0287448 A1 | 11/2008 | Zoller et al. | |
| 2009/0054478 A1 | 2/2009 | Zoller et al. | |
| 2009/0076068 A1 | 3/2009 | Zoller et al. | |

FOREIGN PATENT DOCUMENTS

| | | |
|---|---|---|
| JP | 2004-244320 | 2/2004 |
| WO | WO99/32611 A1 | 7/1999 |
| WO | WO2004/093872 A1 | 11/2004 |
| WO | WO2004/094393 A1 | 11/2004 |
| WO | WO2004/094394 A1 | 11/2004 |
| WO | WO2007/042178 A1 | 4/2007 |
| WO | WO2007/110215 A1 | 10/2007 |
| WO | WO2007/110216 A1 | 10/2007 |
| WO | WO2008/122352 A1 | 10/2008 |
| WO | WO2009/133834 A1 | 5/2009 |
| WO | WO2009/123164 A1 | 8/2009 |
| WO | WO2011/157827 A1 | 12/2011 |

OTHER PUBLICATIONS

English Abstract of JP 2004-244320 from Espacenet (2004).*
Baraldi, P.G. et al., "Design, Synthesis, and Biological Activity of Hybrid Compounds between Uramustine and DNA Minor Groove Binder Distamycin A", J. Med. Chem., vol. 45, pp. 3630-3638 (2002).
Bevilacqua, M.P. et al., "Perspectives: Selectins", J. Clin. Invest., vol. 91, pp. 379-387 (1993).
Britikova, N.E. et al., "5-Aminoorotic Acid Derivatives" Chemistry of Heterocyclic Compounds, vol. 9, pp. 250-252 (1973).
Nielsen, N. et al., "Glycolamide Esters as Biolabile Prodrugs of Carboxylic Acid Agents: Synthesis, Stability, Bioconversion, and Physicochemical Properties", J. of Pharmaceutical Sciences, vol. 77(4), pp. 285-298 (1988).
Bundgaard, H., "Means to Enhance Penetration: Prodrugs as a means to improve the delivery of peptide drugs" Advanced Drug Delivery Reviews, vol. 8, pp. 1-38 (1992).

(Continued)

*Primary Examiner* — Deepak Rao
(74) *Attorney, Agent, or Firm* — Barry H. Jacobsen

(57) ABSTRACT

The present invention provides compounds of Formula (I): (I) as defined in the specification and compositions comprising any of such novel compounds. These compounds are endothelial lipase inhibitors which may be used as medicaments.

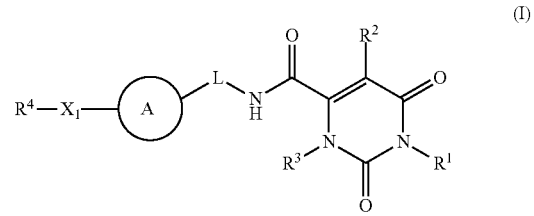

11 Claims, No Drawings

(56) References Cited

OTHER PUBLICATIONS

Cogan, Derek A. et al., "Asymmetric Synthesis of Chiral Amines by Highly Diastereoselective 1,2-Additions of Organometallic Reagents to N-tert-Butanesulfinyl Imines", Tetrahedron, vol. 55(29), pp. 8883-8904 (1999).

Culbertson, T.P., "Synthesis of 5,6-Dihydroxy-2-phenyl-4-pyrimidinecarboxylic Acid, Methyl Ester, a Corrected Structure", J. Heterocyclic Chem., vol. 16, p. 1423 (1979).

deLemos, Andrew S. et al., "Identification of Genetic Variants in Endothelial Lipase in Persons With Elevated High-Density Lipoprotein Cholesterol", Circulation, vol. 106, pp. 1321-1326 (2002).

Dreher, Spencer D. et al., "Highly selective synthesis of 2-substituted-5-hydroxy-6-oxo-1,6-dihydropyrimidine-4-carboxylic acid derivatives using a novel protected dihydroxyfumarate", Tetrahedron Letters, vol. 45, pp. 6023-6025 (2004).

Elzein, E. et al., "Discovery of a Novel $A_{2B}$ Adenosine Receptor Antagonist as a Clinical Candidate for Chronic Inflammatory Airway Diseases", J. Med. Chem., vol. 51, pp. 2267-2278 (2008).

Folkman, J. et al., "Minireview: Angiogenesis", The J. of Biological Chemistry, vol. 267(16), pp. 10931-10934 (1992).

Folkman, J. et al., "Angiogenic Factors", Science, vol. 235, pp. 442-447 (1987).

Gordon, D.J. et al., "High-density lipoprotein cholesterol and cardiovascular disease. Four prospective American studies", Circulation, vol. 79, pp. 8-15 (1989).

Gordon, D.J. et al., "High-Density Lipoprotein—The Clinical Implications of Recent Studies", New England Journal of Medicine, vol. 321(19), pp. 1311-1316 (1989).

Hirata, K. et al., "Cloning of a Unique Lipase from Endothelial Cells Extends the Lipase Gene Family", The J. of Biological Chemistry, vol. 274(20), pp. 14170-14175 (1999).

Janssens, S.P. et al., "Cloning and Expression of a cDNA Encoding Human Endothelium-derived Relaxing Factor/Nitric Oxide Synthase", The J. of Biological Chemistry, vol. 267(21), pp. 14519-14522—(1992).

Jaye, M. et al., "A novel endothelial-derived lipase that modulates HDL metabolism", Nature genetics, vol. 21, pp. 424-428 (1999).

Jin, W. et al., "Lipases and HDL metabolism", TRENDS in Endocrinology & Metabolism, vol. 13(4), pp. 174-178 (2002).

Kakeya, N. et al., "Studies on Prodrugs of Cephalosporins. I. Synthesis and Biological Properties of Glycyloxybenzoyloxymethyl and Glycylaminobenzoyloxmethyl Esters of 7β-[2-(2-Aminothiazol-4-yl)-(Z)-2-methoxyiminoacetamido]-3-methyl-3-cephem-4-carboxylic Acid", Chem. Pharm. Bulletin, vol. 32 (2), pp. 692-698 (1984).

Lamas, S. et al., "Endothelial nitric oxide synthase: Molecular cloning and characterization of a distinct constitutive enzyme isoform", Proc. Natl. Acad. Sci, USA, vol. 89, pp. 6348-6352 (1992).

Liu, G. et al., "Catalytic Asymmetric Synthesis of tert-Butanesulfinamide. Application to the Asymmetric Synthesis of Amines", J. American Chemical Society, vol. 119, pp. 9913-9914 (1997).

Lüscher, T.F. et al., "Endothelium-derived contracting factors." Hypertension, vol. 19, pp. 117-130 (1992).

McCoy, M.G. et al., "Characterization of the lipolytic activity of endothelial lipase", Journal of Lipid Research, vol. 43, pp. 921-929 (2002).

Ross, Russell, The pathogenesis of atherosclerosis: a perspective for the 1990s, Nature, vol. 362, pp. 801-809 (1993).

Strauss, J.G. et al., "Endothelial cell-derived lipase mediates uptake and binding of high-density lipoprotein (HDL) particles and the selective uptake of HDL-associated cholesterol esters independent of its enzymic activity", Biochem, J., vol. 368, pp. 69-79 (2002).

Tao, L. et al., "A Mild and Efficient method for N-Arylnucleobase Synthesis via the Cross-Coupling Reactions of Nucleobases with Arylboronic Acids Catalyzed by Simple Copper Salts", Helvetica Chimica Acta, vol. 91(6), pp. 1008-1014 (2008).

Widder, K.J. et al., "Drug and Enzyme Targeting Part A", Methods in Enzymology, vol. 112 pp. 309-396 (1985).

Williams, T.J. et al., "3. Endothelial Cell Biology: Adhesion Molecules Involved in the Microvascular Inflammatory Response", Am Rev Respir Disease, vol. 146, pp. S45-S50 (1992).

Wong, H. et al., "The lipase gene family", Journal of Lipid Research, vol. 43, pp. 993-999 (2002).

Yanagisawa, M. et al., "A novel potent vasoconstrictor peptide produced by vascular endothelial cells", Nature, vol. 332 (6163), pp. 411-415 (1988).

Yue, Y. et al., "Copper-Catalyzed Cross-Coupling Reactions of Nucleobases with Arylboronic Acids: An Efficient Access to N-Arylnucleobases", Eur. J. Org. Chem., pp. 5154-5157 (2005).

Zajac, M. A. et al., "A Novel Method of Caffeine Synthesis from Uracil", Synthetic Communications, vol. 33(19), pp. 3291-3297 (2003).

Zhang, L. et al., "Microwave-assisted synthesis of 8-mercapto-3-methyl-7-alkyl xanthines—an improved methods", Tetrahedron Letters, vol. 47, pp. 775-778 (2006).

Database Registry [Online], Jun. 7, 2012, Database accession No. 1376334-23-4 (XP-002696249).

* cited by examiner

PYRIMIDINONE CARBOXAMIDE INHIBITORS OF ENDOTHELIAL LIPASE

CROSS-REFERENCE TO RELATED APPLICATIONS

The present application is a 371 of International Application No. PCT/US2013/034786 filed on Apr. 1, 2013, which claims priority benefit of U.S. provisional application Ser. No. 61/619,496, filed Apr. 3, 2012; each of which is fully incorporated by reference herein.

FIELD OF THE INVENTION

The present invention provides novel pyrimidinone carboxamide compounds and analogues, which are endothelial lipase (EL) inhibitors, compositions containing them, and methods of using them, for example, for the treatment and/or prophylaxis of dyslipidemias and the sequelae thereof.

BACKGROUND OF THE INVENTION

Cardiovascular disease is a major health risk throughout the industrialized world. Atherosclerosis, the most prevalent of cardiovascular diseases, is the principal cause of heart attack, and stroke, and thereby the principal cause of death in the United States.

Atherosclerosis is a complex disease involving many cell types and molecular factors (for a detailed review, see Ross, R., *Nature*, 362(6423):801-809 (1993)). Results from epidemiologic studies have clearly established an inverse relationship between levels of high density lipoprotein (HDL), which transports endogenous cholesterol from tissues to the liver as well as mediating selective cholesteryl ester delivery to steroidogenic tissues, and the risk for atherosclerosis (Gordon, D. J. et al., *N Engl. J. Med.*, 321(19):1311-1316 (1989)).

The metabolism of HDL is influenced by several members of the triacylglycerol (TG) lipase family of proteins, which hydrolyze triglycerides, phospholipids, and cholesteryl esters, generating fatty acids to facilitate intestinal absorption, energy production, or storage. Of the TG lipases, lipoprotein lipase (LPL) influences the metabolism of HDL cholesterol by hydrolyzing triglycerides in triglyceride-rich lipoproteins, resulting in the transfer of lipids and apolipoproteins to HDL and is responsible for hydrolyzing chylomicron and very low density lipoprotein (VLDL) in muscle and adipose tissues. Hepatic lipase (HL) hydrolyzes HDL triglyceride and phospholipids, generating smaller, lipid-depleted HDL particles, and plays a role in the uptake of HDL cholesterol (Jin, W. et al., *Trends Endocrinol. Metab.*, 13(4):174-178 (2002); Wong, H. et al., *J. Lipid Res.*, 43:993-999 (2002)). Endothelial lipase (also known as EDL, EL, LIPG, endothelial-derived lipase, and endothelial cell-derived lipase) is synthesized in endothelial cells, a characteristic that distinguishes it from the other members of the family.

Recombinant endothelial lipase protein has substantial phospholipase activity but has been reported to have less hydrolytic activity toward triglyceride lipids (Hirata, K. et al., *J. Biol. Chem.*, 274(20):14170-14175 (1999); Jaye, M. et al., *Nat. Genet.*, 21:424-428 (1999)). However, endothelial lipase does exhibit triglyceride lipase activity ex vivo in addition to its HDL phospholipase activity, and endothelial lipase was found to hydrolyze HDL more efficiently than other lipoproteins (McCoy, M. G. et al., *J. Lipid Res.*, 43:921-929 (2002)). Overexpression of the human endothelial lipase gene in the livers of mice markedly reduces plasma concentrations of HDL cholesterol and its major protein apolipoprotein A-I (apoA-I) (Jaye, M. et al., *Nat. Genet.*, 21:424-428 (1999)).

Various types of compounds have been reported to modulate the expression of endothelial lipase, for example, 3-oxo-1,3-dihydro-indazole-2-carboxamides (WO 2004/093872, US 2006/0211755A1), 3-oxo-3-H-benzo[d]isoxazole-2-carboxamides (WO 2004/094393, U.S. Pat. No. 7,217,727), and benzisothiazol-3-one-2-carboxamides (WO 2004/094394, U.S. Pat. No. 7,595,403) by Eli Lilly & Co.; diacylindazole derivatives (WO 2007/042178, US 2008/0287448A1) and imidazopyridin-2-one derivatives (WO 2007/110215, US 2009/0076068A1), and azolopyridin-3-one derivatives (WO 2007/110216, US 2009/0054478A1) by Sanofi-Aventis; heterocyclic derivatives (WO 2009/123164) and keto-amide derivatives (WO 2009/133834) by Shionogi & Co., Ltd. However, because endothelial lipase is a relatively new member in the lipase gene family, a full understanding of the potential of endothelial lipase inhibitors to human health, as well as the inhibitors of other lipases in general, requires more studies.

Thus, there is a clear need for new types of compounds capable of inhibiting the activity of lipases, particularly endothelial lipase, that would constitute effective treatments to the diseases or disorders associated with the activity of such lipases.

SUMMARY OF THE INVENTION

The present disclosure provides novel pyrimidinone carboxamide compounds and their analogues, including stereoisomers, tautomers, pharmaceutically acceptable salts, or solvates thereof, which are useful as EL inhibitors.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of dyslipidemias and the sequelae thereof.

The compounds of the invention may be used in therapy.

The compounds of the invention may be used for the manufacture of a medicament for the treatment and/or prophylaxis of dyslipidemias and the sequelae thereof.

The compounds of the invention can be used alone, in combination with other compounds of the present invention, or in combination with one or more, preferably one to two, and other agent.

Other features and advantages of the invention will be apparent from the following detailed description and claims.

DETAILED DESCRIPTION OF THE INVENTION

I. Compounds of the Invention

In a first aspect, the present invention provides, inter alia, a compound of Formula (I):

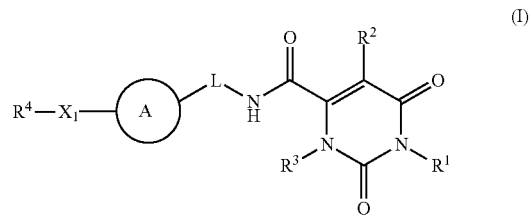

or a stereoisomer, a tautomer, a pharmaceutically acceptable salt, or a solvate thereof, wherein:

ring A is independently selected from the group consisting of: $C_{3-14}$ carbocycle and a 4- to 14-membered heterocycle comprising: carbon atoms and 1-4 heteroatoms selected from N, $NR^e$, O, and $S(O)_p$; wherein said carbocycle and heterocycle are further substituted with 0-4 $R^5$;

$X_1$ is independently selected from the group consisting of: a bond, a hydrocarbon linker and a hydrocarbon-heteroatom linker; wherein said hydrocarbon linker and hydrocarbon-heteroatom linker may be substituted with 0-2 $R^g$; said hydrocarbon linker has one to six carbon atoms and may be saturated or unsaturated; and said hydrocarbon-heteroatom linker may be saturated or unsaturated and has zero to four carbon atoms and one group selected from O, —CO—, S, —SO—, —$SO_2$—, NH, N($C_{1-4}$ alkyl), —NHCO—, —CONH—, —OCONH—, —NHCONH—, and —$SO_2NH$—;

L is independently a hydrocarbon linker substituted with 0-2 $R^g$ or a hydrocarbon-heteroatom linker substituted with 0-2 $R^g$; wherein said hydrocarbon linker has one to eight carbon atoms and may be straight or branched, saturated or unsaturated; and said hydrocarbon-heteroatom linker has one to seven carbon atoms and one group selected from O, —CO—, S, —SO—, —$SO_2$—, NH, N($C_{1-4}$ alkyl), and —NHCO—;

$R^1$ and $R^3$ are each independently selected from the group consisting of: H, $C_{1-6}$ haloalkyl, $C_{1-6}$ alkyl substituted with 0-3 $R^a$, $C_{2-6}$ alkenyl substituted with 0-3 $R^a$,

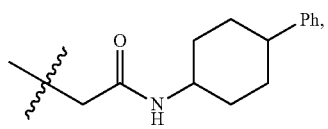 [SMILES: *CC(=O)NC1CCC(c2ccccc2)CC1]

and —$(CH_2)_n$—($C_{3-10}$ carbocycle substituted with 0-3 $R^c$);

$R^2$ is independently selected from the group consisting of: $OR^6$ and $NHR^7$;

$R^4$ is independently selected from the group consisting of: H, =O, halogen, $C_{1-6}$ alkyl substituted with 0-1 OH, $C_{1-4}$ alkoxy, $C_{1-4}$ haloalkyl, $C_{1-4}$ haloalkoxy, CN, $NO_2$, $NH_2$, N($C_{1-4}$ alkyl)$_2$, and a ring moiety substituted with 0-2 $R^h$ and selected from: $C_{3-10}$ carbocycle and a 5- to 10-membered heterocycle comprising: carbon atoms and 1-4 heteroatoms selected from N, $NR^e$, O, and $S(O)_p$;

$R^5$ is, independently at each occurrence, selected from the group consisting of: =O, OH, halogen, $C_{1-6}$ alkyl substituted with 0-1 OH, $C_{1-4}$ alkoxy, $C_{1-4}$ haloalkyl, $C_{1-4}$ haloalkoxy, $SCF_3$, CN, $NH_2$, $NO_2$, NH($C_{1-4}$ alkyl), N($C_{1-4}$ alkyl)$_2$, $CO_2H$, $CO_2(C_{1-4}$ alkyl), —$CH_2CO_2(C_{1-4}$ alkyl), CO($C_{1-4}$ alkyl), $CONH_2$, CONH($C_{1-4}$ alkyl), and CON($C_{1-4}$ alkyl)$_2$;

$R^6$ is independently selected from the group consisting of: H and $C_{1-6}$ alkyl substituted with 0-1 $R^8$;

$R^7$ is independently selected from the group consisting of: H, $COCF_3$, $C_{1-6}$ haloalkyl, $C_{1-6}$ alkyl substituted with 0-1 $R^a$, —$(CHR^f)_n$—($C_{3-10}$ carbocycle substituted with 0-3 $R^b$), and —$(CHR^f)_n$—(5- to 10-membered heterocycle comprising: carbon atoms and 1-4 heteroatoms selected from N, $NR^e$, O, and $S(O)_p$); and wherein said heterocycle is substituted with 0-3 $R^c$;

$R^8$ is independently selected from the group consisting of: $CO_2H$ and OH;

$R^a$ is, independently at each occurrence, selected from the group consisting of: halogen, OH, $C_{1-4}$ alkyl, $C_{1-4}$ alkoxy, $C_{1-4}$ haloalkyl, $C_{1-4}$ haloalkoxy, CN, $NH_2$, $NO_2$, NH($C_{1-4}$ alkyl), N($C_{1-4}$ alkyl)$_2$, $CO_2H$, $CO_2(C_{1-4}$ alkyl), NHCO($C_{1-4}$ alkyl substituted with 0-1 $NH_2$), N($C_{1-4}$ alkyl)CO($C_{1-4}$ alkyl), $NHCO_2(C_{1-4}$ alkyl), $CONHSO_2(C_{1-4}$ alkyl), $SO_2(C_{1-4}$ alkyl), $CONH_2$, CONH($C_{1-4}$ alkyl), $NHSO_2(C_{1-4}$ alkyl), N($C_{1-4}$ alkyl)$SO_2(C_{1-4}$ alkyl), phenoxy, and —CONH(phenylcyclohexyl);

$R^b$ is, independently at each occurrence, selected from the group consisting of: halogen, OH, $C_{1-4}$ alkyl substituted with 0-1 OH, $C_{1-4}$ alkoxy, $C_{1-4}$ haloalkyl, $C_{1-4}$ haloalkoxy, CN, $NH_2$, $NO_2$, NH($C_{1-4}$ alkyl), N($C_{1-4}$ alkyl)$_2$, $CO_2H$, $CO_2(C_{1-4}$ alkyl), $CONH_2$, CONH($C_{1-4}$ alkyl), CON($C_{1-4}$ alkyl)$_2$, $NHCO_2(C_{1-4}$ alkyl), $NHSO_2(C_{1-4}$ alkyl), N($C_{1-4}$ alkyl)$SO_2(C_{1-4}$ alkyl), $SO_2(C_{1-4}$ alkyl), $SO_2NH_2$, phenyl, benzyl, and phenoxy;

$R^c$ is, independently at each occurrence, selected from the group consisting of: =O and $R^b$;

$R^d$ is, independently at each occurrence, selected from the group consisting of: $CONH_2$, $C_{1-4}$ alkyl, —$(CH_2)_2O(CH_2)_2O(C_{1-4}$ alkyl), $C_{3-6}$ carbocycle substituted with 0-2 $R^h$, morpholin-1-yl, 1-$C_{1-4}$ alkyl-piperazin-4-yl, 1-CBz-piperazin-4-yl, pyridyl, indol-3-yl, and benzothiazol-2-yl;

$R^e$ is, independently at each occurrence, selected from the group consisting of: H, $C_{1-4}$ alkyl, CO($C_{1-4}$ alkyl), $CO_2(C_{1-4}$ alkyl), $CO_2$(benzyl), CONH($C_{1-4}$ alkyl), CONH(phenyl substituted with 0-2 halogens), $SO_2(C_{1-4}$ alkyl), and —$(CH_2)$—$R^d$;

$R^f$ is, independently at each occurrence, selected from the group consisting of: H and $C_{1-4}$ alkyl;

$R^g$ is, independently at each occurrence, selected from the group consisting of: halogen, OH, $C_{1-4}$ alkyl, $C_{2-4}$ alkenyl, $C_{1-4}$ haloalkyl, $C_{1-4}$ alkyoxy, $CO_2(C_{1-4}$ alkyl), $C_{3-6}$ cycloalkyl, and phenyl;

$R^h$ is, independently at each occurrence, selected from the group consisting of: H, halogen, $C_{1-6}$ alkyl, $C_{1-6}$ alkoxy, $C_{1-4}$ haloalkyl, $C_{1-4}$ haloalkoxy, —$(CH_2)_2O(C_{1-4}$ alkyl), $CF_3$, $NO_2$, $CONH_2$, OBn, quinolinyl, 1-$C_{1-4}$ alkyl-pyrazolyl, 1-($CH_2CO_2(C_{1-4}$ alkyl))-pyrazolyl, 1-$C_{1-4}$ alkyl-3-$CF_3$-pyrazolyl, 1-(($CH_2)_2$(morpholin-4-yl))-pyrazolyl, 1-(tetrahydro-2H-pyran-2-yl)-pyrazolyl, 1,2,5-tri$C_{1-4}$ alkyl-pyrazolyl, 2-Ph-4-$C_{1-4}$ alkyl-thiazolyl, —$NHSO_2$(phenyl substituted with $C_{1-4}$ alkyl), and —$(CH_2)_{0-2}$-(phenyl substituted with zero to three substituents independently selected from the group consisting of: halogen, $CH_2OH$, $C_{1-4}$ alkyl, $C_{1-4}$ haloalkyl, $C_{1-4}$ alkoxy, $C_{1-4}$ haloalkoxy, N($C_{1-4}$ alkyl)$_2$, $CONH_2$, and NHCO($C_{1-4}$ alkyl));

n is, independently at each occurrence, selected from 0, 1, 2, 3, and 4; and p is, independently at each occurrence, selected from 0, 1, and 2;

provided that the following compounds are excluded:

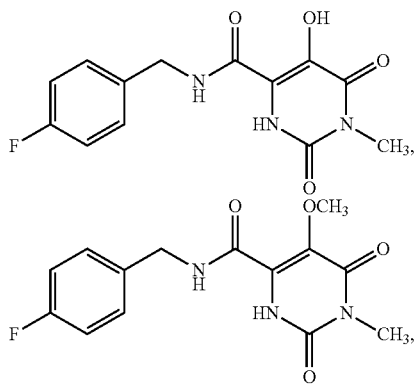

-continued

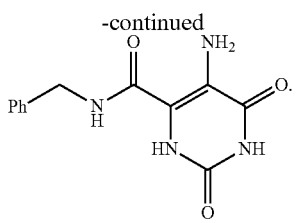

In a second aspect, the present invention includes a compound of Formula (I), or a stereoisomer, a tautomer, a pharmaceutically acceptable salt, or a solvate thereof, within the scope of the first aspect, wherein:

ring A is independently selected from the group consisting of: $C_{3-6}$ cycloalkyl, phenyl, naphthyl, tetrahydronaphthyl, dihydroindenyl, and a 5- to 10-membered heterocycle comprising: carbon atoms and 1-4 heteroatoms selected from N, $NR^e$, O, and $S(O)_p$; and wherein each moiety is substituted with 0-3 $R^5$;

$X_1$ is independently selected from the group consisting of: a bond, a hydrocarbon linker substituted with 0-1 $R^g$ and a hydrocarbon-heteroatom linker substituted with 0-1 $R^g$; wherein said hydrocarbon linker has one to three carbon atoms and may be saturated or unsaturated; and said hydrocarbon-heteroatom linker may be saturated or unsaturated and has zero to three carbon atoms and one group selected from O, CO, —SO$_2$—, —CONH—, and —NHCO—;

L is independently a hydrocarbon linker substituted with 0-1 $R^g$ or a hydrocarbon-heteroatom linker substituted with 0-1 $R^g$; wherein said hydrocarbon linker has one to six carbon atoms and may be straight or branched, saturated or unsaturated; and said hydrocarbon-heteroatom linker has one to five carbon atoms and one group selected from O, —CO—, S, —SO—, —SO$_2$—, NH, N(C$_{1-4}$ alkyl), and —NHCO—; and $R^1$ and $R^3$ are each independently selected from the group consisting of: H, $C_{1-6}$ alkyl substituted with 0-3 $R^a$, $C_{1-6}$ haloalkyl,

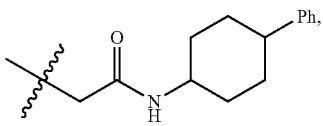 [SMILES: *CC(=O)NC1CCC(c2ccccc2)CC1]

and —(CH$_2$)$_n$-(phenyl substituted with 0-3 $R^c$);

$R^2$ is independently selected from the group consisting of: $OR^6$ and $NHR^7$;

$R^4$ is independently selected from the group consisting of: H, =O, halogen, $C_{1-4}$ alkyl, $C_{1-4}$ alkoxy, $C_{1-4}$ haloalkyl, $C_{1-4}$ haloalkoxy, CN, NO$_2$, NH$_2$, N(C$_{1-4}$ alkyl)$_2$, CO$_2$(C$_{1-4}$ alkyl), —CH$_2$CO$_2$(C$_{1-4}$ alkyl), a ring moiety substituted with 0-2 $R^h$ and selected from: $C_{3-10}$ carbocycle and a 5- to 10-membered heterocycle comprising: carbon atoms and 1-4 heteroatoms selected from N, $NR^e$, O, and $S(O)_p$;

$R^5$ is, independently at each occurrence, selected from the group consisting of: =O, OH, halogen, $C_{1-4}$ alkyl substituted with 0-1 OH, $C_{1-4}$ alkoxy, $C_{1-4}$ haloalkyl, $C_{1-4}$ haloalkoxy, SCF$_3$, CN, NO$_2$, CO$_2$(C$_{1-4}$ alkyl), —CH$_2$CO$_2$(C$_{1-4}$ alkyl), NH$_2$, NH(C$_{1-4}$ alkyl), N(C$_{1-4}$ alkyl)$_2$, CONH$_2$, CONH(C$_{1-4}$ alkyl), and CON(C$_{1-4}$ alkyl)$_2$; and $R^6$ is independently selected from the group consisting of: H and $C_{1-4}$ alkyl substituted with 0-1 CO$_2$H;

provided that the following compounds are excluded:

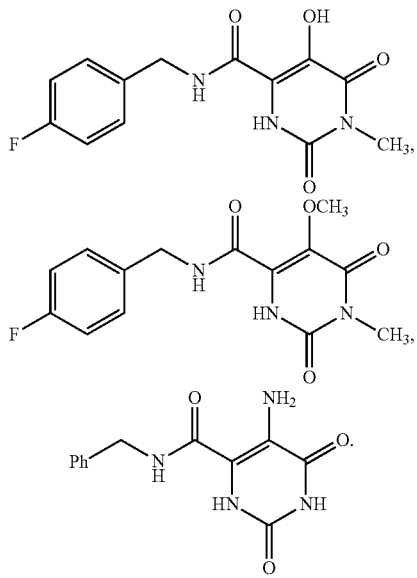

In a third aspect, the present invention includes a compound of Formula (I), or a stereoisomer, a tautomer, a pharmaceutically acceptable salt, or a solvate thereof, within the scope of the first or second aspect, wherein:

L is independently a hydrocarbon linker optionally substituted with 0-1 $R^g$ or a hydrocarbon-heteroatom linker optionally substituted with 0-1 $R^g$; wherein said hydrocarbon linker has one to five carbon atoms and may be straight or branched, saturated or unsaturated; and said hydrocarbon-heteroatom linker has zero to four carbon atoms and one group selected from O, S, —SO—, and —SO$_2$—;

provided that the following compounds are excluded:

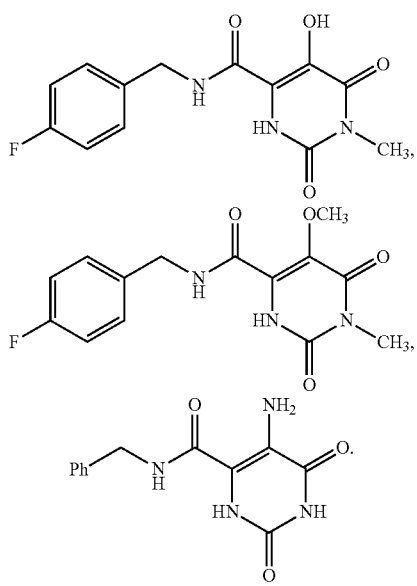

In a fourth aspect, the present invention includes a compound of Formula (I), or a stereoisomer, a tautomer, a pharmaceutically acceptable salt, or a solvate thereof, within the scope of any of the above aspects, wherein:

ring A is independently selected from the group consisting of: $C_{3-6}$ cycloalkyl, phenyl, naphthyl, tetrahydronaphthalenyl, dihydroindenyl, tetrahydroindazolyl, tetrahydroquinolinyl, benzothiazolyl, benzimidazolyl, pyridyl, isoxazolyl, oxadiazolyl, pyrrolidinyl, piperidinyl, pyrazolyl; wherein each moiety is further substituted with 0-3 $R^5$;

$X_1$ is a bond, O, CO, —$(CH_2)_{1-3}$—, —$(CH_2)_{1-2}$O—, —$SO_2$—, —CONH—, and —NHCO—;

L is independently selected from the group consisting of: straight or branched $C_{1-5}$ alkylene, and —O-(straight or branched $C_{1-4}$ alkylene);

$R^1$ and $R^3$ are each independently selected from the group consisting of: H, $C_{1-4}$ alkyl, $C_{1-4}$ haloalkyl, 3-halo-4-halo-phenyl, 3-$CF_3$-5-halo-phenyl, and benzyl;

$R^2$ is independently selected from the group consisting of: OH and $NHR^7$;

$R^4$ is independently selected from the group consisting of: H, =O, halogen, $C_{1-4}$ alkyl, $C_{1-4}$ alkoxy, $C_{1-4}$ haloalkyl, $C_{1-4}$ haloalkoxy, CN, $NO_2$, $NH_2$, $N(C_{1-4}$ alkyl$)_2$, $CO_2(C_{1-4}$ alkyl), $C_{3-6}$ cycloalkyl, morpholinyl, 1-$C_{1-4}$ alkyl-piperazin-4-yl, 1-$CO_2(C_{1-4}$ alkyl)-piperazin-4-yl, 1-CBz-piperazin-4-yl, pyrrolyl, oxadiazolyl, benzimidazolyl,

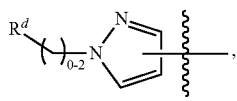

and phenyl substituted with 0-2 $R^h$;

$R^5$ is, independently at each occurrence, selected from the group consisting of: =O, halogen, $C_{1-4}$ alkyl, $C_{1-4}$ alkoxy, $C_{1-4}$ haloalkyl, $C_{1-4}$ haloalkoxy, $SCF_3$, $OCH_2CF_3$, CN, $NH_2$, $NO_2$, $NH(C_{1-4}$ alkyl), $N(C_{1-4}$ alkyl$)_2$, $CO_2(C_{1-4}$ alkyl), —$CH_2CO_2(C_{1-4}$ alkyl), $CONH_2$, $CONH(C_{1-4}$ alkyl), and $CON(C_{1-4}$ alkyl$)_2$;

$R^7$ is independently selected from the group consisting of: H, $C_{1-4}$ alkyl, $C_{1-4}$ haloalkyl, —$(CH_2)_2O(C_{1-4}$ alkyl), $COCF_3$, $C_{1-6}$ alkyl substituted with 0-1 OH, —$(CHR^f)_n$—$(C_{3-6}$ cycloalkyl substituted with 0-1 OH); and —$(CHR^f)_n$-(phenyl substituted with 0-2 $R^b$);

$R^b$ is, independently at each occurrence, selected from the group consisting of: halogen, OH, $C_{1-4}$ alkyl substituted with 0-1 OH, $C_{1-4}$ alkoxy, $C_{1-4}$ haloalkyl, $C_{1-4}$ haloalkoxy, $CF_3$, $OCF_3$, CN, $NH_2$, $NO_2$, $NH(C_{1-4}$ alkyl), $N(C_{1-4}$ alkyl$)_2$, $CO_2H$, $CO_2(C_{1-4}$ alkyl), $CONH_2$, $CONH(C_{1-4}$ alkyl), $CON(C_{1-4}$ alkyl$)_2$, $NHCO_2(C_{1-4}$ alkyl), $SO_2(C_{1-4}$ alkyl), and $SO_2NH_2$;

$R^d$ is, independently at each occurrence, selected from the group consisting of: $CONH_2$, $C_{1-4}$ alkyl, —$(CH_2)_2O(CH_2)_2O(C_{1-4}$ alkyl), $C_{3-6}$ carbocycle substituted with 0-2 $R^h$, morpholin-1-yl, 1-$C_{1-4}$ alkyl-piperazin-4-yl, 1-CBz-piperazin-4-yl, pyridyl, indol-3-yl, and benzothiazol-2-yl;

$R^f$ is, independently at each occurrence, selected from the group consisting of: H and methyl; and n is, independently at each occurrence, selected from 0, 1, 2, and 3;

provided that the following compounds are excluded:

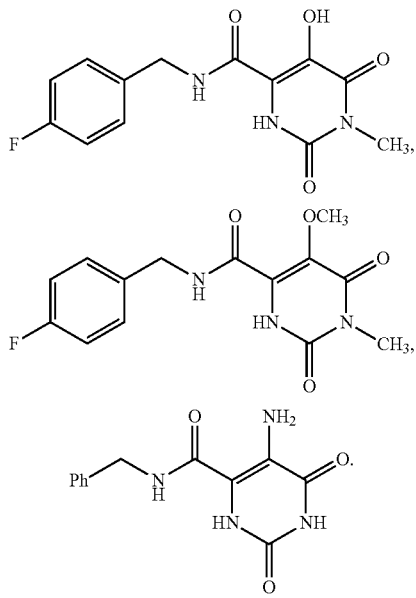

In a fifth aspect, the present invention includes a compound of Formula (I), or a stereoisomer, a tautomer, a pharmaceutically acceptable salt, or a solvate thereof, within the scope of any of the above aspects, wherein:

$R^4$ is independently selected from the group consisting of: H, =O, halogen, $C_{1-4}$ alkyl, $C_{1-4}$ alkoxy, $C_{1-4}$ haloalkyl, $C_{1-4}$ haloalkoxy, CN, $NO_2$, $NH_2$, $N(C_{1-4}$ alkyl$)_2$, $CO_2(C_{1-4}$ alkyl), $C_{3-6}$ cycloalkyl, morpholinyl, 1-$C_{1-4}$ alkyl-piperazin-4-yl, 1-$CO_2(C_{1-4}$ alkyl)-piperazin-4-yl, 1-CBz-piperazin-4-yl, pyrrolyl, oxadiazolyl, benzimidazolyl,

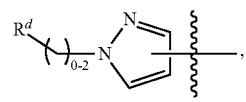

and phenyl substituted with 0-2 $R^h$;

$R^7$ is independently selected from the group consisting of: H, $C_{1-4}$ alkyl, —$(CH_2)_2O(C_{1-4}$ alkyl), $COCF_3$, 4-halo-benzyl, 4-$C_{1-4}$ alkoxy-benzyl, 3-$CF_3$-benzyl, 2-$CH_2OH$-benzyl, 2-halo-phenethyl, 4-halo-phenethyl, and —$(CH_2)_3$Ph; and L is independently selected from the group consisting of: —$CH_2$—, —$CH(CH_3)$—, —$(CH_2)_2$—, —$(CH_2)_3$—, —$(CH_2)_2CH(CH_3)$—, —$OCH_2CH(CH_3)$—, —$OCH(CH_3)CH_2$—, —$O(CH_2)_3$—, and —$O(CH_2)_2CH(CH_3)$—;

provided that the following compounds are excluded:

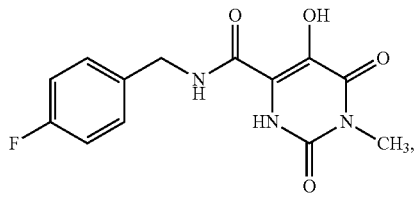

-continued

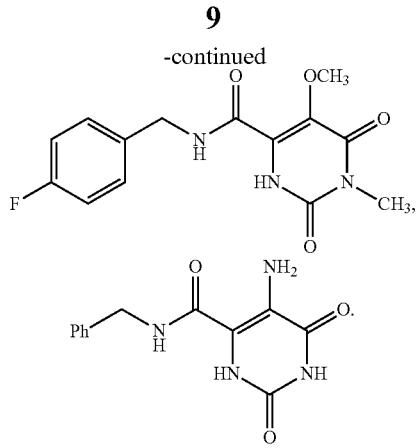

In a sixth aspect, the present invention includes a compound of Formula (I), wherein $R^2$ is $NHR^7$, further characterized by Formula (II):

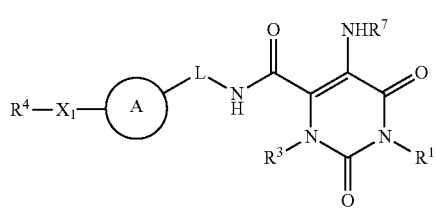

(II)

or a stereoisomer, a tautomer, a pharmaceutically acceptable salt, or a solvate thereof, within the scope of any of the above aspects;
provided that

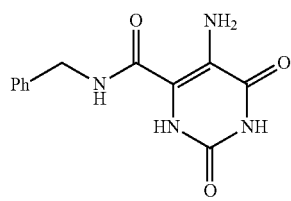 [SMILES: Nc1c(C(=O)NCc2ccccc2)[nH]c(=O)[nH]c1=O]

is excluded.

In a seventh aspect, the present invention includes a compound of Formula (II), or a stereoisomer, a tautomer, a pharmaceutically acceptable salt, or a solvate thereof, within the scope of any of the above aspects, wherein:
ring A is independently selected from the group consisting of: phenyl, naphthyl, dihydroindenyl, tetrahydroindazolyl, benzothiazolyl, tetrahydronaphthalenyl, pyrazolyl, and pyrrolidinyl; wherein each moiety is further substituted with 0-3 $R^5$;
$X_1$ is a bond, O, CO, —$(CH_2)_{1-2}$—, —$CH_2O$—, and —$SO_2$—;
$R^1$ and $R^3$ are each independently selected from the group consisting of: H, $C_{1-4}$ alkyl, $CH_2CF_3$, and benzyl;
$R^4$ is independently selected from the group consisting of: H, halogen, $C_{1-4}$ alkyl, $C_{1-4}$ alkoxy, $C_{1-4}$ haloalkyl, $C_{1-4}$ haloalkoxy, CN, $NO_2$, $NH_2$, $N(C_{1-4}$ alkyl$)_2$, $CO_2(C_{1-4}$ alkyl), $C_{3-6}$ cycloalkyl, morpholinyl, 1-$C_{1-4}$ alkyl-piperazin-4-yl, 1-$CO_2(C_{1-4}$ alkyl)-piperazin-4-yl, 1-CBz-piperazin-4-yl, pyrrol-1-yl, 1,3,4-oxadiazolyl, benzimidazolyl,

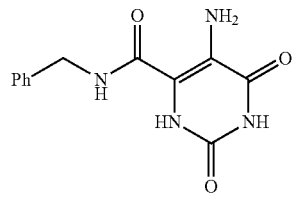

and phenyl substituted with 0-2 $R^h$;
$R^5$ is, independently at each occurrence, selected from the group consisting of: halogen, $C_{1-4}$ alkyl, and $C_{1-4}$ alkoxy;
$R^7$ is independently selected from the group consisting of: H, $C_{1-4}$ alkyl, $COCF_3$, and 4-$C_{1-4}$ alkoxy-benzyl;
L is independently selected from the group consisting of: —$CH_2$—, —$CH(CH_3)$—, —$(CH_2)_2$—, —$(CH_2)_3$—, —$(CH_2)_2CH(CH_3)$—, —$OCH_2CH(CH_3)$—, —$O(CH_2)_3$—, and —$O(CH_2)_2CH(CH_3)$—;
$R^d$ is, independently at each occurrence, selected from the group consisting of: $CONH_2$, $C_{1-4}$ alkyl, —$(CH_2)_2O(CH_2)_2O(C_{1-4}$ alkyl), $C_{3-6}$ cycloalkyl, phenyl substituted with 0-2 $R^h$, morpholin-1-yl, 1-$C_{1-4}$ alkyl-piperazin-4-yl, 1-CBz-piperazin-4-yl, pyridyl, indol-3-yl, and benzothiazol-2-yl; and
$R^h$ is, independently at each occurrence, selected from the group consisting of: H, halogen, $C_{1-4}$ alkyl, $C_{1-4}$ alkoxy, $CF_3$, $OCF_3$, CN, $CO_2(C_{1-4}$ alkyl), $CONH_2$, and phenyl substituted with zero to three substituents independently selected from the group consisting of: halogen, $C_{1-4}$ alkyl, $C_{1-4}$ haloalkyl, and $C_{1-4}$ alkyoxy;
provided that

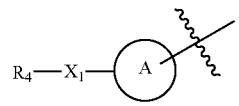

is excluded.

In an eighth aspect, the present invention includes a compound of Formula (II), or a stereoisomer, a tautomer, a pharmaceutically acceptable salt, or a solvate thereof, within the scope of any of the above aspects, wherein:
$R^1$ and $R^3$ are each independently selected from the group consisting of: H and $C_{1-4}$ alkyl;

is independently selected from the group consisting of:

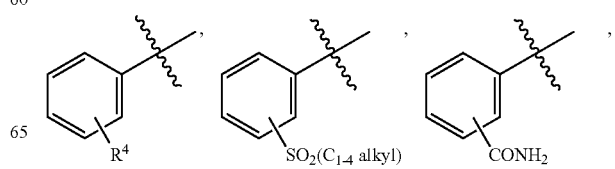

-continued

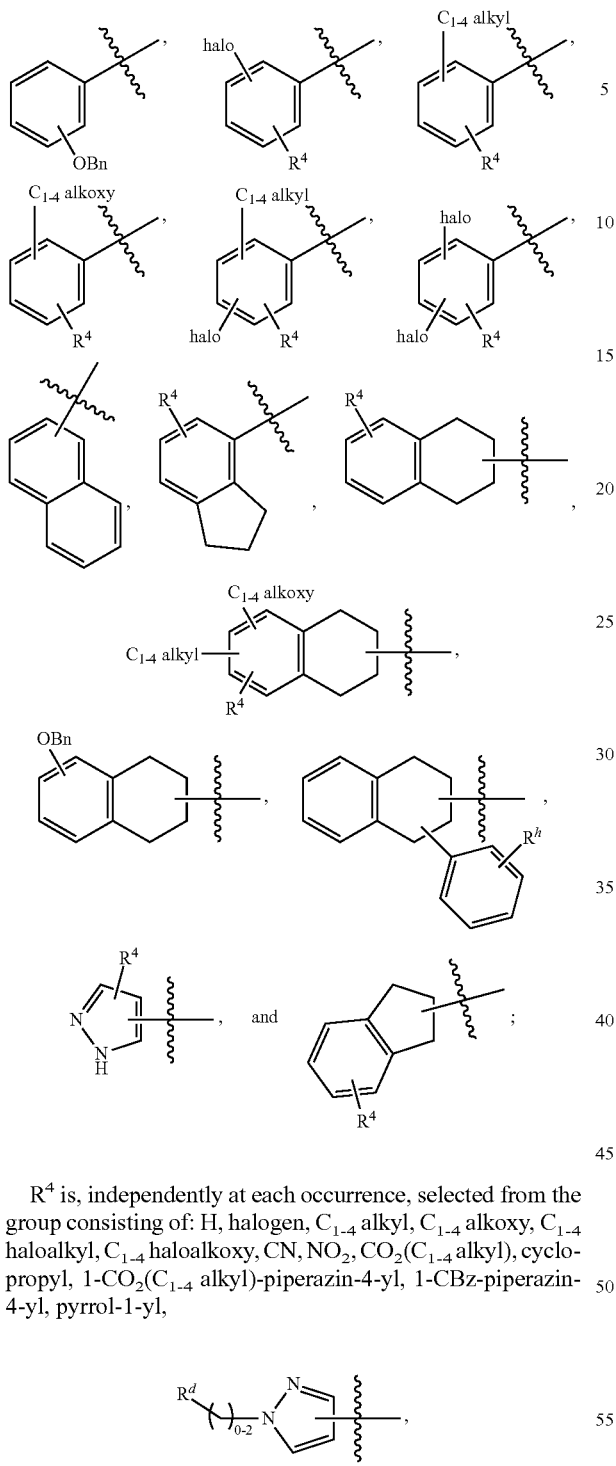

$R^4$ is, independently at each occurrence, selected from the group consisting of: H, halogen, $C_{1-4}$ alkyl, $C_{1-4}$ alkoxy, $C_{1-4}$ haloalkyl, $C_{1-4}$ haloalkoxy, CN, $NO_2$, $CO_2(C_{1-4}$ alkyl), cyclopropyl, 1-$CO_2(C_{1-4}$ alkyl)-piperazin-4-yl, 1-CBz-piperazin-4-yl, pyrrol-1-yl,

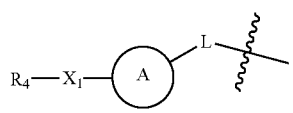

and Ph;

$R^d$ is, independently at each occurrence, selected from the group consisting of: $CONH_2$, $C_{1-4}$ alkyl, $C_{3-6}$ cycloalkyl, phenyl substituted with 0-1 $R^h$, morpholin-1-yl, 1-CBz-piperazin-4-yl, pyridyl, indol-3-yl, and benzothiazol-2-yl; and $R^h$ is, independently at each occurrence, selected from the group consisting of: H, halogen, $C_{1-4}$ alkyl, $C_{1-4}$ alkoxy, $CF_3$, $OCF_3$, CN, $CO_2(C_{1-4}$ alkyl), and $CONH_2$;

provided that

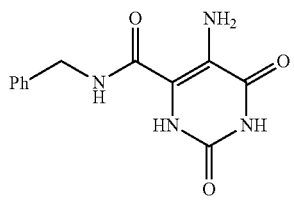 [SMILES: Nc1c(C(=O)NCc2ccccc2)[nH]c(=O)[nH]c1=O]

is excluded.

In a ninth aspect, the present invention includes a compound of Formula (II), or a stereoisomer, a tautomer, a pharmaceutically acceptable salt, or a solvate thereof, within the scope of any of the above aspects, wherein:

$R^1$ and $R^3$ are each independently selected from the group consisting of: H and $C_{1-4}$ alkyl;

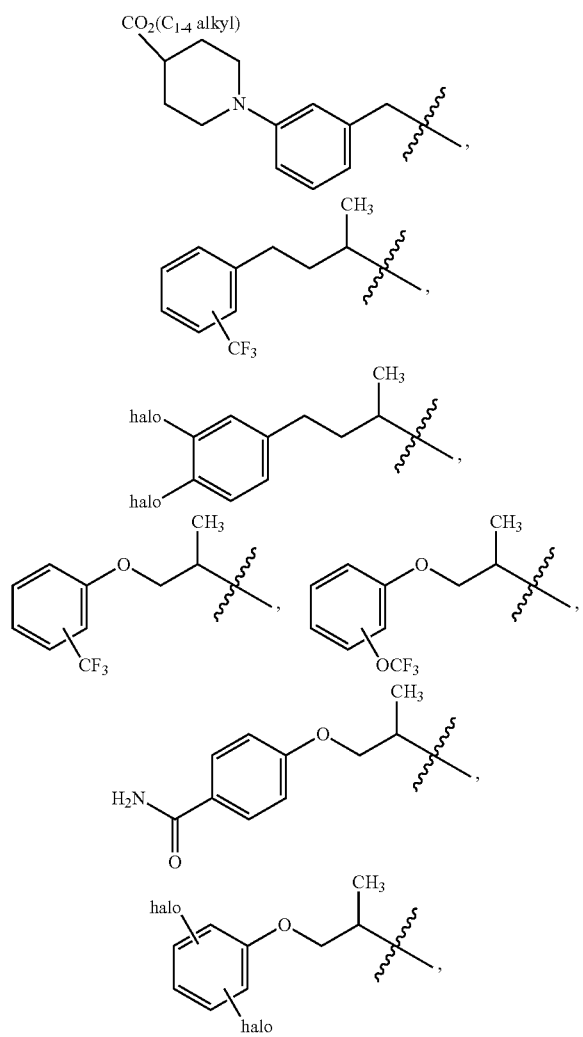

is independently selected from the group consisting of:

-continued

-continued
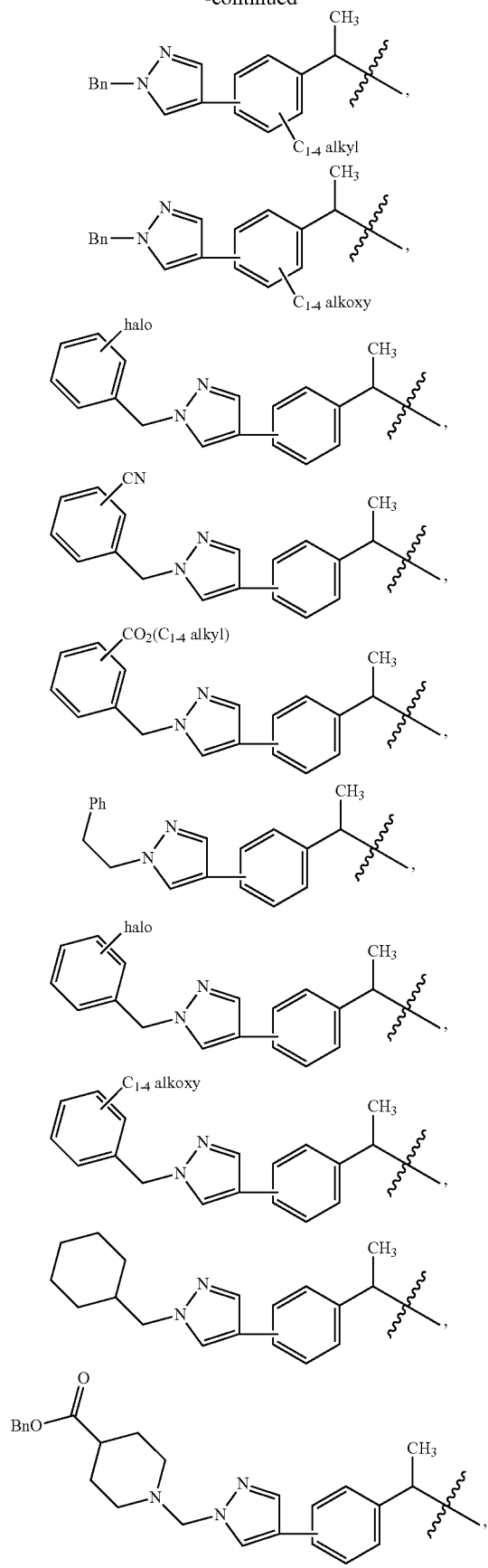
-continued
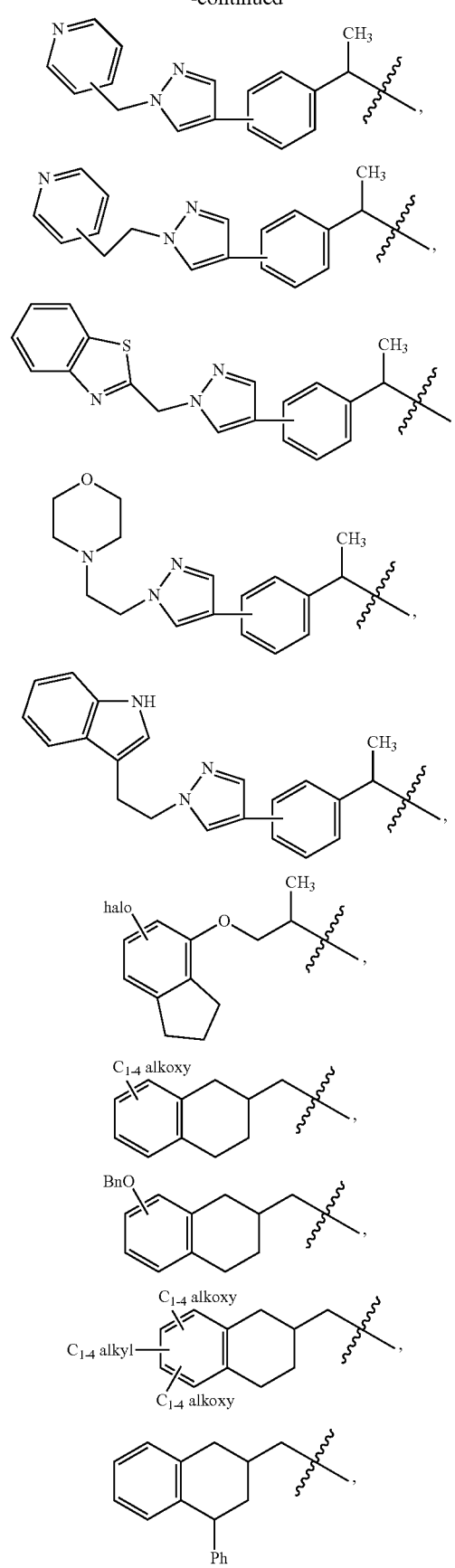

-continued

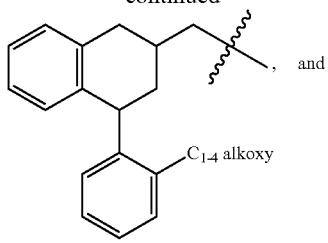
, and

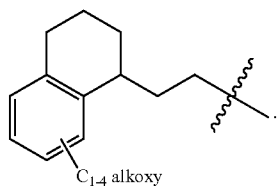
.

In a tenth aspect, the present invention includes a compound of Formula (I), wherein $R^2$ is OH, further characterized by Formula (III):

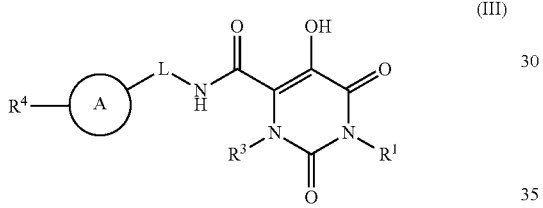
(III)

or a stereoisomer, a tautomer, a pharmaceutically acceptable salt, or a solvate thereof, within the scope of any of the first to fifth aspect;

provided that

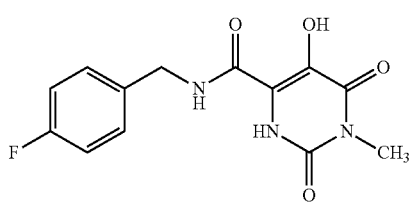 [SMILES: Cn1c(=O)[nH]c(C(=O)NCc2ccc(F)cc2)c(O)c1=O]

is excluded.

In an eleventh aspect, the present invention includes a compound of Formula (III), or a stereoisomer, a tautomer, a pharmaceutically acceptable salt, or a solvate thereof, within the scope of any of the first to fifth or tenth aspect, wherein:

$R^1$ and $R^3$ are each independently selected from the group consisting of: H and $C_{1-4}$ alkyl;

is independently selected from the group consisting of:

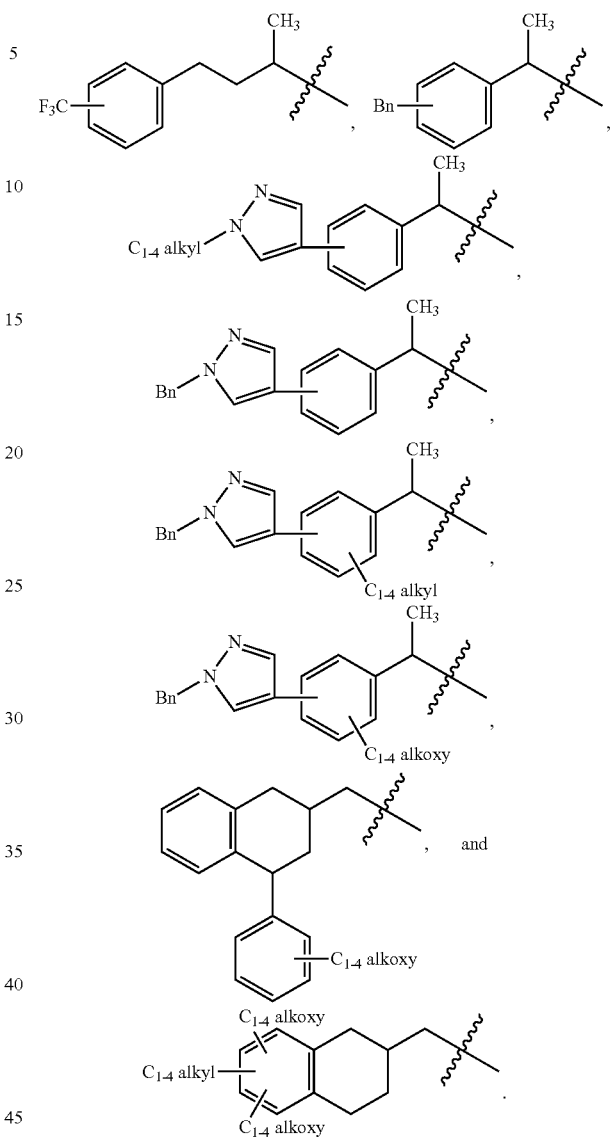

In a twelfth aspect, the present invention provides a compound selected from the exemplified examples or a stereoisomer, a tautomer, a pharmaceutically acceptable salt, or a solvate thereof.

In another aspect, the present invention provides a compound selected from any subset list of compounds within the scope of the twelfth aspect.

In another embodiment, the compounds of the present invention have EL $IC_{50}$ values ≤10 μM.

In another embodiment, the compounds of the present invention have EL $IC_{50}$ values ≤5 μM.

In another embodiment, the compounds of the present invention have EL $IC_{50}$ values ≤1 μM.

In another embodiment, the compounds of the present invention have EL $IC_{50}$ values ≤0.5 μM.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate thereof.

In another embodiment, the present invention provides a pharmaceutical composition, comprising: a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition as defined above further comprising additional therapeutic agent(s).

In another embodiment, the present invention provides a method for the treatment and/or prophylaxis of dyslipidemias and the sequelae thereof comprising administering to a patient in need of such treatment and/or prophylaxis a therapeutically effective amount of at least one of the compounds of the present invention, alone, or, optionally, in combination with another compound of the present invention and/or at least one other type of therapeutic agent.

Examples of diseases or disorders associated with the activity of endothelial lipase that can be prevented, modulated, or treated according to the present invention include, but are not limited to, atherosclerosis, coronary heart disease, coronary artery disease, coronary vascular disease, cerebrovascular disorders, Alzheimer's disease, venous thrombosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity or endotoxemia.

In one embodiment, the present invention provides a method for the treatment and/or prophylaxis of atherosclerosis, coronary heart disease, cerebrovascular disorders and dyslipidemia, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a compound of the present invention for use in therapy for the treatment and/or prophylaxis of dyslipidemias and the sequelae thereof.

In another embodiment, the present invention also provides the use of a compound of the present invention for the manufacture of a medicament for the treatment and/or prophylaxis of dyslipidemias and the sequelae thereof.

In another embodiment, the present invention provides a method for the treatment and/or prophylaxis of dyslipidemias and the sequelae thereof, comprising: administering to a patient in need thereof a therapeutically effective amount of a first and second therapeutic agent, wherein the first therapeutic agent is a compound of the present invention.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment and/or prophylaxis of dyslipidemias and the sequelae thereof.

The compounds of the present invention may be employed in combination with additional therapeutic agent(s) selected from one or more, preferably one to three, of the following therapeutic agents: anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-hypertensive agents, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, treatments for heart failure, treatments for peripheral arterial disease, treatment for malignant tumors, and anti-inflammatory agents.

In another embodiment, additional therapeutic agent(s) used in combined pharmaceutical compositions or combined methods or combined uses, are selected from one or more, preferably one to three, of the following therapeutic agents in treating atherosclerosis: anti-hyperlipidemic agents, plasma HDL-raising agents, anti-hypercholesterolemic agents, cholesterol biosynthesis inhibitors (such as HMG CoA reductase inhibitors), acyl-coenzyme A:cholesterol acyltransferase (ACAT) inhibitors, LXR agonist, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, antioxidant vitamins, β-blockers, anti-diabetes agents, angiotensin II antagonists, angiotensin converting enzyme inhibitors, platelet aggregation inhibitors, fibrinogen receptor antagonists, aspirin or fibric acid derivatives.

In another embodiment, additional therapeutic agent(s) used in combined pharmaceutical compositions or combined methods or combined uses, are selected from one or more, preferably one to three, of the following therapeutic agents in treating cholesterol biosynthesis inhibitor, particularly an HMG-CoA reductase inhibitor. Examples of suitable HMG-CoA reductase inhibitors include, but are not limited to, lovastatin, simvastatin, pravastatin, fluvastatin, atorvastatin, and rivastatin.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_{1-6}$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle," "carbocyclyl," or "carbocyclic residue" is intended to mean any stable 3-, 4-, 5-, 6-, 7-, or 8-membered monocyclic or bicyclic or 7-, 8-, 9-, 10-, 11-, 12-, 13, or 14-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0] bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2] bicyclooctane). Preferred carbocycles, unless otherwise specified, are cyclopropyl, cyclobutyl, cyclopentyl, cyclohexyl, phenyl, indanyl, and tetrahydronaphthyl. When the term "carbocycle" is used, it is intended to include "aryl." A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl. "Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary*, 13th Edition, John Wiley & Sons, Inc., New York (1997). "$C_6$ or $C_{10}$ aryl" or "$C_{6-10}$ aryl" refers to phenyl and naphthyl. Unless otherwise specified, "aryl", "$C_6$ or $C_{10}$ aryl", "$C_{6-10}$ aryl", or "aromatic residue" may be unsubstituted or substituted with 1 to 5 groups, preferably 1 to 3 groups, selected from —OH, —OCH$_3$, —Cl, —F, —Br, —I, —CN, —NO$_2$, —NH$_2$, —N(CH$_3$)H, —N(CH$_3$)$_2$, —CF$_3$, —OCF$_3$, —C(O)CH$_3$, —SCH$_3$, —S(O)CH$_3$, —S(O)$_2$CH$_3$, —CH$_3$, —CH$_2$CH$_3$, —CO$_2$H, and —CO$_2$CH$_3$.

The term "benzyl," as used herein, refers to a methyl group on which one of the hydrogen atoms is replaced by a phenyl group, wherein said phenyl group may optionally be substituted with 1 to 5 groups, preferably 1 to 3 groups, OH, OCH$_3$, Cl, F, Br, I, CN, NO$_2$, NH$_2$, N(CH$_3$)H, N(CH$_3$)$_2$, CF$_3$, OCF$_3$, C(=O)CH$_3$, SCH$_3$, S(=O)CH$_3$, S(=O)$_2$CH$_3$, CH$_3$, CH$_2$CH$_3$, CO$_2$H, and CO$_2$CH$_3$.

As used herein, the term "heterocycle," "heterocyclyl," or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and S(O)$_p$, wherein p is 0, 1 or 2).

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counter ion" is used to represent a negatively charged species such as chloride, bromide, hydroxide, acetate, and sulfate.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R.

Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

As a person of ordinary skill in the art would be able to understand, a ketone (—CH—C=O) group in a molecule may tautomerize to its enol form (—C=C—OH), as shown in the following equation, wherein R=R$^4$—X$_1$-A-L:

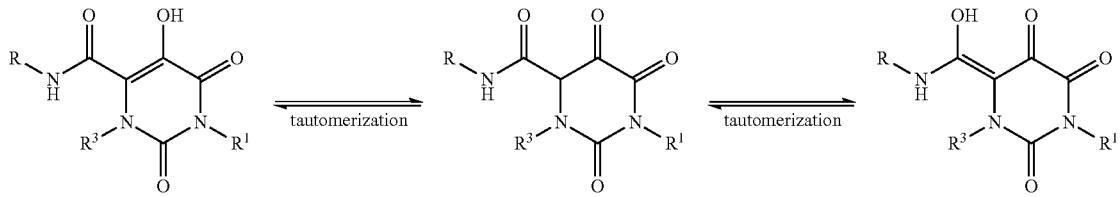

Likewise, an imine (—CH—C=NHR) group in a molecule may tautomerize to its enamine form (—C=C—NHR), as shown in the following equation for illustration purpose:

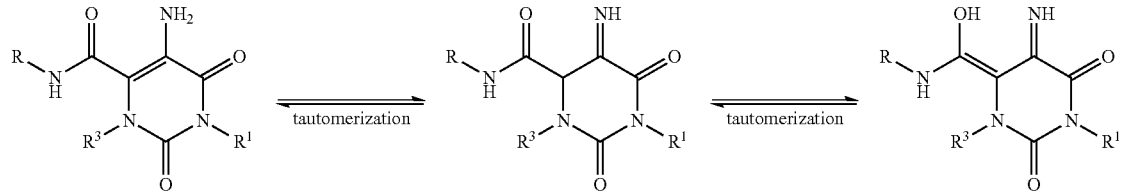

Various tautomerized forms may occur when both R$^1$ and R$^3$ are hydrogen, when R$^1$=H and R$^3$≠H, or when R$^1$≠H and R$^3$=H. For example, some possible tautomerized forms are shown for illustration purpose for the compounds when R$^2$ is OH and both R$^1$ and R$^3$ are hydrogen.

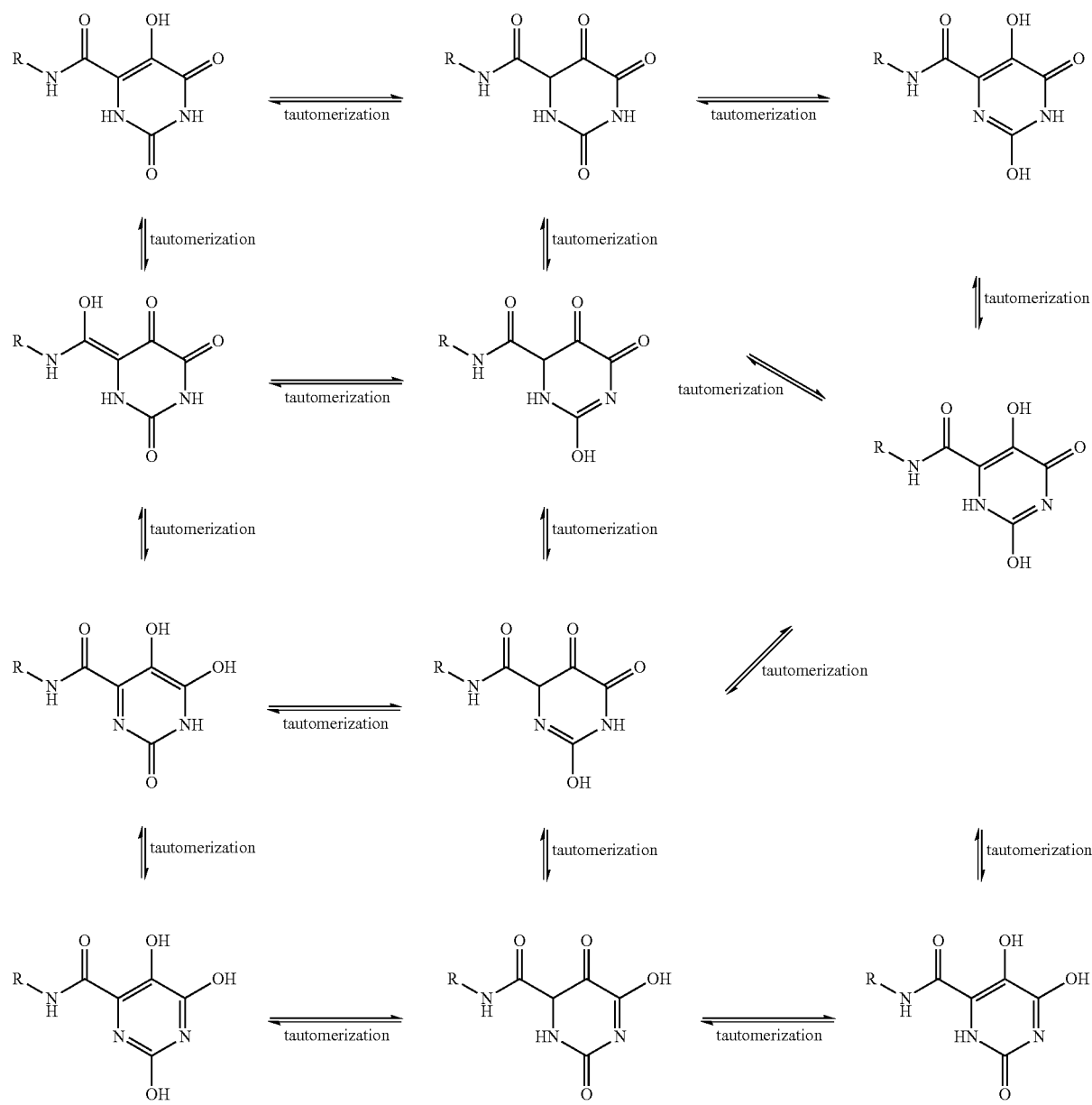
For example, some possible tautomerized forms are shown for illustration purpose for the compounds when $R^2$ is $NH_2$ and both $R^1$ and $R^3$ are hydrogen.
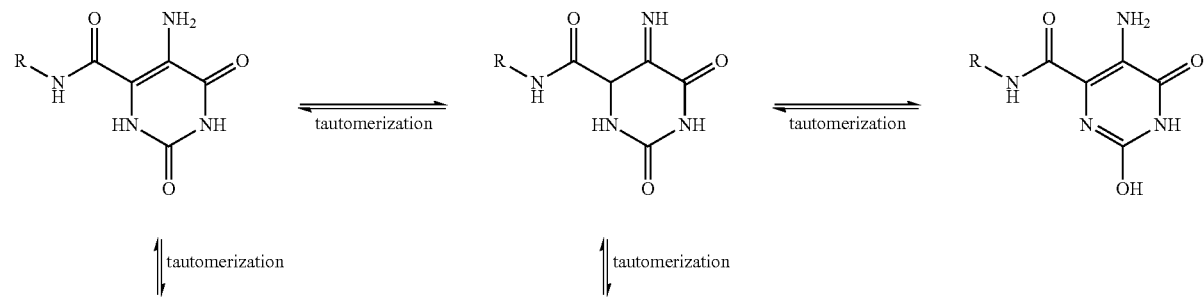

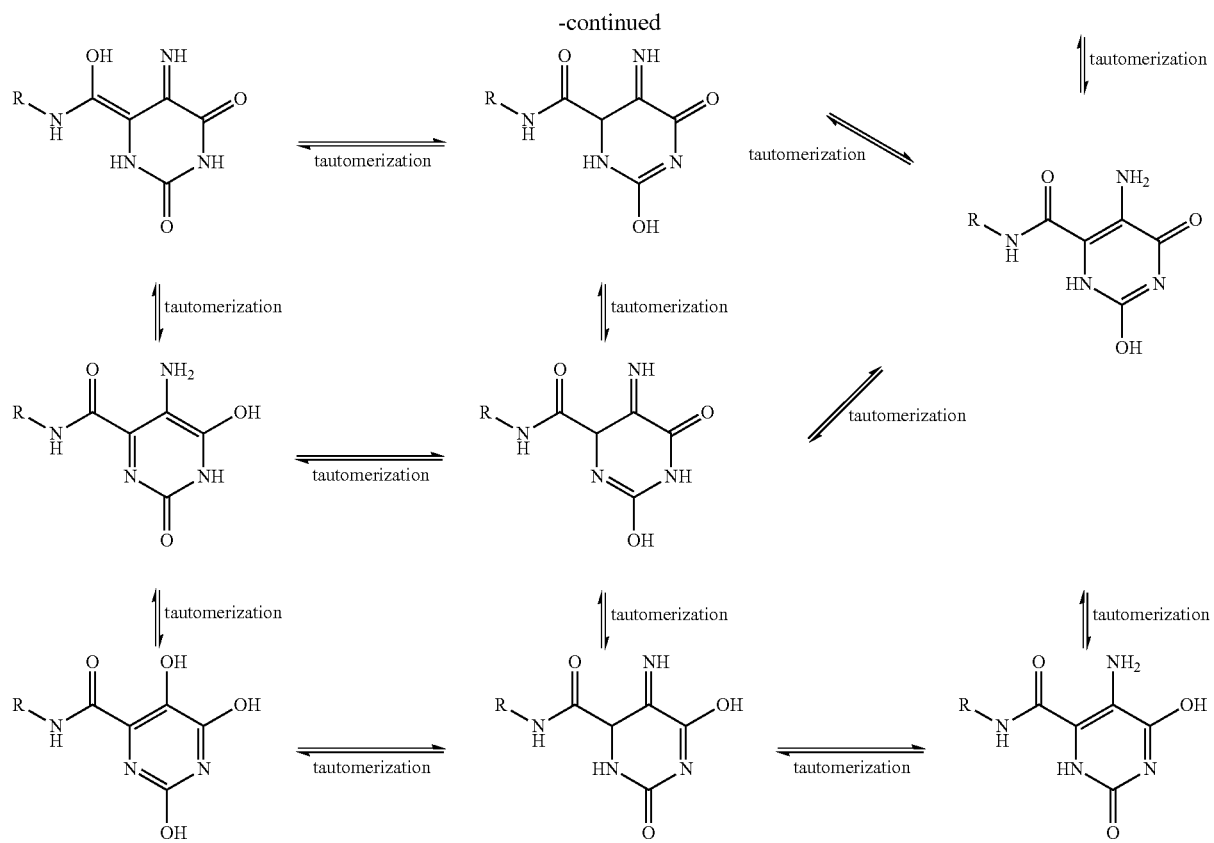

Thus, this disclosure is intended to cover all possible tautomers even when a structure depicts only one of them.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 18th Edition, Mack Publishing Company, Easton, Pa. (1990), the disclosure of which is hereby incorporated by reference.

In addition, compounds of Formula (I), Formula (II), or Formula (III) may have prodrug forms. Any compound that will be converted in vivo to provide the bioactive agent (i.e., a compound of Formula (I), Formula (II) or Formula (III)) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112: 309-396, Academic Press (1985);

b) Bundgaard, H., Chapter 5, "Design and Application of Prodrugs," Krosgaard-Larsen, P. et al., eds., *A Textbook of Drug Design and Development*, pp. 113-191, Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988); and e) Kakeya, N. et al., *Chem. Pharm. Bull.*, 32:692 (1984).

Compounds containing a carboxy group can form physiologically hydrolyzable esters that serve as prodrugs by being hydrolyzed in the body to yield Formula (I), Formula (II), Formula (III), or Formula (IV) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of Formula (I), Formula (II), Formula (III), or Formula (IV) include $C_1$ to $C_6$ alkyl, $C_1$ to $C_6$ alkylbenzyl, 4-methoxybenzyl, indanyl, phthalyl, methoxymethyl, $C_{1-6}$ alkanoyloxy-$C_{1-6}$ alkyl (e.g., acetoxymethyl, pivaloyloxymethyl or propionyloxymethyl), $C_1$ to $C_6$ alkoxycarbonyloxy-$C_1$ to $C_6$ alkyl (e.g., methoxycarbonyloxymethyl or ethoxycarbonyloxymethyl), glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (1994); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more, preferably one to three, solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "nM" for nanomolar, "mol" for mole or moles, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1H$" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Me methyl
Et ethyl
Pr propyl
i-Pr isopropyl
Bu butyl
i-Bu isobutyl
t-Bu tert-butyl
Ph phenyl
Bn benzyl
Boc tert-butyloxycarbonyl
AcOH or HOAc acetic acid
$AlCl_3$ aluminum chloride
$BBr_3$ boron tribromide
$BCl_3$ boron trichloride
BOP reagent benzotriazol-1-yloxytris(dimethylamino)phosphonium hexafluorophosphate
Cbz carbobenzyloxy
$CH_2Cl_2$ dichloromethane
$CH_3CN$ or ACN acetonitrile
$CDCl_3$ deutero-chloroform
$CDCl_3$ chloroform
mCPBA or m-meta-chloroperbenzoic acid
CPBA
$Cs_2CO_3$ cesium carbonate
$Cu(OAc)_2$ copper (II) acetate
DCE 1,2 dichloroethane
DCM dichloromethane
DEA diethylamine
DIAD diisopropyl azodicarboxylate.
DIC or DIPCDI diisopropylcarbodiimide
DIEA, DIPEA or diisopropylethylamine
Hunig's base
DMAP 4-dimethylaminopyridine
DME 1,2-dimethoxyethane
DMF dimethyl formamide
DMSO dimethyl sulfoxide
cDNA complimentary DNA
Dppp (R)-(+)-1,2-bis(diphenylphosphino)propane
EDC N-(3-dimthylaminopropyl)-N'-ethylcarbodiimide
EDTA ethylenediaminetetraacetic acid
$Et_3N$ or TEA triethylamine
EtOAc ethyl acetate
$Et_2O$ diethyl ether
EtOH ethanol
HCl hydrochloric acid
HOBt or HOBT 1-hydroxybenzotriazole
$H_2SO_4$ sulfuric acid
$K_2CO_3$ potassium carbonate
KOAc potassium acetate
$K_3PO_4$ potassium phosphate
LAH lithium aluminum hydride
LG leaving group
LiOH lithium hydroxide MeOH methanol
MgSO$_4$ magnesium sulfate
MsOH or MSA methylsulfonic acid
NaCl sodium chloride
NaH sodium hydride
NaHCO$_3$ sodium bicarbonate
Na$_2$CO$_3$ sodium carbonate
NaOH sodium hydroxide
Na$_2$SO$_3$ sodium sulfite
Na$_2$SO$_4$ sodium sulfate
NBS N-bromosuccinimide
NH$_3$ ammonia
NH$_4$Cl ammonium chloride
NH$_4$OH ammonium hydroxide
OTf triflate or trifluoromethanesulfonate
Pd$_2$(dba)$_3$ tris(dibenzylideneacetone)dipalladium(0)
Pd(OAc)$_2$ palladium(II) acetate
Pd/C palladium on carbon
Pd(dppf)Cl$_2$ [1,1'-bis(diphenylphosphino)-ferrocene]dichloropalladium(II)
Ph$_3$PCl$_2$ triphenylphosphine dichloride
PG protecting group
PMB p-methoxybenzyl
POCl$_3$ phosphorus oxychloride
i-PrOH or IPA isopropanol
PS polystyrene
PS—Pd(Ph$_3$)$_4$ tetrakis(triphenylphosphine)palladium (0) on polystyrene support
PyBOP (benzotriazol-1-yloxy)tripyrrolidinophosphonium hexafluorophosphate
SiO$_2$ silica oxide
SnCl$_2$ tin(II) chloride
TBAF tetra-n-butylammonium fluoride
TBAI tetra-n-butylammonium iodide
TEA triethylamine
TFA trifluoroacetic acid
THF tetrahydrofuran
TMSCHN$_2$ trimethylsilyldiazomethane
Xantphos 4,5-Bis(diphenylphosphino)-9,9-dimethylxanthene
Synthesis The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being affected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

A particularly useful compendium of synthetic methods which may be applicable to the preparation of compounds of the present invention may be found in Larock, R. C., *Comprehensive Organic Transformations*, VCH, New York (1989). Preferred methods include, but are not limited to, those described below. All references cited herein are hereby incorporated in their entirety herein by reference.

The novel compounds of this invention may be prepared using the reactions and techniques described in this section.

Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups In Organic Synthesis*, Wiley and Sons (1991)).

Schemes 1-18 describe synthetic routes for making intermediates and compounds of the present invention. Schemes 1-3 describe preparation of compounds of the present invention from key intermediates 2, 4 or 5. Schemes 4-6 illustrate several preparations for the hydroxypyrimidinedione esters from commercially available starting materials. Scheme 7 describes the preparation of aminopyrimidine dione ester 17 from commercially available starting materials. Schemes 8 and 9 illustrate the synthesis of N-1 substituted or N-3 substituted hydroxypyrimidinedione analogs in the present invention. Schemes 10 and 11 exemplify the preparations of compounds of the present invention wherein $R^2$ is either an NH$_2$ group or a NHR group. Scheme 12 illustrates the selective N-arylation or N-alkenylation of the NH group at the 3 position of the pyrimidine dione core. Scheme 13 describes the general amine intermediates for the preparation of compounds of the present invention. Schemes 14-17 exemplify the preparation of examples of some of these amine intermediates. Scheme 18 describes the conversion of 5-amino to 5-hydroxy group under acidic conditions.

Scheme 1 describes a preparation of compounds of Formula (I) of the present invention from the key intermediate acid 2. The amine intermediates 3 ($R^4$—X$_1$-A-L-NH$_2$) or their HCl or TFA salts are either commercially available or can be readily prepared from commercially available materials by methods known to one skilled in the art of organic synthesis. Reaction of amine 3 with acid 2 can occur under standard amide coupling conditions at temperatures between 0° C. and 100° C. in a variety of solvents such as DMF or dichloromethane. The protocols include, but are not limited to, formation of the acid chloride of 2 using either oxalyl chloride and catalytic DMF in the presence of a suitable solvent such as dichloromethane or thionyl chloride, followed by addition of amine 3 in the presence of a base such as TEA, DIPEA or N-methylmorpholine, or formation of the active ester of intermediate 2 using EDC, HOBt, PyBOP and a base, such as TEA, DIPEA or N-methylmorpholine, in the presence of amine 3.

Scheme 1

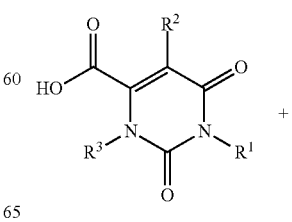

2

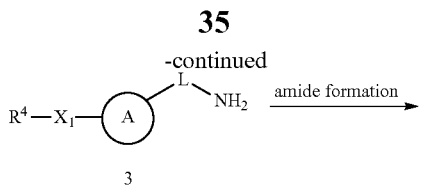

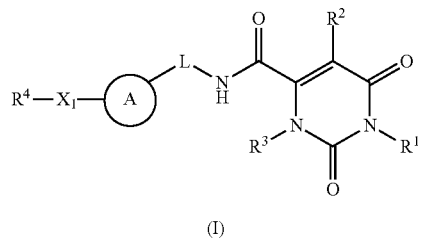

Alternatively, compounds of Formula (I) of the present invention can be prepared by displacement of the methyl ester 4 with the amines 3 in polar solvents such as ethanol, DMF, or neat at elevated temperatures or under microwave irradiation as shown in Scheme 2.

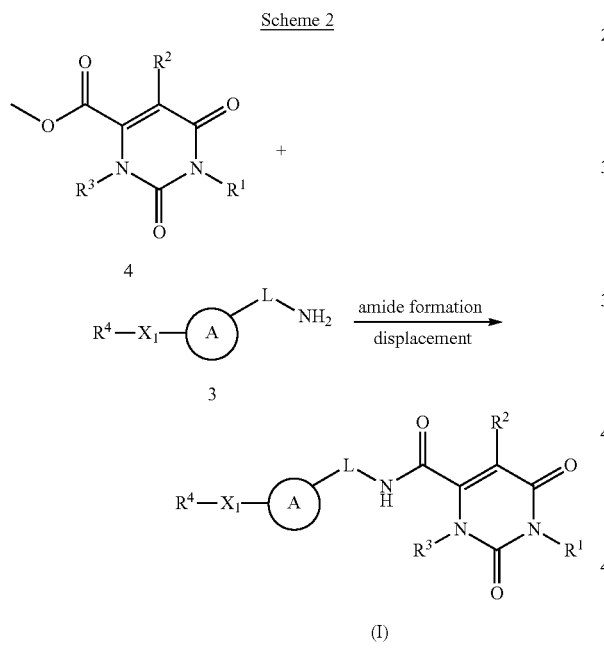

Compounds of Formula (I) wherein $R^2$=OH can be made by the general methods described in Schemes 1 and 2. Alternatively, $R^2$ can be hydroxyl group protected as shown in intermediate 5 (Scheme 3), wherein the protecting group can be methyl, benzyl, allyl, or silyl-based groups. Amide formation between the ester or acid 5 and the amine 3, followed by deprotection to free the hydroxyl group in intermediate 6 can afford the compounds of Formula (I) (wherein $R^2$=OH). When the protecting group on the hydroxyl group is methyl, ethyl, isopropyl, or benzyl, deprotection can occur with $BBr_3$, $BCl_3$, $BBr_3.SMe$, $BCl_3.SMe$ $AlCl_3$, or $BCl_3/TBAI$ at temperatures between −78° C. and refluxing in a solvent such as $CH_2Cl_2$. When heating is required, the reaction can also occur under microwave irradiation to shorten the reaction time. When the protecting group on the hydroxyl group is a benzyl group, debenzylation can also occur by hydrogenation (such as Pd/C, $H_2$) or by heating in TFA under microwave irradiation with or without a solvent, such as $CH_2Cl_2$, or by using $AlCl_3$ in $CH_2Cl_2$ in a variety of solvent such as methanol or EtOAc.

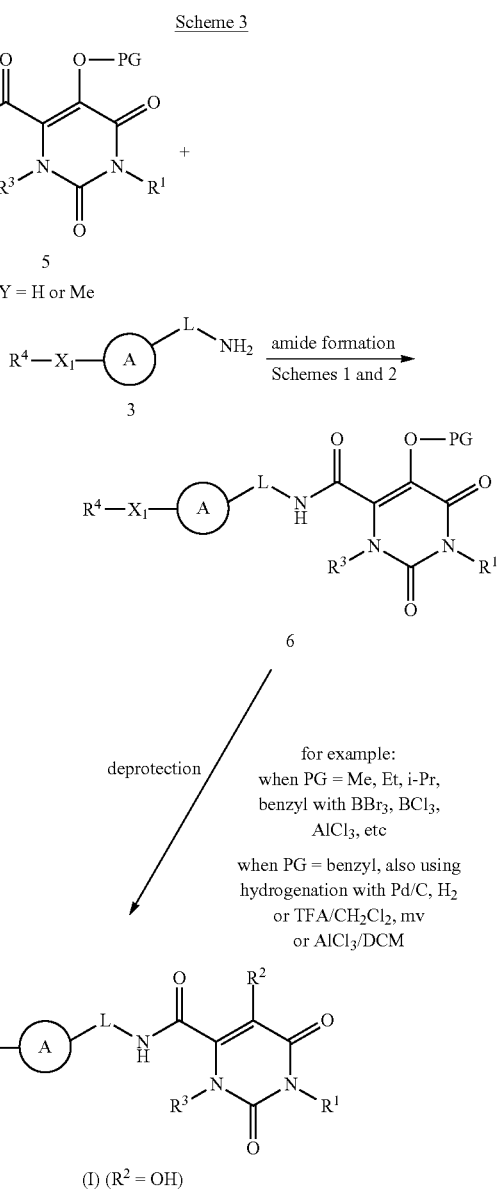

Scheme 4 describes the preparation of 5-hydroxy pyrimidinone carboxylic acid intermediates 7 ($R^2$=OH) by ring construction. An oxalic acid diester is condensed with glycolate using lithium bis(trimethylsilyl)amide or a similar base, followed by reacting with 2-methyl-2-thiopseudourea sulfate in one-pot to give the pyrimidinone intermediate 8 (US 2005/0261322A1 and Dreher, S. D. et al., *Tetrahedron Letters*, 45(31):6023-6025 (2004)). The intermediate methylsulfide 8 can then be oxidized to sulfone 9 by using standard oxidation reagents, such as mCPBA, hydrogen peroxide, or OXONE®. The resulting pyrimidinone sulfone 9 is stirred in the presence of an aqueous base, such as NaOH, KOH in solvent, such as dioxanes, to afford intermediate 7.

Scheme 4

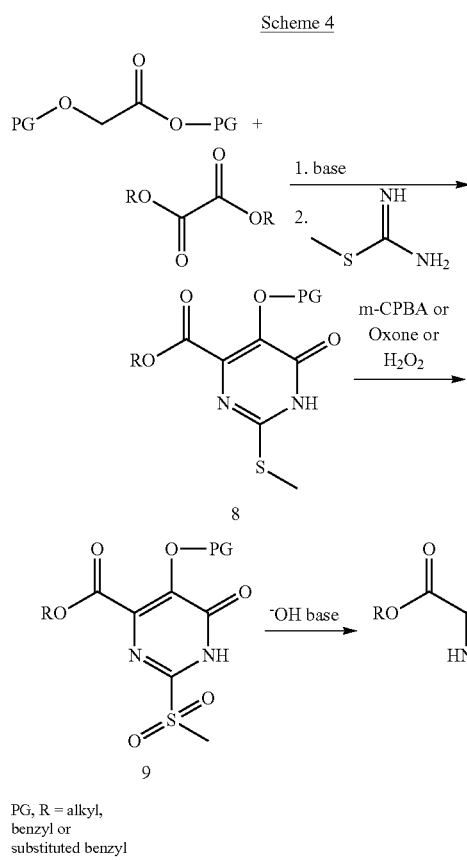

PG, R = alkyl,
benzyl or
substituted benzyl

Alternatively, 2-oxo or 2-thioxo-tetrahydropyrimidinones 10 can be synthesized from the condensation of dihydroxyfumarate derivatives 11 with alkyl/aryl carbamimidates or alkyl/aryl carbamimidothioates 12, followed by deprotection to remove the alkyl or aryl groups on intermediate 13 and tautomerization as shown in Scheme 5.

Scheme 5

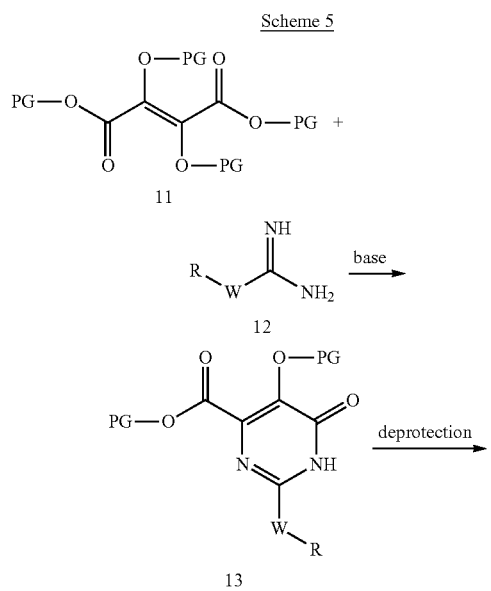

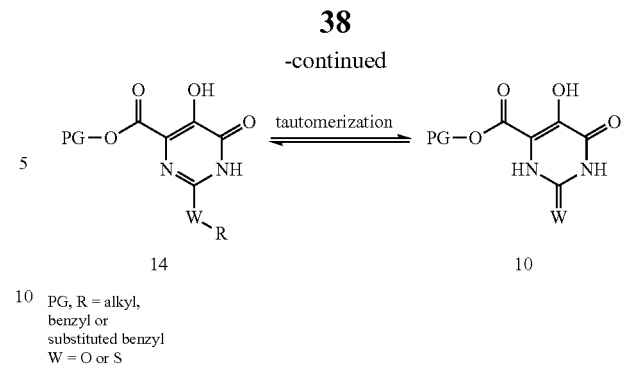

PG, R = alkyl,
benzyl or
substituted benzyl
W = O or S

Alternatively, the pyrimidinone 13 (Scheme 6) can be synthesized as shown in Scheme 6 via Michael addition of N-hydroxy amidine 15 to acetylynic diesters 16, followed by thermal Claisen rearrangement and amide condensation (Culbertson, T. P., *J. Heterocycl. Chem.,* 16:1423-1424 (1979)).

Scheme 6

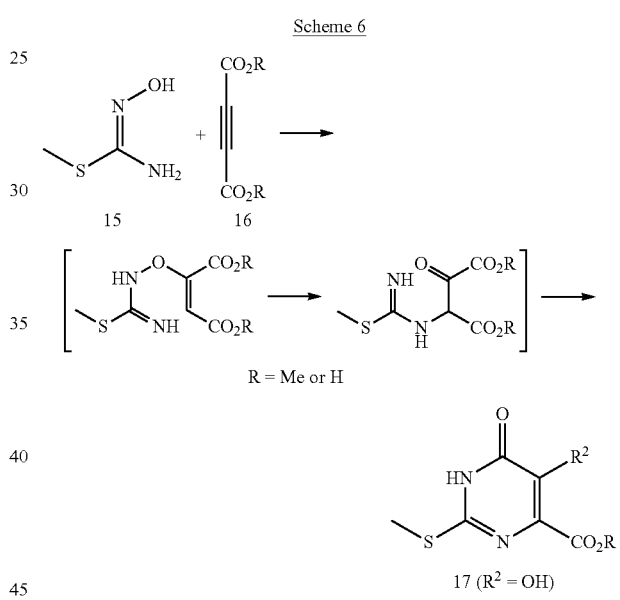

Similarly the corresponding 5-aminopyrimidinone 17 (R=Me or H) can be synthesized as shown in Scheme 7 using an aza-Claisen rearrangement, starting with (E)-methyl carbamohydrazonothioate 18.

Scheme 7

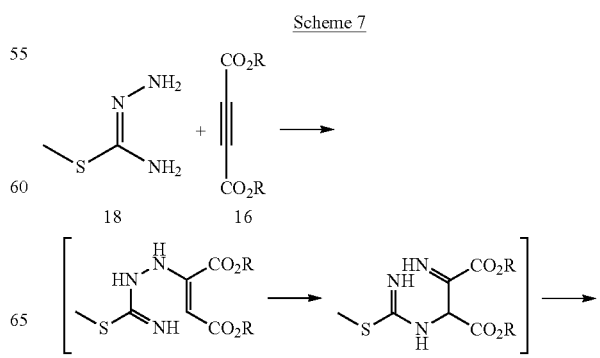

-continued

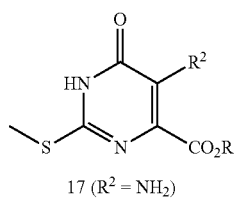

17 (R² = NH₂)

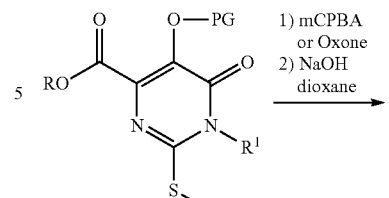

19

The thioether 8 shown in Scheme 8 is an intermediate for the preparation of N-1 or N-3 substituted 5-hydroxypyrimidinediones of Formula (I) of the present invention. Intermediate 8 can be N-1 alkylated with alkyl halides or benzyl halides (X=Br or Cl) in the presence of an inorganic or organic base (such as $K_2CO_3$, $Cs_2CO_3$, $Et_3N$, NaH, LiH). Alternatively, pyrimidinone 8 can be N-1 arylated using Ullmann-Goldberg reaction (CuI, base heating), or Buchwald modified Ullmann reaction (CuI, ligand, base, heating) or Pd C—N cross-coupling reaction (Pd(OAc)₂, or other Pd(0) catalysts, base, ligand, heating) with aryl halides or copper-mediated cross-coupling reaction (Cu(OAc)₂, base (such as $Et_3N$, pyridine) with aryl boronic acids. Alternatively, pyrimidinone 8 can be alkylated by Mitsunobu protocol with a suitable alcohol. For example, alkylation of pyrimidinone 8 with alkyl halides or benzyl halides in the presence of an inorganic or organic base (such as $K_2CO_3$, $Cs_2CO_3$, $Et_3N$, NaH, LiH) can afford both the N-1 alkylated pyrimidinone intermediate 19 and the O-alkylated intermediate 20. Following similar sequences as shown in Scheme 4, the N-1 substituted acid 21 can be obtained. Formation of the amide of intermediate 21 followed by deprotection can provide N-1 substituted compound 22. Alternatively, O-alkylated pyrimidine 20 can be oxidized to the corresponding sulfone then hydrolyzed to pyrimidinone 23. Intermediate 23 can be further alkylated at the N-3 position followed by removal of the R¹ and PG groups to give the N-3 substituted ester 25. Hydrolysis of the ester in intermediate 25 followed by amide formation and then deprotection can provide the corresponding N-3 substituted compound 26.

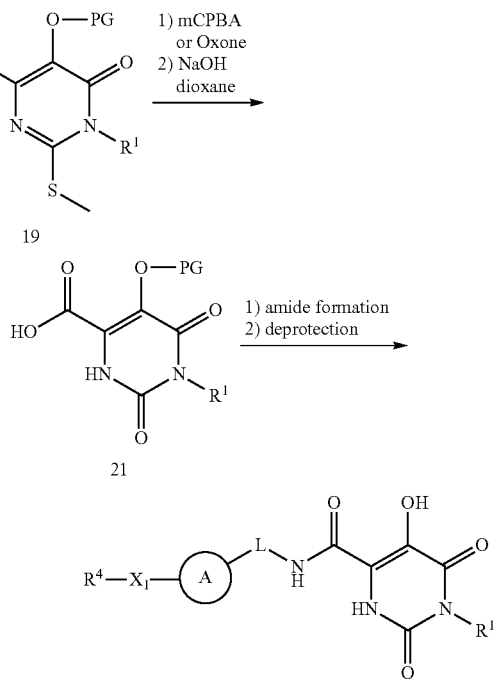

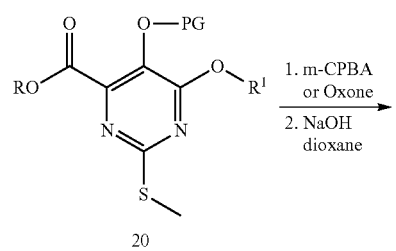

20

Scheme 8

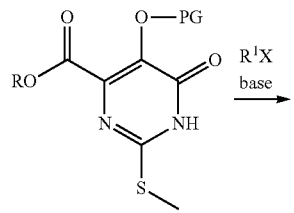

8
R = alkyl or benzyl

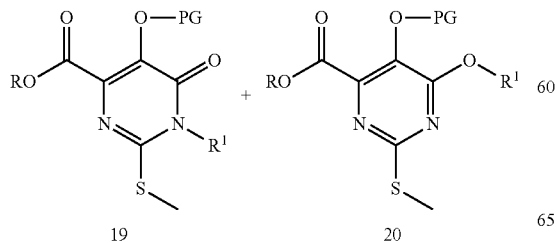

19     20

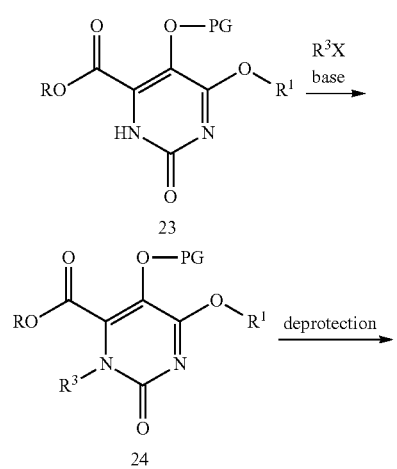

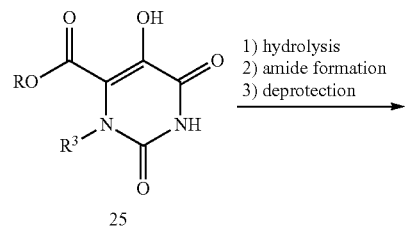

25

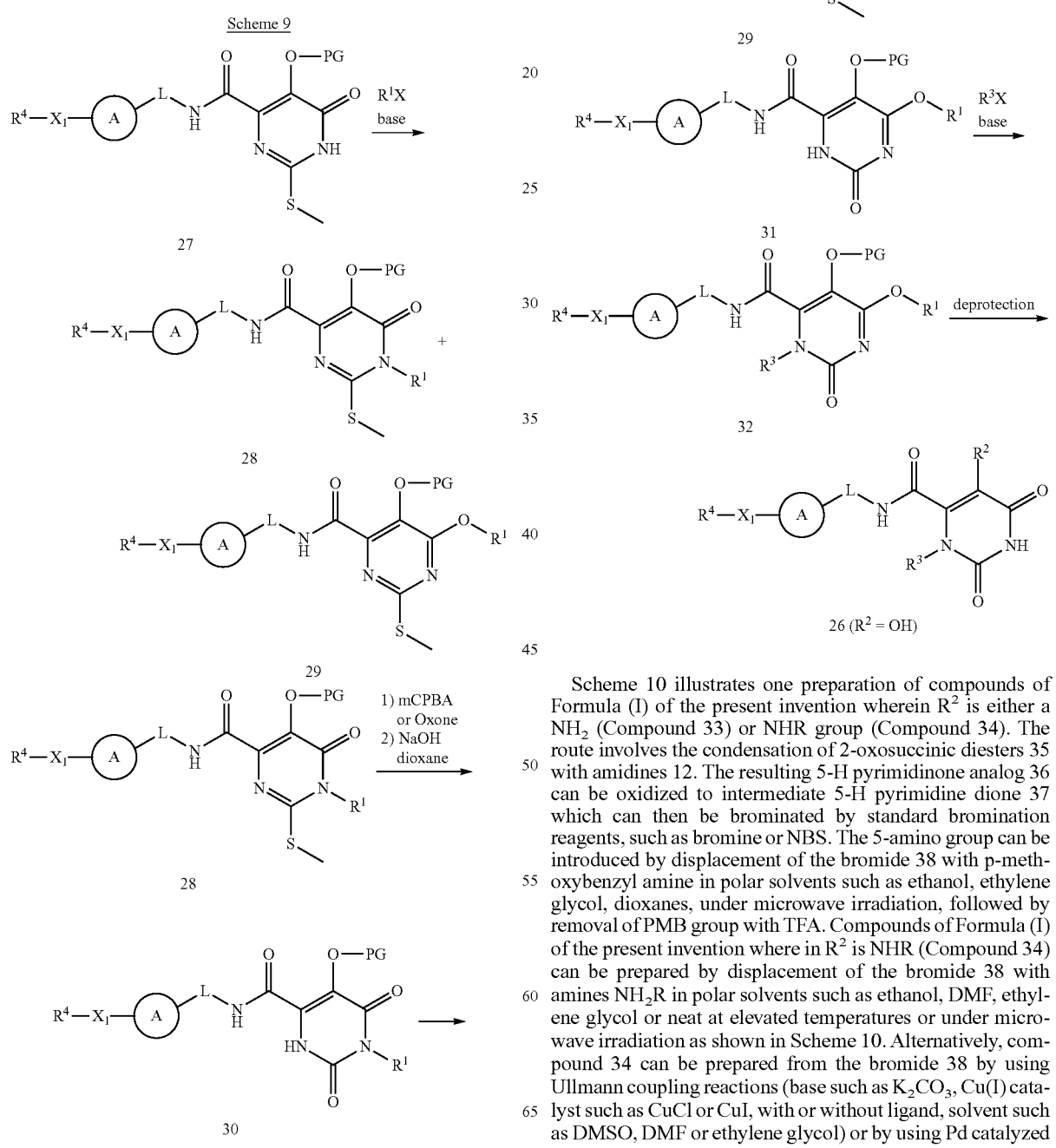

Similarly, the N-1 substituted compound 22 and the N-3 substituted compound 26 can also be prepared using the synthetic route shown in Scheme 9.

Scheme 10 illustrates one preparation of compounds of Formula (I) of the present invention wherein $R^2$ is either a $NH_2$ (Compound 33) or NHR group (Compound 34). The route involves the condensation of 2-oxosuccinic diesters 35 with amidines 12. The resulting 5-H pyrimidinone analog 36 can be oxidized to intermediate 5-H pyrimidine dione 37 which can then be brominated by standard bromination reagents, such as bromine or NBS. The 5-amino group can be introduced by displacement of the bromide 38 with p-methoxybenzyl amine in polar solvents such as ethanol, ethylene glycol, dioxanes, under microwave irradiation, followed by removal of PMB group with TFA. Compounds of Formula (I) of the present invention where in $R^2$ is NHR (Compound 34) can be prepared by displacement of the bromide 38 with amines $NH_2R$ in polar solvents such as ethanol, DMF, ethylene glycol or neat at elevated temperatures or under microwave irradiation as shown in Scheme 10. Alternatively, compound 34 can be prepared from the bromide 38 by using Ullmann coupling reactions (base such as $K_2CO_3$, Cu(I) catalyst such as CuCl or CuI, with or without ligand, solvent such as DMSO, DMF or ethylene glycol) or by using Pd catalyzed Buchwald-Hartwig reaction with suitable amines.

Scheme 10

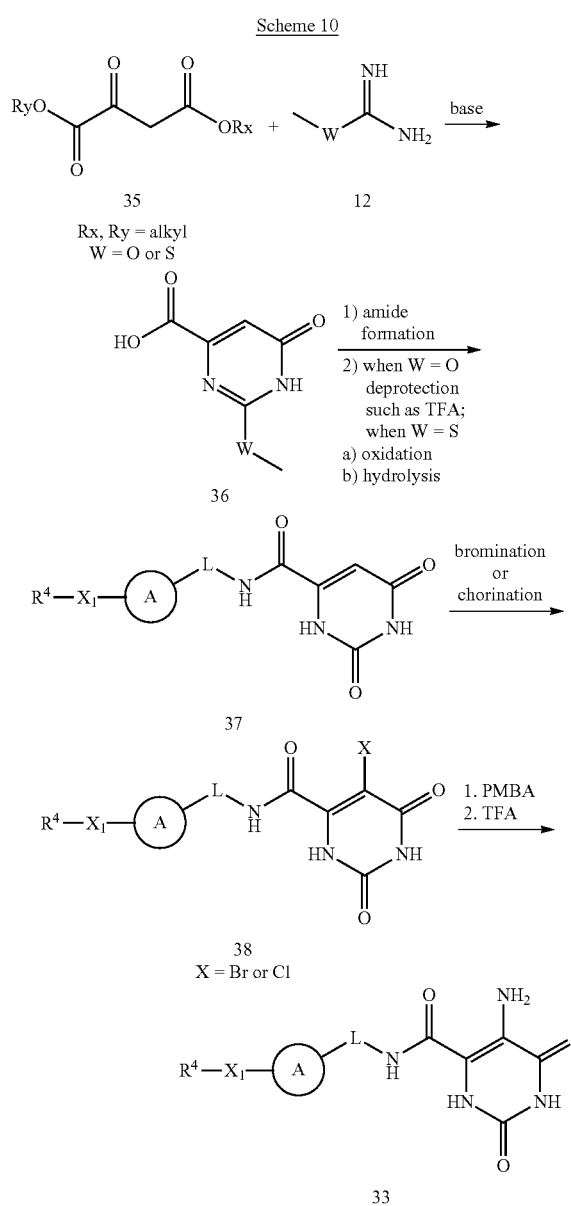

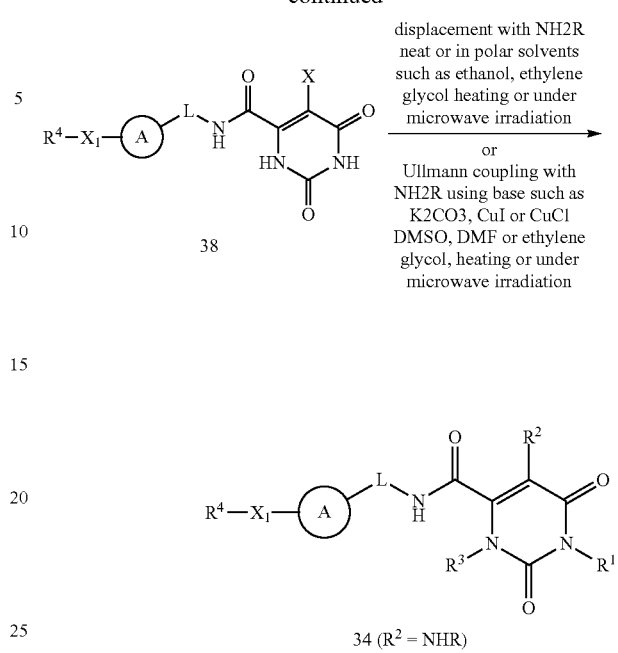

Scheme 11 depicts an alternate synthesis of 5-aminopyrimidinone 33 from 2,6-dioxo-1,2,3,6-tetrahydropyrimidine-4-carboxamide 37 by nitrosation with sodium nitrite in acetic acid followed by reduction of the nitroso group in 39 with sodium dithionite. (Elzein, E. et al., *J. Med. Chem.*, 51: 2267-2278 (2008); Zhang, Y. J., *Tetrahedron Letters*, 47(5):775-778 (2006)). Alternatively 5-aminopyrimidinone can be synthesized from 2,6-dioxo-1,2,3,6-tetrahydropyrimidine-4-carboxamide by nitration using standard nitration condition followed by reduction of nitro group in 40 to the amino group with reducing agents, such as Fe/HCl, or hydrogenation condition, such as Pd/C/hydrogen (Baraldi, P. G. et al., *J. Med. Chem.*, 45(17):3630-3638 (2002); Zajac, M. A. et al., *Synthetic Communications*, 33(19):3291-3297 (2003)).

Scheme 11

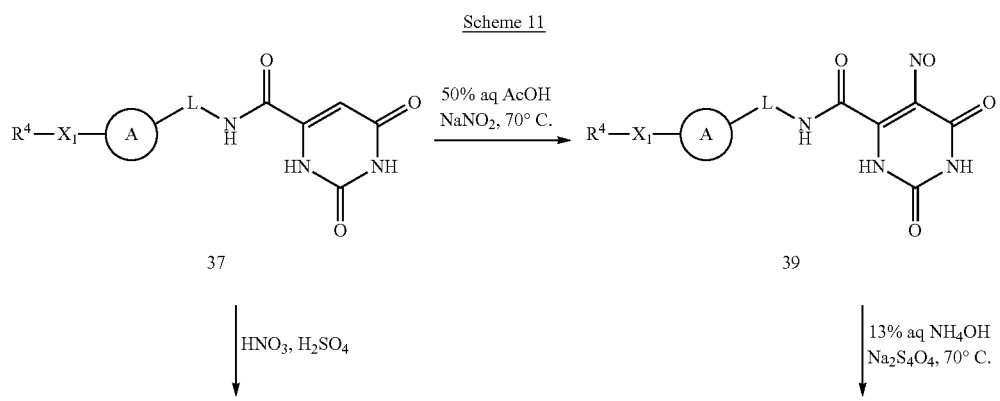

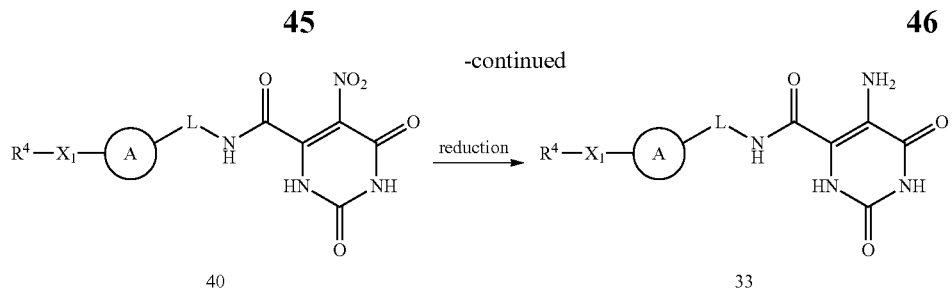

Scheme 12 illustrates one preparation of N-3 substituted analogs 41 from intermediate 42. Regioselective arylation or alkenlation of the N-3 NH group of intermediate 41 can be realized by using modified Chan-Lam Cu-prompted C—N cross-coupling reaction with $R^3$—$B(OH)_2$ and related boron reagents as described in Yang Yue et al., *Eur. J. Org. Chem.*, 5154-5157 (2005); Lan Tao et al., *Helvetica Chimica Acta* 91(6):1008-1014 (2008).

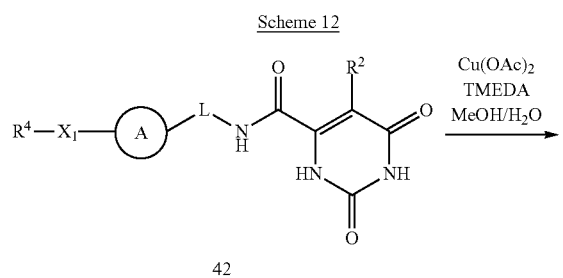

Scheme 13 illustrates examples of amine intermediates $NH_2$—$X_1$-A-L-$R^4$ (compound 3, Scheme 1) that can be used to prepare compounds of the present invention. These intermediates are either commercially available or can be prepared using methods, examples of which are shown in Schemes 14-17, known to those skilled in the art of organic synthesis.

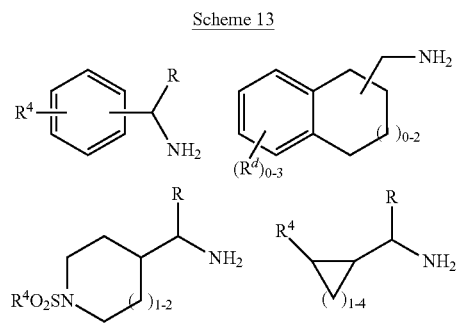

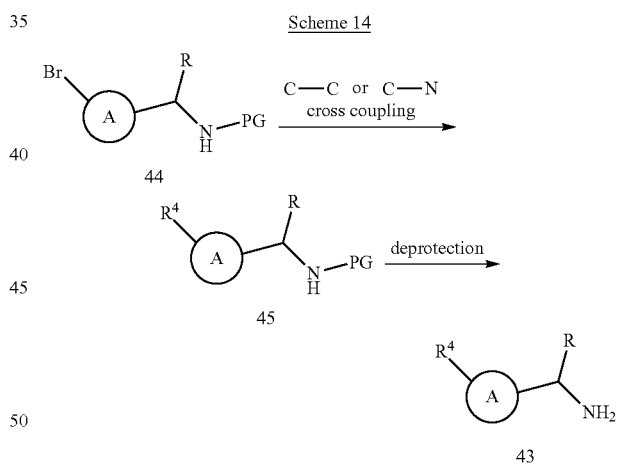

Amine intermediates of formula 43, wherein R=Me or H, ring A and $R^4$ is either an aryl or a heteroaryl, can be synthesized according to Scheme 14. Ring A can be ortho-, meta-, or para position to $R^4$. Compounds of formula 44, synthesized from amines by using standard peptide protocols, can afford compounds of formula 45 by treatment with boronic acids using palladium-catalyzed Suzuki-Miyaura C—C or Buchwald-Hartwig C—N cross coupling conditions. The protective groups of compounds of formula 45 thus formed can be removed by standard protocols to give the compounds of formula 43.

Amines of formula 46 may be synthesized according to Scheme 15. Phenols (X=O) or thiols (X=S) of formula 47 may be coupled to amines of formula 48, where R=H or Me, suitably protected with, for example, phthalimide or Boc, and containing a leaving group (LG) such as bromide. The reaction takes place in the presence of a base such as $Cs_2CO_3$ in a suitable solvent such as DMF. Removal of the protecting group from compounds of formula 49 provides amines of formula 46. When the protecting group is a phthalimide, the typical deprotection procedure employs hydrazine monohydrate in a suitable solvent such as EtOH. When a Boc group is employed as the protecting group, it is typically removed using, for example, 10% TFA in a suitable solvent such as DCM.

Scheme 15

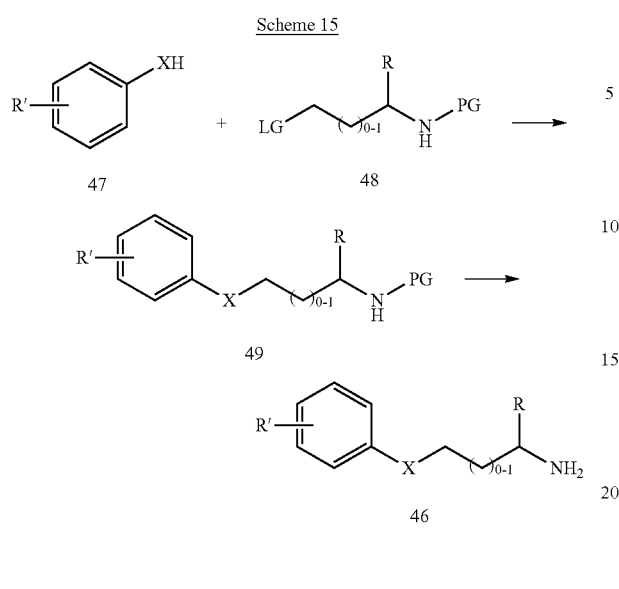

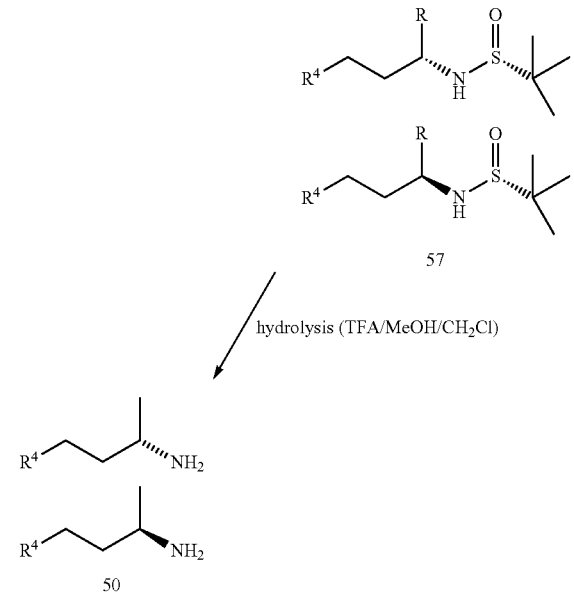

Scheme 16 exemplifies the synthesis of alpha-substituted C$_{2-5}$ alkyl amines 50. Compound 50 is either commercially available or can be readily prepared from commercially available materials by methods described in Scheme 16. Ketone 53 and aldehyde 54 are either commercially available or can be readily prepared from commercially available materials by methods described in Scheme 16. For example, Heck reaction of the corresponding aryl halide (bromide or iodide) 51 with the alcohol 52 can give the corresponding aldehyde 54 or ketone 53. The enantiopure amines 50 can be made from the ketone intermediate 53 by reduction followed by deprotection using methods illustrated in Scheme 16. On the other hand, treatment of aldehyde 54 with Grignard reagent can give the desired diastereomer sulfinamide 56 by using Ellman's methodology (Cogan, D. A. et al., *Tetrahedron* 55(29): 8883-8904 (1999); Li, G. et al., *J. Am. Chem. Soc.* 119(41): 9913-9914 (1997)).

Scheme 17 outlines a possible synthetic route for (R)-1-(3-(1H-pyrazol-4-yl)phenyl)ethanamines 60. Protected 1H-pyrazole can be introduced to 58 via Suzuki reaction. After selective removal of protective group for pyrazole, alkylation of the resulting 59 with alkyl bromide or benzyl bromide under basic condition would afford the various R groups on the pyrazole ring.

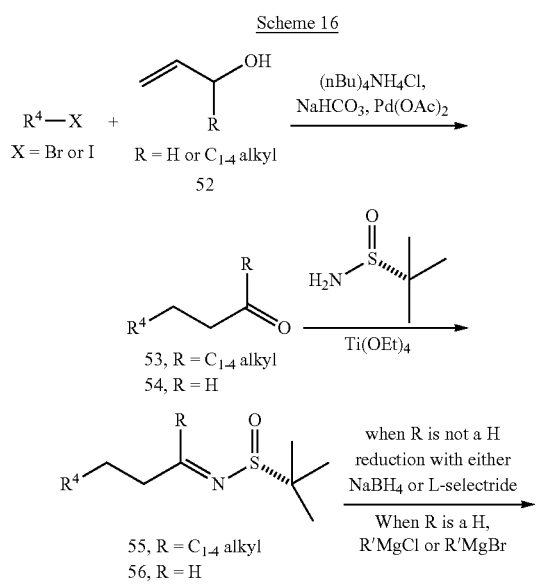

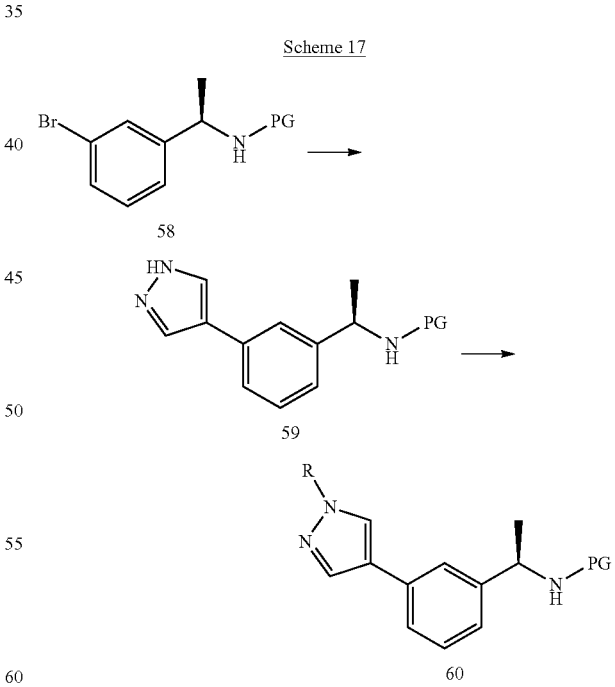

Scheme 18 illustrates that 5-aminoorotic amides can be transformed to 5-hydroxyorotic amides under acidic condition (such as 1 N HCl) with compatible solvents, such as dioxane, ethanol, etc. at reflux, and with or without a catalyst, such as TiCl$_4$.

Scheme 18

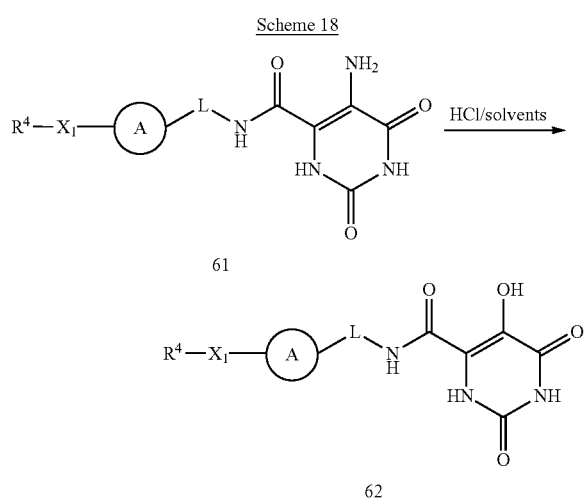

General Methods

The following methods were used in the exemplified Examples, except where noted otherwise.

Products were analyzed by reverse phase analytical HPLC carried out on a Shimadzu Analytical HPLC system running Discovery VP software using Method A: PHENOMENEX® Luna C18 column (4.6×50 mm or 4.6×75 mm) eluted at 4 mL/min with a 2, 4 or 8 min gradient from 100% A to 100% B (A: 10% methanol, 89.9% water, 0.1% TFA; B: 10% water, 89.9% methanol, 0.1% TFA, UV 220 nm), or Method B: PHENOMENEX® Luna C18 column (4.6×50 mm) eluted at 4 mL/min with a 4 min gradient from 100% A to 100% B (A: 10% acetonitrile, 89.9% water, 0.1% TFA; B: 10% water, 89.9% acetonitrile, 0.1% TFA, UV 220 nm) or Method C: PHENOMENEX® Luna C18 column (4.6×50 mm or 4.6×75 mm) eluted at 4 mL/min with a 2, 4 or 8 min gradient from 100% A to 100% B (A: 10% methanol, 89.9% water, 0.1% $H_3PO_4$; B: 10% water, 89.9% methanol, 0.1% $H_3PO_4$, UV 220 nm) or Method D: PHENOMENEX® Luna C18 column (4.6×50 mm or 4.6×75 mm) eluted at 4 mL/min with a 2, 4 or 8 min gradient from 100% A to 100% B (A: 10% methanol, 89.9% water, 0.1% $NH_4OAc$; B:

10% water, 89.9% methanol, 0.1% $NH_4OAc$, UV 220 nm).

Purification of intermediates and final products was carried out via either normal or reverse phase chromatography. Normal phase chromatography was carried out using prepacked $SiO_2$ cartridges eluted with gradients of hexanes and ethyl acetate or methylene chloride and methanol. Reverse phase preparative HPLC was carried out using a Shimadzu Preparative HPLC system running Discovery VP software using Method A: YMC Sunfire 5 nm C18 30×100 mm column with a 10 min gradient at 40 mL/min from 100% A to 100% B (A: 10% methanol, 89.9% water, 0.1% TFA; B: 10% water, 89.9% methanol, 0.1% TFA, UV 220 nm), Method B: PHENOMENEX® Axia Luna 5 µm C18 30×75 mm column with a 10 min gradient at 40 mL/min from 100% A to 100% B (A: 10% acetonitrile, 89.9% water, 0.1% TFA; B: 10% water, 89.9% acetonitrile, 0.1% TFA, UV 220 nm), Method C: PHENOMENEX® Luna 5 µm C18 30×100 mm column with a 10 min gradient at 40 mL/min from 100% A to 100% B (A: 10% acetonitrile, 89.9% water, 0.1% TFA; B: 10% water, 89.9% acetonitrile, 0.1% TFA, UV 220 nm), or Method D: PHENOMENEX® Luna 5 µm C18 30×100 mm column with a 10 min gradient at 40 mL/min from 100% A to 100% B (A: 10% methanol, 89.9% water, 0.1% TFA; B: 10% water, 89.9% methanol, 0.1% TFA, UV 220 nm).

Alternatively, reverse phase preparative HPLC was carried out using a Varian ProStar Preparative HPLC System running Star 6.2 Chromatography Workstation software using Method E: Dynamax 10 µm C18 41.4×250 mm column with a 30 min gradient at 30 mL/min from 10% B to 100% B (A 98% water, 2% acetonitrile, 0.05% TFA; B: 98% acetonitrile, 2% water, 0.05% TFA, UV 254 nm).

LCMS chromatograms were obtained on a Shimadzu HPLC system running Discovery VP software, coupled with a Waters ZQ mass spectrometer running MassLynx version 3.5 software and using the following respective methods. Unless specified otherwise, for each method, the LC column was maintained at room temperature and UV detection was set to 220 nm.

Method A: A linear gradient using solvent A (10% methanol, 90% water, 0.1% of TFA) and solvent B (90% methanol, 10% water, 0.1% of TFA); 0-100% of solvent B over 4 min and then 100% of solvent B over 1 min. Column: PHENOMENEX® Luna 5 µm C18 (4.5×50 mm) Flow rate was 4 mL/min.

Method B: A linear gradient using solvent A (10% methanol, 90% water, 0.1% of TFA) and solvent B (90% methanol, 10% water, 0.1% of TFA); 0-100% of solvent B over 2 min and then 100% of solvent B over 1 min. Column: PHENOMENEX® Luna 5 µm C18 (2.0×30 mm) Flow rate was 1 mL/min.

Method C: A linear gradient using solvent A (10% acetonitrile, 90% water, 10 mM $NH_4OAc$) and solvent B (90% acetonitrile, 10% water, 10 mM $NH_4OAc$); 0-100% of solvent B over 4 min and then 100% of solvent B over 1 min. Column: PHENOMENEX® Luna 5 µm C18 (4.5×50 mm) Flow rate was 4 mL/min.

Method D: A linear gradient using solvent A (10% acetonitrile, 90% water, 0.05% of TFA) and solvent B (90% acetonitrile, 10% water, 0.05% of TFA); 0-100% of solvent B over 2 min and then 100% of solvent B over 1 min. Column: Luna 5 µm C18 (4.5×30 mm) Flow rate was 1 mL/min.

Method E: A linear gradient using solvent A (10% MeOH, 90% water, 10 mM $NH_4OAc$) and solvent B (90% MeOH, 10% water, 10 mM $NH_4OAc$); 0-100% of solvent B over 4 min and then 100% of solvent B over 1 min. Column: PHENOMENEX® Luna 5 µm C18 (4.5×50 mm) Flow rate was 4 mL/min.

Method F: A linear gradient using solvent A (10 mM ammonium acetate, 95% water, 5% ACN) and solvent B (10 mM ammonium acetate, 95% ACN, 5% water); 0-100% of solvent B over 4 min and then 100% of solvent B over 1 min. Column: Mac-Mod Halo (C18, 4.6×50 mm) Flow rate was 4 mL/min.

Method G: A linear gradient using solvent A (10% acetonitrile, 90% water, 0.1% TFA) and solvent B (90% acetonitrile, 10% water, 0.1% TFA); 0-100% of solvent B over 4 min and then 100% of solvent B over 1 min. Column: PHENOMENEX® Luna 3 µm C18 (2.0×50 mm) Flow rate was 4 mL/min.

Method H: A linear gradient using solvent A (10% methanol, 90% water, 0.1% of formic acid) and solvent B (90% methanol, 10% water, 0.1% of formic acid); 0-100% of solvent B over 2 min and then 100% of solvent B over 1 min. Column: PHENOMENEX® Luna 3 µm C18 (2.0×30 mm) Flow rate was 1 mL/min.

Method I: A linear gradient using solvent A (10% MeOH, 90% water, 10 mM $NH_4OAc$) and solvent B (90% MeOH, 10% water, 10 mM $NH_4OAc$); 0-100% of solvent B over 2 min and then 100% of solvent B over 1 min. Column: PHE-NOMENEX® Luna 3 μm C18 (2.0×30 mm) Flow rate was 1 mL/min.

Method J: A linear gradient using solvent A (10% methanol, 90% water, 0.1% of formic acid) and solvent B (90% methanol, 10% water, 0.1% of TFA); 0-100% of solvent B over 4 min and then 100% of solvent B over 1 min. Column: PHENOMENEX® Luna 5 μm C18 (4.5×50 mm) Flow rate was 4 mL/min.

Method K: A linear gradient using solvent A (10 mM ammonium acetate, 95% water, 5% ACN) and solvent B (10 mM ammonium acetate, 95% ACN, 5% water); 0-100% of solvent B over 5.5 min and then 100% of solvent B over 1.5 min. Column: SUPELCO® Ascentis 4.6×50 mm 2.7 μm C18. Flow rate was 4 mL/min.

Method L: A linear gradient using solvent A (5% methanol, 95% water, 0.05% of TFA) and solvent B (95% methanol, 5% water, 0.05% of TFA); 0-100% of solvent B over 4 min and then 100% of solvent B over 1 min. Column: Waters XBridge C18 (4.6×50 mm, 5 μm). Flow rate was 4 mL/min. The LC column was maintained at 35° C.

Method M: A linear gradient using of Solvent A (0.05% TFA, 100% water) and Solvent B (0.05% TFA, 100% ACN); 2 to 98% B over 1 min, with 0.5 min hold time at 98% B. Column: Waters BEH C18 (2.1×50 mm) Flow rate: 0.8 mL/min.

Preparative HPLC methods employed in the purification of products:

Method A: Linear gradient of 0 to 100% B over 10 min, with 5 min hold time at 100% B; Shimadzu LC-8A binary pumps Waters ZQ mass spectrometer using Waters Masslynx 4.0 SP4 MS software UV visualization at 220 nm
Column: Waters XBridge 19×150 mm 5 μm C18
Flow rate: 20 ml/min
Peak collection triggered by mass spectrometry
Solvent A: 0.1% TFA, 10% ACN, 90% water
Solvent B: 0.1% TFA, 90% ACN, 10% water In addition, the following orthogonal HPLC conditions were used to check the purity of the compounds:

Method A: A linear gradient using solvent A (5% acetonitrile, 95% water, 0.05% TFA) and solvent B (95% acetonitrile, 5% water, 0.05% TFA); 10-100% of solvent B over 10 min and then 100% of solvent B over 5 min. Column: Sunfire C18 3.5 μm (4.6×150 mm) Flow rate was 2 ml/min. and UV detection was set to 220 nm. The LC column was maintained at room temperature.

Method B: A linear gradient using solvent A (5% acetonitrile, 95% water, 0.05% TFA) and solvent B (95% acetonitrile, 5% water, 0.05% TFA); 10-100% of solvent B over 10 min and then 100% of solvent B over 5 min. Column: Xbridge Phenyl 3.5 m (4.6×150 mm) Flow rate was 2 ml/min. and UV detection was set to 220 nm. The LC column was maintained at room temperature.

NMR Employed in Characterization of Examples $^1$H NMR spectra were obtained with Bruker or JEOL Fourier transform spectrometers operating at frequencies as follows: $^1$H NMR: 400 MHz (Bruker or JEOL) or 500 MHz (JEOL). $^{13}$C NMR: 100 MHz (Bruker or JEOL). Spectra data are reported in the format: chemical shift (multiplicity, coupling constants, number of hydrogens). Chemical shifts are specified in ppm downfield of a tetramethylsilane internal standard (6 units, tetramethylsilane=0 ppm) and/or referenced to solvent peaks, which in $^1$H NMR spectra appear at 2.49 ppm for $CD_2HSOCD_3$, 3.30 ppm for $CD_2HOD$, and 7.24 ppm for $CHCl_3$, and which in $^{13}$C NMR spectra appear at 39.7 ppm for $CD_3SOCD_3$, 49.0 ppm for $CD_3OD$, and 77.0 ppm for $CDCl_3$. All $^{13}$C NMR spectra were proton decoupled.

Biology

The endothelium occupies a pivotal position at the interface between the circulating humoral and cellular elements of the blood, and the solid tissues which constitute the various organs. In this unique position, endothelial cells regulate a large number of critical processes, including leukocyte adherence and transit through the blood vessel wall, local control of blood vessel tone, modulation of the immune response, the balance between thrombosis and thrombolysis, and new blood vessel development. Thus, endothelial cell dysfunction has been postulated as a central feature of vascular diseases such as hypertension and atherosclerosis. (WO 1999/032611 and references cited therein, e.g., Folkman, J. et al., *Science,* 235:442-447 (1987); Yanagisawa, M. et al., *Nature,* 332(6163):411-415 (1988); Folkman, J. et al., *J. Biol. Chem.,* 267(16):10931-10934 (1992); Janssens, S. P. et al., *J. Biol. Chem.,* 267(21):14519-14522 (1992); Lamas, S. et al., *Proc. Natl. Acad. Sci. U.S.A.,* 89(14):6348-6352 (1992); Luscher, T. F. et al., *Hypertension,* 19(2):117-130 (1992); Williams et al., *Am. Rev. Respir. Dis.,* 146:S45-S50 (1992); and Bevilacqua, M. P. et al., *J. Clin. Invest.,* 91(2):379-387 (1993)).

Atherosclerosis and its associated coronary artery disease (CAD) is the leading cause of mortality in the industrialized world. Despite attempts to modify secondary risk factors (smoking, obesity, lack of exercise) and treatment of dyslipidemia with dietary modification and drug therapy, coronary heart disease (CHD) remains the most common cause of death in the U.S., where cardiovascular disease accounts for 44% of all deaths, with 53% of these associated with atherosclerotic coronary heart disease.

Risk for development of atherosclerosis has been shown to be strongly correlated with certain plasma lipid levels. While elevated low density lipoprotein-cholesterol (LDL-C) may be the most recognized form of dyslipidemia, it is by no means the only significant lipid associated contributor to CHD. Low high density lipoprotein-cholesterol (HDL-C) is also a known risk factor for CHD (Gordon, D. J. et al., *Circulation,* 79(1): 8-15 (1989)).

High LDL-C and triglyceride levels are positively correlated, while high levels of HDL-C are negatively correlated with the risk for developing cardiovascular diseases. Thus, dyslipidemia is not a unitary risk profile for CHD but may be comprised of one or more, preferably one to three, lipid aberrations.

At least 50% of the variation in HDL cholesterol levels is genetically determined. The phenotype of elevated HDL cholesterol is often dominantly inherited, but homozygous deficiency of HL or of the cholesteryl ester transfer protein (CETP), which result in elevated HDL cholesterol, are recessive conditions. Recently, several genetic variations in the human endothelial lipase gene have been identified, six of which potentially produce functional variants of the protein, and the frequencies of these variants were found to be associated with elevated levels of HDL cholesterol in human subjects (deLemos, A. S. et al., *Circulation,* 106(11):1321-1326 (2002)). Notably, the endothelial lipase-mediated binding and uptake of HDL particles and the selective uptake of HDL-derived cholesterol esters have been reported to be independent of its enzymatic lipolytic activity (Strauss, J. G. et al., *Biochem. J.,* 368:69-79 (2002)).

Because of the beneficial effects widely associated with elevated HDL levels, an agent which inhibits EL activity in humans, by virtue of its HDL increasing ability, are expected to be useful for the treatment, prevention, the arrestment and/or regression of atherosclerosis, coronary heart disease, cerebrovascular disorders etc., especially those (but not restricted thereto) which are characterized by one or more of the following factors: (a) high plasma triglyceride concentrations, high postprandial plasma triglyceride concentrations; (b) low HDL cholesterol concentration; (c) low apoA lipoprotein concentrations; (d) high LDL cholesterol concentrations; (e) small dense LDL cholesterol particles; and (f) high apoB lipoprotein concentrations.

The term "modulator" refers to a chemical compound with capacity to either enhance (e.g., "agonist" activity) or partially enhance (e.g., "partial agonist" activity) or inhibit (e.g., "antagonist" activity or "inverse agonist" activity) a functional property of biological activity or process (e.g., enzyme activity or receptor binding); such enhancement or inhibition may be contingent on the occurrence of a specific event, such as activation of a signal transduction pathway, receptor internalization, and/or may be manifest only in particular cell types.

It is also desirable and preferable to find compounds with advantageous and improved characteristics compared with known anti-atherosclerosis agents, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood drug concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) improved therapeutic index.

As used herein, the term "patient" encompasses all mammalian species.

As used herein, the term "subject" refers to any human or non-human organism that could potentially benefit from treatment with an anti-atherosclerosis agent, e.g., an endothelial lipase inhibitor. Exemplary subjects include human beings of any age with risk factors for atherosclerosis and its associated coronary artery disease. Common risk factors include, but are not limited to, age, sex, weight, and family history.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" or "prevention" covers the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit endothelial lipase and/or to prevent or treat the disorders listed herein. When applied to a combination, the term refers to combined amounts of the active ingredients that result in the preventive or therapeutic effect, whether administered in combination, serially, or simultaneously.

Biological Activity

Endothelial lipase activity was measured using a fluorescent substrate, A10070, (Invitrogen, CA) doped into an artificial vesicle containing DMPG (Avanti Polar Lipids) as the excipient. Vesicles were prepared by combining 285 µL of 1 mM DMPG in a 1:1 mixture of MeOH and CHCl$_3$ with 15 µL of 1 mM A10070 in a 1:1 mixture of MeOH and CHCl$_3$. The mixture was dried under nitrogen and resuspended in 150 µL of 50 mM HEPES pH 8.0 buffer containing 100 mM NaCl and 0.2 mM EDTA. The sample was allowed to sit at rt for 15 min and then was sonicated 3×4 mins on ice with a Branson Sonicator using duty cycle 1. This preparation provides vesicles with a mole fraction of 0.05 for the FRET substrate.

The enzymatic assay was measured using white, opaque 96-well half area plates. Each well contained 60 µL of assay buffer (50 mM HEPES pH 8.0, 50 mM NaCl and 1 mM CaCl$_2$) and 2 ul of a DMSO solution containing compound of interest. Conditioned media obtained from HT-1080 cells, which were transformed by RAGE technology (Athersys) to overexpress endogenous EL, was added and the reaction was allowed to incubate for 20 min at 37° C. with gentle agitation. The reaction was started by the addition of 20 µL of a 1:4 dilution of vesicles. The final total reaction volume was 100 µL. The reaction rates were measured on a Gemini plate reader with an excitation wavelength of 488 nm and a emission of 530 nm. Readings were taken every 20 seconds for 10 min with agitation between each reading. The slope of the linear portion of the readout was used to calculate the rate of the reaction.

The exemplified examples disclosed in the present invention were tested in the EL assay described above and found having EL inhibitory activity. A range of EL IC$_{50}$ values of ≤10 µM (10000 nM) was observed. The EL IC$_{50}$ values measured for the following examples are listed in Table 1.

TABLE 1

| Ex. No. | ELIC$_{50}$ (nM) |
| --- | --- |
| 1 | 80 |
| 2 | 149 |
| 14 | 7512 |
| 15 | 9926 |
| 25 | 4254 |
| 28 | 2199 |
| 29 | 7405 |
| 30 | 612 |
| 32 | 703 |
| 33 | 266 |
| 37 | 3173 |
| 44 | 3072 |
| 45 | 78 |
| 46 | 207 |
| 50 | 2483 |
| 54 | 11 |
| 65 | 223 |
| 72 | 1386 |
| 84 | 1996 |
| 88 | 509 |
| 103 | 559 |
| 115 | 4987 |
| 120 | 5397 |
| 136 | 20 |
| 141 | 883 |
| 143 | 6958 |
| 155 | 422 |
| 160 | 369 |
| 161 | 441 |

TABLE 1-continued

| Ex. No. | ELIC$_{50}$ (nM) |
|---|---|
| 171 | 358 |
| 176 | 4639 |
| 181 | 10 |
| 182 | 10 |

Accordingly, the compounds of the present invention can be administered to mammals, preferably humans, for the treatment of a variety of conditions and disorders, including, but not limited to, atherosclerosis, coronary heart disease, coronary artery disease, coronary vascular disease, cerebrovascular disorders, Alzheimer's disease, venous thrombosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity or endotoxemia.

VI. Pharmaceutical Compositions, Formulations and Combinations

The compounds of this invention can be administered for any of the uses described herein by any suitable means, for example, orally, such as tablets, capsules (each of which includes sustained release or timed release formulations), pills, powders, granules, elixirs, tinctures, suspensions, syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 18th Edition (1990).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.01 to about 5000 mg per day, preferably between about 0.1 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more, preferably one to three, other therapeutic agent(s), e.g., HMG-CoA reductase inhibitors or other pharmaceutically active material.

The compounds of the present invention may be employed in combination with other EL inhibitors or one or more, preferably one to three, other suitable therapeutic agents useful in the treatment of the aforementioned disorders including: anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-hypertensive agents, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, treatments for heart failure, treatments for peripheral arterial disease, treatment for malignant tumors, and anti-inflammatory agents.

The compounds of the present invention may be employed in combination with additional therapeutic agent(s) selected from one or more, preferably one to three, of the following therapeutic agents in treating atherosclerosis: anti-hyperlipidemic agents, plasma HDL-raising agents, anti-hypercholesterolemic agents, cholesterol biosynthesis inhibitors (such as HMG CoA reductase inhibitors), acyl-coenzyme A:cholesterol acyltransferase (ACAT) inhibitors, LXR agonist, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, anti-oxidant vitamins, β-blockers, anti-diabetes agents, angiotensin II antagonists, angiotensin converting enzyme inhibitors, platelet aggregation inhibitors, fibrinogen receptor antagonists, aspirin or fibric acid derivatives.

The compounds of the present invention may be employed in combination with additional therapeutic agent(s) selected from one or more, preferably one to three, of the following therapeutic agents in treating cholesterol biosynthesis inhibitor, particularly an HMG-CoA reductase inhibitor. Examples of suitable HMG-CoA reductase inhibitors include, but are not limited to, lovastatin, simvastatin, pravastatin, fluvastatin, atorvastatin, and rivastatin.

The term HMG-CoA reductase inhibitor is intended to include all pharmaceutically acceptable salt, ester, free acid and lactone forms of compounds which have HMG-CoA reductase inhibitory activity and, therefore, the use of such salts, esters, free acids and lactone forms is included within the scope of this invention. Compounds which have inhibitory activity for HMG-CoA reductase can be readily identified using assays well-known in the art.

The compounds of the invention may be used in combination with one or more, preferably one to three, of the following anti-diabetic agents depending on the desired target therapy. Studies indicate that diabetes and hyperlipidemia modulation can be further improved by the addition of a second agent to the therapeutic regimen. Examples of anti-diabetic agents include, but are not limited to, sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone), and related insulin sensitizers, such as selective and non-selective activators of PPARα, PPARβ and PPARγ; dehydroepiandrosterone (also referred to as DHEA or its conjugated sulphate ester, DHEA-$50_4$); anti-glucocorticoids; TNFα inhibitors; α-glucosidase inhibitors (such as acarbose, miglitol, and voglibose), pramlintide (a synthetic analog of the human hormone amylin), other insulin secretagogues (such as repaglinide, gliquidone, and nateglinide), insulin, as well as the therapeutic agents discussed above for treating atherosclerosis.

The compounds of the invention may be used in combination with one or more, preferably one to three, of the following anti-obesity agents selected from phenylpropanolamine, phentermine, diethylpropion, mazindol, fenfluramine, dexfenfluramine, phentiramine, $β_3$-adrenoreceptor agonist agents; sibutramine, gastrointestinal lipase inhibitors (such as orlistat), and leptins. Other agents used in treating obesity or obesity-related disorders include neuropeptide Y, enterostatin, cholecytokinin, bombesin, amylin, histamine $H_3$ receptors, dopamine $D_2$ receptor modulators, melanocyte stimulating hormone, corticotrophin releasing factor, galanin and gamma amino butyric acid (GABA).

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more, preferably one to three, additional therapeutic agents. By "administered in combination" or "combination therapy" it is meant that the compound of the present invention and one or more, preferably one to three, additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the endothelial lipase. Such compounds may be provided in a commercial kit, for example, for use in pharmaceutical research involving endothelial lipase or HDL activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness. The compounds of the present invention may also be used in diagnostic assays involving endothelial lipase.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment and/or prophylaxis of dyslipidemias and the sequelae thereof. In another embodiment, the package insert states that the pharmaceutical composition can be used in combination (as defined previously) with a second therapeutic agent for the treatment and/or prophylaxis of dyslipidemias and the sequelae thereof. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention should become apparent in the course of the above descriptions of exemplary embodiments that are given for illustration of the invention and are not intended to be limiting thereof.

EXAMPLES

The following Examples have been prepared, isolated and characterized using the methods disclosed herein. The following examples demonstrate a partial scope of the invention and are not meant to be limiting of the scope of the invention.

Intermediate 1.
3-(3,4-Dichlorophenyl)propan-1-amine hydrochloride

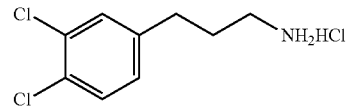

Intermediate 1A.
3-(3,4-Dichlorophenyl)propanamide

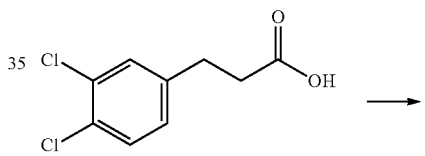

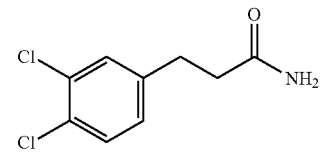

To a solution of 3-(3,4-dichlorophenyl)propanoic acid (12.4 g, 56.6 mmol) in $CH_2Cl_2$ (150 mL) was added oxalyl chloride (5.95 mL, 67.9 mmol) dropwise, followed by addition of DMF (0.044 mL, 0.57 mmol) at 0° C. The ice bath was removed after 30 min, and the mixture was stirred at rt for 3 h. The reaction mixture was concentrated, and dried under vacuum for 0.5 h. The acid chloride was diluted in ca. 20 mL of $Et_2O$. The $Et_2O$ solution was added portion-wise to the stirred solution of concentrated aqueous ammonium hydroxide (ca. 30% of $NH_3$, 180 mL) at 0° C. A white precipitate formed during the addition. The ice bath was removed, and the mixture was stirred at rt for 2 h. The white precipitate was filtered, washed with $H_2O$, and dried under vacuum for 16 h to give Intermediate 1A (11.9 g, 54.6 mmol, 96.0% yield) as a white crystalline solid. LC-MS: 218.3 (M+H), 216.2 (M−H). RT=2.60 min (Method E).

Intermediate 1

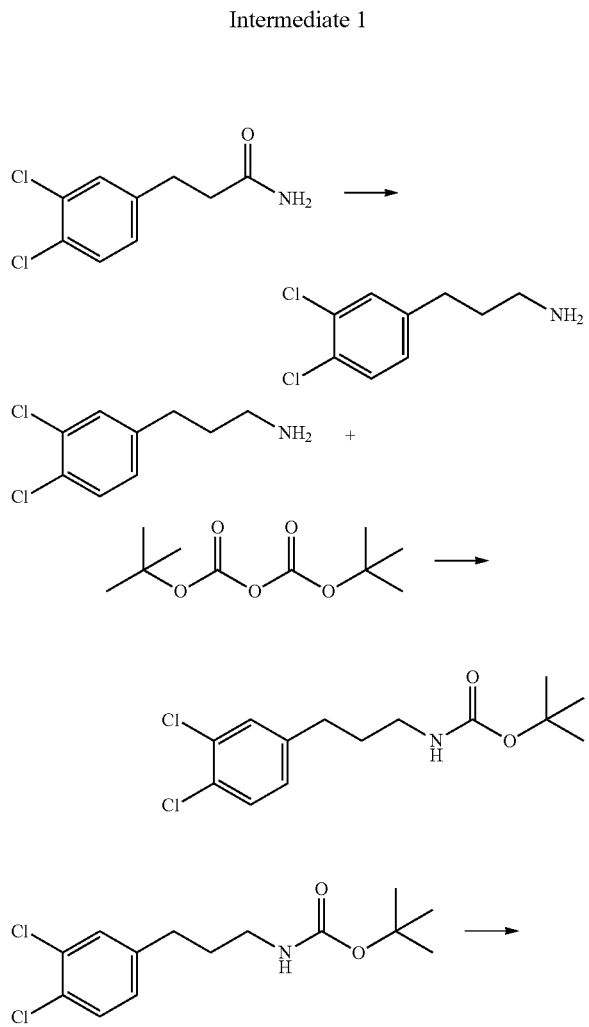

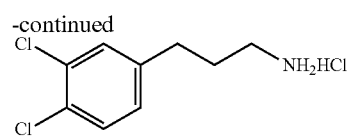

To a solution of Intermediate 1A (8.0 g, 37 mmol) in THF (35 mL) was added LAH (40 mL, 2 M in THF, 81 mmol) dropwise for 40 min at 0° C. under Ar. The colorless solution turned yellowish brown, and a precipitate formed after stirring at rt for 30 min. The suspension was stirred at rt for 6 h. The reaction mixture was cooled to 0° C. and quenched by careful addition of $H_2O$ (3 mL), 15% NaOH (3 mL) and then $H_2O$ (9 mL). $Et_2O$ (ca. 100 mL) was added. The mixture was stirred at rt for 20 min then filtered through Celite® and rinsed with $Et_2O$ (ca. 150 mL). The filtrate was concentrated. The residue was dissolved in $Et_2O$ (100 mL) and $CH_2Cl_2$ (10 mL), dried over $Na_2SO_4$, filtered and concentrated to give a light tan oil after drying under vacuum. This crude was taken to the next step without further purification. LC-MS: 203.9 (M+H), RT=2.76 min (Method A). TEA (8.36 mL, 60.0 mmol) was added to 3-(3,4-dichlorophenyl)propan-1-amine (6.8 g, 33 mmol) in THF (100 mL) followed by the addition of di-tert-butyl dicarbonate (8.22 g, 37.6 mmol) and the reaction mixture was stirred at rt for 16 h. The solvent was removed under vacuum and $Et_2O$ was added. The organic solution was washed with $H_2O$ and then brine. The organic layer was dried over $MgSO_4$, filtered and concentrated. The residue was purified by flash chromatography using hexanes/EtOAc to give the product tert-butyl 3-(3,4-dichlorophenyl)propylcarbamate (6.9 g, 23 mmol, 68% yield) as a colorless oil. LC-MS (ESI) 248.0 (M-tBu+H), RT=3.85 min (Method A). tert-Butyl 3-(3,4-dichlorophenyl)propylcarbamate (3.48 g, 11.4 mmol) was stirred in 4N HCl in dioxane (20 mL) at rt for 2 h. The volume of the mixture was reduced under reduced pressure, and $Et_2O$ was added. The reaction mixture was stirred at rt for 30 min. The resulting precipitate was filtered and rinsed with $Et_2O$ to give Intermediate 1 (1.95 g, 8.11 mmol, 70.9% yield). LCMS=203.9 [M+1], RT=1.51 min (Method B).

Intermediates 2-3 were prepared according to the procedures described in Intermediate 1 using corresponding acid as the starting material.

| Intermediate # | Structure | Name | LC-MS [M + 1]/RT |
| --- | --- | --- | --- |
| 2 | 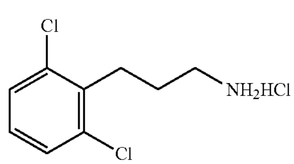 | 3-(2,6-dichlorophenyl)propan-1-amine hydrochloride | 204.0/1.46 min (Method B) |
| 3 | 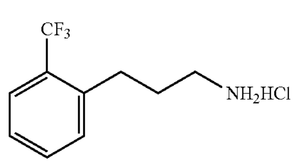 | 3-(2-(trifluoromethyl)phenyl)propan-1-amine hydrochloride | 204.0/1.40 min (Method B) |

Intermediate 4.
(R)-4-(3,4-Dichlorophenyl)butan-2-amine hydrochloride

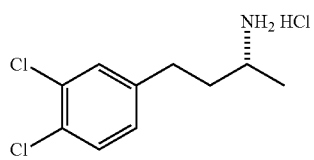

Intermediate 4A. 4-(3,4-Dichlorophenyl)butan-2-one

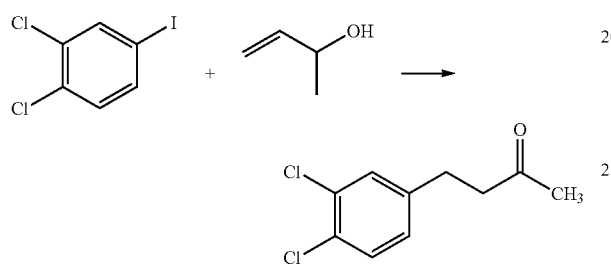

A microwave vial was charged with palladium acetate (0.165 g, 0.733 mmol), 1,2-dichloro-4-iodobenzene (2.00 g, 7.33 mmol), but-3-en-2-ol (0.793 g, 11.0 mmol), tetrabutylammonium chloride, hydrate (2.17 g, 7.33 mmol), and sodium bicarbonate (1.539 g, 18.32 mmol). DMF (5 mL) was added via syringe and the reaction mixture was degassed three times. The mixture was heated at 60° C. for 16 h. The reaction mixture was allowed to cool to room temperature, and diluted with ether. The organic layer was washed with water, separated, dried with MgSO$_4$, filtered and concentrated. The crude residue was purified by silica gel chromatography with an eluant of 10% ethyl acetate/hexanes to afford the desired product Intermediate 4A (1.4 g, 6.5 mmol, 88% yield). LC-MS (ESI) m/z 216.9 (M+H), RT=2.01 min (Method B).

Intermediate 4B. (S)—N—((R)-4-(3,4-Dichlorophenyl)butan-2-yl)-2-methylpropane-2-sulfinamide

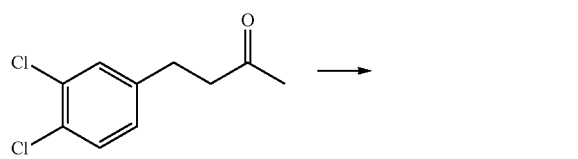

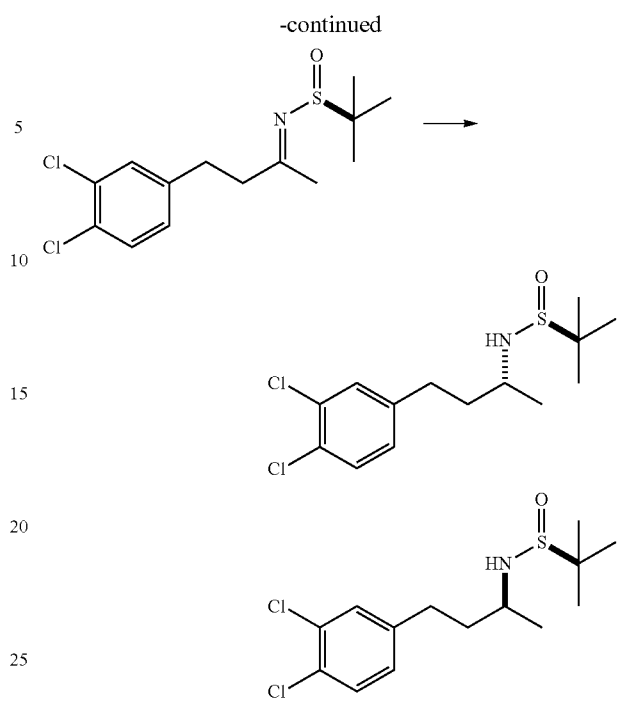

To a stirred solution of (S)-2-methylpropane-2-sulfinamide (373 mg, 3.08 mmol) and Intermediate 4A (700 mg, 3.22 mmol) in THF (2 mL) at rt was added tetraethoxytitanium (1.22 mL, 5.86 mmol). The reaction mixture was heated at 75° C. for 16 h, and allowed to cool and stay at rt for 72 h. Another equivalent of Ti(OEt)$_4$ (1.22 mL, 5.86 mmol) and (S)-2-methylpropane-2-sulfinamide (373 mg, 3.08 mmol) were added. The reaction mixture was heated at 75° C. for 16 h before cooled down. This THF solution was stirred in a round-bottomed flask under argon at −40 to −50° C. L-Selectride (2016 μL, 2.016 mmol) was added dropwise. The resulting mixture was then warmed up to 0° C. during a 1.5 h period. It was cooled in dry ice and MeOH was added dropwise until gas evolution stopped. The mixture was stirred at rt for 20 min. It was filtered through Celite and rinsed with CH$_2$Cl$_2$ and the filtrate was washed with brine (2×) and dried over Na$_2$SO$_4$, filtered and concentrated. The residue was purified on flash chromatography (0-100% hexanes/EtOAc) to give Intermediate 4B (620 mg, 1.92 mmol, 59.6% yield) as slightly tan oil (slow eluent) and an impure (S)—N—((S)-4-(3,4-dichlorophenyl)butan-2-yl)-2-methylpropane-2-sulfinamide. LC-MS (ESI) m/z 322.0 (M+H), RT=2.34 min (Method B).

Intermediate 4

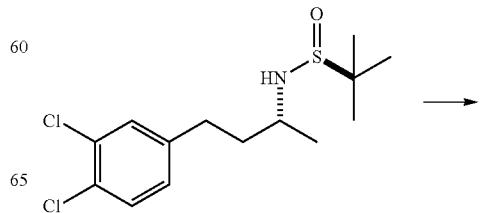

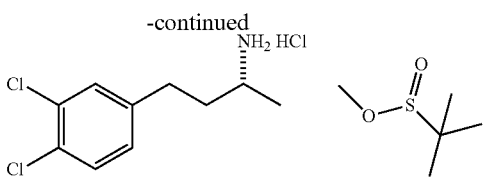

Intermediate 4B (600 mg, 1.86 mmol) was stirred in MeOH (10 mL) at rt. 4N HCl in dioxane (5 mL) was added. The resulting mixture was stirred at rt for 20 min. The solvents were evaporated and CH$_2$Cl$_2$ (3×) was added and evaporated. The resulting white solids were vacuum dried for 5 h to give Intermediate 4(0.46 g, 1.8 mmol, 97% yield) as off-white solids. The HCl salt was used without further purification. LC-MS (ESI) m/z 218.0 (M+H), RT=1.61 min (Method B).

Intermediate 5. (R)-4-(3-(Trifluoromethyl)phenyl)butan-2-amine hydrochloride

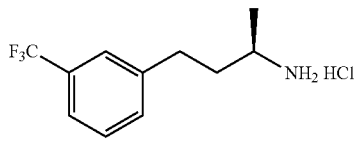

Intermediate 5 (55 mg, 0.25 mmol, 88% yield) was prepared as a white powder following the procedure described for Intermediate 4 by replacing 2,6-dichlorophenol with 2-trifluromethylphenol. LC-MS (ESI) 218.1 (M+H), RT=1.60 min (Method B).

Intermediate 6. 3-(2-(Trifluoromethyl)phenoxy)propan-1-amine

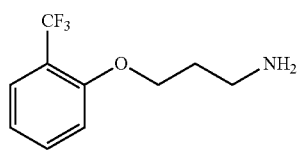 [SMILES: NCCCOc1ccccc1C(F)(F)F]

Intermediate 6A. 2-(3-(2-(Trifluoromethyl)phenoxy)propyl)isoindoline-1,3-dione

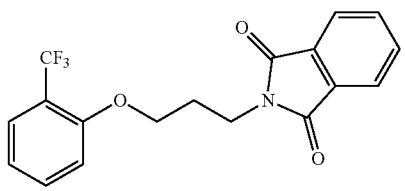 [SMILES: O=C1c2ccccc2C(=O)N1CCCOc1ccccc1C(F)(F)F]

A solution of 2-(trifluoromethyl)phenol (250 mg, 1.54 mmol), tetrabutyl ammonium iodide (114 mg, 1.31 mmol) and 2-(3-bromopropyl)isoindoline-1,3-dione (455 mg, 1.70 mmol) was stirred in THF (10 mL) at rt. Cs$_2$CO$_3$ (904 mg, 2.78 mmol) was added. The resulting mixture was stirred at 60° C. for 16 h. H$_2$O was added to the reaction mixture and the aqueous layer was extracted with EtOAc. The organic layer was dried over MgSO$_4$, filtered and concentrated. The residue was purified by triturating with Et$_2$O to yield Intermediate 6A (0.50 g, 1.4 mmol, 93% yield) as a white powder. LC-MS (ESI) 350 (M+H), RT=3.41 min (Method B).

Intermediate 6

To a solution of Intermediate 6A (203 mg, 0.559 mmol) in EtOH (1 mL) was added hydrazine (0.106 mL, 2.88 mmol). The reaction mixture was stirred at 60° C. for 3 h, allowed to cool to rt, and diluted with ether. The resulting precipitate was filtered and washed with ether. The filtrate was evaporated under reduced pressure to give Intermediate 6 (0.12 g, 0.52 mmol, 92% yield). LC-MS (ESI) 234 (M+H), RT=1.42 min (Method B).

Intermediate 7. (R)-1-(2,6-Dichlorophenoxy)propan-2-amine, trifluoroacetic acid salt

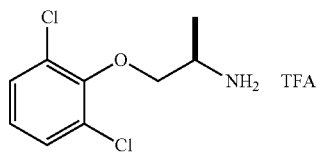

Intermediate 7A. (R)-tert-Butyl 1-bromopropan-2-ylcarbamate

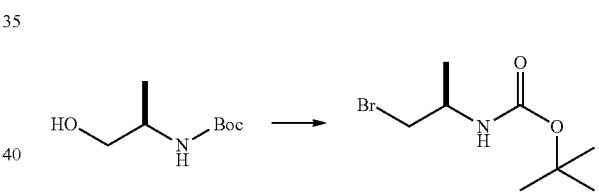

(R)-tert-Butyl 1-hydroxypropan-2-ylcarbamate (1.00 g, 5.71 mmol) and carbon tetrabromide (2.84 g, 8.56 mmol) were stirred in CH$_2$Cl$_2$ (20 mL) at −20° C. under argon. A solution of triphenylphosphine (2.40 g, 9.13 mmol) in CH$_2$Cl$_2$ (5 mL) was added dropwise. The reaction was allowed to reach rt and stirred for 14 h. H$_2$O (50 mL) was added to the reaction mixture and then the aqueous layer was removed and the CH$_2$Cl$_2$ layer was dried over Na$_2$SO$_4$, filtered, and evaporated. The residue was applied to a silica gel column and eluted with 5:1 hexanes/EtOAc. Intermediate 7A (0.68 g, 2.86 mmol, 50% yield) was isolated as a white solid. LC-MS (ESI) 183.9 (M-tBu+H), RT=1.76 min (Method B).

Intermediate 7B. (R)-tert-Butyl 1-(2,6-dichlorophenoxy)propan-2-ylcarbamate

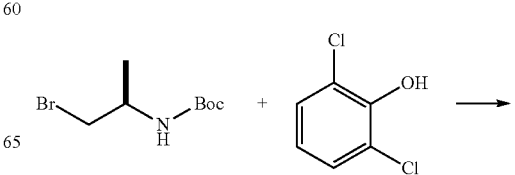

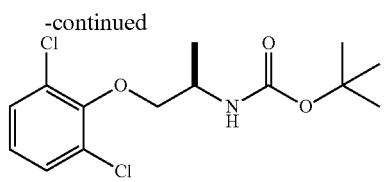

Intermediate 7A (230 mg, 0.970 mmol), cesium carbonate (409 mg, 1.26 mmol) and 2,6-dichlorophenol (157 mg, 0.970 mmol) were heated in acetone (1 mL) under microwave irradiation at 100° C. for 30 min. The solvents were removed and CH$_2$Cl$_2$ was added. The organic phase was washed with H$_2$O, dried over Na$_2$SO$_4$, filtered and concentrated. The colorless oil was purified by flash chromatography (hexanes/EtOAc) to give Intermediate 7B (100 mg, 0.312 mmol, 32.3% yield). LC-MS 219.9 (M-Boc+H), RT=2.23 min (Method B).

Intermediate 7

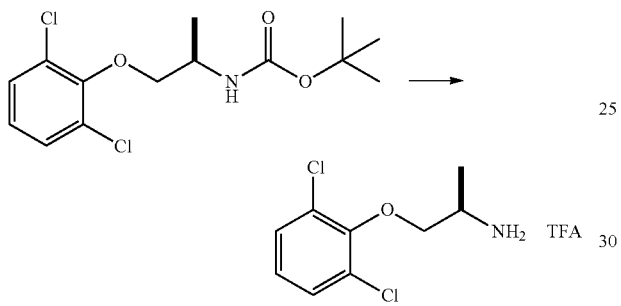

Intermediate 7B (95 mg, 0.30 mmol) was stirred in CH$_2$Cl$_2$ (1 mL) and TFA (1 mL) was added. The reaction was stirred at rt until LC-MS showed the completion of the reaction. The reaction mixture was concentrated and diluted with CH$_2$Cl$_2$. The organic phase was washed with saturated NaHCO$_3$ and H$_2$O and brine, dried over Na$_2$SO$_4$, filtered, and concentrated. Intermediate 7 was used directly for the next step after vacuum drying as the TFA salt (85 mg, 90%). MS (ESI) m/z 219.9, 222.0 (M+H)$^+$, RT=1.34 min (Method B).

Intermediate 8.
(R)-4-(2,6-Dichlorophenoxy)butan-2-amine

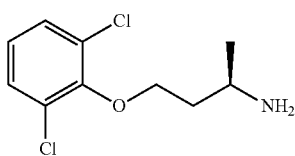

Intermediate 8A. (R)-2-(4-(2,6-Dichlorophenoxy)butan-2-yl)isoindoline-1,3-dione

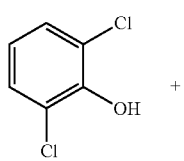

To a solution of 2,6-dichlorophenol (14.9 mg, 0.0910 mmol) in THF (1.5 mL) was added (R)-2-(4-hydroxybutan-2-yl)isoindoline-1,3-dione (20 mg, 0.091 mmol) and triphenylphosphine (47.9 mg, 0.182 mmol) and the reaction mixture was cooled to 0° C. in an ice/water bath. DIAD (0.035 mL, 0.18 mmol) was added drop wise and the reaction mixture was stirred at 0° C. for 1 h. The reaction mixture was allowed to warm to rt and stirred at rt for 16 h. The reaction mixture was concentrated under vacuum to yield a yellow oil that was purified by flash chromatography. Intermediate 8A (0.10 g, 96% yield) was isolated as a clear oil. LC-MS (ESI) 365 (M+H), RT=2.84 min (Method A).

Intermediate 8

To a solution of Intermediate 8A (33 mg, 0.091 mmol) in EtOH (1 mL) was added hydrazine (0.017 mL, 0.54 mmol). The reaction mixture was stirred at 60° C. for 3 h, allowed to cool to rt, and diluted with EtOAc. The precipitate was filtered and washed with MeOH. The filtrate was dried over Na$_2$SO$_4$ and evaporated under reduced pressure to give Intermediate 8 (18 mg, 0.077 mmol, 85% yield). LC-MS (ESI) 235 (M+H), RT=1.39 min (Method B).

Intermediate 9. (1-(3,4-Dichlorophenylsulfonyl)piperidin-4-yl)methanamine

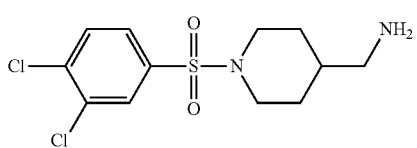 [SMILES: NCC1CCN(S(=O)(=O)c2ccc(Cl)c(Cl)c2)CC1]

Intermediate 9A. tert-Butyl(1-(3,4-dichlorophenyl-sulfonyl)piperidin-4-yl)methylcarbamate

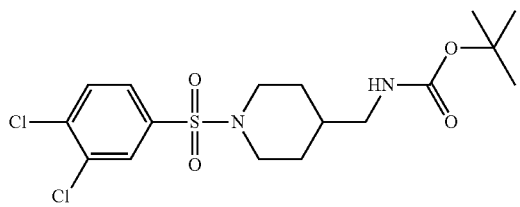 [SMILES: CC(C)(C)OC(=O)NCC1CCN(S(=O)(=O)c2ccc(Cl)c(Cl)c2)CC1]

To a solution of 3,4-dichlorobenzene-1-sulfonyl chloride (470 mg, 1.91 mmol) was added tert-butyl piperidin-4-ylmethylcarbamate (410 mg, 1.91 mmol), followed by triethylamine (0.267 mL, 1.91 mmol). The reaction mixture was stirred for 16 h then diluted with DCM. The organic phase was washed with 1 N HCl, H$_2$O, and brine, dried over Na$_2$SO$_4$, and then filtered. The solvent was evaporated under reduced pressure and the residue was purified on a 24 g cartridge using 0 to 100% EtOAc in hexanes and then 0 to 20% MeOH in DCM to yield Intermediate 9A (0.80 g, 1.9 mmol, 99% yield). LC-MS (ESI) 324.1. (M+H-Boc), RT=1.55 min (Method B).

Intermediate 9

To a solution of Intermediate 9A (100 mg, 0.236 mmol) in DCM (1 mL) was added 4 N HCl in dioxane (0.118 mL, 0.472 mmol). The reaction mixture was stirred at rt for 16 h. The reaction mixture was evaporated to dryness and the residue was titurated with Et$_2$O. The solid was collected by filtration and dried to give Intermediate 9 (75 mg, 0.23 mmol, 98% yield). LC-MS (ESI) 324.1 (M+H), retention time=2.74 min (Method A).

Intermediate 10. (R)-Benzyl 4-(3-(1-aminoethyl)phenyl)piperazine-1-carboxylate

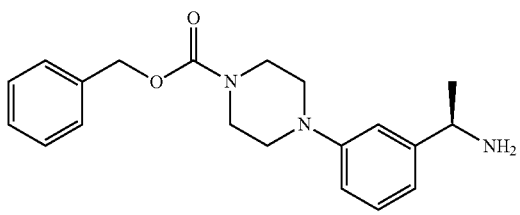 [SMILES: C[C@@H](N)c1cccc(N2CCN(C(=O)OCc3ccccc3)CC2)c1]

Intermediate 10A. (R)-tert-Butyl 1-(3-bromophenyl)ethylcarbamate

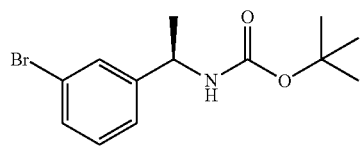 [SMILES: C[C@@H](NC(=O)OC(C)(C)C)c1cccc(Br)c1]

To a solution of (R)-1-(3-bromophenyl)ethanamine (0.10 g, 0.50 mmol) in tetrahydrofuran (4 mL) was added Et$_3$N (0.10 mL, 0.75 mmol), followed by di-tert-butyl dicarbonate (0.13 g, 0.60 mmol). The reaction mixture was stirred at rt for 3 h. The solvent was removed under reduced pressure. The crude residue was diluted with Et$_2$O and washed with 1 N HCl, H$_2$O then dried over Na$_2$SO$_4$. The Et$_2$O layer was concentrated in vacuum to give the crude Intermediate 10A (150 mg, 0.500 mmol, 100% yield). LC-MS (ESI) m/z 245.9 (M-Boc+H), RT=2.13 min (Method B).

Intermediate 10B. (R)-Benzyl 4-(3-(1-(tert-butoxycarbonylamino)ethyl)phenyl)-piperazine-1-carboxylate

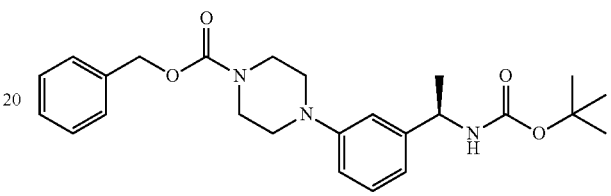

To a suspension of Intermediate 10A (50 mg, 0.17 mmol) and Pd$_2$(dba)$_3$ (15 mg, 0.017 mmol) in toluene (2 mL) was added Xantphos (29 mg, 0.050 mmol), benzyl piperazine-1-carboxylate (37 mg, 0.17 mmol), followed by sodium tert-butoxide (48 mg, 0.50 mmol). The reaction mixture was stirred at 70° C. for 16 h, and then filtered. The filtrate was concentrated and purified by flash chromatography using a 15 min gradient from 0 to 100% EtOAc in hexanes to give Intermediate 10B (70 mg, 0.16 mmol, 96% yield). LC-MS (ESI) m/z 440.1 (M+H), RT=2.27 min (Method B).

Intermediate 10

To a solution of Intermediate 10B (35 mg, 0.080 mmol) in DCM (0.2 mL) was added 4 N HCl in dioxane (100 µL, 0.400 mmol). The reaction mixture was stirred at rt for 2 h. Intermediate 10 (25 mg, 0.074 mmol, 92% yield) was obtained by triturating the crude residue with Et$_2$O. LC-MS (ESI) m/z 340.1 (M+H), RT=1.63 min (Method B).

Intermediate 11. (R)-1-(3-(1-Phenethyl-1H-pyrazol-4-yl)phenyl)ethanamine

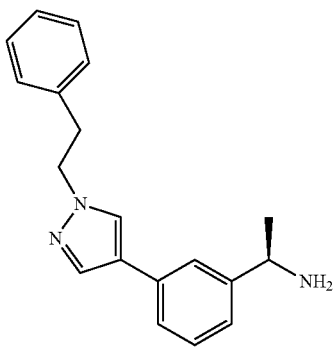 [SMILES: C[C@@H](N)c1cccc(-c2cnn(CCc3ccccc3)c2)c1]

Intermediate 11A. (R)-tert-Butyl 1-(3-bromophenyl)ethylcarbamate

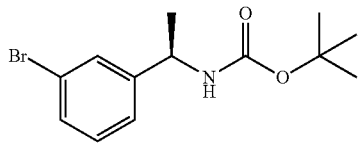 [SMILES: C[C@@H](NC(=O)OC(C)(C)C)c1cccc(Br)c1]

To a solution of (R)-1-(3-bromophenyl)ethanamine (2.0 g, 10 mmol) in tetrahydrofuran (5 mL) was added $Na_2CO_3$ (1.059 g, 10.00 mmol), followed by di-tert-butyl dicarbonate (2.62 g, 12.0 mmol) at 0° C. The reaction mixture was stirred at rt for 2 h. The solvent was removed under reduced pressure and DCM was added. The $Et_2O$ was washed with 1 N HCl and $H_2O$ then dried over $Na_2SO_4$, filtered and concentrated to give the crude product Intermediate 11A (3.0 g, 10 mmol) as a colorless oil. LCMS=1.04 min [M+2H]=302.0; [M-tBu+2]=246.0 (Method M).

Intermediate 11B. (R)-tert-Butyl 1-(3-(1H-pyrazol-4-yl)phenyl)ethylcarbamate

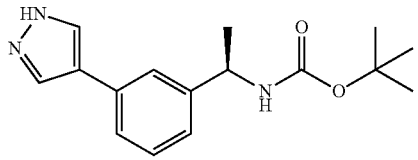 [SMILES: C[C@@H](NC(=O)OC(C)(C)C)c1cccc(-c2cn[nH]c2)c1]

To a degassed solution of Intermediate 11A (3.00 g, 9.99 mmol), tert-butyl 4-(4,4,5,5-tetramethyl-1,3,2-dioxaborolan-2-yl)-1H-pyrazole-1-carboxylate (4.410 g, 14.99 mmol) and potassium carbonate (4.14 g, 30.0 mmol) in dioxane (20 mL)/water (8 mL) was added Tetrakis (0.577 g, 0.500 mmol). The vial was purged with argon, sealed and stirred at 90° C. for 16 h. Another 20% of tetrakis and boronic ester were added and the reaction mixture was degassed and heated at 90° C. for 24 h. The reaction was cooled down to rt and NaOH (14.99 mL, 14.99 mmol) was added and the reaction was stirred at 50° C. for 5 h. The mixture was partitioned between EtOAc and water. The organic layer was separated. The aqueous phase was extracted with EtOAc, and the combined organic layers were dried over $MgSO_4$ and concentrated in vacuo. The crude material was purified by flash chromatography over 120 g of silica gel (15 min gradient, with 0-100% ethyl acetate in hexanes) to afford Intermediate 11B (2.14 g, 7.45 mmol, 74.5% yield) as a white solid. LCMS=1.86 min [M+1]=288.2 (Method B).

Intermediate 11C. (R)-tert-Butyl 1-(3-(1-phenethyl-1H-pyrazol-4-yl)phenyl)ethylcarbamate

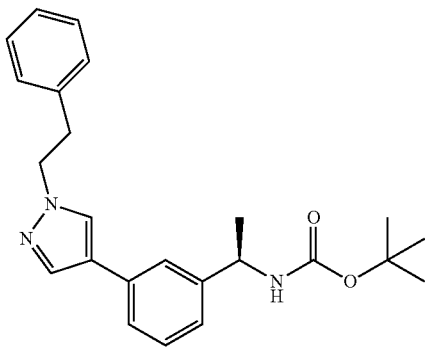 [SMILES: C[C@@H](NC(=O)OC(C)(C)C)c1cccc(-c2cnn(CCc3ccccc3)c2)c1]

To a vial was added Intermediate 11B (110 mg, 0.383 mmol) in acetonitrile (0.7 mL) and DMF (0.7 mL) and potassium carbonate (159.0 mg, 1.148 mmol). The reaction was stirred for 10 min before (2-bromoethyl)benzene (106 mg, 0.574 mmol) was added. The resulting mixture was heated at 50° C. for 16 h. The reaction was quenched with water and extracted with EtOAc. The combined organics were dried over $Na_2SO_4$ and concentrated. The crude was purified by flash chromatography to give Intermediate 11C (116 mg, 0.296 mmol, 77.0% yield) as a white solid. LCMS=2.20 min [M+1]=392.3 (Method B).

Intermediate 11

Intermediate 11C (116 mg, 0.296 mmol) was stirred in $CH_2Cl_2$ (1 mL) at rt. 4 N HCl in dioxane (0.148 mL, 0.593 mmol) was added. The resulting mixture was stirred at rt till TLC showed completion of the reaction. The solvents were evaporated and $CH_2Cl_2$ (3×) was added and evaporated. The resulting white solids were vacuum dried for 1 h to give Intermediate 11 as a white solid. The HCl salt was used directly in the next step. LCMS=3.18 min [M+1-$NH_2$]=275.1 (Method A).

Intermediate 12. (R)-tert-Butyl 1-(3-(1-benzyl-1H-pyrazol-4-yl)-2-methylphenyl)ethylcarbamate

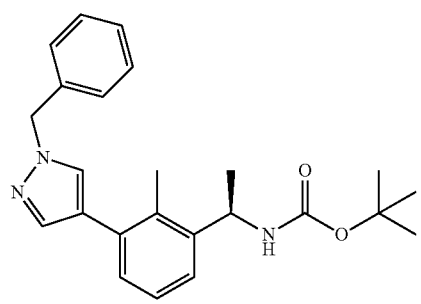 [SMILES: Cc1c(-c2cnn(Cc3ccccc3)c2)cccc1[C@@H](C)NC(=O)OC(C)(C)C]

Intermediate 12A. 1-(3-Bromo-2-methylphenyl)ethanone

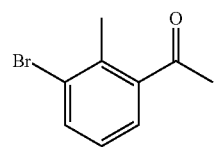

3-Bromo-2-methylbenzonitrile (810 mg, 4.13 mmol) was stirred in THF (5 mL) at 0° C. under argon, and methylmagnesium bromide (1.6 mL, 4.8 mmol) (3.0 M solution in $Et_2O$). The reaction was stirred at 45-50° C. for 2 h. The reaction was cooled to 0° C. and 6 N HCl (5 mL) was added carefully. The reaction mixture was stirred at 40-50° C. for 2 h. After cooling, the mixture was extracted with $Et_2O$ (2×). The organic layers were washed with $H_2O$, brine, dried over $MgSO_4$, filtered and concentrated to give Intermediate 12A (600 mg, 2.82 mmol, 68.2% yield) as yellowish oil. LCMS=1.27 min [M+1]=211.9, 213.9 (Method B).

Intermediate 12B. (R,E)-N-(1-(3-Bromo-2-methylphenyl)ethylidene)-2-methylpropane-2-sulfinamide

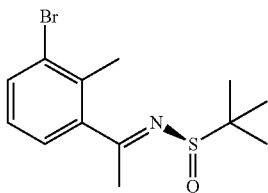 [SMILES: C/C(=N\[S@](=O)C(C)(C)C)c1cccc(Br)c1C]

To a stirring solution of (R)-2-methylpropane-2-sulfinamide (326 mg, 2.69 mmol) and Intermediate 12A (600 mg, 2.82 mmol) in THF (2 mL) at rt was added tetraethoxytitanium (1.06 mL, 5.12 mmol). The reaction mixture was heated at 75° C. for 16 h. The reaction mixture was cooled and used directly in the next step. LCMS=2.12 min [M+1]=318.0 (Method B).

Intermediate 12C. (R)—N-(1-(3-Bromo-2-methylphenyl)ethyl)-2-methylpropane-2-sulfonamide

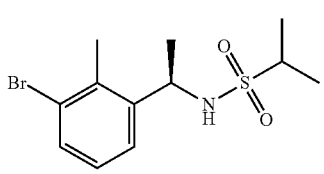 [SMILES: Cc1c(Br)cccc1[C@@H](C)NS(=O)(=O)C(C)C]

Sodium borohydride (397 mg, 10.5 mmol) was stirred in a round-bottomed flask under argon at −40 to −50° C. The reaction mixture of Intermediate 12B was added dropwise to the flask, and the vesicle was rinsed with THF (1 mL) and added to the reaction mixture. The resulting mixture was warmed up to 0° C. during 1.5 h period. It was cooled in dry ice and MeOH was added dropwise till gas evolution stopped. The mixture was stirred at rt for 20 min, and filtered through Celite and rinsed with EtOAc then CH$_2$Cl$_2$. The filtrate was washed with brine (2×) and dried over MgSO$_4$, filtered and concentrated. The residue was purified on flash chromatography (hexanes/EtOAc) to give Intermediate 12C (320 mg, 1.01 mmol, 39.3% yield) as colorless crystals.

Intermediate 12D. (R)-1-(3-Bromo-2-methylphenyl)ethanamine

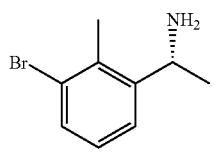

Intermediate 12C (320 mg, 1.01 mmol) was stirred in MeOH (5 mL) and 4N HCl in dioxane (2 mL) was added. The mixture was stirred at rt for 0.5 h and the solvents were evaporated. The residue was added CH$_2$Cl$_2$ (2×) and evaporated, then vacuum dried for 1 h to give off-white solids as Intermediate 12D. LCMS=1.50 min [M+1-NH$_2$]=196.9 (Method B).

Intermediate 12E. (R)-tert-Butyl 1-(3-bromo-2-methylphenyl)ethylcarbamate

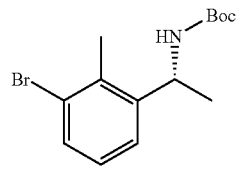 [SMILES: Cc1c(Br)cccc1[C@@H](C)NC(=O)OC(C)(C)C]

Intermediate 12D (250 mg, 0.998 mmol) and di-tert-butyl dicarbonate (261 mg, 1.20 mmol) were stirred at DCM (8 mL) at rt. Triethylamine (0.415 mL, 2.99 mmol) was added dropwise and the mixture was stirred at rt for 20 h. H$_2$O was added and the mixture was extracted twice with CH$_2$Cl$_2$. The organics were combined, washed with brine, dried over Na$_2$SO$_4$, filtered and concentrated. The residue was purified by flash chromatography (40 g column) with hexanes/EtOAc as eluants to give pure Intermediate 12E (186 mg, 0.591 mmol, 59.2% yield). LCMS=2.23 min [M+Na]=338.0 (Method B).

Intermediate 12

To a degassed mixture of Intermediate 12E (186 mg, 0.591 mmol), 1-benzyl-4-(4,4,5,5-tetramethyl-1,3,2-dioxaborolan-2-yl)-1H-pyrazole (140 mg, 0.493 mmol) were added PdCl$_2$ (dppf)-CH$_2$Cl$_2$ adduct (40 mg, 0.049 mmol), dioxane (3 mL) and Na$_2$CO$_3$ (0.493 mmol). The reaction was purged with Ar and the vial was then sealed. The reaction was heated at 95° C. for 7 h. The mixture was quenched with water and extracted with ethyl acetate. The organic extract was dried, stripped and purified with SiO$_2$ column, 0-100% ethyl acetate/hexanes, to give Intermediate 12 (100 mg, 0.255 mmol, 51.8% yield) as a white solid. LCMS=2.20 min [M+H]=392.2 (Method B).

Intermediate 13. (R)-tert-Butyl 1-(3-bromo-4-methoxyphenyl)ethylcarbamate

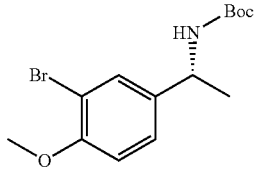 [SMILES: COc1ccc([C@@H](C)NC(=O)OC(C)(C)C)cc1Br]

Intermediate 13A. (R)-tert-Butyl 1-(4-methoxyphenyl)ethylcarbamate

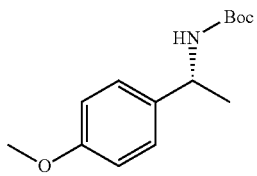 [SMILES: COc1ccc([C@@H](C)NC(=O)OC(C)(C)C)cc1]

To a solution of (R)-1-(4-methoxyphenyl)ethanamine (1.00 g, 6.61 mmol) in tetrahydrofuran (10 mL) was added Na₂CO₃ (0.771 g, 7.27 mmol), followed by di-tert-butyl dicarbonate (1.59 g, 7.27 mmol). The reaction mixture was stirred at rt overnight. The solvent was removed under reduced pressure and Et₂O was added. The Et₂O was washed with 1 N HCl and H₂O then dried over Na₂SO₄, filtered and concentrated to give the crude product as Intermediate 13A (1.70 g, 6.76 mmol, 102% yield) as a white solid. LCMS=1.98 min [M+Na]=274.1 (Method B).

Intermediate 13

To a solution of Intermediate 13A (1.65 g, 6.57 mmol) in acetone (25 mL) and 1 N HCl (0.7 mL, 0.7 mmol) was added NBS (1.17 g, 6.57 mmol) and the reaction mixture was stirred at room temperature for 2 h. Hexanes were added. The resulting precipitate was filtered to give Intermediate 13 (900 mg, 2.73 mmol, 41.5% yield) as white solids. LCMS=2.05 min [M+Na]=354.0 (Method B).

Example 1

(R)-5-Amino-2,6-dioxo-N-(4-(3-(trifluoromethyl)phenyl)butan-2-yl)-1,2,3,6-tetrahydropyrimidine-4-carboxamide

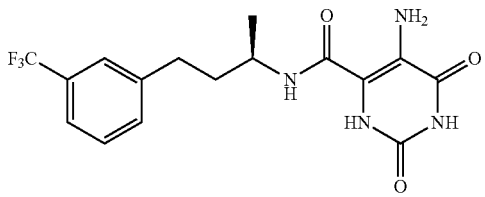 [SMILES: C[C@H](CCc1cccc(C(F)(F)F)c1)NC(=O)c1[nH]c(=O)[nH]c(=O)c1N]

To a 10-mL microwave reaction vial charged with 5-amino-2,6-dioxo-1,2,3,6-tetrahydropyrimidine-4-carboxylic acid (25 mg, 0.15 mmol) in DMF (1 mL) was added EDC (35 mg, 0.18 mmol), HOBt (28 mg, 0.18 mmol), and Intermediate 5 (37 mg, 0.15 mmol) followed by DIEA (0.13 mL, 0.73 mmol). The resulting solution was stirred at rt for 14 h. The reaction was diluted with MeOH and purified by Prep HPLC (0-75% B over 12 min, Column: PHENOMENEX® Luna Axia 5u C18 30×100 mm; Solvent A: 10% ACN-90% H₂O—0.1% TFA; Solvent B: 90% ACN-10% H₂O-0.1% TFA, flow rate=40 mL/min) to give Example 1 (25 mg, 0.067 mmol, 46% yield) as a white solid. LCMS=371.0 [M+1] RT=1.93 min (Method B); Orthogonal HPLC (150×4.6 mm 3 Sum, 254 nm): Sunfire {RT=8.02 min, 100%, Method A}; Xbridge {RT=7.33 min, 99.2%, Method B). ¹H NMR (400 MHz, acetone-d₆) δ ppm 7.58 (1H, s), 7.47-7.57 (4H, m), 5.68 (2H, br. s.), 4.06-4.28 (1H, m), 2.81-2.93 (2H, m), 1.85-2.03 (2H, m), 1.27 (3H, d, J=6.82 Hz).

Examples 2-52 were prepared according the procedures described for Example 1 by using the appropriate intermediate amines and acids.

Example 53

(R)-5-Amino-N-(1-(2-chloro-3-(trifluoromethyl)phenoxy)propan-2-yl)-2,6-dioxo-1,2,3,6-tetrahydropyrimidine-4-carboxamide

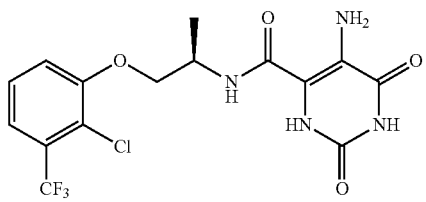 [SMILES: C[C@H](COc1cccc(C(F)(F)F)c1Cl)NC(=O)c1[nH]c(=O)[nH]c(=O)c1N]

Example 53A (R)-tert-Butyl 1-(2-chloro-3-(trifluoromethyl)phenoxy)propan-2-ylcarbamate

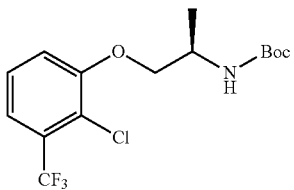

(R)-tert-Butyl 1-hydroxypropan-2-ylcarbamate (220 mg, 1.26 mmol) and 2-chloro-3-(trifluoromethyl)phenol (247 mg, 1.26 mmol) were stirred in a 20-mL vial a 0° C. Triphenylphosphine (494 mg, 1.88 mmol) was added followed by the addition of DIAD (366 µl, 1.88 mmol). The resulting mixture was stirred at rt for 24 h. The reaction mixture was concentrated, dissolved in a small amount of CH₂Cl₂, and then purified by flash chromatography (hexanes/EtOAc=0-100%) to give Example 53A (370 mg, 1.05 mmol, 83.0% yield) as slightly tan viscous oil. LC-MS (ESI) m/z 376.0 (M+Na), RT=2.27 min (Method B).

Example 53B (R)-1-(2-Chloro-3-(trifluoromethyl)phenoxy)propan-2-amine hydrochloride

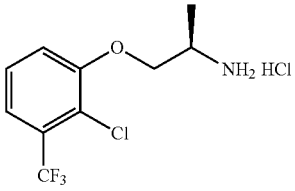

Example 53A (365 mg, 1.03 mmol) was stirred in 4 N HCl in dioxane (10 mL) at rt for 14 h. The solvents were evaporated and dried under vacuum to give Example 53B (290 mg, 1.00 mmol, 97.0% yield) as a white solid and it was used directly in the next reaction without further purification. LC-MS (ESI) m/z 254.0 (M+H), RT=1.56 min (Method B).

Example 53

To a 10 mL microwave reaction vial charged with 5-amino-2,6-dioxo-1,2,3,6-tetrahydropyrimidine-4-carboxylic acid (27 mg, 0.16 mmol) and DMF (0.5 mL) was added EDC (25 mg, 0.13 mmol), HOBt (20 mg, 0.13 mmol), and Example 53B (30 mg, 0.10 mmol) followed by DIEA (0.090 mL, 0.52 mmol). The resulting mixture was stirred at rt for 14 h. It was diluted with MeOH and purified by Prep HPLC (ACN/H$_2$O/TFA, 10-100% B over 16 min) to give Example 53 (13.4 mg, 31.8%). LC-MS (ESI) m/z 407.0 (M+H), RT=1.89 min (Method B); Orthogonal HPLC (150×4.6 mm 3 Sum, 254 nm): Sunfire {RT=7.71 min, 100%, Method A}; Xbridge {RT=6.91 min, 100%, Method B).

Examples 54-130 were prepared according the procedures described for Example 53 by using the appropriate intermediate amines and acids and by using either PS-triphenylphosphine instead or triphenylphosphine.

Examples 131-168 were prepared according the procedures described for Example 1 by using the appropriate intermediate amines and acids.

Example 169

5-(Butylamino)-N-(3-(3,4-dichlorophenyl)propyl)-1,3-dimethyl-2,6-dioxo-1,2,3,6-tetrahydropyrimidine-4-carboxamide

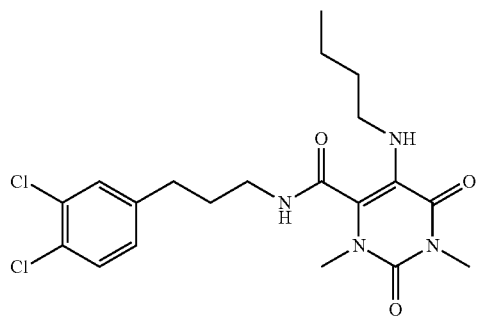 [SMILES: CCCCNc1c(C(=O)NCCCc2ccc(Cl)c(Cl)c2)n(C)c(=O)n(C)c1=O]

Example 169A

5-Bromo-N-(3-(3,4-dichlorophenyl)propyl)-2,6-dioxo-1,2,3,6-tetrahydropyrimidine-4-carboxamide

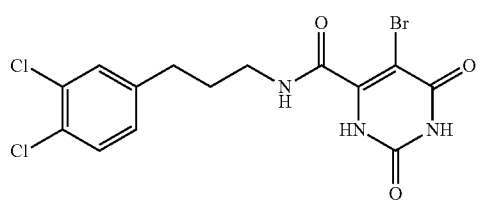 [SMILES: O=C(NCCCc1ccc(Cl)c(Cl)c1)c1[nH]c(=O)[nH]c(=O)c1Br]

Example 169A (0.15 g, 0.36 mmol, 17% yield) was prepared from Intermediate 1 as a white powder following the procedure described for Example 1. LC-MS (ESI) m/z 421.7 (M+H), RT=1.92 min (Method B).

Example 169B

5-Bromo-N-(3-(3,4-dichlorophenyl)propyl)-1,3-dimethyl-2,6-dioxo-1,2,3,6-tetrahydropyrimidine-4-carboxamide

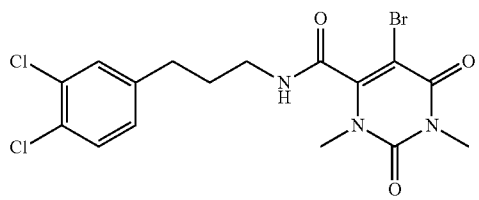 [SMILES: Cn1c(C(=O)NCCCc2ccc(Cl)c(Cl)c2)c(Br)c(=O)n(C)c1=O]

The mixture of Example 169A (50 mg, 0.12 mmol) and cesium carbonate (97 mg, 0.30 mmol) in DMSO (0.5 mL) were stirred at rt for 0.5 h. Iodomethane (0.020 mL, 0.32 mmol) was added dropwise. The resulting mixture was stirred at 50° C. for 14 h. The mixture was concentrated, diluted with water, and extracted with EtOAc (3×). The organics were combined, concentrated and purified by HPLC (20-100% B over 12 min, Column: PHENOMENEX® Luna Axia 5u C18 30×100 mm; Solvent A: 10% ACN-90% H$_2$O—0.1% TFA; Solvent B: 90% ACN-10% H$_2$O-0.1% TFA, flow rate=40 mL/min) to give Example 169B (26 mg, 0.057 mmol, 48% yield) as a white solid. LCMS=449.8 [M+1] RT=1.97 min (Method B); Orthogonal HPLC (150×4.6 mm 3 Sum, 254 nm): Sunfire {RT=9.94 min, 98.6%, Method A}; Xbridge {RT=9.01 min, 98.2%, Method B}. $^1$H NMR (400 MHz, DMSO-d$_6$) δ ppm 9.20 (1H, t, J=5.50 Hz), 7.55 (1H, d, J=8.24 Hz), 7.53 (1H, d, J=2.20 Hz), 7.24 (1H, d, J=8.24 Hz), 3.86-3.95 (2H, m), 3.68-3.79 (2H, m), 3.15-3.33 (2H, m), 2.67 (2H, t, J=7.70 Hz), 1.74-1.85 (2H, m), 1.20 (3H, t, J=6.87 Hz), 1.11 (3H, t, J=6.87 Hz).

Example 169

To a 5-mL microwave reaction vial charged with Example 169B (51 mg, 0.12 mmol) and tetrakis(triphenylphosphine)palladium(0) (26 mg, 0.023 mmol) was added butyl amine (0.5 mL). The contents were heated in the microwave to 100° C. for 35 minutes. The reaction was filtered, concentrated, and purified by HPLC (25-100% B over 15 min, Column: PHENOMENEX® Luna Axia 5u C18 30×100 mm; Solvent A: 10% MeOH-90% H$_2$O—0.1% TFA; Solvent B: 90% MeOH-10% H$_2$O-0.1% TFA, flow rate=40 mL/min, then 10-90% B over 15 min, Column: PHENOMENEX® Luna Axia 5u C18 30×100 mm; Solvent A: 10% ACN-90% H$_2$O—0.1% TFA; Solvent B: 90% ACN-10% H$_2$O-0.1% TFA, flow rate=40 mL/min) to give Example 169 (8.0 mg, 0.018 mmol, 16% yield). LCMS=441.0 [M+1], RT=2.20 min (Method B); Orthogonal HPLC (150×4.6 mm 3 Sum, 254 nm): Sunfire {RT=10.35 min, 100%, Method A}; Xbridge {RT=9.23 min, 100%, Method B}. $^1$H NMR (400 MHz, acetone-d$_6$) δ ppm 7.49 (1H, d, J=4.04 Hz), 7.48 (1H, d, J=2.02 Hz), 7.26 (1H, dd, J=8.21, 1.89 Hz), 3.41-3.48 (2H, m), 3.31 (3H, s), 3.27 (3H, s), 2.94 (2H, t, J=7.07 Hz), 2.78 (2H, t, J=7.58 Hz), 2.06-2.10 (2H, m), 1.92-2.03 (2H, m, J=7.45, 7.45, 7.33, 7.07 Hz), 1.46 (2H, qd, J=7.33, 7.07 Hz), 1.25-1.38 (2H, m), 0.86 (3H, t, J=7.20 Hz).

Example 170

N-(3-(3,4-Dichlorophenyl)propyl)-5-(4-methoxybenzylamino)-1,3-dimethyl-2,6-dioxo-1,2,3,6-tetrahydropyrimidine-4-carboxamide

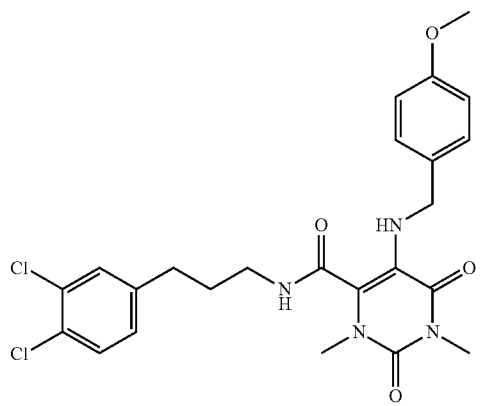 [SMILES: COc1ccc(CNc2c(C(=O)NCCCc3ccc(Cl)c(Cl)c3)n(C)c(=O)n(C)c2=O)cc1]

The reaction mixture of Example 169B (7.0 mg, 0.016 mmol) and (4-methoxyphenyl)methanamine (106 mg, 0.771 mmol) in dioxane (0.5 mL) was heated at 120° C. under microwave irradiation for 2 h. The reaction mixture was concentrated, and purified by HPLC (0-100% B over 10 min, Column: PHENOMENEX® Luna Axia 5u C18 30×100 mm; Solvent A: 10% MeOH-90% H$_2$O—0.1% TFA; Solvent B: 90% MeOH-10% H$_2$O-0.1% TFA, flow rate=40 mL/min) to give Example 170 (6.1 mg, 0.011 mmol, 74% yield) as a colorless oil. LCMS=505.1 [M+1], RT=2.23 min (Method B); Orthogonal HPLC (150×4.6 mm 3 Sum, 254 nm): Sunfire {RT=10.74 min, 95.8%, Method A}; Xbridge {RT=9.63 min, 94.4%, Method B}. $^1$H NMR (400 MHz, acetone-d$_6$) δ ppm 7.43-7.47 (2H, m), 7.20-7.27 (3H, m), 6.80-6.86 (2H, m), 4.05 (2H, s), 3.75 (3H, s), 3.39-3.45 (2H, m), 3.31 (3H, s), 3.25 (3H, s), 2.72-2.81 (2H, m), 1.95 (2H, ddd, J=14.97, 7.39, 7.20 Hz).

Example 171

(R)—N-(4-(3,4-Dichlorophenyl)butan-2-yl)-5-(4-methoxybenzylamino)-1-methyl-2,6-dioxo-1,2,3,6-tetrahydropyrimidine-4-carboxamide

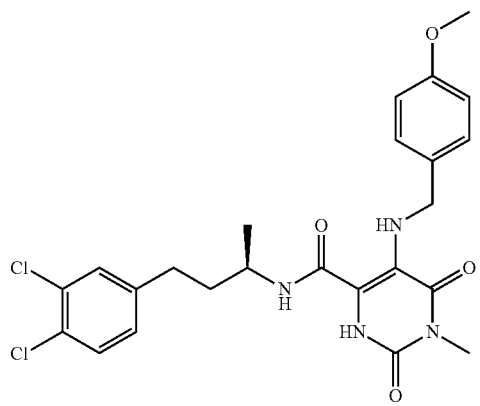 [SMILES: COc1ccc(CNc2c(C(=O)N[C@H](C)CCc3ccc(Cl)c(Cl)c3)[nH]c(=O)n(C)c2=O)cc1]

Example 171A (R)—N-(4-(3,4-Dichlorophenyl)butan-2-yl)-1-methyl-2,6-dioxo-1,2,3,6-tetrahydropyrimidine-4-carboxamide

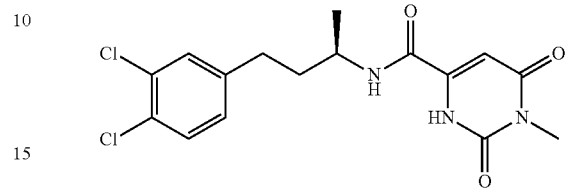

Example 171A (35 mg, 0.083 mmol, 36% yield) was prepared as a white solid following the procedure described for Example 1 with Intermediate 4. LCMS=370.0 [M+1], RT=2.04 min (Method B).

Example 171B (R)-5-Bromo-N-(4-(3,4-dichlorophenyl)butan-2-yl)-1-methyl-2,6-dioxo-1,2,3,6-tetrahydropyrimidine-4-carboxamide

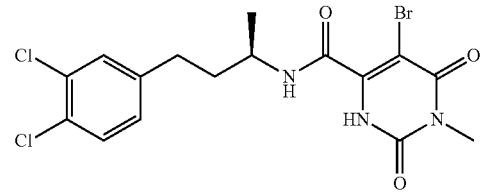 [SMILES: C[C@H](CCc1ccc(Cl)c(Cl)c1)NC(=O)c1[nH]c(=O)n(C)c(=O)c1Br]

To a vigorously stirred solution of Example 171A (50 mg, 0.14 mmol) in acetic acid (1.5 mL) was added bromine (7.0 μl, 0.14 mmol) dropwise. The reaction was stirred for 30 min. Water (2 mL) was added to the reaction, and the resulting precipitate was filtered and washed with water (2×) and Et$_2$O (2×). The filter cake was dried under reduced vacuum to yield Example 171B (52 mg, 0.12 mmol, 86% yield) as a white solid. LCMS=449.7 [M+1], RT=2.13 min (Method B). Orthogonal HPLC (150×4 6 mm 3.5 um, 254 nm): Sunfire {RT=9.04 min, 95.7%, Method A}; Xbridge {RT=8.19 min, 93.4%, Method B).

Example 171

To a solution of Example 171B (20 mg, 0.045 mmol) in dioxane (0.5 mL) was added (4-methoxyphenyl)methanamine (0.1 mL). The reaction mixture was heated in microwave at 120° C. for 25 min. The reaction mixture was concentrated and purified by Prep HPLC (0-100% B over 10 min, Column: PHENOMENEX® Luna Axia 5u C18 30×100 mm; Solvent A: 10% ACN-90% H$_2$O—0.1% TFA; Solvent B: 90% ACN-10% H$_2$O-0.1% TFA, flow rate=40 mL/min) to give Example 171 (13 mg, 0.026 mmol, 58% yield) as a white solid. LCMS=504.9 [M+1] RT=2.36 min (Method B).

Example 172

(R)-5-Amino-N-(4-(3,4-dichlorophenyl)butan-2-yl)-1-methyl-2,6-dioxo-1,2,3,6-tetrahydropyrimidine-4-carboxamide

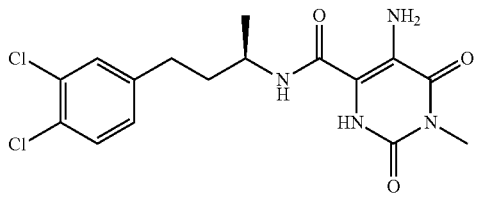 [SMILES: C[C@H](CCc1ccc(Cl)c(Cl)c1)NC(=O)c1[nH]c(=O)n(C)c(=O)c1N]

and

Example 173

(R)—N-(4-(3,4-Dichlorophenyl)butan-2-yl)-1-methyl-2,6-dioxo-5-(2,2,2-trifluoroacetamido)-1,2,3,6-tetrahydropyrimidine-4-carboxamide

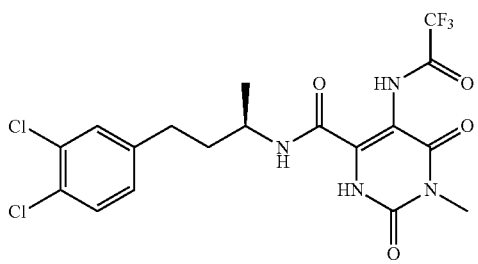 [SMILES: C[C@H](CCc1ccc(Cl)c(Cl)c1)NC(=O)c1[nH]c(=O)n(C)c(=O)c1NC(=O)C(F)(F)F]

To a solution of Example 171 (10 mg, 0.020 mmol) in CH₂Cl₂ (0.5 mL) was added TFA (0.20 mL, 2.6 mmol). The reaction was stirred at rt for 4 h. The reaction was concentrated and the residue was diluted with MeOH and purified by Prep HPLC (0-100% B over 10 min, Column: PHENOMENEX® Luna Axia 5u C18 30×100 mm; Solvent A: 10% ACN-90% H₂O—0.1% TFA; Solvent B: 90% ACN-10% H₂O-0.1% TFA, flow rate=40 mL/min) to give Example 172 (6.2 mg, 0.015 mmol, 76% yield) and Example 173 (2.0 mg, 3.9 μmol, 20% yield).

Example 172

LCMS=384.8 [M+1] RT=2.05 min (Method B). Orthogonal HPLC (150×4.6 mm 3 5um, 254 nm): Sunfire {RT=8.69 min, 93.2%, Method A}; Xbridge {RT=7.62 min, 93.7%, Method B). ¹H NMR (400 MHz, chloroform-d) δ ppm 6.91-7.00 (2H, m), 6.72 (1H, dd, J=8.24, 2.20 Hz), 5.08 (1H, br. s.), 3.81 (1H, ddd, J=13.88, 7.15, 7.01 Hz), 2.95 (3H, s), 2.32 (2H, t, J=7.97 Hz), 1.42-1.55 (2H, m), 0.88 (3H, d, J=6.60 Hz).

Example 173

LCMS=480.8 [M+1] RT=2.11 min (Method B). Orthogonal HPLC (150×4.6 mm 3 5um, 254 nm): Sunfire {RT=9.06 min, 93.1%, Method A}; Xbridge {RT=8.02 min, 93.3%, Method B).

Example 174

(R)—N-(1-(3-(1-(3-Carbamoylbenzyl)-1H-pyrazol-4-yl)phenyl)ethyl)-2,6-dioxo-5-(2,2,2-trifluoroacetamido)-1,2,3,6-tetrahydropyrimidine-4-carboxamide

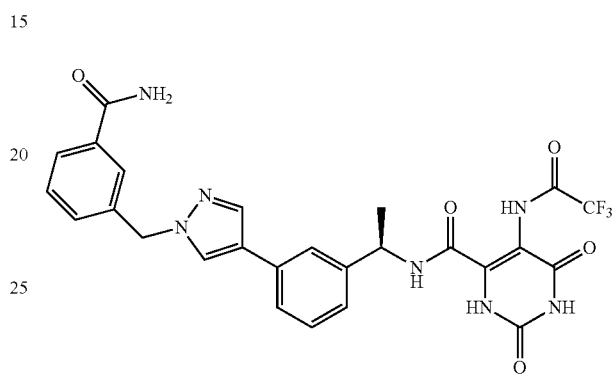

Example 174 was obtained in a similar procedure as Example 173 from Example 141 as the starting material. LCMS=570.0 [M+1] RT=0.69 min (Method M). Orthogonal HPLC (150×4.6 mm 3 5um, 254 nm): Sunfire {RT=6.90 min, 97.5%, Method A}; Xbridge {RT=7.14 min, 96.2%, Method B).

Example 175

(R)-5-Hydroxy-2,6-dioxo-N-(4-(3-(trifluoromethyl)phenyl)butan-2-yl)-1,2,3,6-tetrahydropyrimidine-4-carboxamide

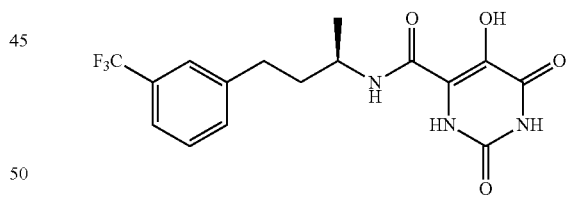

To a reaction vial charged with Example 1 (18 mg, 0.049 mmol) was added 1N HCl (1.215 mL, 1.215 mmol). The resulting mixture was stirred at 100° C. for 2 h. The reaction was cooled down to rt and the solvents were evaporated. The residue was dissolved in MeOH and DIEA (2 drops) and purified by Prep HPLC (0-100% B over 10 min, ACN/H₂O/TFA) to give Example 175 (14 mg, 0.034 mmol, 71% yield) as white solids. LC-MS (ESI) 372.3 (M+H), retention time=3.63 min (Method J).

Examples 176-188 were prepared according the procedures described for Example 175 by using the appropriate 1,2,3,6-tetrahydropyrimidine-4-carboxamides.

The analytical data (mass, retention time, and conditions of LC-MS) of Examples 2-52, 54-130, 131-168, and 176-188 are listed in Table 2.

TABLE 2

| Ex. No. | Structure | Name | LC-MS [M + 1]/RT | Purity (%) |
|---|---|---|---|---|
| 2 | 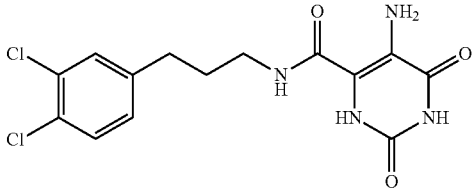 [SMILES: Nc1c(C(=O)NCCCc2ccc(Cl)c(Cl)c2)[nH]c(=O)[nH]c1=O] | 5-amino-N-(3-(3,4-dichlorophenyl)propyl)-2,6-dioxo-1,2,3,6-tetrahydropyrimidine-4-carboxamide | 357.1/1.91 min (Method B) | RT = 7.81 min, 100% (Method A) RT = 7.30 min, 100% (Method B) |
| 3 | 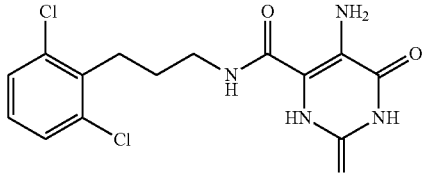 | 5-amino-N-(3-(2,6-dichlorophenyl)propyl)-2,6-dioxo-1,2,3,6-tetrahydropyrimidine-4-carboxamide | 356.9/1.92 min (Method B) | RT = 7.27 min, 94.4% (Method A) RT = 6.81 min, 98.4% (Method B) |
| 4 | 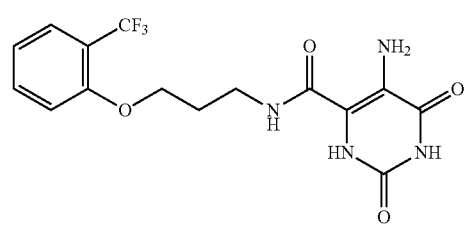 [SMILES: Nc1c(C(=O)NCCCOc2ccccc2C(F)(F)F)[nH]c(=O)[nH]c1=O] | 5-amino-2,6-dioxo-N-(3-(2-(trifluoromethyl)phenoxy)propyl)-1,2,3,6-tetrahydropyrimidine-4-carboxamide | 373.0/1.78 min (Method B) | RT = 7.33 min, 99.4% (Method A) RT = 6.82 min, 99.8% (Method B) |
| 5 | 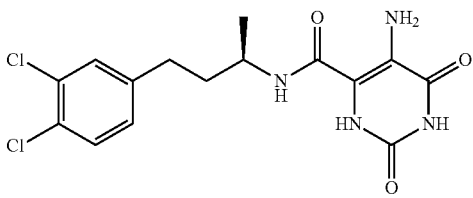 [SMILES: C[C@H](CCc1ccc(Cl)c(Cl)c1)NC(=O)c1[nH]c(=O)[nH]c(=O)c1N] | (R)-5-amino-N-(4-(3,4-dichlorophenyl)butan-2-yl)-2,6-dioxo-1,2,3,6-tetrahydropyrimidine-4-carboxamide | 371.4/1.97 min (Method B) | RT = 8.31 min, 100% (Method A) RT = 7.63 min, 100% (Method B) |
| 6 | 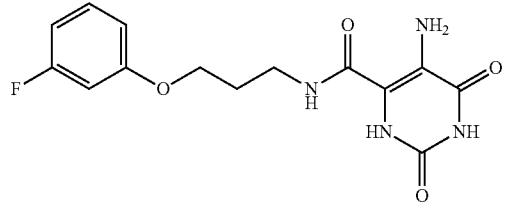 [SMILES: Nc1c(C(=O)NCCCOc2cccc(F)c2)[nH]c(=O)[nH]c1=O] | 5-amino-N-(3-(3-fluorophenoxy)propyl)-2,6-dioxo-1,2,3,6-tetrahydropyrimidine-4-carboxamide | 323.0/1.49 min (Method F) | 94.9 |
| 7 | 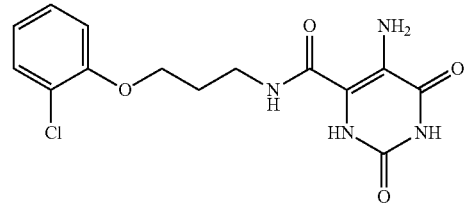 [SMILES: Nc1c(C(=O)NCCCOc2ccccc2Cl)[nH]c(=O)[nH]c1=O] | 5-amino-N-(3-(2-chlorophenoxy)propyl)-2,6-dioxo-1,2,3,6-tetrahydropyrimidine-4-carboxamide | 339.0/1.58 min (Method F) | 96.3 |
| 8 | 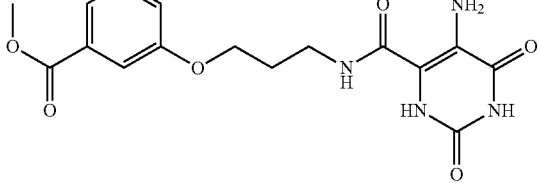 | methyl 3-(3-(5-amino-2,6-dioxo-1,2,3,6-tetrahydropyrimidine-4-carboxamido)propoxy)benzoate | 363.0/1.44 min (Method F) | 98.0 |

TABLE 2-continued

| Ex. No. | Structure | Name | LC-MS [M + 1]/RT | Purity (%) |
|---|---|---|---|---|
| 9 | 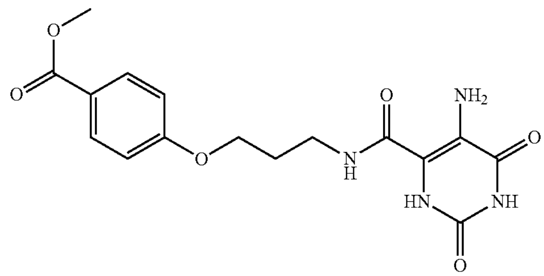 [SMILES: COC(=O)c1ccc(OCCCNC(=O)c2[nH]c(=O)[nH]c(=O)c2N)cc1] | methyl 4-(3-(5-amino-2,6-dioxo-1,2,3,6-tetrahydropyrimidine-4-carboxamido)propoxy)benzoate | 363.0/1.4 min (Method F) | 100 |
| 10 | 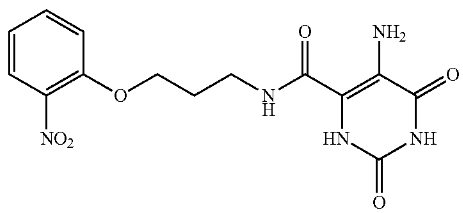 [SMILES: Nc1c(C(=O)NCCCOc2ccccc2[N+](=O)[O-])[nH]c(=O)[nH]c1=O] | 5-amino-N-(3-(2-nitrophenoxy)propyl)-2,6-dioxo-1,2,3,6-tetrahydropyrimidine-4-carboxamide | 350.0/1.31 min (Method F) | 97.9 |
| 11 | 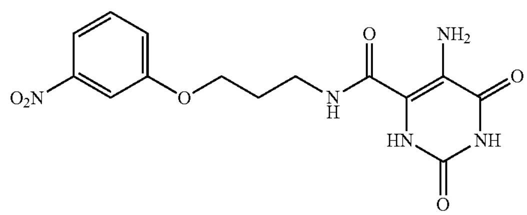 [SMILES: Nc1c(C(=O)NCCCOc2cccc([N+](=O)[O-])c2)[nH]c(=O)[nH]c1=O] | 5-amino-N-(3-(3-nitrophenoxy)propyl)-2,6-dioxo-1,2,3,6-tetrahydropyrimidine-4-carboxamide | 350.0/1.45 min (Method F) | 100 |
| 12 | 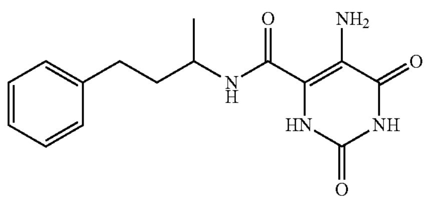 [SMILES: CC(CCc1ccccc1)NC(=O)c1[nH]c(=O)[nH]c(=O)c1N] | 5-amino-2,6-dioxo-N-(4-phenylbutan-2-yl)-1,2,3,6-tetrahydropyrimidine-4-carboxamide | 303.1/1.6 min (Method F) | 100 |
| 13 | 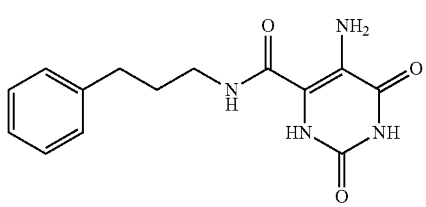 [SMILES: Nc1c(C(=O)NCCCc2ccccc2)[nH]c(=O)[nH]c1=O] | 5-amino-2,6-dioxo-N-(3-phenylpropyl)-1,2,3,6-tetrahydropyrimidine-4-carboxamide | 289.1/1.42 min (Method F) | 98.9 |
| 14 | 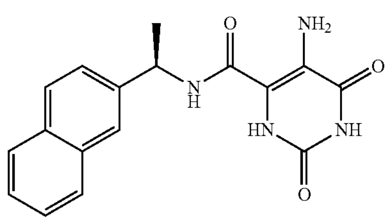 [SMILES: C[C@@H](NC(=O)c1[nH]c(=O)[nH]c(=O)c1N)c1ccc2ccccc2c1] | (R)-5-amino-N-(1-(naphthalen-2-yl)ethyl)-2,6-dioxo-1,2,3,6-tetrahydropyrimidine-4-carboxamide | 325.1/1.73 min (Method F) | 97.9 |

TABLE 2-continued

| Ex. No. | Structure | Name | LC-MS [M + 1]/RT | Purity (%) |
|---|---|---|---|---|
| 15 | 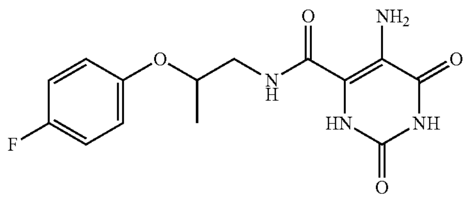 [SMILES: CC(CNC(=O)c1[nH]c(=O)[nH]c(=O)c1N)Oc1ccc(F)cc1] | 5-amino-N-(2-(4-fluorophenoxy)propyl)-2,6-dioxo-1,2,3,6-tetrahydropyrimidine-4-carboxamide | 323.1/1.33 min (Method F) | 98.9 |
| 16 | 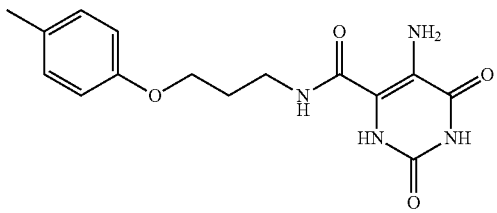 [SMILES: Cc1ccc(OCCCNC(=O)c2[nH]c(=O)[nH]c(=O)c2N)cc1] | 5-amino-2,6-dioxo-N-(3-(p-tolyloxy)propyl)-1,2,3,6-tetrahydropyrimidine-4-carboxamide | 319.1/1.59 min (Method F) | 97.5 |
| 17 | 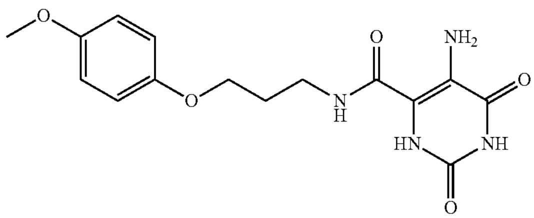 [SMILES: COc1ccc(OCCCNC(=O)c2[nH]c(=O)[nH]c(=O)c2N)cc1] | 5-amino-N-(3-(4-methoxyphenoxy)propyl)-2,6-dioxo-1,2,3,6-tetrahydropyrimidine-4-carboxamide | 335.1/1.31 min (Method F) | 100 |
| 18 | 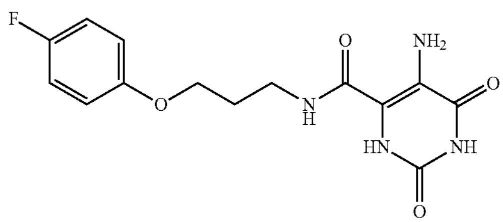 [SMILES: Nc1c(C(=O)NCCCOc2ccc(F)cc2)[nH]c(=O)[nH]c1=O] | 5-amino-N-(3-(4-fluorophenoxy)propyl)-2,6-dioxo-1,2,3,6-tetrahydropyrimidine-4-carboxamide | 323.1/1.43 min (Method F) | 97.8 |
| 19 | 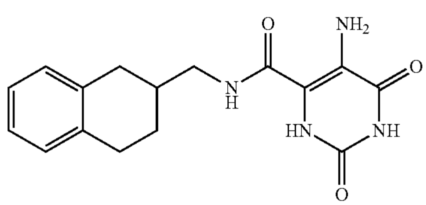 [SMILES: Nc1c(C(=O)NCC2CCc3ccccc3C2)[nH]c(=O)[nH]c1=O] | 5-amino-2,6-dioxo-N-((1,2,3,4-tetrahydronaphthalen-2-yl)methyl)-1,2,3,6-tetrahydropyrimidine-4-carboxamide | 315.1/1.65 min (Method F) | 100 |
| 20 | 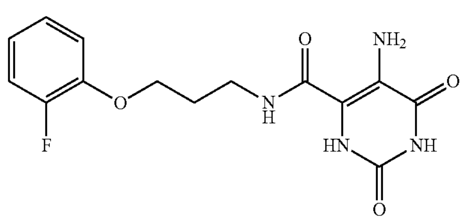 [SMILES: Nc1c(C(=O)NCCCOc2ccccc2F)[nH]c(=O)[nH]c1=O] | 5-amino-N-(3-(2-fluorophenoxy)propyl)-2,6-dioxo-1,2,3,6-tetrahydropyrimidine-4-carboxamide | 323.0/1.38 min (Method F) | 100 |
| 21 | 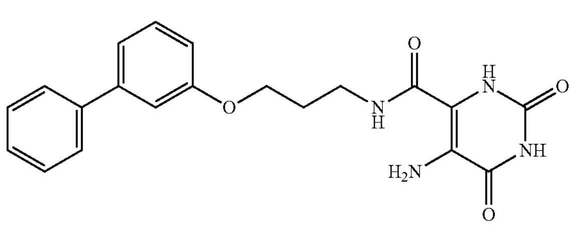 [SMILES: Nc1c(C(=O)NCCCOc2cccc(-c3ccccc3)c2)[nH]c(=O)[nH]c1=O] | 5-amino-N-(3-(biphenyl-3-yloxy)propyl)-2,6-dioxo-1,2,3,6-tetrahydropyrimidine-4-carboxamide | 381.1/2.03 min (Method F) | 100 |

TABLE 2-continued

| Ex. No. | Structure | Name | LC-MS [M + 1]/RT | Purity (%) |
|---|---|---|---|---|
| 22 | 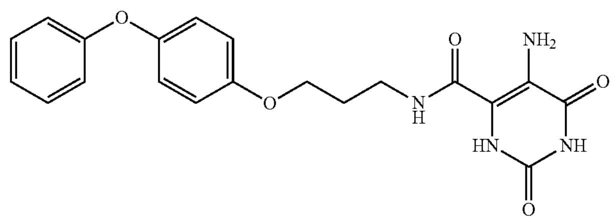 [SMILES: Nc1c(C(=O)NCCCOc2ccc(Oc3ccccc3)cc2)[nH]c(=O)[nH]c1=O] | 5-amino-2,6-dioxo-N-(3-(4-phenoxyphenoxy)propyl)-1,2,3,6-tetrahydropyrimidine-4-carboxamide | 397.1/2.04 min (Method F) | 100 |
| 23 | 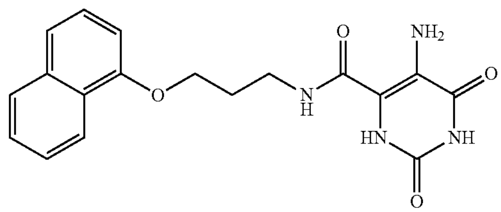 [SMILES: Nc1c(C(=O)NCCCOc2cccc3ccccc23)[nH]c(=O)[nH]c1=O] | 5-amino-N-(3-(naphthalen-1-yloxy)propyl)-2,6-dioxo-1,2,3,6-tetrahydropyrimidine-4-carboxamide | 355.1/1.82 min (Method F) | 95.2 |
| 24 | 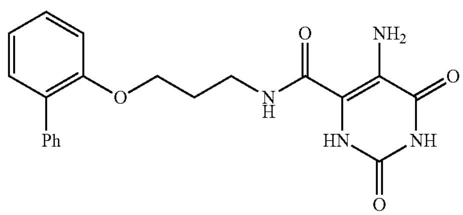 [SMILES: Nc1c(C(=O)NCCCOc2ccccc2-c2ccccc2)[nH]c(=O)[nH]c1=O] | 5-amino-N-(3-(biphenyl-2-yloxy)propyl)-2,6-dioxo-1,2,3,6-tetrahydropyrimidine-4-carboxamide | 381.1/1.97 min (Method F) | 100 |
| 25 | 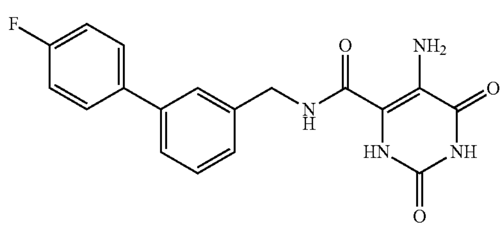 [SMILES: Nc1c(C(=O)NCc2cccc(-c3ccc(F)cc3)c2)[nH]c(=O)[nH]c1=O] | 5-amino-N-((4'-fluorobiphenyl-3-yl)methyl)-2,6-dioxo-1,2,3,6-tetrahydropyrimidine-4-carboxamide | 355.0/1.90 min (Method B) | RT = 7.64 min, 93.6% (Method A) RT = 7.20 min, 98.3% (Method B) |
| 26 | 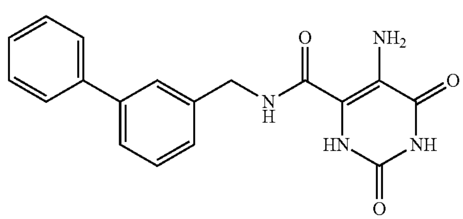 [SMILES: Nc1c(C(=O)NCc2cccc(-c3ccccc3)c2)[nH]c(=O)[nH]c1=O] | 5-amino-N-(biphenyl-3-ylmethyl)-2,6-dioxo-1,2,3,6-tetrahydropyrimidine-4-carboxamide | 337.0/1.77 min (Method B) | RT = 7.43 min, 93.8% (Method A) RT = 7.02 min, 82.4% (Method B) |
| 27 | 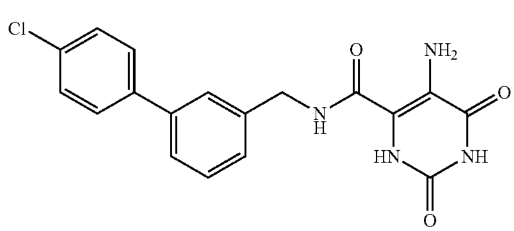 [SMILES: Nc1c(C(=O)NCc2cccc(-c3ccc(Cl)cc3)c2)[nH]c(=O)[nH]c1=O] | 5-amino-N-((4'-chlorobiphenyl-3-yl)methyl)-2,6-dioxo-1,2,3,6-tetrahydropyrimidine-4-carboxamide | 370.9/1.92 min (Method B) | RT = 8.36 min, 95.2% (Method A) RT = 7.80 min, 97.7% (Method B) |

TABLE 2-continued

| Ex. No. | Structure | Name | LC-MS [M + 1]/RT | Purity (%) |
|---|---|---|---|---|
| 28 | 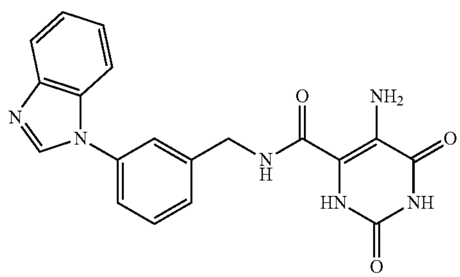 [SMILES: Nc1c(C(=O)NCc2cccc(-n3cnc4ccccc43)c2)[nH]c(=O)[nH]c1=O] | N-(3-(1H-benzo[d]imidazol-1-yl)benzyl)-5-amino-2,6-dioxo-1,2,3,6-tetrahydropyrimidine-4-carboxamide | 377.1/1.38 min (Method F) | 92.7 |
| 29 | 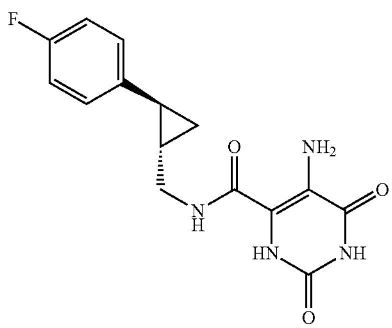 [SMILES: Nc1c(C(=O)NC[C@H]2C[C@@H]2c2ccc(F)cc2)[nH]c(=O)[nH]c1=O] | 5-amino-N-(((1S,2S)-2-(4-fluorophenyl)cyclopropyl)methyl)-2,6-dioxo-1,2,3,6-tetrahydropyrimidine-4-carboxamide | 319.1/1.59 min (Method F) | 95.9 |
| 30 | 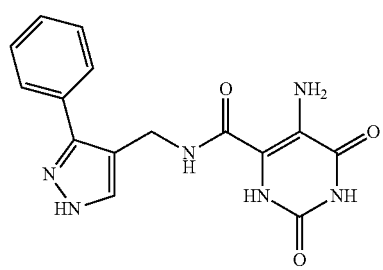 [SMILES: Nc1c(C(=O)NCc2c[nH]nc2-c2ccccc2)[nH]c(=O)[nH]c1=O] | 5-amino-2,6-dioxo-N-((3-phenyl-1H-pyrazol-4-yl)methyl)-1,2,3,6-tetrahydropyrimidine-4-carboxamide | 327.1/1.05 min (Method F) | 96.4 |
| 31 | 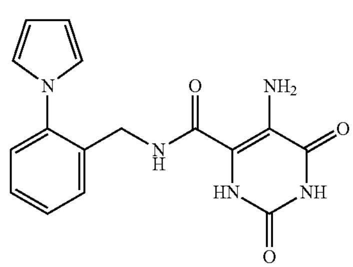 [SMILES: Nc1c(C(=O)NCc2ccccc2-n2cccc2)[nH]c(=O)[nH]c1=O] | N-(2-(1H-pyrrol-1-yl)benzyl)-5-amino-2,6-dioxo-1,2,3,6-tetrahydropyrimidine-4-carboxamide | 326.1/1.53 min (Method F) | 100 |
| 32 | 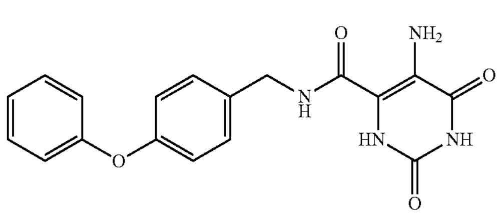 [SMILES: Nc1c(C(=O)NCc2ccc(Oc3ccccc3)cc2)[nH]c(=O)[nH]c1=O] | 5-amino-2,6-dioxo-N-(4-phenoxybenzyl)-1,2,3,6-tetrahydropyrimidine-4-carboxamide | 353.0/1.83 min (Method F) | 100 |

TABLE 2-continued

| Ex. No. | Structure | Name | LC-MS [M + 1]/RT | Purity (%) |
|---|---|---|---|---|
| 33 | 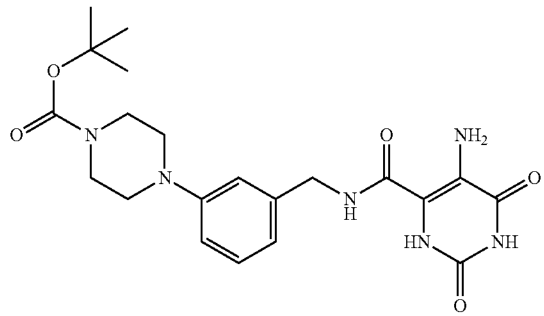 [SMILES: CC(C)(C)OC(=O)N1CCN(c2cccc(CNC(=O)c3[nH]c(=O)[nH]c(=O)c3N)c2)CC1] | tert-butyl 4-(3-((5-amino-2,6-dioxo-1,2,3,6-tetrahydro-pyrimidine-4-carboxamido)methyl)phenyl)piperazine-1-carboxylate | 445.2/1.83 min (Method F) | 100 |
| 34 | 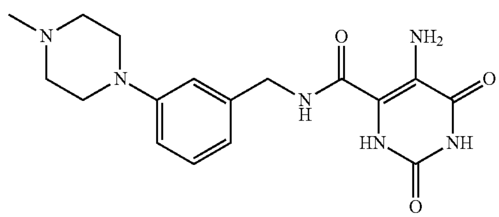 [SMILES: CN1CCN(c2cccc(CNC(=O)c3[nH]c(=O)[nH]c(=O)c3N)c2)CC1] | 5-amino-N-(3-(4-methylpiperazin-1-yl)benzyl)-2,6-dioxo-1,2,3,6-tetrahydropyrimidine-4-carboxamide | 359.2/0.92 min (Method F) | 95.2 |
| 35 | 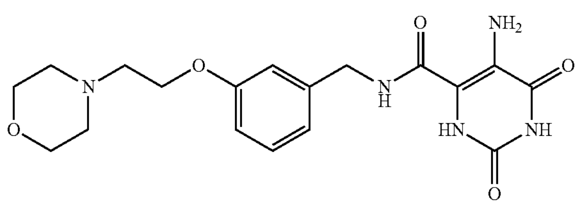 [SMILES: Nc1c(C(=O)NCc2cccc(OCCN3CCOCC3)c2)[nH]c(=O)[nH]c1=O] | 5-amino-N-(3-(2-morpholinoethoxy)benzyl)-2,6-dioxo-1,2,3,6-tetrahydropyrimidine-4-carboxamide | 390.1/1.10 min (Method F) | 100 |
| 36 | 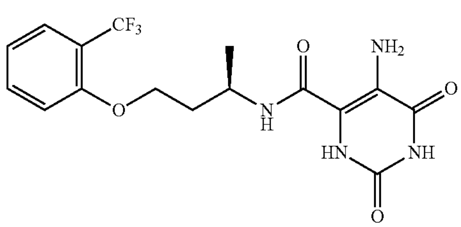 | (R)-5-amino-2,6-dioxo-N-(4-(2-(trifluoromethyl)phenoxy)butan-2-yl)-1,2,3,6-tetrahydropyrimidine-4-carboxamide | 387/2.38 min (Method A) | RT = 8.5 min, 95% (Method A) RT = 8.1 min, 93% (Method B) |
| 37 | 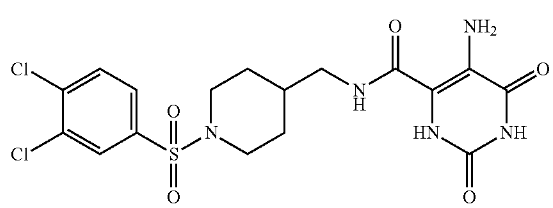 [SMILES: Nc1c(C(=O)NCC2CCN(S(=O)(=O)c3ccc(Cl)c(Cl)c3)CC2)[nH]c(=O)[nH]c1=O] | 5-amino-N-((1-(3,4-dichloro-phenylsulfonyl)piperidin-4-yl)methyl)-2,6-dioxo-1,2,3,6-tetrahydropyrimidine-4-carboxamide | 476.1/2.39 min (Method A) | RT = 7.9 min, 88% (Method A) RT = 7.5 min, 92.6% (Method B) |
| 38 | 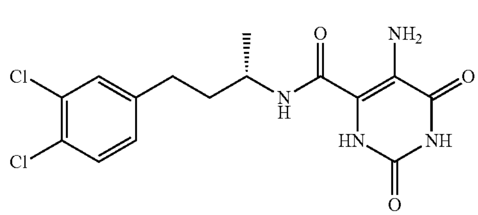 [SMILES: C[C@@H](CCc1ccc(Cl)c(Cl)c1)NC(=O)c1[nH]c(=O)[nH]c(=O)c1N] | (S)-5-amino-N-(4-(3,4-dichlorophenyl)butan-2-yl)-2,6-dioxo-1,2,3,6-tetrahydropyrimidine-4-carboxamide | 370.8/2.07 min (Method B) | RT = 8.34 min, 94.5% (Method A) RT = 7.68 min, 93.6% (Method B) |

TABLE 2-continued

| Ex. No. | Structure | Name | LC-MS [M + 1]/RT | Purity (%) |
|---|---|---|---|---|
| 39 | 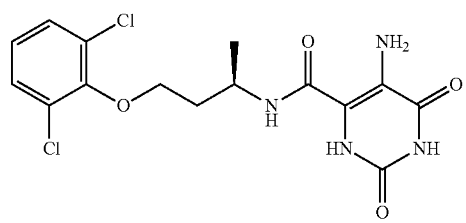 [SMILES: C[C@H](CCOc1c(Cl)cccc1Cl)NC(=O)c1[nH]c(=O)[nH]c(=O)c1N] | (R)-5-amino-N-(4-(2,6-dichloro-phenoxy)butan-2-yl)-2,6-dioxo-1,2,3,6-tetra-hydropyrimidine-4-carboxamide | 387.0/2.30 min (Method G) | RT = 7.6 min, 95.4% (Method A) RT = 7.03 min, 95.3% (Method B) |
| 40 | 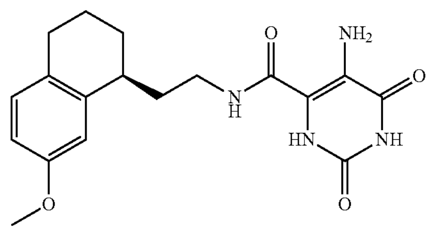 [SMILES: COc1ccc2c(c1)[C@H](CCNC(=O)c1[nH]c(=O)[nH]c(=O)c1N)CCC2] | (S)-5-amino-N-(2-(7-methoxy-1,2,3,4-tetrahydronaphthalen-1-yl)ethyl)-2,6-dioxo-1,2,3,6-tetrahydropyrimidine-4-carboxamide | 359.4/1.97 min (Method B) | RT = 7.42 min, 98.1% (Method A) RT = 6.93 min, 100% (Method B) |
| 41 | 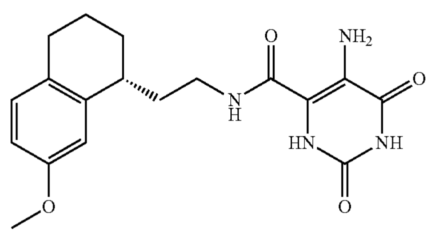 [SMILES: COc1ccc2c(c1)[C@@H](CCNC(=O)c1[nH]c(=O)[nH]c(=O)c1N)CCC2] | (R)-5-amino-N-(2-(7-methoxy-1,2,3,4-tetrahydro-naphthalen-1-yl)ethyl)-2,6-dioxo-1,2,3,6-tetrahydropyrimidine-4-carboxamide | 359.4/1.93 min (Method B) | RT = 7.12 min, 96.2% (Method A) RT = 6.60 min, 100% (Method B) |
| 42 | 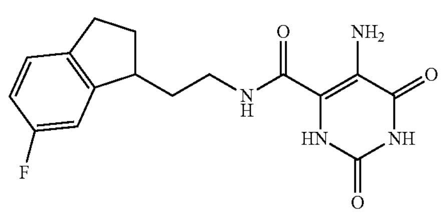 [SMILES: Nc1c(C(=O)NCCC2CCc3ccc(F)cc32)[nH]c(=O)[nH]c1=O] | 5-amino-N-(2-(6-fluoro-2,3-dihydro-1H-inden-1-yl)ethyl)-2,6-dioxo-1,2,3,6-tetrahydropyrimidine-4-carboxamide | 333.4/1.83 min (Method B) | RT = 6.88 min, 98.2% (Method A) RT = 6.42 min, 100% (Method B) |
| 43 | 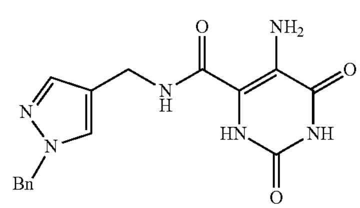 [SMILES: Nc1c(C(=O)NCc2cnn(Cc3ccccc3)c2)[nH]c(=O)[nH]c1=O] | 5-amino-N-((1-benzyl-1H-pyrazol-4-yl)methyl)-2,6-dioxo-1,2,3,6-tetrahydropyrimidine-4-carboxamide | 341.1/2.39 min (Method A) | NA |
| 44 | 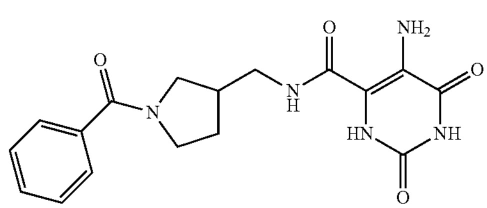 [SMILES: Nc1c(C(=O)NCC2CCN(C(=O)c3ccccc3)C2)[nH]c(=O)[nH]c1=O] | 5-amino-N-((1-benzoylpyrrolidin-3-yl)methyl)-2,6-dioxo-1,2,3,6-tetrahydropyrimidine-4-carboxamide | 358.2/1.33 min (Method B) | RT = 5.91 min, 97.5% (Method A) RT = 6.05 min, 98.6% (Method B) |

TABLE 2-continued

| Ex. No. | Structure | Name | LC-MS [M + 1]/RT | Purity (%) |
|---|---|---|---|---|
| 45 | 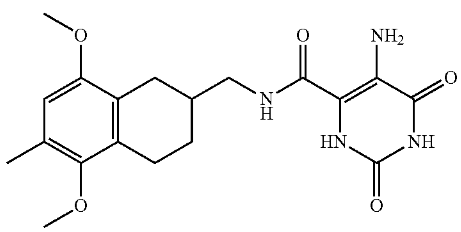 [SMILES: COc1cc(C)c(OC)c2c1CC(CNC(=O)c1[nH]c(=O)[nH]c(=O)c1N)CC2] | 5-amino-N-((5,8-dimethoxy-6-methyl-1,2,3,4-tetrahydronaphthalen-2-yl)methyl)-2,6-dioxo-1,2,3,6-tetrahydropyrimidine-4-carboxamide | 389.1/1.84 min (Method B) | RT = 8.77 min, 99.3% (Method A) RT = 8.66 min, 100% (Method B) |
| 46 | 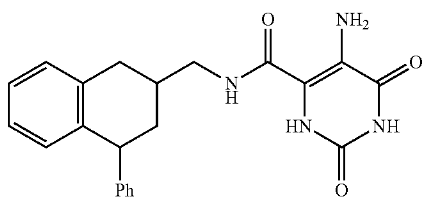 [SMILES: Nc1c(C(=O)NCC2Cc3ccccc3C(c3ccccc3)C2)[nH]c(=O)[nH]c1=O] | 5-amino-2,6-dioxo-N-((4-phenyl-1,2,3,4-tetrahydronaphthalen-2-yl)methyl)-1,2,3,6-tetrahydropyrimidine-4-carboxamide | 391.1/2.08 min (Method B) | RT = 10.53 min, 98.4% (Method A) RT = 10.25 min, 100% (Method B) |
| 47 | 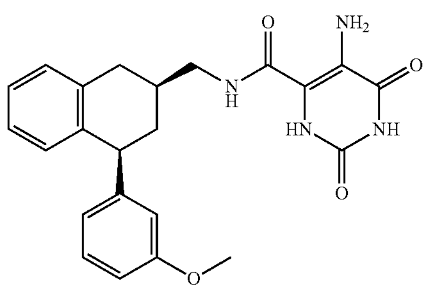 [SMILES: COc1cccc([C@@H]2C[C@H](CNC(=O)c3[nH]c(=O)[nH]c(=O)c3N)Cc3ccccc32)c1] | 5-amino-N-(((2S,4S)-4-(3-methoxyphenyl)-1,2,3,4-tetrahydronaphthalen-2-yl)methyl)-2,6-dioxo-1,2,3,6-tetrahydropyrimidine-4-carboxamide | 421.1/2.06 min (Method B) | RT = 9.99 min, 99.3% (Method A) RT = 9.71 min, 100% (Method B) |
| 48 | 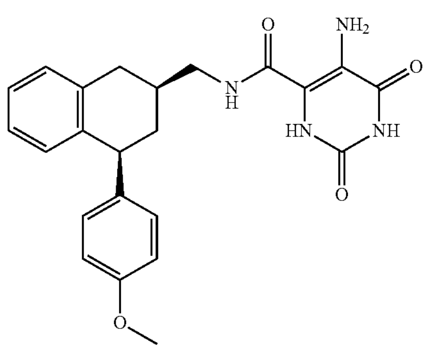 [SMILES: COc1ccc([C@@H]2C[C@H](CNC(=O)c3[nH]c(=O)[nH]c(=O)c3N)Cc3ccccc32)cc1] | 5-amino-N-(((2S,4S)-4-(4-methoxyphenyl)-1,2,3,4-tetrahydronaphthalen-2-yl)methyl)-2,6-dioxo-1,2,3,6-tetrahydropyrimidine-4-carboxamide | 421.0/2.07 min (Method B) | RT = 9.90 min, 98.0% (Method A) RT = 9.69 min, 98.4% (Method B) |
| 49 | 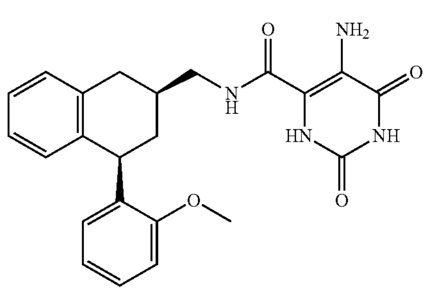 [SMILES: COc1ccccc1[C@@H]1C[C@H](CNC(=O)c2[nH]c(=O)[nH]c(=O)c2N)Cc2ccccc21] | 5-amino-N-(((2S,4R)-4-(2-methoxyphenyl)-1,2,3,4-tetrahydronaphthalen-2-yl)methyl)-2,6-dioxo-1,2,3,6-tetrahydropyrimidine-4-carboxamide | 421.2/2.18 min (Method B) | RT = 10.21 min, 98.8% (Method A) RT = 9.94, 99.8% (Method B) |

TABLE 2-continued

| Ex. No. | Structure | Name | LC-MS [M + 1]/RT | Purity (%) |
|---|---|---|---|---|
| 50 | 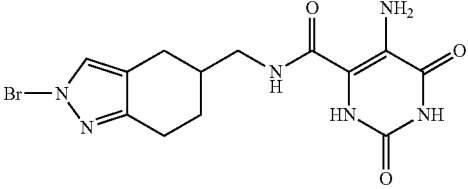 [SMILES: Nc1c(C(=O)NCC2CCc3nn(Br)cc3C2)[nH]c(=O)[nH]c1=O] | 5-amino-N-((2-benzyl-4,5,6,7-tetrahydro-2H-indazol-5-yl)methyl)-2,6-dioxo-1,2,3,6-tetrahydropyrimidine-4-carboxamide | 395.2/1.50 min (Method B) | RT = 6.68 min, 100% (Method A) RT = 7.02 min, 100% (Method B) |
| 51 | 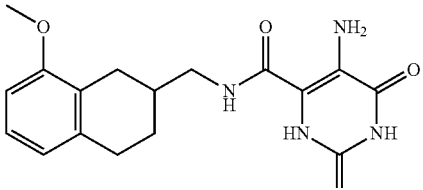 | 5-amino-N-((8-methoxy-1,2,3,4-tetrahydronaphthalen-2-yl)methyl)-2,6-dioxo-1,2,3,6-tetrahydropyrimidine-4-carboxamide | 345.1/1.94 min (Method B) | RT = 8.41 min, 100% (Method A) RT = 8.49 min, 100% (Method B) |
| 52 | 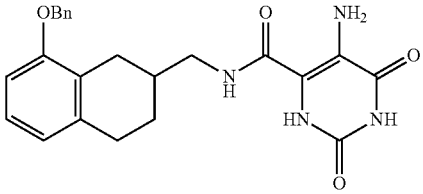 [SMILES: Nc1c(C(=O)NCC2CCc3cccc(OCc4ccccc4)c3C2)[nH]c(=O)[nH]c1=O] | 5-amino-N-((8-(benzyloxy)-1,2,3,4-tetrahydronaphthalen-2-yl)methyl)-2,6-dioxo-1,2,3,6-tetrahydropyrimidine-4-carboxamide | 421.1/2.18 min (Method B) | RT = 10.47 min, 99.0% (Method A) RT = 10.18 min, 97.3% (Method B) |
| 54 | 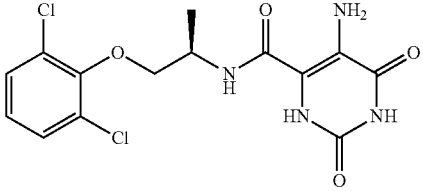 [SMILES: C[C@H](COc1c(Cl)cccc1Cl)NC(=O)c1[nH]c(=O)[nH]c(=O)c1N] | (R)-5-amino-N-(1-(2,6-dichlorophenoxy)propan-2-yl)-2,6-dioxo-1,2,3,6-tetrahydropyrimidine-4-carboxamide | 373.0/2.20 min (Method G) | RT = 7.23 min, 98.9% (Method A) RT = 6.71 min, 97.8% (Method B) |
| 55 | 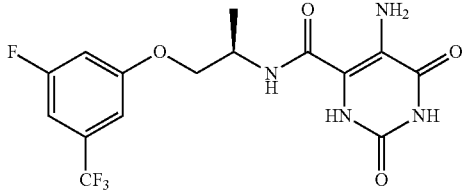 [SMILES: C[C@H](COc1cc(F)cc(C(F)(F)F)c1)NC(=O)c1[nH]c(=O)[nH]c(=O)c1N] | (R)-5-amino-N-(1-(3-fluoro-5-(trifluoromethyl)phenoxy)propan-2-yl)-2,6-dioxo-1,2,3,6-tetrahydropyrimidine-4-carboxamide | 391.0/1.99 (Method B) | RT = 8.02 min, 100% (Method A) RT = 7.13 min, 100% (Method B) |
| 56 | 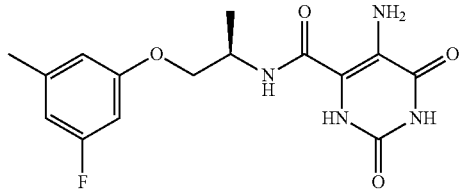 [SMILES: Cc1cc(F)cc(OC[C@@H](C)NC(=O)c2[nH]c(=O)[nH]c(=O)c2N)c1] | (R)-5-amino-N-(1-(3-fluoro-5-methylphenoxy)propan-2-yl)-2,6-dioxo-1,2,3,6-tetrahydropyrimidine-4-carboxamide | 337.1/1.82 (Method K) | 100 |
| 57 | 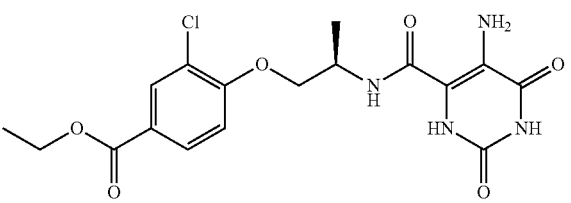 [SMILES: CCOC(=O)c1ccc(OC[C@@H](C)NC(=O)c2[nH]c(=O)[nH]c(=O)c2N)c(Cl)c1] | (R)-ethyl 4-(2-(5-amino-2,6-dioxo-1,2,3,6-tetrahydropyrimidine-4-carboxamido)propoxy)-3-chlorobenzoate | 411.0/1.96 (Method K) | 92.4 |

| Ex. No. | Structure | Name | LC-MS [M + 1]/RT | Purity (%) |
|---|---|---|---|---|
| 58 | 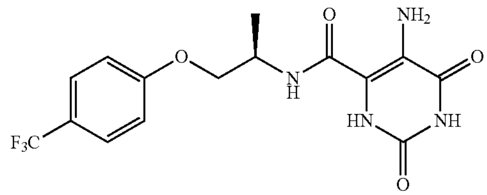 [SMILES: C[C@H](COc1ccc(C(F)(F)F)cc1)NC(=O)c1[nH]c(=O)[nH]c(=O)c1N] | (R)-5-amino-2,6-dioxo-N-(1-(4-(trifluoromethyl)phenoxy)propan-2-yl)-1,2,3,6-tetrahydropyrimidine-4-carboxamide | 373.0/1.96 (Method K) | 87.6 |
| 59 | 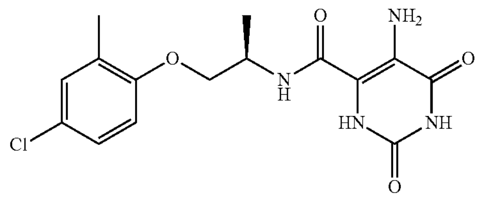 [SMILES: Cc1cc(Cl)ccc1OC[C@@H](C)NC(=O)c1[nH]c(=O)[nH]c(=O)c1N] | (R)-5-amino-N-(1-(4-chloro-2-methylphenoxy)propan-2-yl)-2,6-dioxo-1,2,3,6-tetrahydropyrimidine-4-carboxamide | 353.0/2.02 (Method K) | 98.8 |
| 60 | 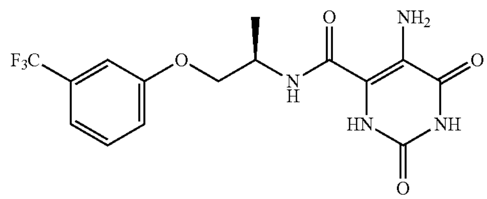 [SMILES: C[C@H](COc1cccc(C(F)(F)F)c1)NC(=O)c1[nH]c(=O)[nH]c(=O)c1N] | (R)-5-amino-2,6-dioxo-N-(1-(3-(trifluoromethoxy)phenoxy)propan-2-yl)-1,2,3,6-tetrahydropyrimidine-4-carboxamide | 389.0/2.02 (Method K) | 95.6 |
| 61 | 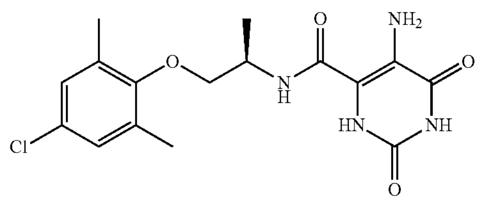 [SMILES: Cc1cc(Cl)cc(C)c1OC[C@@H](C)NC(=O)c1[nH]c(=O)[nH]c(=O)c1N] | (R)-5-amino-N-(1-(4-chloro-2,6-dimethylphenoxy)propan-2-yl)-2,6-dioxo-1,2,3,6-tetrahydropyrimidine-4-carboxamide | 367.0/2.10 (Method K) | 94.3 |
| 62 | 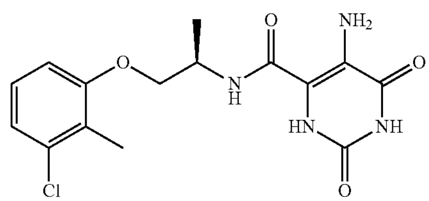 [SMILES: Cc1c(Cl)cccc1OC[C@@H](C)NC(=O)c1[nH]c(=O)[nH]c(=O)c1N] | (R)-5-amino-N-(1-(3-chloro-2-methylphenoxy)propan-2-yl)-2,6-dioxo-1,2,3,6-tetrahydropyrimidine-4-carboxamide | 353.0/2.01 (Method K) | 94.2 |
| 63 | 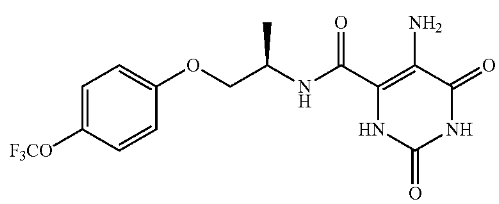 [SMILES: C[C@H](COc1ccc(OC(F)(F)F)cc1)NC(=O)c1[nH]c(=O)[nH]c(=O)c1N] | (R)-5-amino-2,6-dioxo-N-(1-(4-(trifluoromethoxy)phenoxy)propan-2-yl)-1,2,3,6-tetrahydropyrimidine-4-carboxamide | 389.0/2.02 (Method K) | 98.7 |
| 64 | 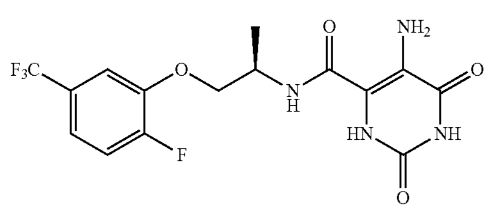 [SMILES: C[C@H](COc1cc(C(F)(F)F)ccc1F)NC(=O)c1[nH]c(=O)[nH]c(=O)c1N] | (R)-5-amino-N-(1-(2-fluoro-5-(trifluoromethyl)phenoxy)propan-2-yl)-2,6-dioxo-1,2,3,6-tetrahydropyrimidine-4-carboxamide | 391.0/1.95 (Method K) | 94.1 |

TABLE 2-continued

| Ex. No. | Structure | Name | LC-MS [M + 1]/RT | Purity (%) |
|---|---|---|---|---|
| 65 | 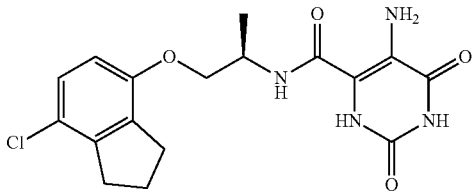 [SMILES: C[C@H](COc1ccc(Cl)c2c1CCC2)NC(=O)c1[nH]c(=O)[nH]c(=O)c1N] | (R)-5-amino-N-(1-(7-chloro-2,3-dihydro-1H-inden-4-yloxy)propan-2-yl)-2,6-dioxo-1,2,3,6-tetrahydropyrimidine-4-carboxamide | 379.1/2.22 (Method K) | 90.6 |
| 66 | 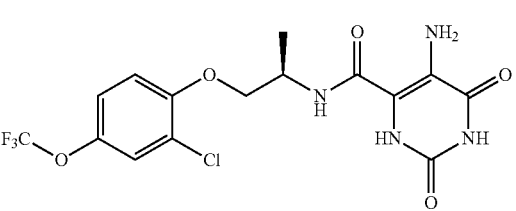 [SMILES: C[C@H](COc1ccc(OC(F)(F)F)cc1Cl)NC(=O)c1[nH]c(=O)[nH]c(=O)c1N] | (R)-5-amino-N-(1-(2-chloro-4-(trifluoromethoxy)phenoxy)propan-2-yl)-2,6-dioxo-1,2,3,6-tetrahydropyrimidine-4-carboxamide | 423.0/2.2 (Method K) | 93.9 |
| 67 | 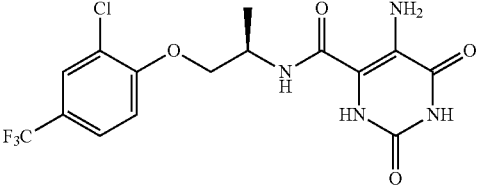 [SMILES: C[C@H](COc1ccc(C(F)(F)F)cc1Cl)NC(=O)c1[nH]c(=O)[nH]c(=O)c1N] | (R)-5-amino-N-(1-(2-chloro-4-(trifluoromethyl)phenoxy)propan-2-yl)-2,6-dioxo-1,2,3,6-tetrahydropyrimidine-4-carboxamide | 407.0/2.12 (Method K) | 94.6 |
| 68 | 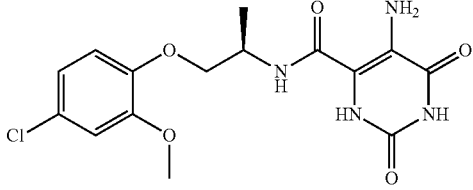 [SMILES: COc1cc(Cl)ccc1OC[C@@H](C)NC(=O)c1[nH]c(=O)[nH]c(=O)c1N] | (R)-5-amino-N-(1-(4-chloro-2-methoxyphenoxy)propan-2-yl)-2,6-dioxo-1,2,3,6-tetrahydropyrimidine-4-carboxamide | 369.0/1.76 (Method K) | 94.0 |
| 69 | 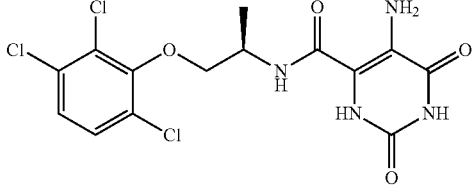 [SMILES: C[C@H](COc1c(Cl)ccc(Cl)c1Cl)NC(=O)c1[nH]c(=O)[nH]c(=O)c1N] | (R)-5-amino-2,6-dioxo-N-(1-(2,3,6-trichlorophenoxy)propan-2-yl)-1,2,3,6-tetrahydropyrimidine-4-carboxamide | 406.9/2.05 (Method K) | 100 |
| 70 | 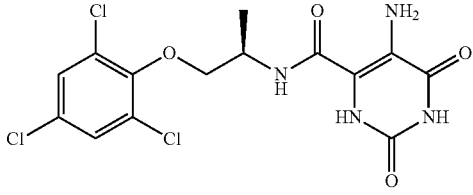 [SMILES: C[C@H](COc1c(Cl)cc(Cl)cc1Cl)NC(=O)c1[nH]c(=O)[nH]c(=O)c1N] | (R)-5-amino-2,6-dioxo-N-(1-(2,4,6,-trichlorophenoxy)propan-2-yl)-1,2,3,6-tetrahydropyrimidine-4-carboxamide | 406.9/2.14 (Method K) | 94.6 |
| 71 | 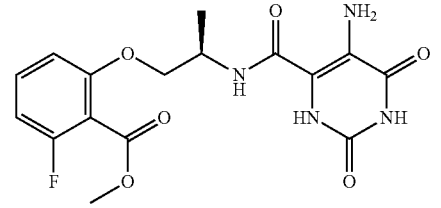 [SMILES: COC(=O)c1c(F)cccc1OC[C@@H](C)NC(=O)c1[nH]c(=O)[nH]c(=O)c1N] | (R)-methyl 2-(2-(5-amino-2,6-dioxo-1,2,3,6-tetrahydropyrimidine-4-carboxamido)propoxy)-6-fluorobenzoate | 381.0/1.52 (Method K) | 100 |

TABLE 2-continued

| Ex. No. | Structure | Name | LC-MS [M + 1]/RT | Purity (%) |
|---|---|---|---|---|
| 72 | 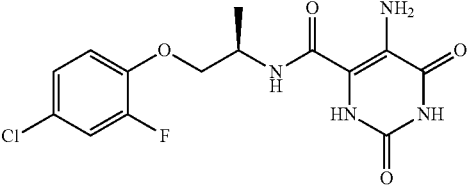 [SMILES: C[C@H](COc1ccc(Cl)cc1F)NC(=O)c1[nH]c(=O)[nH]c(=O)c1N] | (R)-5-amino-N-(1-(4-chloro-2-fluoro-phenoxy)propan-2-yl)-2,6-dioxo-1,2,3,6-tetrahydropyrimidine-4-carboxamide | 357.0/1.78 (Method K) | 99.3 |
| 73 | 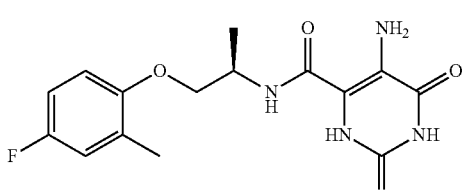 | (R)-5-amino-N-(1-(4-fluoro-2-methylphenoxy)propan-2-yl)-2,6-dioxo-1,2,3,6-tetrahydropyrimidine-4-carboxamide | 337.1/1.75 (Method K) | 96.7 |
| 74 | 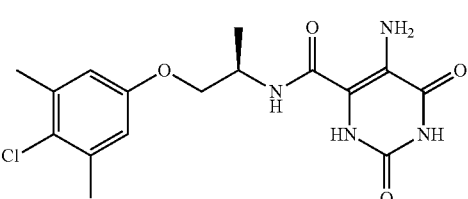 | (R)-5-amino-N-(1-(4-chloro-3,5-dimethylphenoxy)propan-2-yl)-2,6-dioxo-1,2,3,6-tetrahydropyrimidine-4-carboxamide | 367.0/2.10 (Method K) | 90.9 |
| 75 | 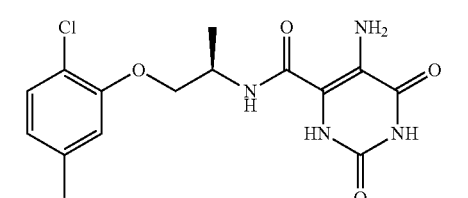 | (R)-5-amino-N-(1-(2-chloro-5-methylphenoxy)propan-2-yl)-2,6-dioxo-1,2,3,6-tetrahydropyrimidine-4-carboxamide | 353.0/1.84 (Method K) | 100 |
| 76 | 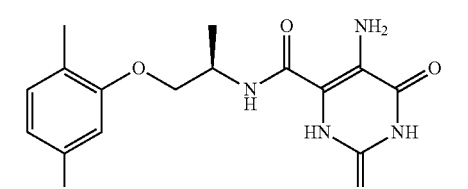 | (R)-5-amino-N-(1-(5-chloro-2-methylphenoxy)propan-2-yl)-2,6-dioxo-1,2,3,6-tetrahydropyrimidine-4-carboxamide | 353.0/1.96 (Method K) | 100 |
| 77 | 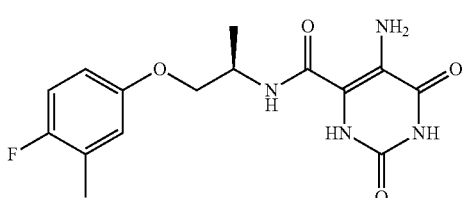 | (R)-5-amino-N-(1-(4-fluoro-3-methylphenoxy)propan-2-yl)-2,6-dioxo-1,2,3,6-tetrahydropyrimidine-4-carboxamide | 337.1/1.74 (Method K) | 97.3 |
| 78 | 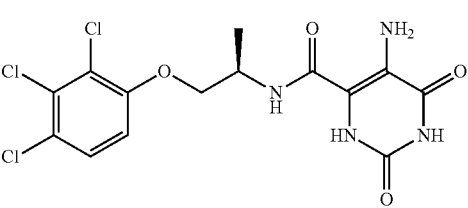 [SMILES: C[C@H](COc1ccc(Cl)c(Cl)c1Cl)NC(=O)c1[nH]c(=O)[nH]c(=O)c1N] | (R)-5-amino-2,6-dioxo-N-(1-(2,3,4-trichlorophenoxy)propan-2-yl)-1,2,3,6-tetrahydropyrimidine-4-carboxamide | 406.9/2.10 (Method K) | 100 |

TABLE 2-continued

| Ex. No. | Structure | Name | LC-MS [M + 1]/RT | Purity (%) |
|---|---|---|---|---|
| 79 | 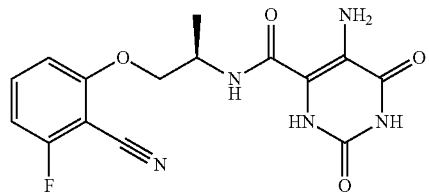 [SMILES: C[C@H](COc1cccc(F)c1C#N)NC(=O)c1[nH]c(=O)[nH]c(=O)c1N] | (R)-5-amino-N-(1-(2-cyano-3-fluorophenoxy)propan-2-yl)-2,6-dioxo-1,2,3,6-tetrahydropyrimidine-4-carboxamide | 348.0/1.48 (Method K) | 91.9 |
| 80 | 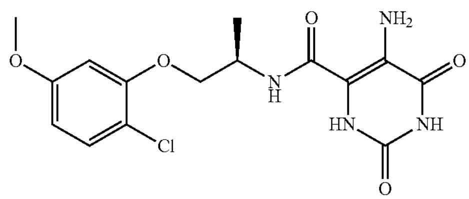 [SMILES: COc1ccc(Cl)c(OC[C@@H](C)NC(=O)c2[nH]c(=O)[nH]c(=O)c2N)c1] | (R)-5-amino-N-(1-(2-chloro-5-methoxyphenoxy)propan-2-yl)-2,6-dioxo-1,2,3,6-tetrahydropyrimidine-4-carboxamide | 369.0/1.73 (Method K) | 96.9 |
| 81 | 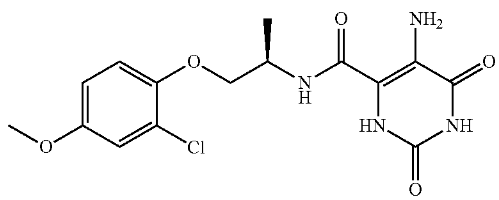 [SMILES: COc1ccc(OC[C@@H](C)NC(=O)c2[nH]c(=O)[nH]c(=O)c2N)c(Cl)c1] | (R)-5-amino-N-(1-(2-chloro-4-methoxyphenoxy)propan-2-yl)-2,6-dioxo-1,2,3,6-tetrahydropyrimidine-4-carboxamide | 369.0/1.69 (Method K) | 97.7 |
| 82 | 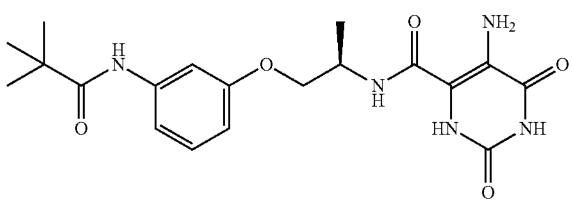 [SMILES: C[C@H](COc1cccc(NC(=O)C(C)(C)C)c1)NC(=O)c1[nH]c(=O)[nH]c(=O)c1N] | (R)-5-amino-2,6-dioxo-N-(1-(3-pivalamidophenoxy)propan-2-yl)-1,2,3,6-tetrahydropyrimidine-4-carboxamide | 404.1/1.61 (Method K) | 98.0 |
| 83 | 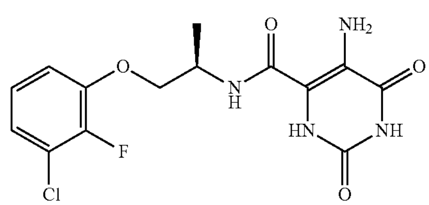 [SMILES: C[C@H](COc1cccc(Cl)c1F)NC(=O)c1[nH]c(=O)[nH]c(=O)c1N] | (R)-5-amino-N-(1-(3-chloro-2-fluorophenoxy)propan-2-yl)-2,6-dioxo-1,2,3,6-tetrahydropyrimidine-4-carboxamide | 357.0/1.76 (Method K) | 98.4 |
| 84 | 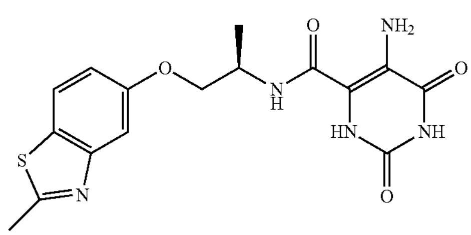 [SMILES: Cc1nc2cc(OC[C@@H](C)NC(=O)c3[nH]c(=O)[nH]c(=O)c3N)ccc2s1] | (R)-5-amino-N-(1-(2-methylbenzo[d]thiazol-5-yloxy)propan-2-yl)-2,6-dioxo-1,2,3,6-tetrahydropyrimidine-4-carboxamide | 376.0/1.49 (Method K) | 100 |
| 85 | 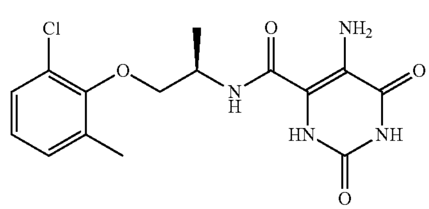 [SMILES: Cc1cccc(Cl)c1OC[C@@H](C)NC(=O)c1[nH]c(=O)[nH]c(=O)c1N] | (R)-5-amino-N-(1-(2-chloro-6-methylphenoxy)propan-2-yl)-2,6-dioxo-1,2,3,6-tetrahydropyrimidine-4-carboxamide | 353.0/1.83 (Method K) | 100 |

TABLE 2-continued

| Ex. No. | Structure | Name | LC-MS [M + 1]/RT | Purity (%) |
|---|---|---|---|---|
| 86 | 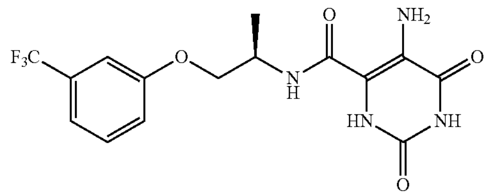 [SMILES: C[C@H](COc1cccc(C(F)(F)F)c1)NC(=O)c1[nH]c(=O)[nH]c(=O)c1N] | (R)-5-amino-2,6-dioxo-N-(1-(3-(trifluoromethyl)phenoxy)propan-2-yl)-1,2,3,6-tetrahydropyrimidine-4-carboxamide | 373.0/1.92 (Method K) | 100 |
| 87 | 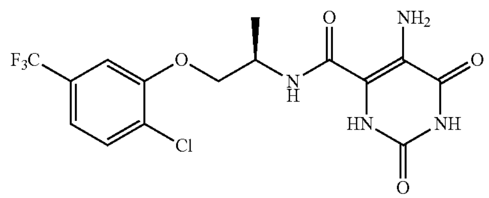 [SMILES: C[C@H](COc1cc(C(F)(F)F)ccc1Cl)NC(=O)c1[nH]c(=O)[nH]c(=O)c1N] | (R)-5-amino-N-(1-(2-chloro-5-(trifluoromethyl)phenoxy)propan-2-yl)-2,6-dioxo-1,2,3,6-tetrahydropyrimidine-4-carboxamide | 406.9/2.1 (Method K) | 97.1 |
| 88 | 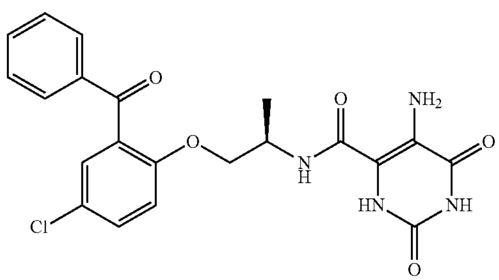 [SMILES: C[C@H](COc1ccc(Cl)cc1C(=O)c1ccccc1)NC(=O)c1[nH]c(=O)[nH]c(=O)c1N] | (R)-5-amino-N-(1-(2-benzoyl-4-chlorophenoxy)propan-2-yl)-2,6-dioxo-1,2,3,6-tetrahydropyrimidine-4-carboxamide | 442.9/2.07 (Method K) | 92.5 |
| 89 | 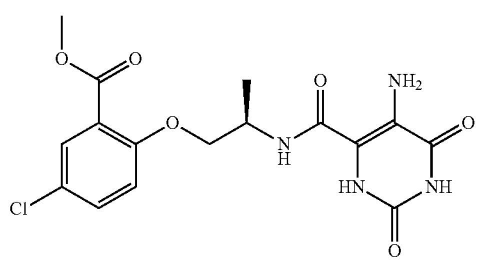 [SMILES: COC(=O)c1cc(Cl)ccc1OC[C@@H](C)NC(=O)c1[nH]c(=O)[nH]c(=O)c1N] | (R)-methyl 2-(2-(5-amino-2,6-dioxo-1,2,3,6-tetrahydropyrimidine-4-carboxamido)propoxy)-5-chlorobenzoate | 397.0/1.81 (Method K) | 100 |
| 90 | 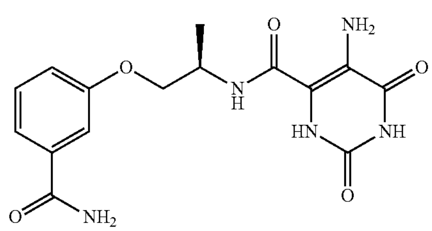 [SMILES: C[C@H](COc1cccc(C(N)=O)c1)NC(=O)c1[nH]c(=O)[nH]c(=O)c1N] | (R)-5-amino-N-(1-(3-carbamoylphenoxy)propan-2-yl)-2,6-dioxo-1,2,3,6-tetrahydropyrimidine-4-carboxamide | 348/1.08 (Method K) | 92.0 |
| 91 | 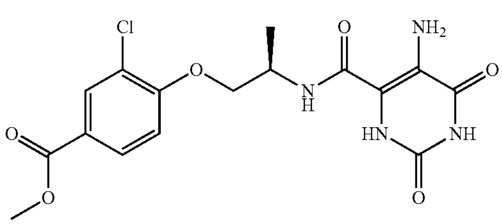 [SMILES: COC(=O)c1ccc(OC[C@@H](C)NC(=O)c2[nH]c(=O)[nH]c(=O)c2N)c(Cl)c1] | (R)-methyl 4-(2-(5-amino-2,6-dioxo-1,2,3,6-tetrahydropyrimidine-4-carboxamido)propoxy)-3-chlorobenzoate | 397/1.74 (Method K) | 100 |

TABLE 2-continued

| Ex. No. | Structure | Name | LC-MS [M + 1]/RT | Purity (%) |
|---|---|---|---|---|
| 92 | 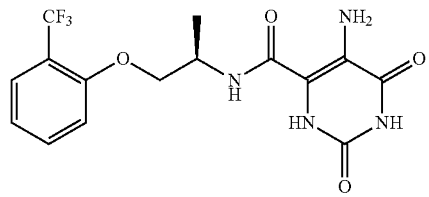 [SMILES: C[C@H](COc1ccccc1C(F)(F)F)NC(=O)c1[nH]c(=O)[nH]c(=O)c1N] | (R)-5-amino-2,6-dioxo-N-(1-(2-(trifluoromethyl)phenoxy)propan-2-yl)-1,2,3,6-tetrahydropyrimidine-4-carboxamide | 373/1.86 (Method K) | 95.7 |
| 93 | 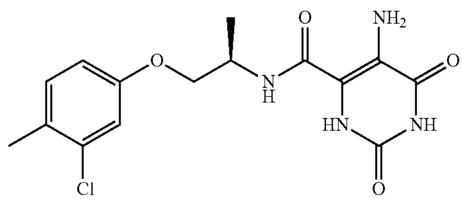 [SMILES: Cc1ccc(OC[C@@H](C)NC(=O)c2[nH]c(=O)[nH]c(=O)c2N)cc1Cl] | (R)-5-amino-N-(1-(3-chloro-4-methylphenoxy)propan-2-yl)-2,6-dioxo-1,2,3,6-tetrahydropyrimidine-4-carboxamide | 353.0/1.97 (Method K) | 99.2 |
| 94 | 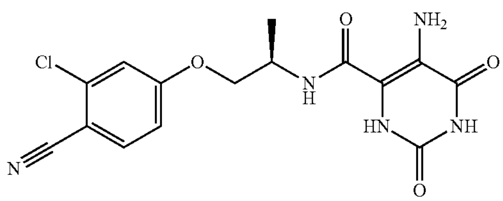 [SMILES: C[C@H](COc1ccc(C#N)c(Cl)c1)NC(=O)c1[nH]c(=O)[nH]c(=O)c1N] | (R)-5-amino-N-(1-(3-chloro-4-cyanophenoxy)propan-2-yl)-2,6-dioxo-1,2,3,6-tetrahydropyrimidine-4-carboxamide | 363.9/1.64 (Method K) | 100 |
| 95 | 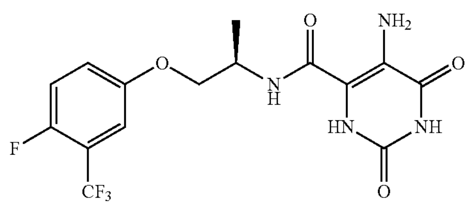 [SMILES: C[C@H](COc1ccc(F)c(C(F)(F)F)c1)NC(=O)c1[nH]c(=O)[nH]c(=O)c1N] | (R)-5-amino-N-(1-(4-fluoro-3-(trifluoromethyl)phenxoy)propan-2-yl)-2,6-dioxo-1,2,3,6-tetrahydropyrimidine-4-carboxamide | 391/1.97 (Method K) | 100 |
| 96 | 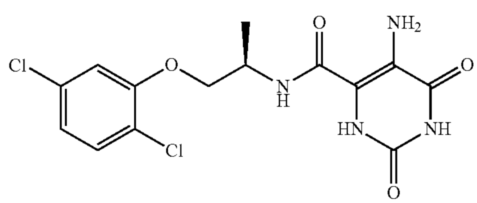 [SMILES: C[C@H](COc1cc(Cl)ccc1Cl)NC(=O)c1[nH]c(=O)[nH]c(=O)c1N] | (R)-5-amino-N-(1-(2,5-dichlorophenoxy)propan-2-yl)-2,6-dioxo-1,2,3,6-tetrahydropyrimidine-4-carboxamide | 379.9/1.93 (Method K) | 100 |
| 97 | 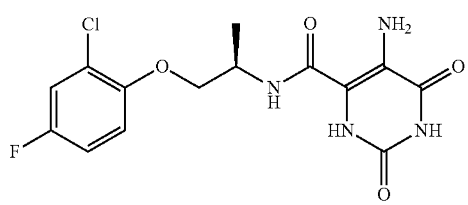 [SMILES: C[C@H](COc1ccc(F)cc1Cl)NC(=O)c1[nH]c(=O)[nH]c(=O)c1N] | (R)-5-amino-N-(1-(2-chloro-4-fluorophenoxy)propan-2-yl)-2,6-dioxo-1,2,3,6-tetrahydropyrimidine-4-carboxamide | 356.9/1.76 (Method K) | 100 |
| 98 | 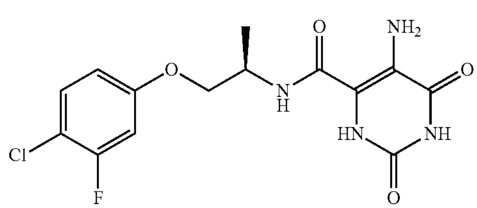 [SMILES: C[C@H](COc1ccc(Cl)c(F)c1)NC(=O)c1[nH]c(=O)[nH]c(=O)c1N] | (R)-5-amino-N-(1-(4-chloro-3-fluorophenoxy)propan-2-yl)-2,6-dioxo-1,2,3,6-tetrahydropyrimidine-4-carboxamide | 357/1.85 (Method K) | 93.6 |

TABLE 2-continued

| Ex. No. | Structure | Name | LC-MS [M + 1]/RT | Purity (%) |
|---|---|---|---|---|
| 99 | 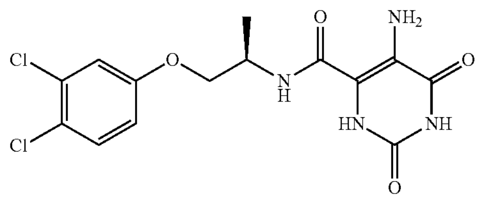 [SMILES: C[C@H](COc1ccc(Cl)c(Cl)c1)NC(=O)c1[nH]c(=O)[nH]c(=O)c1N] | (R)-5-amino-N-(1-(3,4-dichlorophenoxy)propan-2-yl)-2,6-dioxo-1,2,3,6-tetrahydropyrimidine-4-carboxamide | 373/2 (Method K) | 100 |
| 100 | 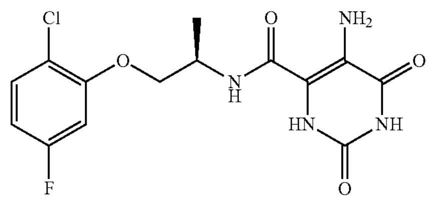 [SMILES: C[C@H](COc1cc(F)ccc1Cl)NC(=O)c1[nH]c(=O)[nH]c(=O)c1N] | (R)-5-amino-N-(1-(2-chloro-5-fluorophenoxy)propan-2-yl)-2,6-dioxo-1,2,3,6-tetrahydropyrimidine-4-carboxamide | 357.0/1.76 (Method K) | 100 |
| 101 | 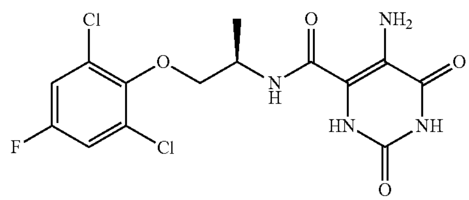 [SMILES: C[C@H](COc1c(Cl)cc(F)cc1Cl)NC(=O)c1[nH]c(=O)[nH]c(=O)c1N] | (R)-5-amino-N-(1-(2,6-dichloro-4-fluorophenoxy)propan-2-yl)-2,6-dioxo-1,2,3,6-tetrahydropyrimidine-4-carboxamide | 391/1.9 (Method K) | 100 |
| 102 | 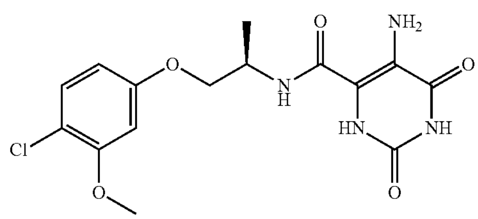 [SMILES: COc1cc(OC[C@@H](C)NC(=O)c2[nH]c(=O)[nH]c(=O)c2N)ccc1Cl] | (R)-5-amino-N-(1-(4-chloro-3-methoxyphenoxy)propan-2-yl)-2,6-dioxo-1,2,3,6-tetrahydropyrimidine-4-carboxamide | 369/1.76 (Method K) | 100 |
| 103 | 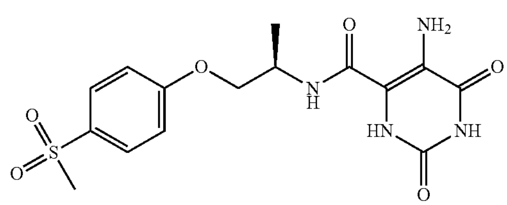 [SMILES: C[C@H](COc1ccc(S(C)(=O)=O)cc1)NC(=O)c1[nH]c(=O)[nH]c(=O)c1N] | (R)-5-amino-N-(1-(4-(methylsulfonyl)phenoxy)propan-2-yl)-2,6-dioxo-1,2,3,6-tetrahydropyrimidine-4-carboxamide | 383/1.2 (Method K) | 100 |
| 104 | 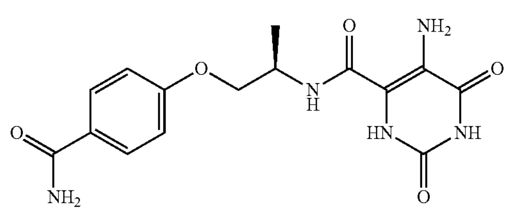 [SMILES: C[C@H](COc1ccc(C(N)=O)cc1)NC(=O)c1[nH]c(=O)[nH]c(=O)c1N] | (R)-5-amino-N-(1-(4-carbamoylphenoxy)propan-2-yl)-2,6-dioxo-1,2,3,6-tetrahydropyrimidine-4-carboxamide | 348.1/1.03 (Method K) | 100 |
| 105 | 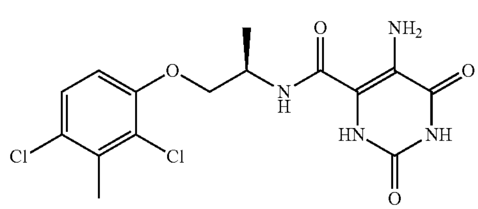 [SMILES: Cc1c(Cl)ccc(OC[C@@H](C)NC(=O)c2[nH]c(=O)[nH]c(=O)c2N)c1Cl] | (R)-5-amino-N-(1-(2,4-dichloro-3-methylphenoxy)propan-2-yl)-2,6-dioxo-1,2,3,6-tetrahydropyrimidine-4-carboxamide | 387.0/2.1 (Method K) | 93.0 |

TABLE 2-continued

| Ex. No. | Structure | Name | LC-MS [M + 1]/RT | Purity (%) |
|---|---|---|---|---|
| 106 | 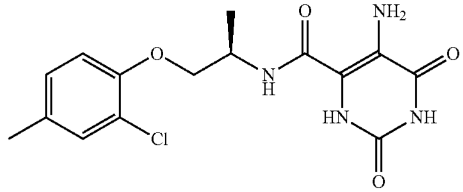 [SMILES: Cc1ccc(OC[C@@H](C)NC(=O)c2[nH]c(=O)[nH]c(=O)c2N)c(Cl)c1] | (R)-5-amino-N-(1-(2-chloro-4-methylphenoxy)propan-2-yl)-2,6-dioxo-1,2,3,6-tetrahydropyrimidine-4-carboxamide | 353.0/1.89 | 100 |
| 107 | 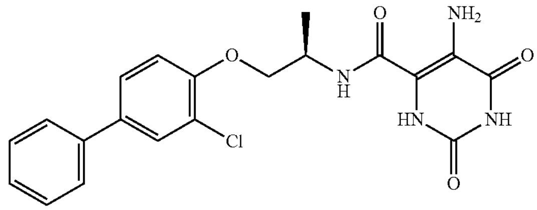 [SMILES: C[C@H](COc1ccc(-c2ccccc2)cc1Cl)NC(=O)c1[nH]c(=O)[nH]c(=O)c1N] | (R)-5-amino-N-(1-(3-chlorobiphenyl-4-yloxy)propan-2-yl)-2,6-dioxo-1,2,3,6-tetrahydropyrimidine-4-carboxamide | 415/2.31 (Method K) | 98.9 |
| 108 | 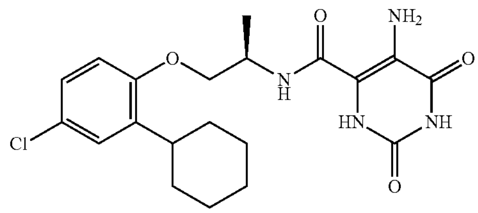 [SMILES: C[C@H](COc1ccc(Cl)cc1C1CCCCC1)NC(=O)c1[nH]c(=O)[nH]c(=O)c1N] | (R)-5-amino-N-(1-(4-chloro-2-cyclohexylphenoxy)propan-2-yl)-2,6-dioxo-1,2,3,6-tetrahydropyrimidine-4-carboxamide | 421.0/2.65 (Method K) | 97.6 |
| 109 | 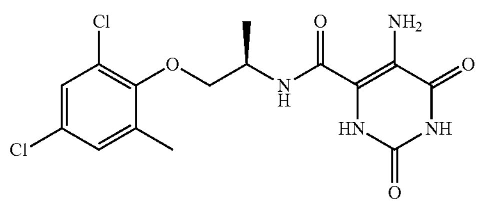 [SMILES: Cc1cc(Cl)cc(Cl)c1OC[C@@H](C)NC(=O)c1[nH]c(=O)[nH]c(=O)c1N] | (R)-5-amino-N-(1-(2,4-dichloro-6-methylphenoxy)propan-2-yl)-2,6-dioxo-1,2,3,6-tetrahydropyrimidine-4-carboxamide | 386.9/2.09 (Method K) | 96.2 |
| 110 | 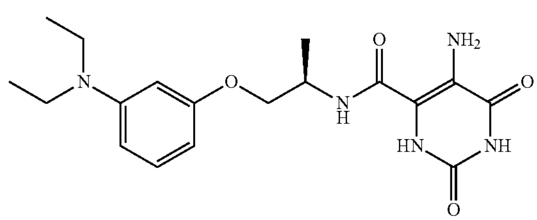 [SMILES: CCN(CC)c1cccc(OC[C@@H](C)NC(=O)c2[nH]c(=O)[nH]c(=O)c2N)c1] | (R)-5-amino-N-(1-(3-(diethylamino)phenoxy)propan-2-yl)-2,6-dioxo-1,2,3,6-tetrahydropyrimidine-4-carboxamide | 376.1/2.04 (Method K) | 100 |
| 111 | 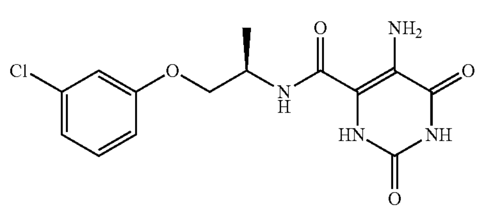 [SMILES: C[C@H](COc1cccc(Cl)c1)NC(=O)c1[nH]c(=O)[nH]c(=O)c1N] | (R)-5-amino-N-(1-(3-chlorophenoxy)propan-2-yl)-2,6-dioxo-1,2,3,6-tetrahydropyrimidine-4-carboxamide | 339/1.78 (Method K) | 100 |
| 112 | 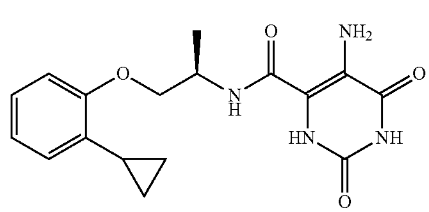 [SMILES: C[C@H](COc1ccccc1C1CC1)NC(=O)c1[nH]c(=O)[nH]c(=O)c1N] | (R)-5-amino-N-(1-(2-cyclopropylphenoxy)propan-2-yl)-2,6-dioxo-1,2,3,6-tetrahydropyrimidine-4-carboxamide | 345.1/1.96 (Method K) | 100 |

TABLE 2-continued

| Ex. No. | Structure | Name | LC-MS [M + 1]/RT | Purity (%) |
|---|---|---|---|---|
| 113 | 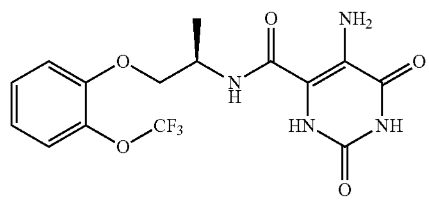 [SMILES: C[C@H](COc1ccccc1OC(F)(F)F)NC(=O)c1[nH]c(=O)[nH]c(=O)c1N] | (R)-5-amino-2,6-dioxo-N-(1-(2-(trifluoromethoxy)phenoxy)propan-2-yl)-1,2,3,6-tetrahydropyrimidine-4-carboxamide | 389.1/1.97 (Method K) | 100 |
| 114 | 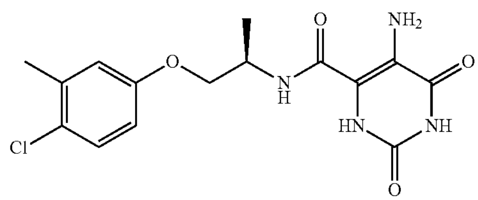 [SMILES: Cc1cc(OC[C@@H](C)NC(=O)c2[nH]c(=O)[nH]c(=O)c2N)ccc1Cl] | (R)-5-amino-N-(1-(4-chloro-3-methylphenoxy)propan-2-yl)-2,6-dioxo-1,2,3,6-tetrahydropyrimidine-4-carboxamide | 353.1/2.01 (Method K) | 100 |
| 115 | 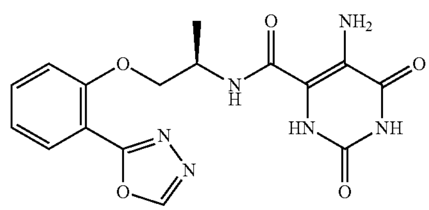 [SMILES: C[C@H](COc1ccccc1-c1nnco1)NC(=O)c1[nH]c(=O)[nH]c(=O)c1N] | (R)-N-(1-(2-(1,3,4-oxadiazol-2-yl)phenoxy)propan-2-yl)-5-amino-2,6-dioxo-1,2,3,6-tetrahydropyrimidine-4-carboxamide | 373.1/1.39 (Method K) | 100 |
| 116 | 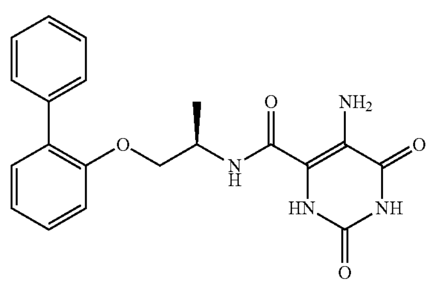 [SMILES: C[C@H](COc1ccccc1-c1ccccc1)NC(=O)c1[nH]c(=O)[nH]c(=O)c1N] | (R)-5-amino-N-(1-(biphenyl-2-yloxy)propan-2-yl)-2,6-dioxo-1,2,3,6-tetrahydropyrimidine-4-carboxamide | 381.1/2.09 (Method K) | 100 |
| 117 | 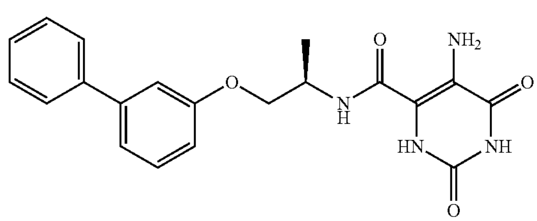 [SMILES: C[C@H](COc1cccc(-c2ccccc2)c1)NC(=O)c1[nH]c(=O)[nH]c(=O)c1N] | (R)-5-amino-N-(1-(biphenyl-3-yloxy)propan-2-yl)-2,6-dioxo-1,2,3,6-tetrahydropyrimidine-4-carboxamide | 381.1/2.2 (Method K) | 100 |
| 118 | 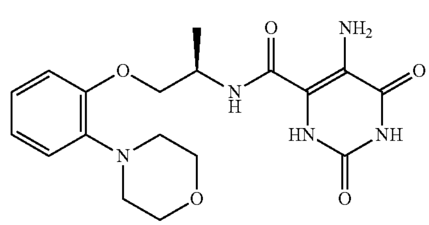 [SMILES: C[C@H](COc1ccccc1N1CCOCC1)NC(=O)c1[nH]c(=O)[nH]c(=O)c1N] | (R)-5-amino-N-(1-(2-morpholinophenoxy)propan-2-yl)-2,6-dioxo-1,2,3,6-tetrahydropyrimidine-4-carboxamide | 390.2/1.58 (Method K) | 95.3 |

TABLE 2-continued

| Ex. No. | Structure | Name | LC-MS [M + 1]/RT | Purity (%) |
|---|---|---|---|---|
| 119 | 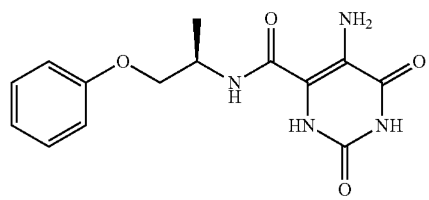 [SMILES: C[C@H](COc1ccccc1)NC(=O)c1[nH]c(=O)[nH]c(=O)c1N] | (R)-5-amino-2,6-dioxo-N-(1-phenoxypropan-2-yl)-1,2,3,6-tetrahydropyrimidine-4-carboxamide | 305.1/1.58 (Method K) | 100 |
| 120 | 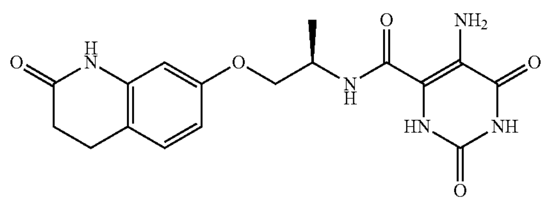 [SMILES: C[C@H](COc1ccc2c(c1)NC(=O)CC2)NC(=O)c1[nH]c(=O)[nH]c(=O)c1N] | (R)-5-amino-2,6-dioxo-N-(1-(2-oxo-1,2,3,4-tetrahydroquinolin-7-yloxy)propan-2-yl)-1,2,3,6-tetrahydropyrimidine-4-carboxamide | 374.1/1.34 (Method K) | 100 |
| 121 | 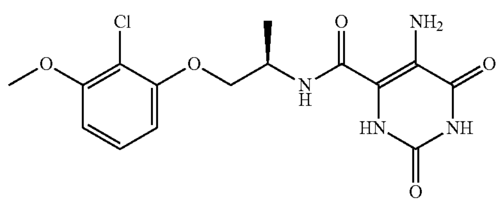 [SMILES: COc1cccc(OC[C@@H](C)NC(=O)c2[nH]c(=O)[nH]c(=O)c2N)c1Cl] | (R)-5-amino-N-(1-(2-chloro-3-methoxyphenoxy)propan-2-yl)-2,6-dioxo-1,2,3,6-tetrahydropyrimidine-4-carboxamide | 369.1/1.68 (Method K) | 100 |
| 122 | 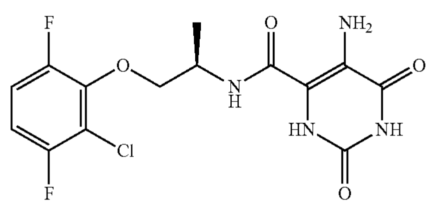 [SMILES: C[C@H](COc1c(F)ccc(F)c1Cl)NC(=O)c1[nH]c(=O)[nH]c(=O)c1N] | (R)-5-amino-N-(1-(2-chloro-3,6-difluorophenoxy)propan-2-yl)-2,6-dioxo-1,2,3,6-tetrahydropyrimidine-4-carboxamide | 375.1/1.81 (Method K) | 100 |
| 123 | 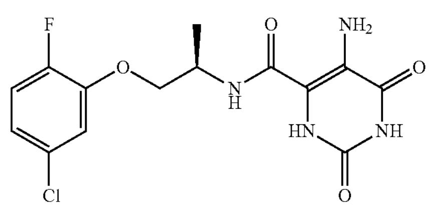 [SMILES: C[C@H](COc1cc(Cl)ccc1F)NC(=O)c1[nH]c(=O)[nH]c(=O)c1N] | (R)-5-amino-N-(1-(5-chloro-2-fluorophenoxy)propan-2-yl)-2,6-dioxo-1,2,3,6-tetrahydropyrimidine-4-carboxamide | 357.1/1.85 (Method K) | 100 |
| 124 | 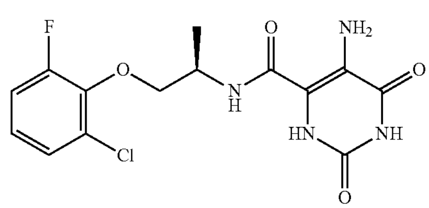 [SMILES: C[C@H](COc1c(F)cccc1Cl)NC(=O)c1[nH]c(=O)[nH]c(=O)c1N] | (R)-5-amino-N-(1-(2-chloro-6-fluorophenoxy)propan-2-yl)-2,6-dioxo-1,2,3,6-tetrahydropyrimidine-4-carboxamide | 357.1/1.76 (Method K) | 100 |
| 125 | 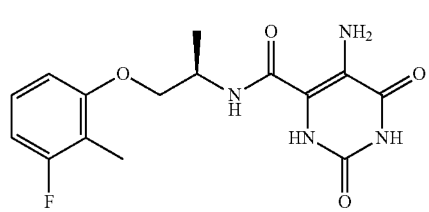 [SMILES: Cc1c(F)cccc1OC[C@@H](C)NC(=O)c1[nH]c(=O)[nH]c(=O)c1N] | (R)-5-amino-N-(1-(3-fluoro-2-methylphenoxy)propan-2-yl)-2,6-dioxo-1,2,3,6-tetrahydropyrimidine-4-carboxamide | 337.2/1.87 (Method K) | 100 |

TABLE 2-continued

| Ex. No. | Structure | Name | LC-MS [M + 1]/RT | Purity (%) |
|---|---|---|---|---|
| 126 | 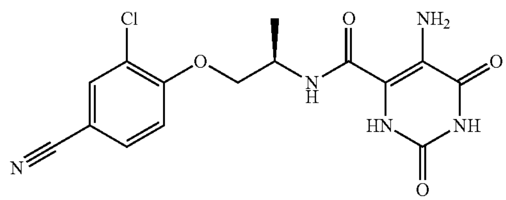 [SMILES: C[C@H](COc1ccc(C#N)cc1Cl)NC(=O)c1[nH]c(=O)[nH]c(=O)c1N] | (R)-5-amino-N-(1-(2-chloro-4-cyanophenoxy)propan-2-yl)-2,6-dioxo-1,2,3,6-tetrahydropyrimidine-4-carboxamide | 364.1/1.67 (Method K) | 100 |
| 127 | 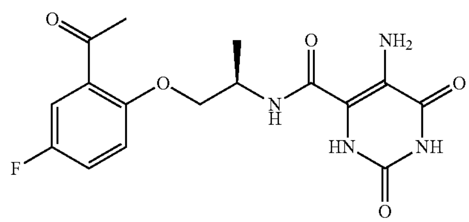 [SMILES: CC(=O)c1cc(F)ccc1OC[C@@H](C)NC(=O)c1[nH]c(=O)[nH]c(=O)c1N] | (R)-N-(1-(2-acetyl-4-fluorophenoxy)propan-2-yl)-5-amino-2,6-dioxo-1,2,3,6-tetrahydropyrimidine-4-carboxamide | 365.1/1.59 (Method K) | 100 |
| 128 | 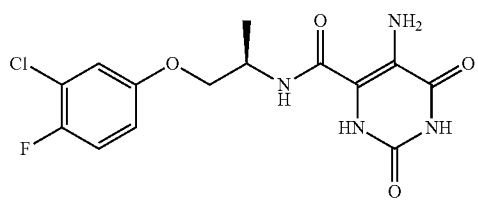 [SMILES: C[C@H](COc1ccc(F)c(Cl)c1)NC(=O)c1[nH]c(=O)[nH]c(=O)c1N] | (R)-5-amino-N-(1-(3-chloro-4-fluorophenoxy)propan-2-yl)-2,6-dioxo-1,2,3,6-tetrahydropyrimidine-4-carboxamide | 357.1/1.83 (Method K) | 100 |
| 129 | 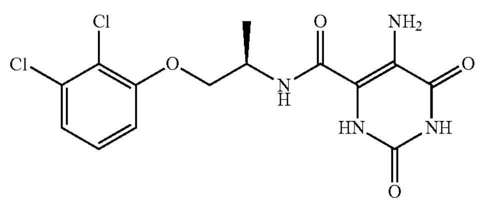 [SMILES: C[C@H](COc1cccc(Cl)c1Cl)NC(=O)c1[nH]c(=O)[nH]c(=O)c1N] | (R)-5-amino-N-(1-(2,3-dichlorophenoxy)propan-2-yl)-2,6-dioxo-1,2,3,6-tetrahydropyrimidine-4-carboxamide | 372.9/1.9 (Method K) | 100 |
| 130 | 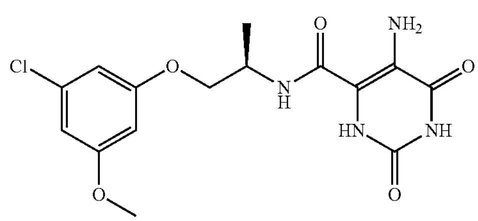 [SMILES: COc1cc(Cl)cc(OC[C@@H](C)NC(=O)c2[nH]c(=O)[nH]c(=O)c2N)c1] | (R)-5-amino-N-(1-(3-chloro-5-methoxyphenoxy)propan-2-yl)-2,6-dioxo-1,2,3,6-tetrahydropyrimidine-4-carboxamide | 369.1/1.89 (Method K) | 100 |
| 131 | 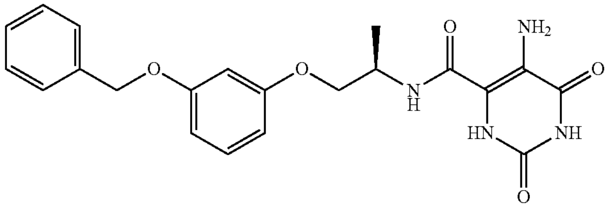 [SMILES: C[C@H](COc1cccc(OCc2ccccc2)c1)NC(=O)c1[nH]c(=O)[nH]c(=O)c1N] | (R)-5-amino-N-(1-(3-(benzyloxy)phenyl)ethyl)-2,6-dioxo-1,2,3,6-tetrahydropyrimidine-4-carboxamide | 381.0/1.92 (Method B) | RT = 9.81 min, 98.8% (Method A) RT = 9.68 min, 98.3% (Method B) |

TABLE 2-continued

| Ex. No. | Structure | Name | LC-MS [M + 1]/RT | Purity (%) |
|---|---|---|---|---|
| 132 | 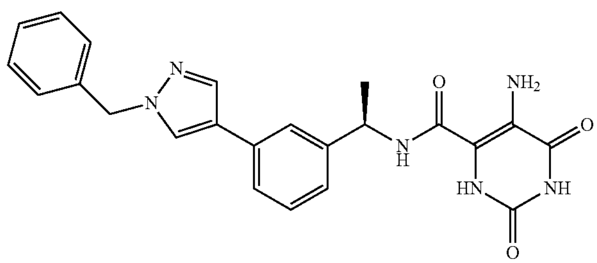 [SMILES: C[C@@H](NC(=O)c1[nH]c(=O)[nH]c(=O)c1N)c1cccc(-c2cnn(Cc3ccccc3)c2)c1] | (R)-5-amino-N-(1-(3-(1-benzyl-1H-pyrazol-4-yl)phenyl)ethyl)-2,6-dioxo-1,2,3,6-tetrahydro-pyrimidine-4-carboxamide | 431.1/1.85 (Method B) | RT = 8.87 min, 90.7% (Method A) RT = 8.96 min, 90.1% (Method B) |
| 133 | 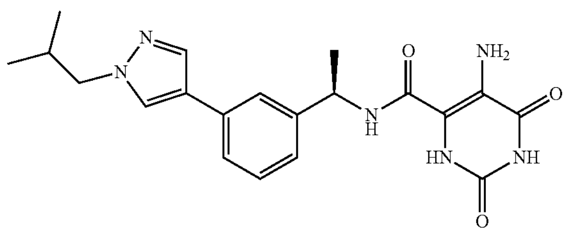 [SMILES: CC(C)Cn1cc(-c2cccc([C@@H](C)NC(=O)c3[nH]c(=O)[nH]c(=O)c3N)c2)cn1] | (R)-5-amino-N-(1-(3-(1-isobutyl-1H-pyrazol-4-yl)phenyl)ethyl)-2,6-dioxo-1,2,3,6-tetrahydro-pyrimidine-4-carboxamide | 397.1/1.86 (Method B) | RT = 7.43 min, 95.2% (Method A) RT = 7.42 min, 93.8% (Method B) |
| 134 | 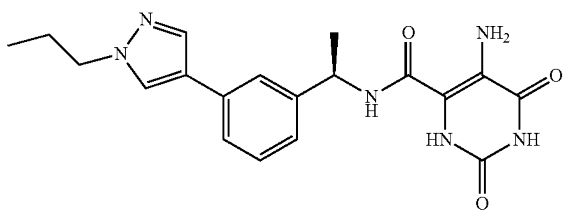 [SMILES: CCCn1cc(-c2cccc([C@@H](C)NC(=O)c3[nH]c(=O)[nH]c(=O)c3N)c2)cn1] | (R)-5-amino-2,6-dioxo-N-(1-(3-(1-propyl-1H-pyrazol-4-yl)phenyl)ethyl)-1,2,3,6-tetrahydro-pyrimidine-4-carboxamide | 383.1/1.85 (Method B) | RT = 6.76 min, 98.7% (Method A) RT = 6.91 min, 100% (Method B) |
| 135 | 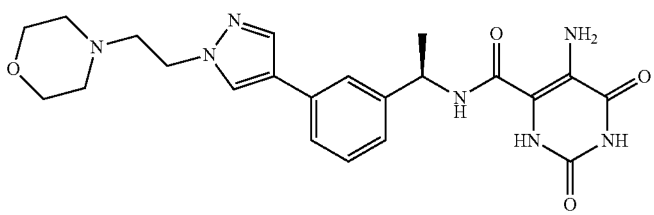 [SMILES: C[C@@H](NC(=O)c1[nH]c(=O)[nH]c(=O)c1N)c1cccc(-c2cnn(CCN3CCOCC3)c2)c1] | (R)-5-amino-N-(1-(3-(1-(2-morpholinoethyl)-1H-pyrazol-4-yl)phenyl)ethyl)-2,6-dioxo-1,2,3,6-tetrahydro-pyrimidine-4-carboxamide | 454.1/1.33 (Method B) | RT = 3.58 min, 99.3% (Method A) RT = 4.81 min, 100% (Method B) |
| 136 | 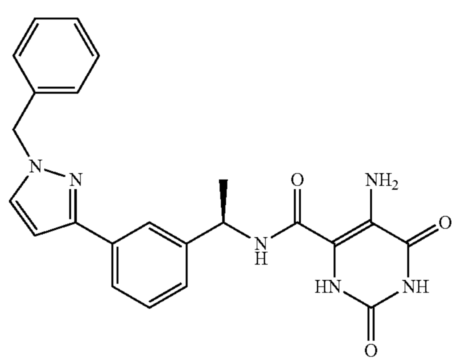 [SMILES: C[C@@H](NC(=O)c1[nH]c(=O)[nH]c(=O)c1N)c1cccc(-c2ccn(Cc3ccccc3)n2)c1] | (R)-5-amino-N-(1-(3-(1-benzyl-1H-pyrazol-3-yl)phenyl)ethyl)-2,6-dioxo-1,2,3,6-tetrahydro-pyrimidine-4-carboxamide | 431.1/3.48 (Method A) | RT = 8.49 min, 92.4% (Method A) RT = 8.52 min, 93.1% (Method B) |

TABLE 2-continued

| Ex. No. | Structure | Name | LC-MS [M + 1]/RT | Purity (%) |
|---|---|---|---|---|
| 137 | 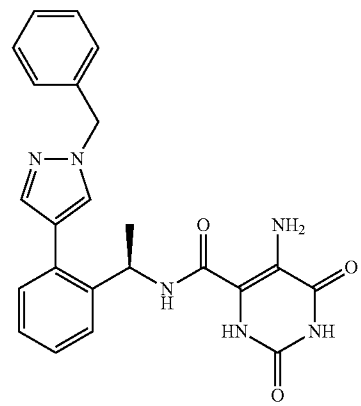 [SMILES: C[C@@H](NC(=O)c1[nH]c(=O)[nH]c(=O)c1N)c1ccccc1-c1cnn(Cc2ccccc2)c1] | (R)-5-amino-N-(1-(2-(1-benzyl-1H-pyrazol-4-yl)phenyl)ethyl)-2,6-dioxo-1,2,3,6-tetrahydro-pyrimidine-4-carboxamide | 431.2/1.89 (Method B) | RT = 8.80 min, 97.7% (Method A) RT = 8.96 min, 98.3% (Method B) |
| 138 | 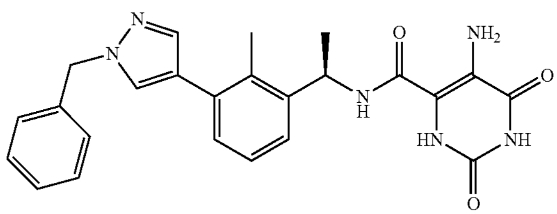 [SMILES: Cc1c(-c2cnn(Cc3ccccc3)c2)cccc1[C@@H](C)NC(=O)c1[nH]c(=O)[nH]c(=O)c1N] | (R)-5-amino-N-(1-(3-(1-benzyl-1H-pyrazol-4-yl)-2-methylphenyl)ethyl)-2,6-dioxo-1,2,3,6-tetrahydro-pyrimidine-4-carboxamide | 445.2/1.96 (Method B) | RT = 7.89 min, 95.8% (Method A) RT = 8.00 min, 93.7% (Method B) |
| 139 | 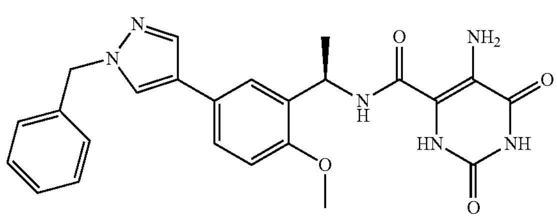 [SMILES: COc1ccc(-c2cnn(Cc3ccccc3)c2)cc1[C@@H](C)NC(=O)c1[nH]c(=O)[nH]c(=O)c1N] | (R)-5-amino-N-(1-(5-(1-benzyl-1H-pyrazol-4-yl)-2-methoxyphenyl)ethyl)-2,6-dioxo-1,2,3,6-tetrahydro-pyrimidine-4-carboxamide | 461.2/1.90 (Method B) | RT = 7.33 min, 91.1% (Method A) |
| 140 | 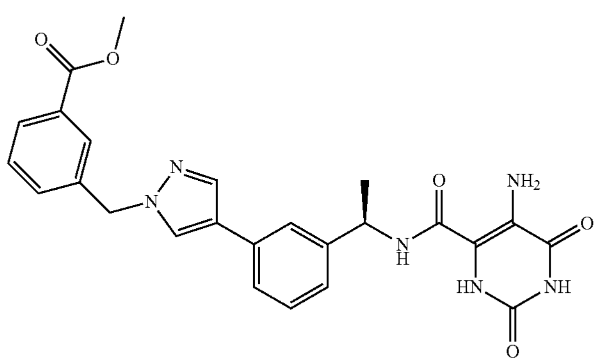 [SMILES: COC(=O)c1cccc(Cn2cc(-c3cccc([C@@H](C)NC(=O)c4[nH]c(=O)[nH]c(=O)c4N)c3)cn2)c1] | (R)-methyl 3-((4-(3-(1-(5-amino-2,6-dioxo-1,2,3,6-tetrahydro-pyrimidine-4-carboxamido)ethyl)phenyl)-1H-pyrazol-1-yl)methyl)benzoate | 489.2/1.86 (Method B) | RT = 8.59 min, 95.7% (Method A) RT = 8.67 min, 94.7% (Method B) |
| 141 | 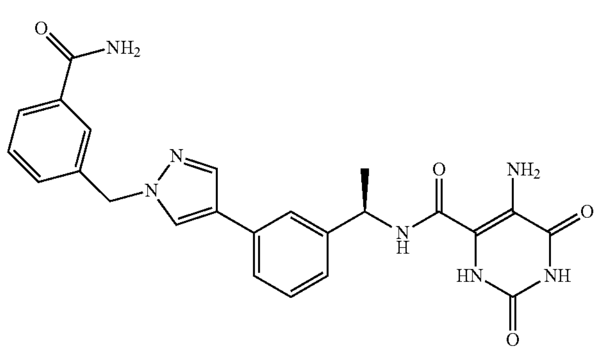 [SMILES: C[C@@H](NC(=O)c1[nH]c(=O)[nH]c(=O)c1N)c1cccc(-c2cnn(Cc3cccc(C(N)=O)c3)c2)c1] | (R)-5-amino-N-(1-(3-(1-(3-carbamoylbenzyl)-1H-pyrazol-4-yl)phenyl)ethyl)-2,6-dioxo-1,2,3,6-tetrahydro-pyrimidine-4-carboxamide | 474.0/0.65 (Method B) | RT = 6.33 min, 99.2% (Method A) RT = 6.67 min, 99.2% (Method B) |

TABLE 2-continued

| Ex. No. | Structure | Name | LC-MS [M + 1]/RT | Purity (%) |
|---|---|---|---|---|
| 142 | 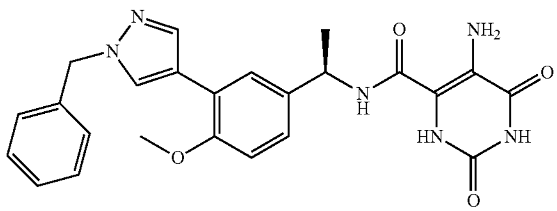 [SMILES: COc1ccc([C@@H](C)NC(=O)c2[nH]c(=O)[nH]c(=O)c2N)cc1-c1cnn(Cc2ccccc2)c1] | (R)-5-amino-N-(1-(3-(1-benzyl-1H-pyrazol-4-yl)-4-methoxyphenyl)ethyl)-2,6-dioxo-1,2,3,6-tetrahydro-pyrimidine-4-carboxamide | 421.1/2.13 (Method B) | RT = 9.87 min, 99.2% (Method A) RT = 9.52 min, 100% (Method B) |
| 143 | 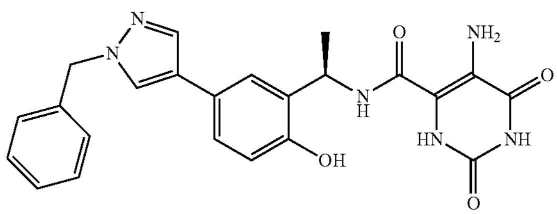 [SMILES: C[C@@H](NC(=O)c1[nH]c(=O)[nH]c(=O)c1N)c1cc(-c2cnn(Cc3ccccc3)c2)ccc1O] | (R)-5-amino-N-(1-(5-(1-benzyl-1H-pyrazol-4-yl)-2-hydroxyphenyl)ethyl)-2,6-dioxo-1,2,3,6-tetrahydro-pyrimidine-4-carboxamide | 447.2/1.74 (Method B) | RT = 7.99 min, 99.2% (Method A) RT = 8.30 min, 100% (Method B) |
| 144 | 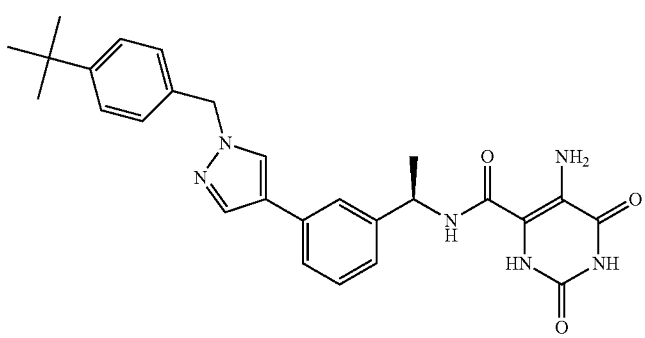 [SMILES: C[C@@H](NC(=O)c1[nH]c(=O)[nH]c(=O)c1N)c1cccc(-c2cnn(Cc3ccc(C(C)(C)C)cc3)c2)c1] | (R)-5-amino-N-(1-(3-(1-(4-tert-butylbenzyl)-1H-pyrazol-4-yl)phenyl)ethyl)-2,6-dioxo-1,2,3,6-tetrahydropyrimidine-4-carboxamide | 487.3/1.99 (Method K) | 98.6 |
| 145 | 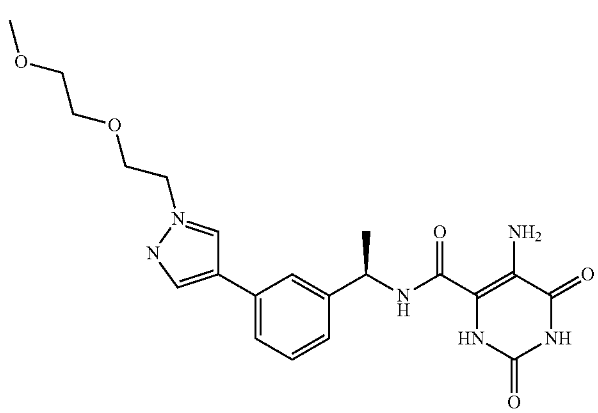 | (R)-5-amino-N-(1-(3-(1-(2-(2-methoxyethoxy)ethyl)-1H-pyrazol-4-yl)phenyl)ethyl)-2,6-dioxo-1,2,3,6-tetrahydro-pyrimidine-4-carboxamide | 443.3/1.18 (Method K) | 97.8 |

TABLE 2-continued

| Ex. No. | Structure | Name | LC-MS [M + 1]/RT | Purity (%) |
|---|---|---|---|---|
| 146 | 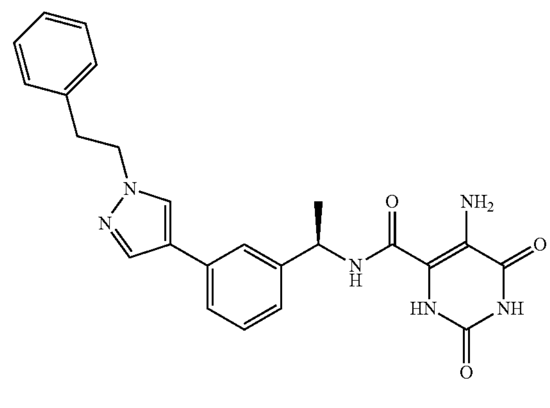 [SMILES: C[C@@H](NC(=O)c1[nH]c(=O)[nH]c(=O)c1N)c1cccc(-c2cnn(CCc3ccccc3)c2)c1] | (R)-5-amino-2,6-dioxo-N-(1-(3-(1-phenethyl-1H-pyrazol-4-yl)phenyl)ethyl)-1,2,3,6-tetrahydro-pyrimidine-4-carboxamide | 445.3/1.61 (Method K) | 100 |
| 147 | 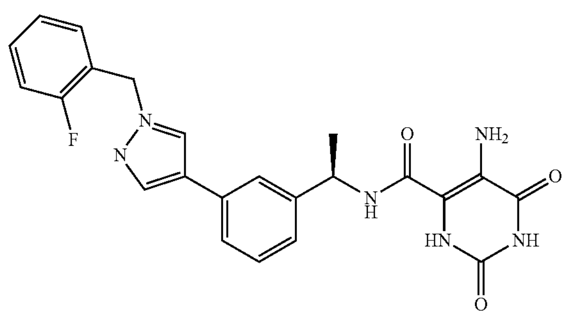 | (R)-5-amino-N-(1-(3-(1-(2-fluorobenzyl)-1H-pyrazol-4-yl)phenyl)ethyl)-2,6-dioxo-1,2,3,6-tetrahydro-pyrimidine-4-carboxamide | 449.3/1.56 (Method K) | 100 |
| 148 | 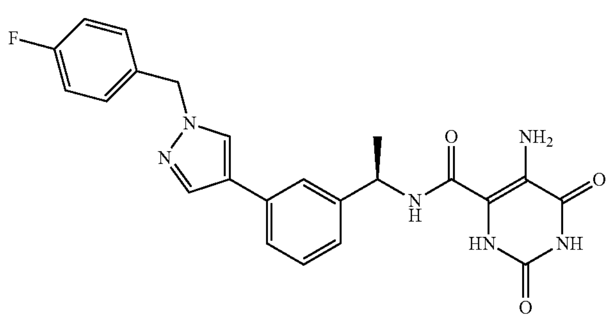 [SMILES: C[C@@H](NC(=O)c1[nH]c(=O)[nH]c(=O)c1N)c1cccc(-c2cnn(Cc3ccc(F)cc3)c2)c1] | (R)-5-amino-N-(1-(3-(1-(4-fluorobenzyl)-1H-pyrazol-4-yl)phenyl)ethyl)-2,6-dioxo-1,2,3,6-tetrahydro-pyrimidine-4-carboxamide | 449.3/1.46 (Method K) | 97.7 |
| 149 | 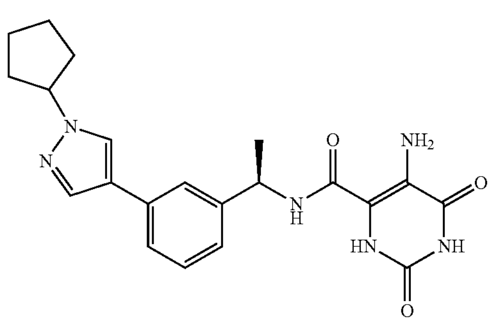 [SMILES: C[C@@H](NC(=O)c1[nH]c(=O)[nH]c(=O)c1N)c1cccc(-c2cnn(C3CCCC3)c2)c1] | (R)-5-amino-N-(1-(3-(1-cyclopentyl-1H-pyrazol-4-yl)phenyl)ethyl)-2,6-dioxo-1,2,3,6-tetra-hydropyrimidine-4-carboxamide | 449.3/1.46 (Method K) | 96.1 |

TABLE 2-continued

| Ex. No. | Structure | Name | LC-MS [M + 1]/RT | Purity (%) |
|---|---|---|---|---|
| 150 | 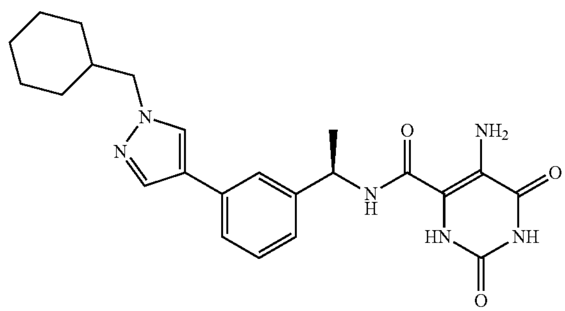 [SMILES: C[C@@H](NC(=O)c1[nH]c(=O)[nH]c(=O)c1N)c1cccc(-c2cnn(CC3CCCCC3)c2)c1] | (R)-5-amino-N-(1-(3-(1-(cyclohexylmethyl)-1H-pyrazol-4-yl)phenyl)ethyl)-2,6-dioxo-1,2,3,6-tetrahydro-pyrimidine-4-carboxamide | 437.3/1.78 (Method K) | 100 |
| 151 | 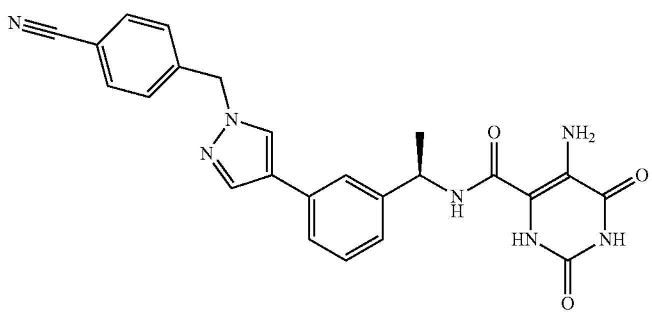 [SMILES: C[C@@H](NC(=O)c1[nH]c(=O)[nH]c(=O)c1N)c1cccc(-c2cnn(Cc3ccc(C#N)cc3)c2)c1] | (R)-5-amino-N-(1-(3-(1-(4-cyanobenzyl)-1H-pyrazol-4-yl)phenyl)ethyl)-2,6-dioxo-1,2,3,6-tetrahydropyrimidine-4-carboxamide | 456.3/1.42 (Method K) | 95.3 |
| 152 | 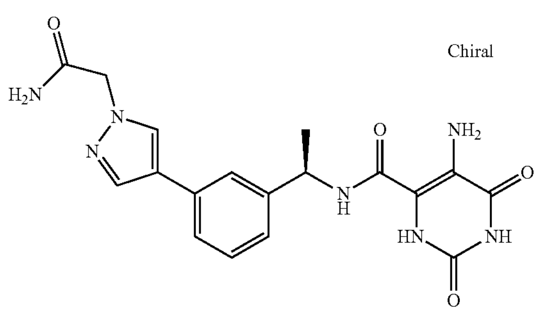 [SMILES: C[C@@H](NC(=O)c1[nH]c(=O)[nH]c(=O)c1N)c1cccc(-c2cnn(CC(N)=O)c2)c1] | (R)-5-amino-N-(1-(3-(1-(2-amino-2-oxoethyl)-1H-pyrazol-4-yl)phenyl)ethyl)-2,6-dioxo-1,2,3,6-tetrahydro-pyrimidine-4-carboxamide | 398.3/1.1 (Method K) | 96.6 |
| 153 | 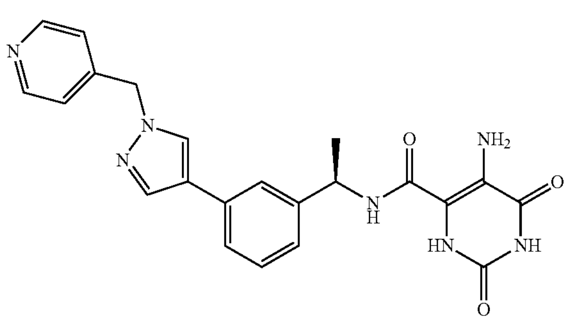 [SMILES: C[C@@H](NC(=O)c1[nH]c(=O)[nH]c(=O)c1N)c1cccc(-c2cnn(Cc3ccncc3)c2)c1] | (R)-5-amino-2,6-dioxo-N-(1-(3-(1-(pyridin-4-ylmethyl)-1H-pyrazol-4-yl)phenyl)ethyl)-1,2,3,6-tetrahydro-pyrimidine-4-carboxamide | 432.3/1.13 (Method K) | 96 |

TABLE 2-continued

| Ex. No. | Structure | Name | LC-MS [M + 1]/RT | Purity (%) |
|---|---|---|---|---|
| 154 | 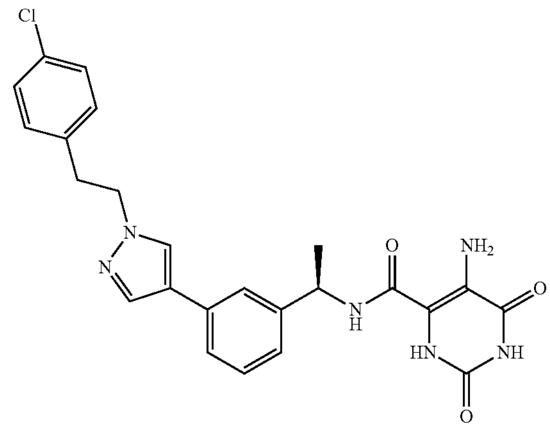 [SMILES: C[C@@H](NC(=O)c1[nH]c(=O)[nH]c(=O)c1N)c1cccc(-c2cnn(CCc3ccc(Cl)cc3)c2)c1] | (R)-5-amino-N-(1-(3-(1-(4-chlorophenethyl)-1H-pyrazol-4-yl)phenyl)ethyl)-2,6-dioxo-1,2,3,6-tetrahydropyrimidine-4-carboxamide | 479.3/1.75 (Method K) | 98 |
| 155 | 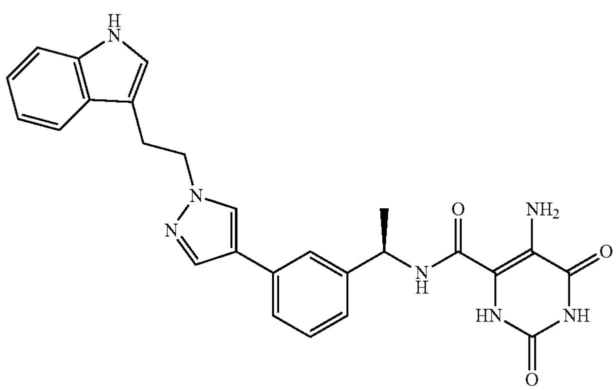 [SMILES: C[C@@H](NC(=O)c1[nH]c(=O)[nH]c(=O)c1N)c1cccc(-c2cnn(CCc3c[nH]c4ccccc34)c2)c1] | (R)-N-(1-(3-(1-(2-(1H-indol-3-yl)ethyl)-1H-pyrazol-4-yl)phenyl)ethyl)-5-amino-2,6-dioxo-1,2,3,6-tetrahydropyrimidine-4-carboxamide | 484.4/1.56 (Method K) | 96.4 |
| 156 | 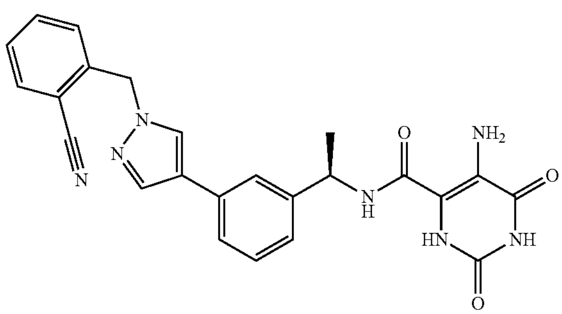 [SMILES: C[C@@H](NC(=O)c1[nH]c(=O)[nH]c(=O)c1N)c1cccc(-c2cnn(Cc3ccccc3C#N)c2)c1] | (R)-5-amino-N-(1-(3-(1-(2-cyanobenzyl)-1H-pyrazol-4-yl)phenyl)ethyl)-2,6-dioxo-1,2,3,6-tetrahydropyrimidine-4-carboxamide | 456.3/1.48 (Method K) | 100 |
| 157 | 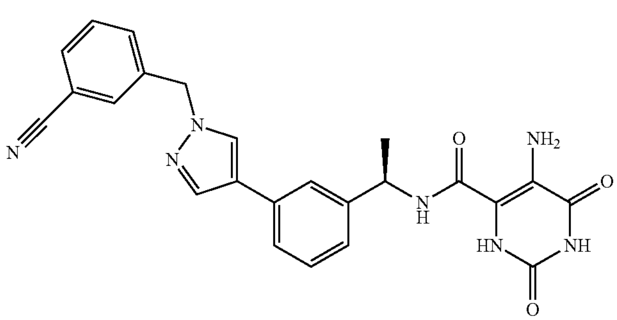 [SMILES: C[C@@H](NC(=O)c1[nH]c(=O)[nH]c(=O)c1N)c1cccc(-c2cnn(Cc3cccc(C#N)c3)c2)c1] | (R)-5-amino-N-(1-(3-(1-(3-cyanobenzyl)-1H-pyrazol-4-yl)phenyl)ethyl)-2,6-dioxo-1,2,3,6-tetrahydropyrimidine-4-carboxamide | 456.3/1.47 (Method K) | 98.5 |

TABLE 2-continued

| Ex. No. | Structure | Name | LC-MS [M + 1]/RT | Purity (%) |
|---|---|---|---|---|
| 158 | 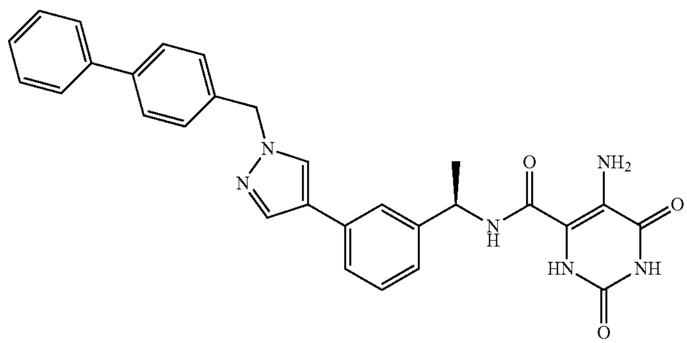 [SMILES: C[C@@H](NC(=O)c1[nH]c(=O)[nH]c(=O)c1N)c1cccc(-c2cnn(Cc3ccc(-c4ccccc4)cc3)c2)c1] | (R)-5-amino-N-(1-(3-(1-(biphenyl-4-ylmethyl)-1H-pyrazol-4-yl)phenyl)ethyl)-2,6-dioxo-1,2,3,6-tetrahydro-pyrimidine-4-carboxamide | 507.3/1.95 (Method K) | 100 |
| 159 | 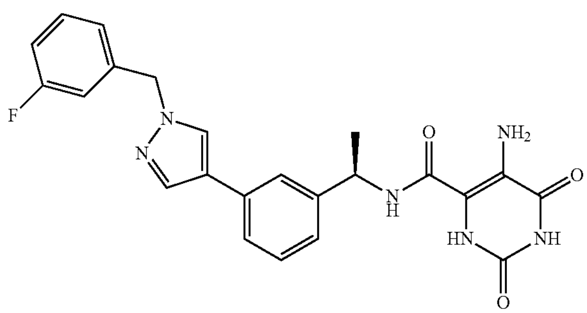 [SMILES: C[C@@H](NC(=O)c1[nH]c(=O)[nH]c(=O)c1N)c1cccc(-c2cnn(Cc3cccc(F)c3)c2)c1] | (R)-5-amino-N-(1-(3-(1-(3-fluorobenzyl)-1H-pyrazol-4-yl)phenyl)ethyl)-2,6-dioxo-1,2,3,6-tetra-hydropyrimidine-4-carboxamide | 449.3/1.59 (Method K) | 97.4 |
| 160 | 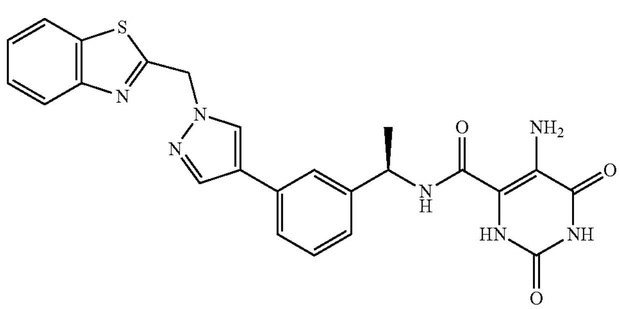 [SMILES: C[C@@H](NC(=O)c1[nH]c(=O)[nH]c(=O)c1N)c1cccc(-c2cnn(Cc3nc4ccccc4s3)c2)c1] | (R)-5-amino-N-(1-(3-(1-(benzo[d]thiazol-2-ylmethyl)-1H-pyrazol-4-yl)phenyl)ethyl)-2,6-dioxo-1,2,3,6-tetra-hydropyrimidine-4-carboxamide | 488.2/1.58 (Method K) | 100 |
| 161 | 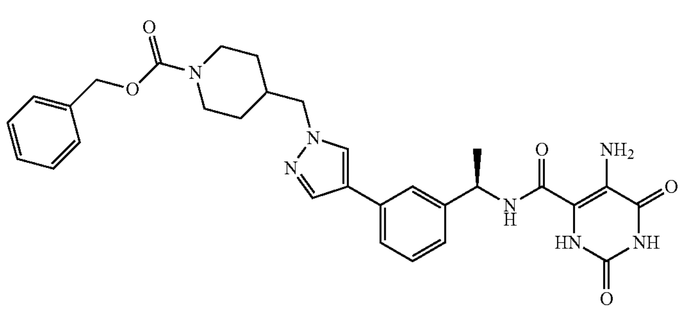 [SMILES: C[C@@H](NC(=O)c1[nH]c(=O)[nH]c(=O)c1N)c1cccc(-c2cnn(CC3CCN(C(=O)OCc4ccccc4)CC3)c2)c1] | (R)-benzyl 4-((4-(3-(1-(5-amino-2,6-dioxo-1,2,3,6-tetra-hydropyrimidine-4-carboxamido)ethyl)phenyl)-1H-pyrazol-1-yl)methyl)piperidine-1-carboxylate | 572.4/1.78 (Method K) | 96.1 |

TABLE 2-continued

| Ex. No. | Structure | Name | LC-MS [M + 1]/RT | Purity (%) |
|---|---|---|---|---|
| 162 | 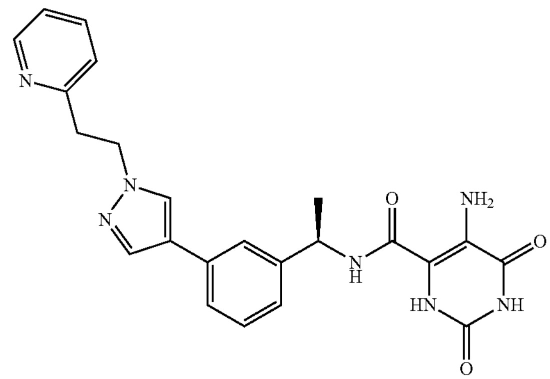 [SMILES: C[C@@H](NC(=O)c1[nH]c(=O)[nH]c(=O)c1N)c1cccc(-c2cnn(CCc3ccccn3)c2)c1] | (R)-5-amino-2,6-dioxo-N-(1-(3-(1-(2-(pyridin-2-yl)ethyl)-1H-pyrazol-4-yl)phenyl)ethyl)-1,2,3,6-tetrahydropyrimidine-4-carboxamide | 446.3/0.93 (Method K) | 98.7 |
| 163 | 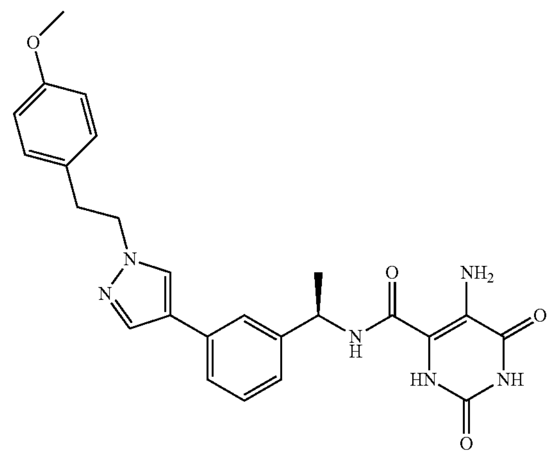 [SMILES: COc1ccc(CCn2cc(-c3cccc([C@@H](C)NC(=O)c4[nH]c(=O)[nH]c(=O)c4N)c3)cn2)cc1] | (R)-5-amino-N-(1-(3-(1-(4-methoxyphenethyl)-1H-pyrazol-4-yl)phenyl)ethyl)-2,6-dioxo-1,2,3,6-tetrahydropyrimidine-4-carboxamide | 475.3/1.62 (Method K) | 98.5 |
| 164 | 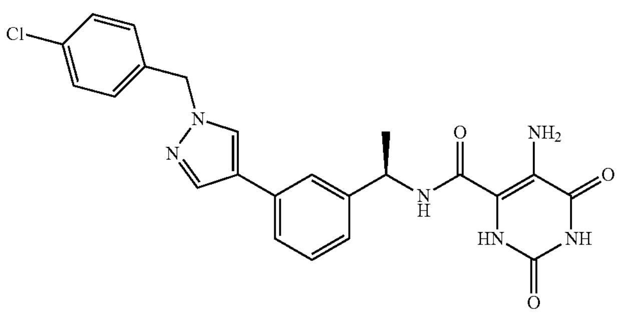 [SMILES: C[C@@H](NC(=O)c1[nH]c(=O)[nH]c(=O)c1N)c1cccc(-c2cnn(Cc3ccc(Cl)cc3)c2)c1] | (R)-5-amino-N-(1-(3-(1-(4-chlorobenzyl)-1H-pyrazol-4-yl)phenyl)ethyl)-2,6-dioxo-1,2,3,6-tetrahydropyrimidine-4-carboxamide | 464.9/1.77 (Method K) | 100 |
| 165 | 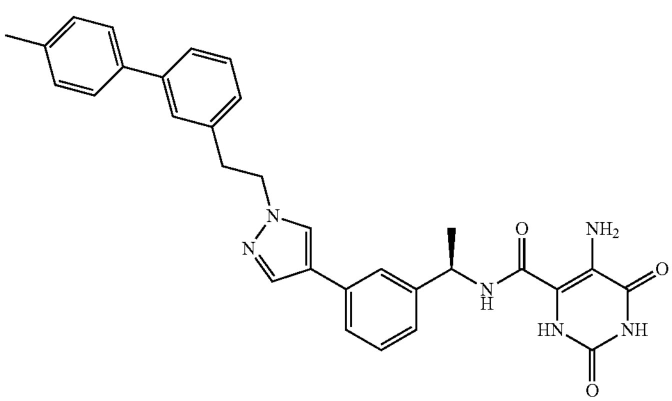 [SMILES: Cc1ccc(-c2cccc(CCn3cc(-c4cccc([C@@H](C)NC(=O)c5[nH]c(=O)[nH]c(=O)c5N)c4)cn3)c2)cc1] | (R)-5-amino-N-(1-(3-(1-(2-(4'-methylbiphenyl-3-yl)ethyl)-1H-pyrazol-4-yl)phenyl)ethyl)-2,6-dioxo-1,2,3,6-tetrahydropyrimidine-4-carboxamide | 535.0/2.11 (Method K) | 100 |

TABLE 2-continued

| Ex. No. | Structure | Name | LC-MS [M + 1]/RT | Purity (%) |
|---|---|---|---|---|
| 166 | 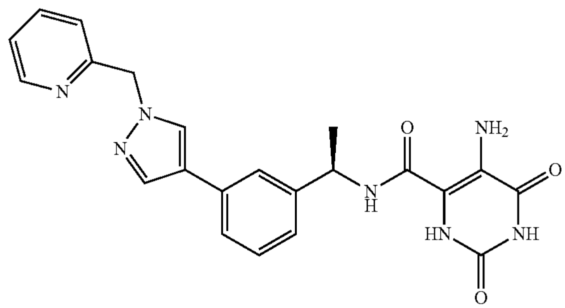 [SMILES: C[C@@H](NC(=O)c1[nH]c(=O)[nH]c(=O)c1N)c1cccc(-c2cnn(Cc3ccccn3)c2)c1] | (R)-5-amino-2,6-dioxo-N-(1-(3-(1-(pyridin-2-ylmethyl)-1H-pyrazol-4-yl)phenyl)ethyl)-1,2,3,6-tetrahydro-pyrimidine-4-carboxamide | 431.9/1.26 (Method K) | 100 |
| 167 | 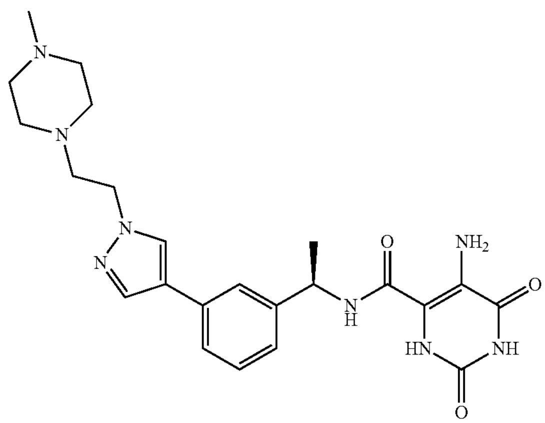 [SMILES: C[C@@H](NC(=O)c1[nH]c(=O)[nH]c(=O)c1N)c1cccc(-c2cnn(CCN3CCN(C)CC3)c2)c1] | (R)-5-amino-N-(1-(3-(1-(2-(4-methylpiperazin-1-yl)ethyl)-1H-pyrazol-4-yl)phenyl)ethyl)-2,6-dioxo-1,2,3,6-tetrahydro-pyrimidine-4-carboxamide | 467.0/1 (Method K) | 100 |
| 168 | 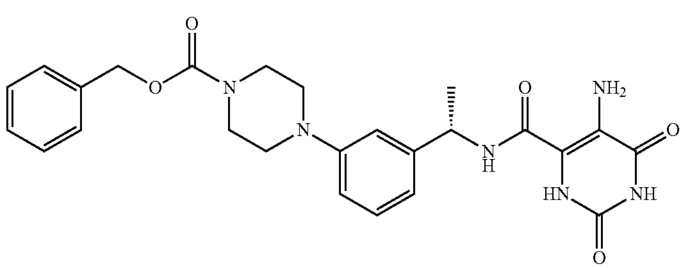 [SMILES: C[C@H](NC(=O)c1[nH]c(=O)[nH]c(=O)c1N)c1cccc(N2CCN(C(=O)OCc3ccccc3)CC2)c1] | (S)-benzyl 4-(3-(1-(5-amino-2,6-dioxo-1,2,3,6-tetrahydro-pyrimidine-4-carboxamido)ethyl)phenyl)piperazine-1-carboxylate | 493/1.86 min (Method B) | RT = 6.99 min, 89% (Method A) RT = 6.99 min, 94.5% (Method B) |
| 176 | 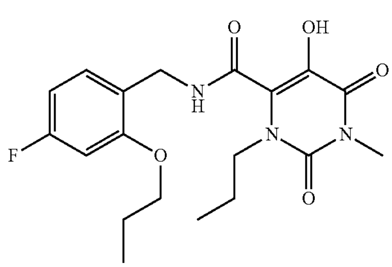 [SMILES: CCCOc1cc(F)ccc1CNC(=O)c1c(O)c(=O)n(C)c(=O)n1CCC] | N-(4-fluoro-2-propoxybenzyl)-5-hydroxy-1-methyl-2,6-dioxo-3-propyl-1,2,3,6-tetra-hydropyrimidine-4-carboxamide | 394 (M + H)/1.93 (Method B) | NA |
| 177 | 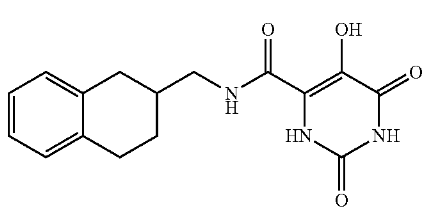 [SMILES: O=C(NCC1CCc2ccccc2C1)c1[nH]c(=O)[nH]c(=O)c1O] | 5-hydroxy-2,6-dioxo-N-((1,2,3,4-tetrahydro-naphthalen-2-yl)methyl)-1,2,3,6-tetrahydro-pyrimidine-4-carboxamide | 316.1/1.93 min (Method B) | RT = 6.74 min, 100% (Method A) RT = 6.41 min, 100% (Method B) |

| Ex. No. | Structure | Name | LC-MS [M + 1]/RT | Purity (%) |
|---|---|---|---|---|
| 178 | 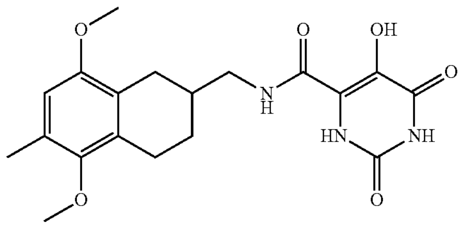 [SMILES: COc1cc(C)c(OC)c2c1CC(CNC(=O)c1[nH]c(=O)[nH]c(=O)c1O)CC2] | N-((5,8-dimethoxy-6-methyl-1,2,3,4-tetrahydronaphthalen-2-yl)methyl)-5-hydroxy-2,6-dioxo-1,2,3,6-tetrahydropyrimidine-4-carboxamide | 390.1/1.87 min (Method B) | RT = 6.99 min, 88.7% (Method A) RT = 6.57 min, 100% (Method B) |
| 179 | 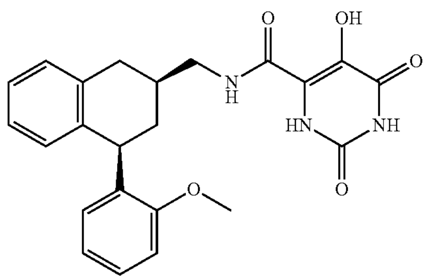 [SMILES: COc1ccccc1[C@@H]1C[C@H](CNC(=O)c2[nH]c(=O)[nH]c(=O)c2O)Cc2ccccc21] | 5-hydroxy-N-(((2S,4R)-4-(2-methoxyphenyl)-1,2,3,4-tetrahydro-naphthalen-2-yl)methyl)-2,6-dioxo-1,2,3,6-tetrahydropyrimidine-4-carboxamide | 422.1/2.11 min (Method B) | RT = 9.84 min, 98.6% (Method A) RT = 9.69 min, 100% (Method B) |
| 180 | 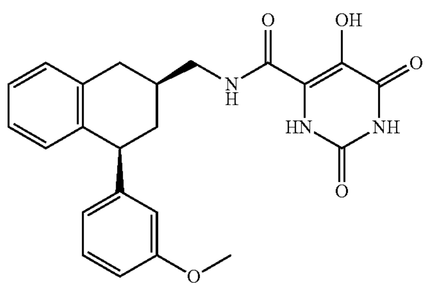 [SMILES: COc1cccc([C@@H]2C[C@H](CNC(=O)c3[nH]c(=O)[nH]c(=O)c3O)Cc3ccccc32)c1] | 5-hydroxy-N-(((2S,4S)-4-(3-methoxyphenyl)-1,2,3,4-tetrahydronaphthalen-2-yl)methyl)-2,6-dioxo-1,2,3,6-tetrahydropyrimidine-4-carboxamide | 422.1/2.08 min (Method B) | RT = 9.62 min, 100% (Method A) RT = 9.51 min, 100% (Method B) |
| 181 | 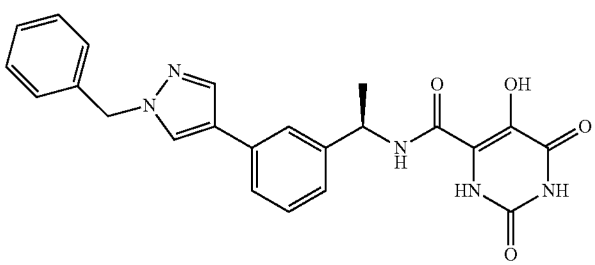 [SMILES: C[C@@H](NC(=O)c1[nH]c(=O)[nH]c(=O)c1O)c1cccc(-c2cnn(Cc3ccccc3)c2)c1] | (R)-N-(1-(3-(1-benzyl-1H-pyrazol-4-yl)phenyl)ethyl)-5-hydroxy-2,6-dioxo-1,2,3,6-tetrahydropyrimidine-4-carboxamide | 432.1/1.91 min (Method B) | RT = 8.50 min, 92.7% (Method A) RT = 8.63 min, 96.3% (Method B) |
| 182 | 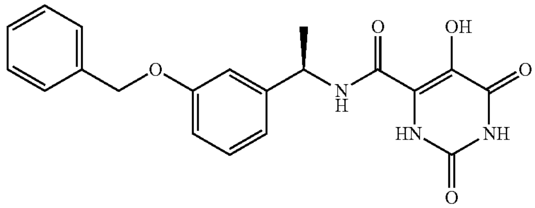 [SMILES: C[C@@H](NC(=O)c1[nH]c(=O)[nH]c(=O)c1O)c1cccc(OCc2ccccc2)c1] | (R)-N-(1-(3-(benzyloxy)phenyl)ethyl)-5-hydroxy-2,6-dioxo-1,2,3,6-tetrahydropyrimidine-4-carboxamide | 382.0/2.06 min (Method B) | RT = 9.24 min, 85.8% (Method A) RT = 9.14 min, 100% (Method B) |
| 183 | 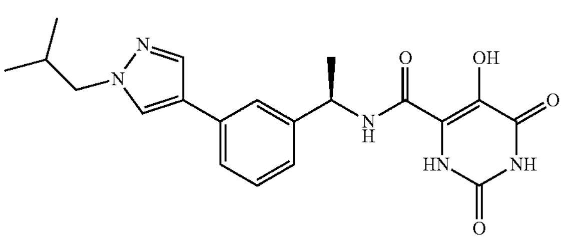 [SMILES: CC(C)Cn1cc(-c2cccc([C@@H](C)NC(=O)c3[nH]c(=O)[nH]c(=O)c3O)c2)cn1] | (R)-5-hydroxy-N-(1-(3-(1-isobutyl-1H-pyrazol-4-yl)phenyl)ethyl)-2,6-dioxo-1,2,3,6-tetrahydropyrimidine-4-carboxamide | 398.1/1.90 min (Method B) | RT = 8.17 min, 94.0% (Method A) RT = 8.23 min, 93.3% (Method B) |

TABLE 2-continued

| Ex. No. | Structure | Name | LC-MS [M + 1]/RT | Purity (%) |
|---|---|---|---|---|
| 184 | 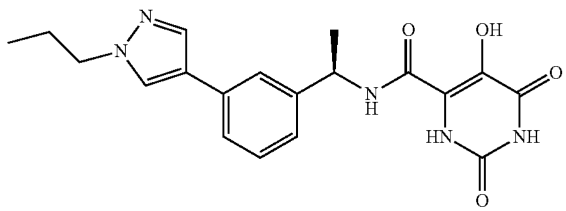 [SMILES: CCCn1cc(-c2cccc([C@@H](C)NC(=O)c3[nH]c(=O)[nH]c(=O)c3O)c2)cn1] | (R)-5-hydroxy-2,6-dioxo-N-(1-(3-(1-propyl-1H-pyrazol-4-yl)phenyl)ethyl)-1,2,3,6-tetrahydropyrimidine-4-carboxamide | 384.1/1.79 min (Method B) | RT = 7.51 min, 96.8% (Method A) RT = 7.70 min, 100% (Method B) |
| 185 | 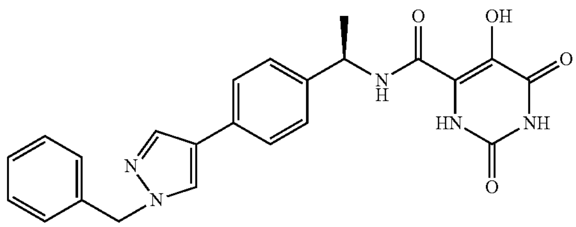 [SMILES: C[C@@H](NC(=O)c1[nH]c(=O)[nH]c(=O)c1O)c1ccc(-c2cnn(Cc3ccccc3)c2)cc1] | (R)-N-(1-(4-(1-benzyl-1H-pyrazol-4-yl)phenyl)ethyl)-5-hydroxy-2,6-dioxo-1,2,3,6-tetrahydropyrimidine-4-carboxamide | 432.2/1.88 min (Method B) | RT = 7.81 min, 88.0% (Method A) RT = 7.70 min, 85.2% (Method B) |
| 186 | 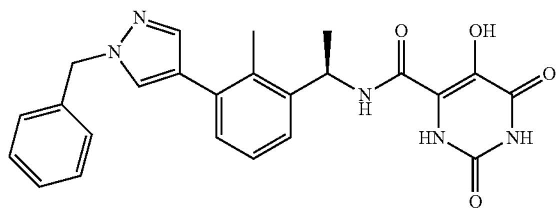 [SMILES: Cc1c(-c2cnn(Cc3ccccc3)c2)cccc1[C@@H](C)NC(=O)c1[nH]c(=O)[nH]c(=O)c1O] | (R)-N-(1-(3-(1-benzyl-1H-pyrazol-4-yl)-2-methylphenyl)ethyl)-5-hydroxy-2,6-dioxo-1,2,3,6-tetrahydropyrimidine-4-carboxamide | 446.2/1.93 min (Method B) | RT = 8.10 min, 98.1% (Method A) RT = 7.96 min, 93.0% (Method B) |
| 187 | 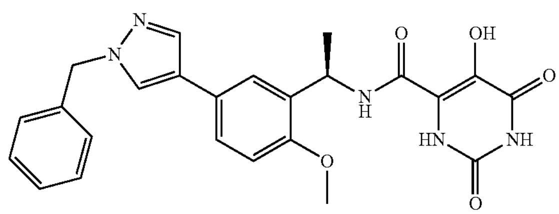 [SMILES: COc1ccc(-c2cnn(Cc3ccccc3)c2)cc1[C@@H](C)NC(=O)c1[nH]c(=O)[nH]c(=O)c1O] | (R)-N-(1-(5-(1-benzyl-1H-pyrazol-4-yl)-2-methoxyphenyl)ethyl)-5-hydroxy-2,6-dioxo-1,2,3,6-tetrahydropyrimidine-4-carboxamide | 462.1/1.99 min (Method B) | RT = 8.42 min, 95% (Method A) RT = 8.63 min, 100% (Method B) |
| 188 | 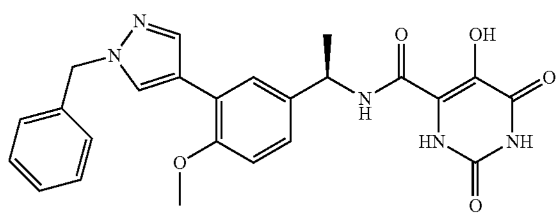 [SMILES: COc1ccc([C@@H](C)NC(=O)c2[nH]c(=O)[nH]c(=O)c2O)cc1-c1cnn(Cc2ccccc2)c1] | (R)-N-(1-(3-(1-benzyl-1H-pyrazol-4-yl)-4-methoxyphenyl)ethyl)-5-hydroxy-2,6-dioxo-1,2,3,6-tetrahydropyrimidine-4-carboxamide | 462.2/1.93 min (Method B) | RT = 8.38 min, 99.7% (Method A) RT = 9.52 min, 99.4% (Method B) |

What is claimed is:

1. A compound of Formula (II):

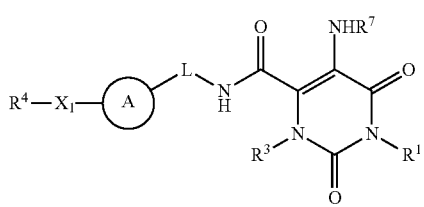

(II)

or a stereoisomer, a tautomer, or a pharmaceutically acceptable salt thereof, wherein:

ring A is independently selected from the group consisting of: $C_{3-14}$ carbocycle and a 4- to 14-membered heterocycle comprising: carbon atoms and 1-4 heteroatoms selected from N, $NR^e$, O, and $S(O)_p$; wherein said carbocycle and heterocycle are further substituted with 0-4 $R^5$;

$X_1$ is independently selected from the group consisting of: a bond, a hydrocarbon linker and a hydrocarbon-heteroatom linker; wherein said hydrocarbon linker and hydrocarbon-heteroatom linker may be substituted with 0-2 $R^g$; said hydrocarbon linker has one to six carbon atoms and may be saturated or unsaturated; and said hydrocarbon-heteroatom linker may be saturated or unsaturated and has zero to four carbon atoms and one group selected from O, —CO—, S, —SO—, —SO$_2$—, NH, N(C$_{1-4}$ alkyl), —NHCO—, —CONH—, —OCONH—, —NHCONH—, and —SO$_2$NH—;

L is independently a hydrocarbon linker substituted with 0-2 R$^g$ or a hydrocarbon-heteroatom linker substituted with 0-2 R$^g$; wherein said hydrocarbon linker has one to eight carbon atoms and may be straight or branched, saturated or unsaturated; and said hydrocarbon-heteroatom linker has one to seven carbon atoms and one group selected from O, —CO—, S, —SO—, —SO$_2$—, NH, N(C$_{1-4}$ alkyl), and —NHCO—;

R$^1$ and R$^3$ are each independently selected from the group consisting of: H, C$_{1-6}$ haloalkyl, C$_{1-6}$ alkyl substituted with 0-3 R$^a$, C$_{2-6}$ alkenyl substituted with 0-3 R$^a$,

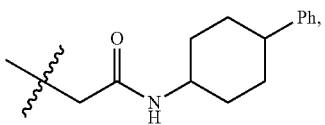 [SMILES: *CC(=O)NC1CCC(c2ccccc2)CC1]

and —(CH$_2$)$_n$—(C$_{3-10}$ carbocycle substituted with 0-3 R$^c$);

R$^4$ is independently selected from the group consisting of: H, =O, halogen, C$_{1-6}$ alkyl substituted with 0-1 OH, C$_{1-4}$ alkoxy, C$_{1-4}$ haloalkyl, C$_{1-4}$ haloalkoxy, CN, NO$_2$, NH$_2$, N(C$_{1-4}$ alkyl)$_2$, and a ring moiety substituted with 0-2 R$^h$ and selected from: C$_{3-10}$ carbocycle and a 5- to 10-membered heterocycle comprising: carbon atoms and 1-4 heteroatoms selected from N, NR$^e$, O, and S(O)$_p$;

R$^5$ is, independently at each occurrence, selected from the group consisting of: =O, OH, halogen, C$_{1-6}$ alkyl substituted with 0-1 OH, C$_{1-4}$ alkoxy, C$_{1-4}$ haloalkyl, C$_{1-4}$ haloalkoxy, SCF$_3$, CN, NH$_2$, NO$_2$, NH(C$_{1-4}$ alkyl), N(C$_{1-4}$ alkyl)$_2$, CO$_2$H, CO$_2$(C$_{1-4}$ alkyl), —CH$_2$CO$_2$(C$_{1-4}$ alkyl), CO(C$_{1-4}$ alkyl), CONH$_2$, CONH(C$_{1-4}$ alkyl), and CON(C$_{1-4}$ alkyl)$_2$;

R$^7$ is independently selected from the group consisting of: H, COCF$_3$, C$_{1-6}$ haloalkyl, C$_{1-6}$ alkyl substituted with 0-1 R$^a$, —(CHR$^f$)$_n$—(C$_{3-10}$ carbocycle substituted with 0-3 R$^b$), and —(CHR$^f$)$_n$—(5- to 10-membered heterocycle comprising: carbon atoms and 1-4 heteroatoms selected from N, NR$^e$, O, and S(O)$_p$); and wherein said heterocycle is substituted with 0-3 R$^c$;

R$^a$ is, independently at each occurrence, selected from the group consisting of: halogen, OH, C$_{1-4}$ alkyl, C$_{1-4}$ alkoxy, C$_{1-4}$ haloalkyl, C$_{1-4}$ haloalkoxy, CN, NH$_2$, NO$_2$, NH(C$_{1-4}$ alkyl), N(C$_{1-4}$ alkyl)$_2$, CO$_2$H, CO$_2$(C$_{1-4}$ alkyl), NHCO(C$_{1-4}$ alkyl substituted with 0-1 NH$_2$), N(C$_{1-4}$ alkyl)CO(C$_{1-4}$ alkyl), NHCO$_2$(C$_{1-4}$ alkyl), CONHSO$_2$(C$_{1-4}$ alkyl), SO$_2$(C$_{1-4}$ alkyl), CONH$_2$, CONH(C$_{1-4}$ alkyl), NHSO$_2$(C$_{1-4}$ alkyl), N(C$_{1-4}$ alkyl)SO$_2$(C$_{1-4}$ alkyl), phenoxy, and —CONH(phenylcyclohexyl);

R$^b$ is, independently at each occurrence, selected from the group consisting of: halogen, OH, C$_{1-4}$ alkyl substituted with 0-1 OH, C$_{1-4}$ alkoxy, C$_{1-4}$ haloalkyl, C$_{1-4}$ haloalkoxy, CN, NH$_2$, NO$_2$, NH(C$_{1-4}$ alkyl), N(C$_{1-4}$ alkyl)$_2$, CO$_2$H, CO$_2$(C$_{1-4}$ alkyl), CONH$_2$, CONH(C$_{1-4}$ alkyl), CON(C$_{1-4}$ alkyl)$_2$, NHCO$_2$(C$_{1-4}$ alkyl), NHSO$_2$(C$_{1-4}$ alkyl), N(C$_{1-4}$ alkyl)SO$_2$(C$_{1-4}$ alkyl), SO$_2$(C$_{1-4}$ alkyl), SO$_2$NH$_2$, phenyl, benzyl, and phenoxy;

R$^c$ is, independently at each occurrence, selected from the group consisting of: =O and R$^b$;

R$^d$ is, independently at each occurrence, selected from the group consisting of: CONH$_2$, C$_{1-4}$ alkyl, —(CH$_2$)$_2$O(C$_{1-4}$ alkyl), C$_{3-6}$ carbocycle substituted with 0-2 R$^h$, morpholin-1-yl, 1-C$_{1-4}$ alkyl-piperazin-4-yl, 1-CBz-piperazin-4-yl, pyridyl, indol-3-yl, and benzothiazol-2-yl;

R$^e$ is, independently at each occurrence, selected from the group consisting of: H, C$_{1-4}$ alkyl, CO(C$_{1-4}$ alkyl), CO$_2$(C$_{1-4}$ alkyl), CO$_2$(benzyl), CONH(C$_{1-4}$ alkyl), CONH(phenyl substituted with 0-2 halogens), SO$_2$(C$_{1-4}$ alkyl), and —(CH$_2$)$_n$R$^d$;

R$^f$ is, independently at each occurrence, selected from the group consisting of: H and C$_{1-4}$ alkyl;

R$^g$ is, independently at each occurrence, selected from the group consisting of: halogen, OH, C$_{1-4}$ alkyl, C$_{2-4}$ alkenyl, C$_{1-4}$ haloalkyl, C$_{1-4}$ alkyoxy, CO$_2$(C$_{1-4}$ alkyl), C$_{3-6}$ cycloalkyl, and phenyl;

R$^h$ is, independently at each occurrence, selected from the group consisting of: H, halogen, C$_{1-6}$ alkyl, C$_{1-6}$ alkoxy, C$_{1-4}$ haloalkyl, C$_{1-4}$ haloalkoxy, —(CH$_2$)$_2$O(C$_{1-4}$ alkyl), CF$_3$, NO$_2$, CONH$_2$, OBn, quinolinyl, 1-C$_{1-4}$ alkyl-pyrazolyl, 1-(CH$_2$CO$_2$(C$_{1-4}$ alkyl))-pyrazolyl, 1-C$_{1-4}$ alkyl-3-CF$_3$-pyrazolyl, 1-((CH$_2$)$_2$(morpholin-4-yl))-pyrazolyl, 1-(tetrahydro-2H-pyran-2-yl)-pyrazolyl, 1,2,5-triC$_{1-4}$ alkyl-pyrazolyl, 2-Ph-4-C$_{1-4}$ alkyl-thiazolyl, —NHSO$_2$(phenyl substituted with C$_{1-4}$ alkyl), and —(CH$_2$)$_{0-2}$-(phenyl substituted with zero to three substituents independently selected from the group consisting of: halogen, CH$_2$OH, C$_{1-4}$ alkyl, C$_{1-4}$ haloalkyl, C$_{1-4}$ alkoxy, C$_{1-4}$ haloalkoxy, N(C$_{1-4}$ alkyl)$_2$, CONH$_2$, and NHCO(C$_{1-4}$ alkyl));

n is, independently at each occurrence, selected from 0, 1, 2, 3, and 4; and p is, independently at each occurrence, selected from 0, 1, and 2;

provided that the following compound is excluded:

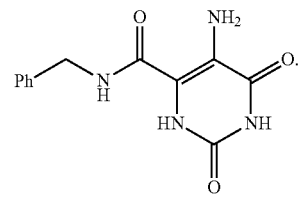 [SMILES: Nc1c(C(=O)NCc2ccccc2)[nH]c(=O)[nH]c1=O]

2. A compound according to claim 1, wherein:

ring A is independently selected from the group consisting of: C$_{3-6}$ cycloalkyl, phenyl, naphthyl, tetrahydronaphthyl, dihydroindenyl, and a 5- to 10-membered heterocycle comprising: carbon atoms and 1-4 heteroatoms selected from N, NR$^e$, O, and S(O)$_p$; and wherein each moiety is substituted with 0-3 R$^5$;

X$_1$ is independently selected from the group consisting of: a bond, a hydrocarbon linker substituted with 0-1 R$^g$ and a hydrocarbon-heteroatom linker substituted with 0-1 R$^g$; wherein said hydrocarbon linker has one to three carbon atoms and may be saturated or unsaturated; and said hydrocarbon-heteroatom linker may be saturated or unsaturated and has zero to three carbon atoms and one group selected from O, CO, —SO$_2$—, —CONH—, and —NHCO—;

L is independently a hydrocarbon linker substituted with 0-1 R$^g$ or a hydrocarbon-heteroatom linker substituted with 0-1 R$^g$; wherein said hydrocarbon linker has one to six carbon atoms and may be straight or branched, saturated or unsaturated; and said hydrocarbon-heteroatom linker has one to five carbon atoms and one group selected from O, —CO—, S, —SO—, —SO$_2$—, NH, N(C$_{1-4}$ alkyl), and —NHCO—; and R$^1$ and R$^3$ are each independently selected from the group consisting of: H, C$_{1-6}$ alkyl substituted with 0-3 R$^a$, C$_{1-6}$ haloalkyl,

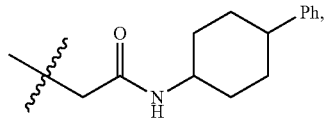

and —(CH$_2$)$_n$-(phenyl substituted with 0-3 R$^c$);

R$^4$ is independently selected from the group consisting of: H, =O, halogen, C$_{1-4}$ alkyl, C$_{1-4}$ alkoxy, C$_{1-4}$ haloalkyl, C$_{1-4}$ haloalkoxy, CN, NO$_2$, NH$_2$, N(C$_{1-4}$ alkyl)$_2$, CO$_2$(C$_{1-4}$ alkyl), —CH$_2$CO$_2$(C$_{1-4}$ alkyl), a ring moiety substituted with 0-2 R$^h$ and selected from: C$_{3-10}$ carbocycle and a 5- to 10-membered heterocycle comprising: carbon atoms and 1-4 heteroatoms selected from N, NR$^e$, O, and S(O)$_p$;

R$^5$ is, independently at each occurrence, selected from the group consisting of: =O, OH, halogen, C$_{1-4}$ alkyl substituted with 0-1 OH, C$_{1-4}$ alkoxy, C$_{1-4}$ haloalkyl, C$_{1-4}$ haloalkoxy, SCF$_3$, CN, NO$_2$, CO$_2$(C$_{1-4}$ alkyl), —CH$_2$CO$_2$(C$_{1-4}$ alkyl), NH$_2$, NH(C$_{1-4}$ alkyl), N(C$_{1-4}$ alkyl)$_2$, CONH$_2$, CONH(C$_{1-4}$ alkyl), and CON(C$_{1-4}$ alkyl)$_2$; and provided that the following compound is excluded:

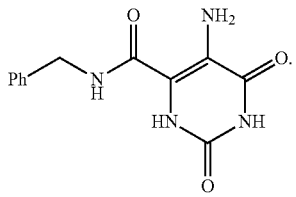

3. A compound according to claim 2, wherein:

L is independently a hydrocarbon linker optionally substituted with 0-1 R$^g$ or a hydrocarbon-heteroatom linker optionally substituted with 0-1 R$^g$; wherein said hydrocarbon linker has one to five carbon atoms and may be straight or branched, saturated or unsaturated; and said hydrocarbon-heteroatom linker has zero to four carbon atoms and one group selected from O, S, —SO—, and —SO$_2$—;

provided that the following compound is excluded:

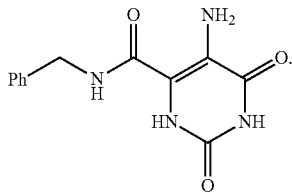 [SMILES: Nc1c(C(=O)NCc2ccccc2)[nH]c(=O)[nH]c1=O]

4. A compound according to claim 3, wherein:

ring A is independently selected from the group consisting of: C$_{3-6}$ cycloalkyl, phenyl, naphthyl, tetrahydronaphthalenyl, dihydroindenyl, tetrahydroindazolyl, tetrahydroquinolinyl, benzothiazolyl, benzimidazolyl, pyridyl, isoxazolyl, oxadiazolyl, pyrrolidinyl, piperidinyl, pyrazolyl; wherein each moiety is further substituted with 0-3 R$^5$;

X$_1$ is a bond, O, CO, —(CH$_2$)$_{1-3}$—, —(CH$_2$)$_{1-2}$O—, —SO$_2$—, —CONH—, and —NHCO—;

L is independently selected from the group consisting of: straight or branched C$_{1-5}$ alkylene, and —O-(straight or branched C$_{1-4}$ alkylene);

R$^1$ and R$^3$ are each independently selected from the group consisting of: H, C$_{1-4}$ alkyl, C$_{1-4}$ haloalkyl, 3-halo-4-halo-phenyl, 3-CF$_3$-5-halo-phenyl, and benzyl;

R$^4$ is independently selected from the group consisting of: H, =O, halogen, C$_{1-4}$ alkyl, C$_{1-4}$ alkoxy, C$_{1-4}$ haloalkyl, C$_{1-4}$ haloalkoxy, CN, NO$_2$, NH$_2$, N(C$_{1-4}$ alkyl)$_2$, CO$_2$(C$_{1-4}$ alkyl), C$_{3-6}$ cycloalkyl, morpholinyl, 1-C$_{1-4}$ alkyl-piperazin-4-yl, 1-CO$_2$(C$_{1-4}$ alkyl)-piperazin-4-yl, 1-CBz-piperazin-4-yl, pyrrolyl, oxadiazolyl, benzimidazolyl,

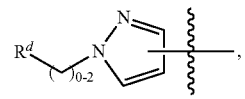

and phenyl substituted with 0-2 R$^h$;

R$^5$ is, independently at each occurrence, selected from the group consisting of: =O, halogen, C$_{1-4}$ alkyl, C$_{1-4}$ alkoxy, C$_{1-4}$ haloalkyl, C$_{1-4}$ haloalkoxy, SCF$_3$, OCH$_2$CF$_3$, CN, NH$_2$, NO$_2$, NH(C$_{1-4}$ alkyl), N(C$_{1-4}$ alkyl)$_2$, CO$_2$(C$_{1-4}$ alkyl), —CH$_2$CO$_2$(C$_{1-4}$ alkyl), CONH$_2$, CONH(C$_{1-4}$ alkyl), and CON(C$_{1-4}$ alkyl)$_2$;

R$^7$ is independently selected from the group consisting of: H, C$_{1-4}$ alkyl, C$_{1-4}$ haloalkyl, —(CH$_2$)$_2$O(C$_{1-4}$ alkyl), COCF$_3$, C$_{1-6}$ alkyl substituted with 0-1 OH, —(CHR$^f$)$_n$—(C$_{3-6}$ cycloalkyl substituted with 0-1 OH); and —(CHR$^f$)$_n$-(phenyl substituted with 0-2 R$^b$);

R$^b$ is, independently at each occurrence, selected from the group consisting of: halogen, OH, C$_{1-4}$ alkyl substituted with 0-1 OH, C$_{1-4}$ alkoxy, C$_{1-4}$ haloalkyl, C$_{1-4}$ haloalkoxy, CF$_3$, OCF$_3$, CN, NH$_2$, NO$_2$, NH(C$_{1-4}$ alkyl), N(C$_{1-4}$ alkyl)$_2$, CO$_2$H, CO$_2$(C$_{1-4}$ alkyl), CONH$_2$, CONH(C$_{1-4}$ alkyl), CON(C$_{1-4}$ alkyl)$_2$, NHCO$_2$(C$_{1-4}$ alkyl), SO$_2$(C$_{1-4}$ alkyl), and SO$_2$NH$_2$;

R$^d$ is, independently at each occurrence, selected from the group consisting of: CONH$_2$, C$_{1-4}$ alkyl, —(CH$_2$)$_2$O(CH$_2$)$_2$O(C$_{1-4}$ alkyl), C$_{3-6}$ carbocycle substituted with 0-2 R$^h$, morpholin-1-yl, 1-C$_{1-4}$ alkyl-piperazin-4-yl, 1-CBz-piperazin-4-yl, pyridyl, indol-3-yl, and benzothiazol-2-yl;

R$^f$ is, independently at each occurrence, selected from the group consisting of: H and methyl; and n is, independently at each occurrence, selected from 0, 1, 2, and 3;

provided that the following compounds are compound is excluded:

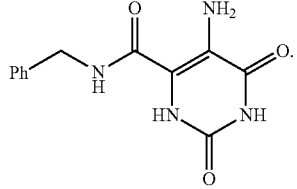 [SMILES: Nc1c(C(=O)NCc2ccccc2)[nH]c(=O)[nH]c1=O]

5. A compound according to claim 4, wherein:

$R^4$ is independently selected from the group consisting of: H, =O, halogen, $C_{1-4}$ alkyl, $C_{1-4}$ alkoxy, $C_{1-4}$ haloalkyl, $C_{1-4}$ haloalkoxy, CN, $NO_2$, $NH_2$, $N(C_{1-4}$ alkyl$)_2$, $CO_2(C_{1-4}$ alkyl), $C_{3-6}$ cycloalkyl, morpholinyl, 1-$C_{1-4}$ alkyl-piperazin-4-yl, 1-$CO_2(C_{1-4}$ alkyl)-piperazin-4-yl, 1-CBz-piperazin-4-yl, pyrrolyl, oxadiazolyl, benzimidazolyl,

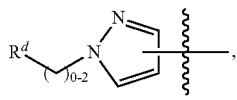

and phenyl substituted with 0-2 $R^h$;

$R^7$ is independently selected from the group consisting of: H, $C_{1-4}$ alkyl, —$(CH_2)_2O(C_{1-4}$ alkyl), $COCF_3$, 4-halo-benzyl, 4-$C_{1-4}$ alkoxy-benzyl, 3-$CF_3$-benzyl, 2-$CH_2OH$-benzyl, 2-halo-phenethyl, 4-halo-phenethyl, and —$(CH_2)_3Ph$; and L is independently selected from the group consisting of: —$CH_2$—, —$CH(CH_3)$—, —$(CH_2)_2$—, —$(CH_2)_3$—, —$(CH_2)_2CH(CH_3)$—, —$OCH_2CH(CH_3)$—, —$OCH(CH_3)CH_2$—, —$O(CH_2)_3$—, and —$O(CH_2)_2CH(CH_3)$—;

provided that the following compound is excluded:

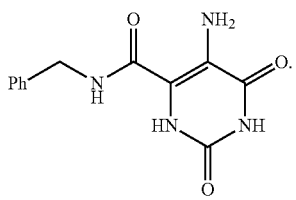

6. A compound according to claim 1, wherein:

ring A is independently selected from the group consisting of: phenyl, naphthyl, dihydroindenyl, tetrahydroindazolyl, benzothiazolyl, tetrahydronaphthalenyl, pyrazolyl, and pyrrolidinyl; wherein each moiety is further substituted with 0-3 $R^5$;

$X_1$ is a bond, O, CO, —$(CH_2)_{1-2}$—, —$CH_2O$—, and —$SO_2$—;

$R^1$ and $R^3$ are each independently selected from the group consisting of: H, $C_{1-4}$ alkyl, $CH_2CF_3$, and benzyl;

$R^4$ is independently selected from the group consisting of: H, halogen, $C_{1-4}$ alkyl, $C_{1-4}$ alkoxy, $C_{1-4}$ haloalkyl, $C_{1-4}$ haloalkoxy, CN, $NO_2$, $NH_2$, $N(C_{1-4}$ alkyl$)_2$, $CO_2(C_{1-4}$ alkyl), $C_{3-6}$ cycloalkyl, morpholinyl, 1-$C_{1-4}$ alkyl-piperazin-4-yl, 1-$CO_2(C_{1-4}$ alkyl)-piperazin-4-yl, 1-CBz-piperazin-4-yl, pyrrol-1-yl, 1,3,4-oxadiazolyl, benzimidazolyl,

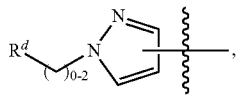

and phenyl substituted with 0-2 $R^h$;

$R^5$ is, independently at each occurrence, selected from the group consisting of: halogen, $C_{1-4}$ alkyl, and $C_{1-4}$ alkoxy;

$R^7$ is independently selected from the group consisting of: H, $C_{1-4}$ alkyl, $COCF_3$, and 4-$C_{1-4}$ alkoxy-benzyl;

L is independently selected from the group consisting of: —$CH_2$—, —$CH(CH_3)$—, —$(CH_2)_2$—, —$(CH_2)_3$—, —$(CH_2)_2CH(CH_3)$—, —$OCH_2CH(CH_3)$—, —$O(CH_2)_3$—, and —$O(CH_2)_2CH(CH_3)$—;

$R^d$ is, independently at each occurrence, selected from the group consisting of: $CONH_2$, $C_{1-4}$ alkyl, —$(CH_2)_2O(CH_2)_2O(C_{1-4}$ alkyl), $C_{3-6}$ cycloalkyl, phenyl substituted with 0-2 $R^h$, morpholin-1-yl, 1-$C_{1-4}$ alkyl-piperazin-4-yl, 1-CBz-piperazin-4-yl, pyridyl, indol-3-yl, and benzothiazol-2-yl; and $R^h$ is, independently at each occurrence, selected from the group consisting of: H, halogen, $C_{1-4}$ alkyl, $C_{1-4}$ alkoxy, $CF_3$, $OCF_3$, CN, $CO_2(C_{1-4}$ alkyl), $CONH_2$, and phenyl substituted with zero to three substituents independently selected from the group consisting of: halogen, $C_{1-4}$ alkyl, $C_{1-4}$ haloalkyl, and $C_{1-4}$ alkyoxy; provided that

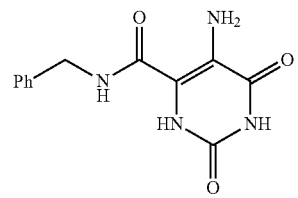 [SMILES: Nc1c(C(=O)NCc2ccccc2)[nH]c(=O)[nH]c1=O]

is excluded.

7. A compound according to claim 6, wherein:

$R^1$ and $R^3$ are each independently selected from the group consisting of: H and $C_{1-4}$ alkyl;

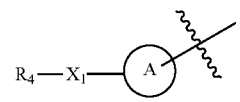

is independently selected from the group consisting of:

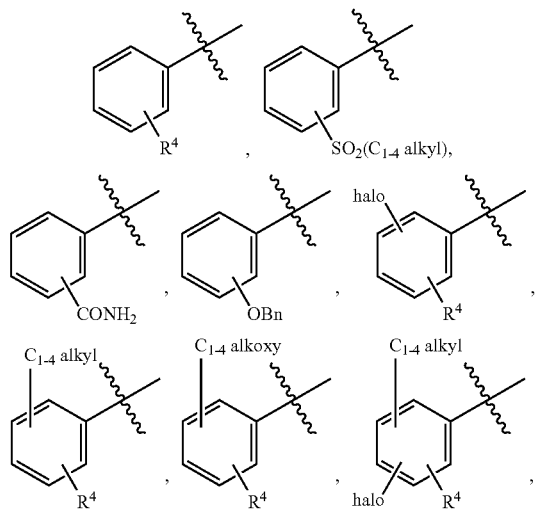

-continued

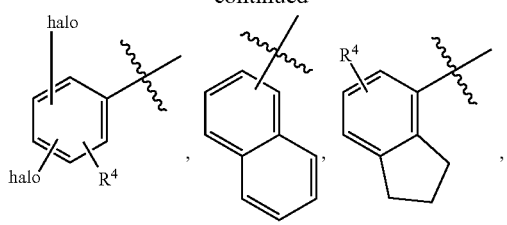

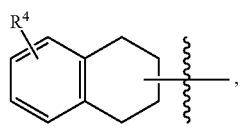

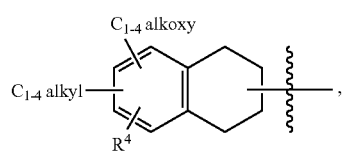

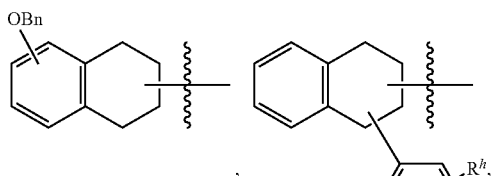

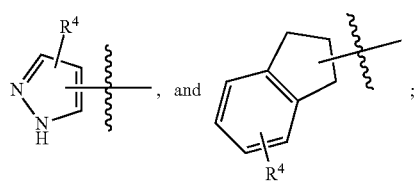

R⁴ is, independently at each occurrence, selected from the group consisting of: H, halogen, $C_{1-4}$ alkyl, $C_{1-4}$ alkoxy, $C_{1-4}$ haloalkyl, $C_{1-4}$ haloalkoxy, CN, NO₂, CO₂($C_{1-4}$ alkyl), cyclopropyl, 1-CO₂($C_{1-4}$ alkyl)-piperazin-4-yl, 1-CBz-piperazin-4-yl, pyrrol-1-yl,

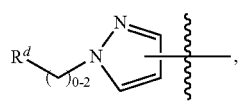

and Ph;

$R^d$ is, independently at each occurrence, selected from the group consisting of: CONH₂, $C_{1-4}$ alkyl, $C_{3-6}$ cycloalkyl, phenyl substituted with 0-1 $R^h$, morpholin-1-yl, 1-CBz-piperazin-4-yl, pyridyl, indol-3-yl, and benzothiazol-2-yl; and $R^h$ is, independently at each occurrence, selected from the group consisting of: H, halogen, $C_{1-4}$ alkyl, $C_{1-4}$ alkoxy, CF₃, OCF₃, CN, CO₂($C_{1-4}$ alkyl), and CONH₂; provided that

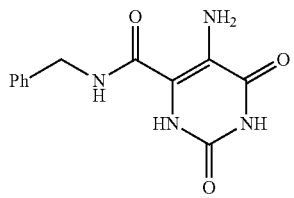 [SMILES: Nc1c(C(=O)NCc2ccccc2)[nH]c(=O)[nH]c1=O]

is excluded.

8. A compound according to claim 7, wherein:
R¹ and R³ are each independently selected from the group consisting of: H and $C_{1-4}$ alkyl;

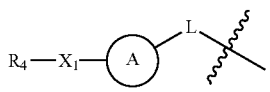

is independently selected from the group consisting of:

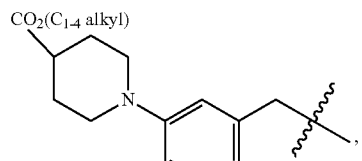

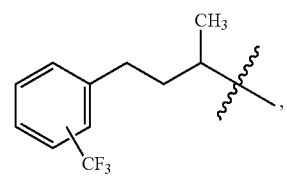

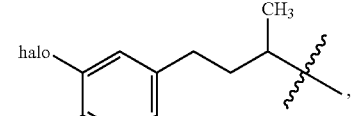

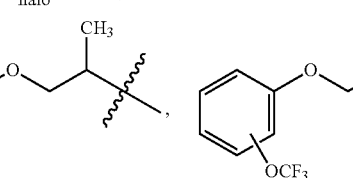

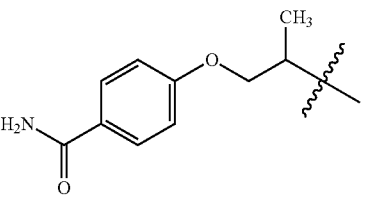

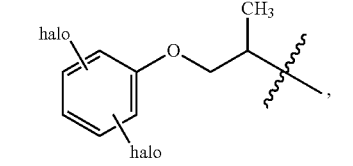

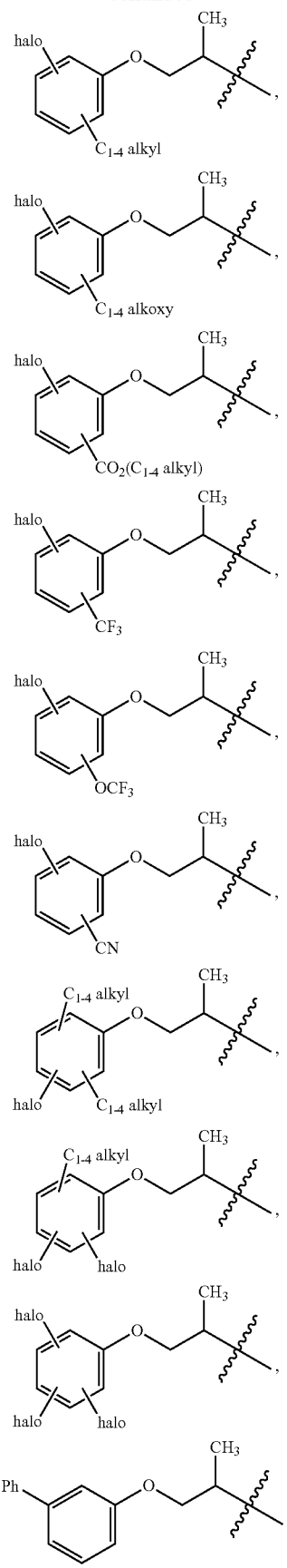
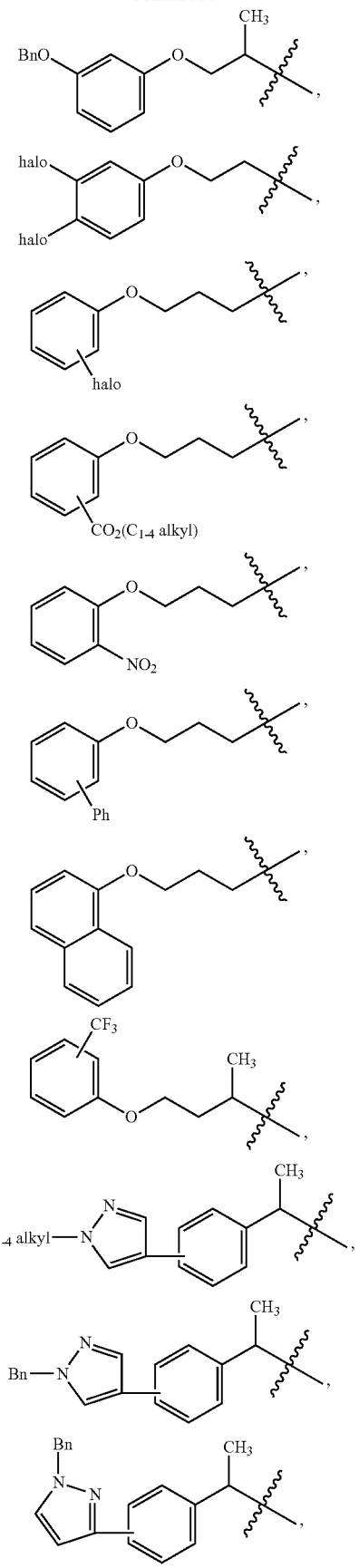

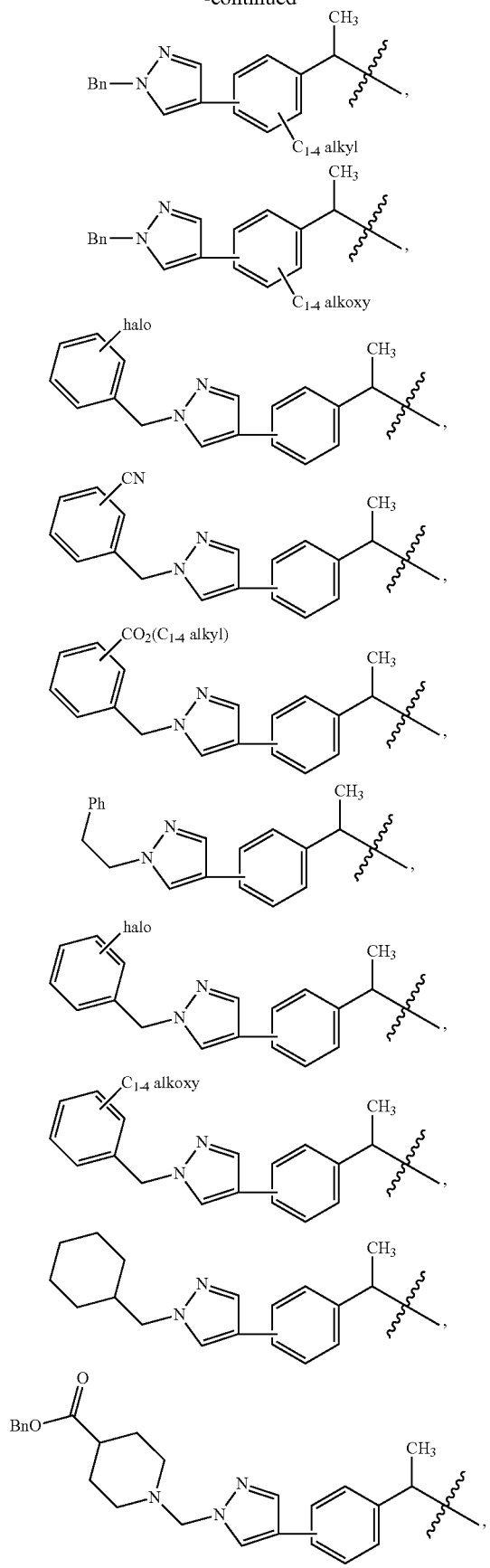
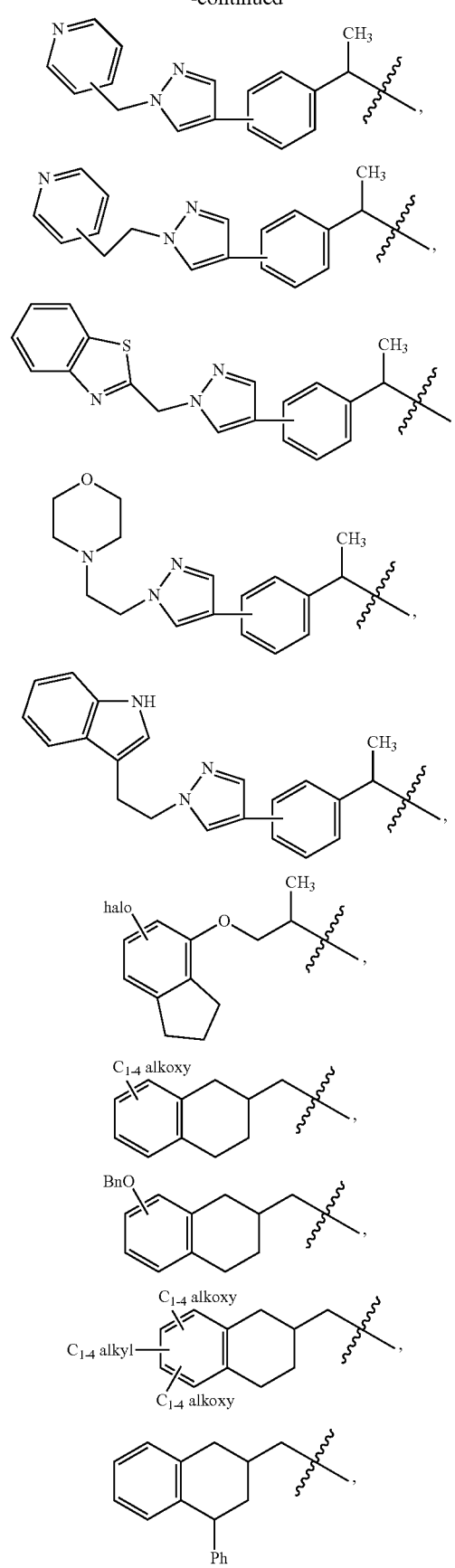

157
-continued
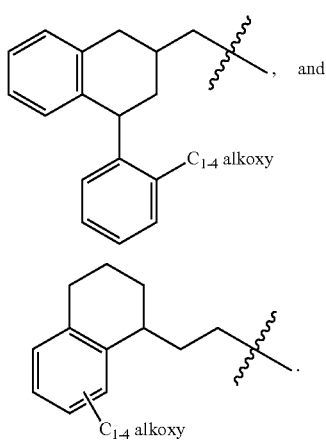, and
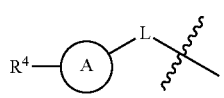.
9. A compound according to claim 1, wherein:
R$^1$ and R$^3$ are each independently selected from the group consisting of: H and C$_{1-4}$ alkyl;
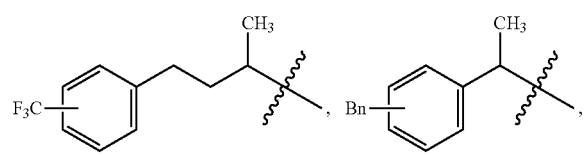
is independently selected from the group consisting of:
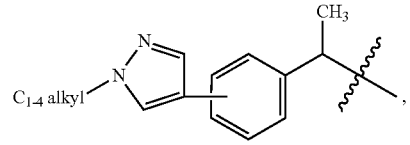,
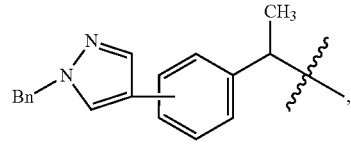,
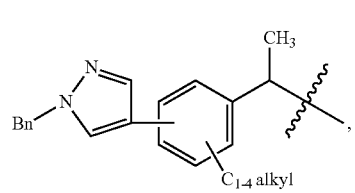,
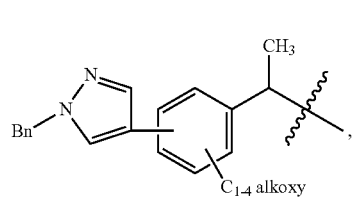,
158
-continued
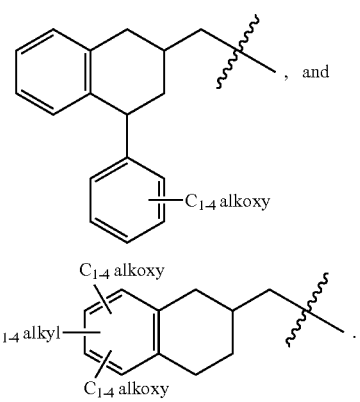, and
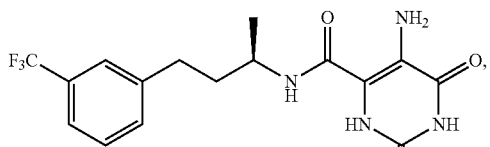.
10. A compound selected from:
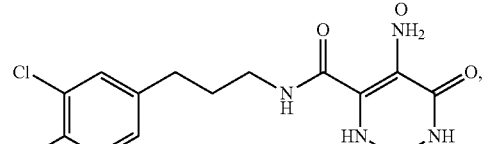,
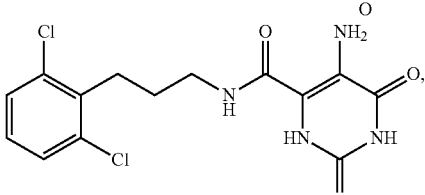,
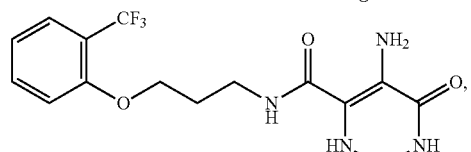,
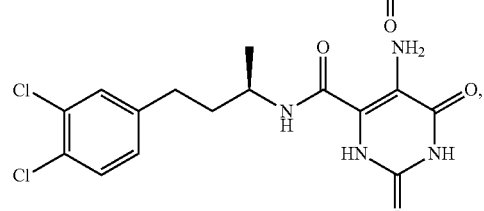,
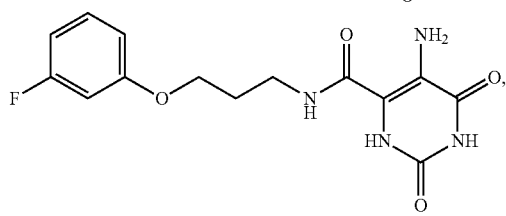,

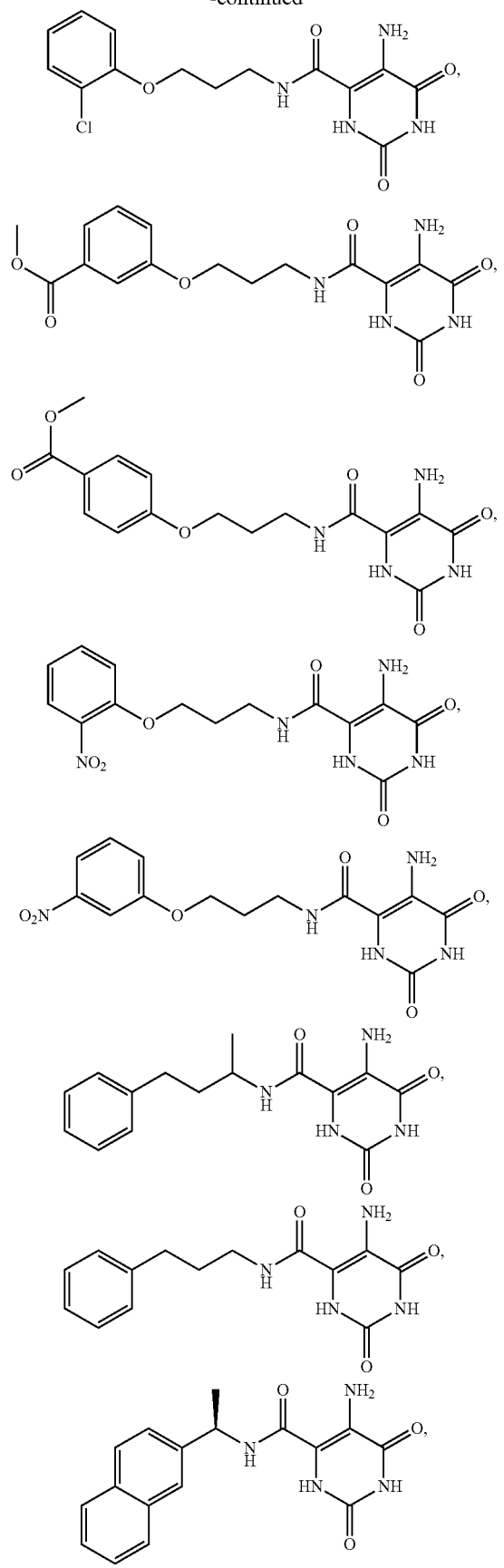

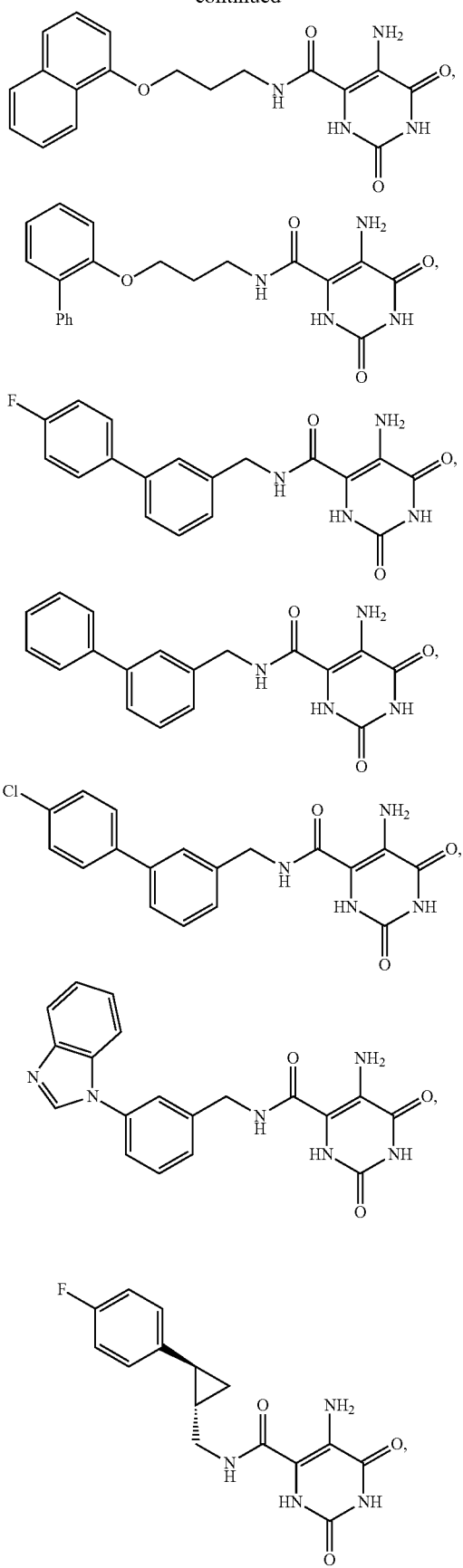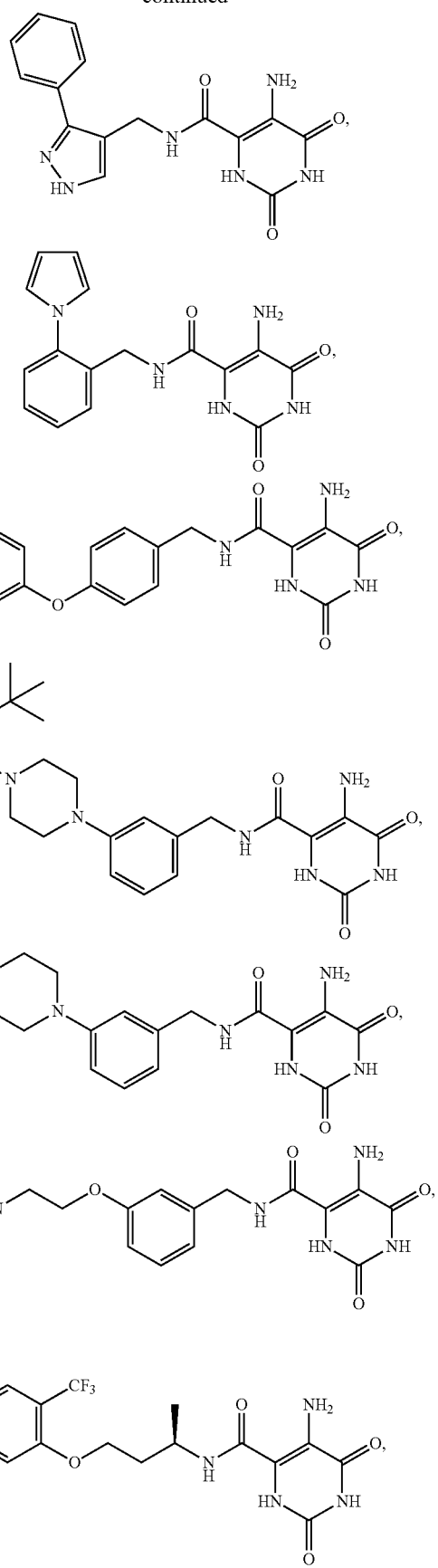

163
-continued
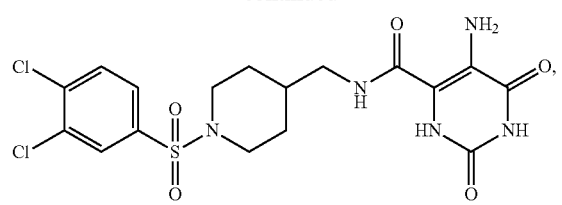
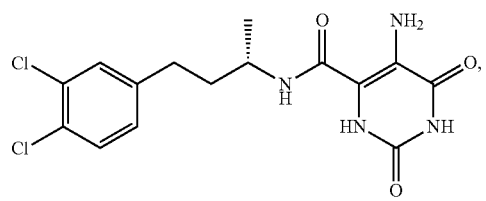
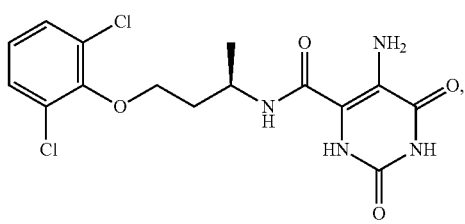
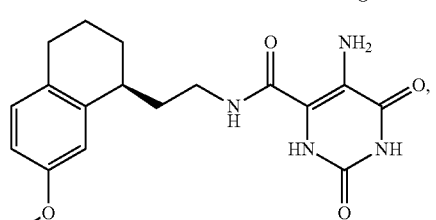
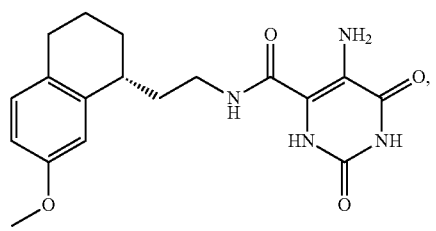
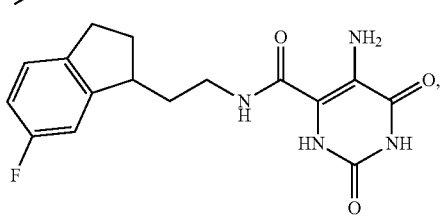
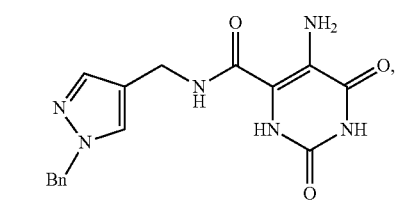
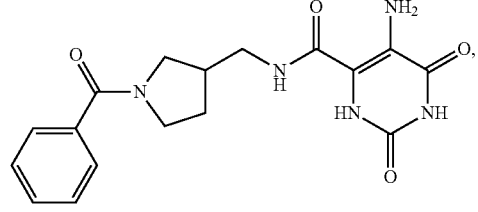
164
-continued
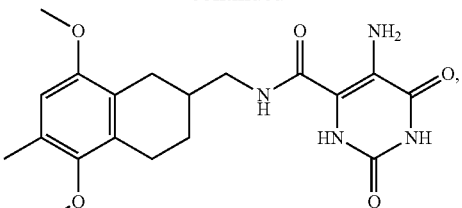
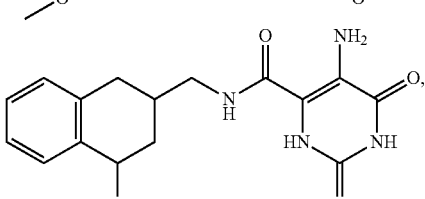
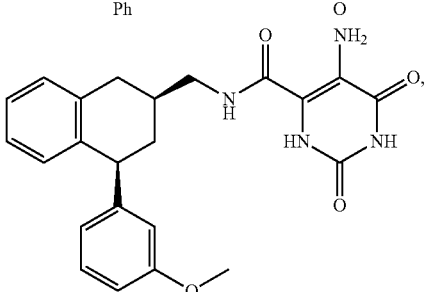
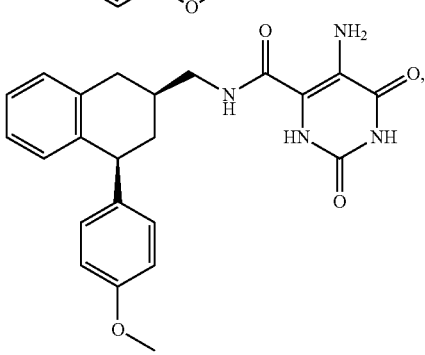
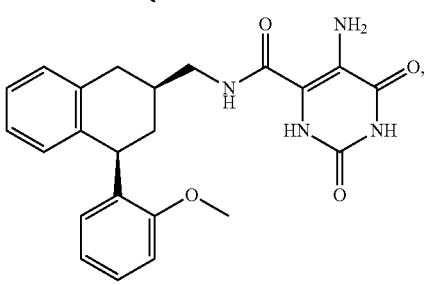
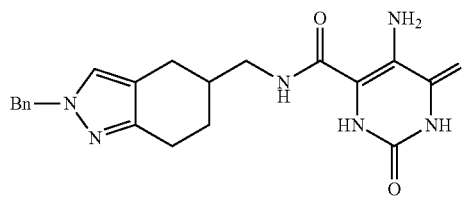
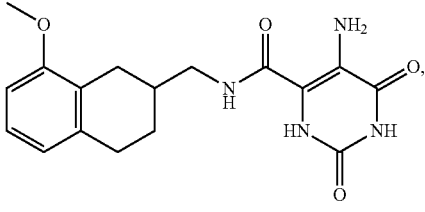

165
-continued
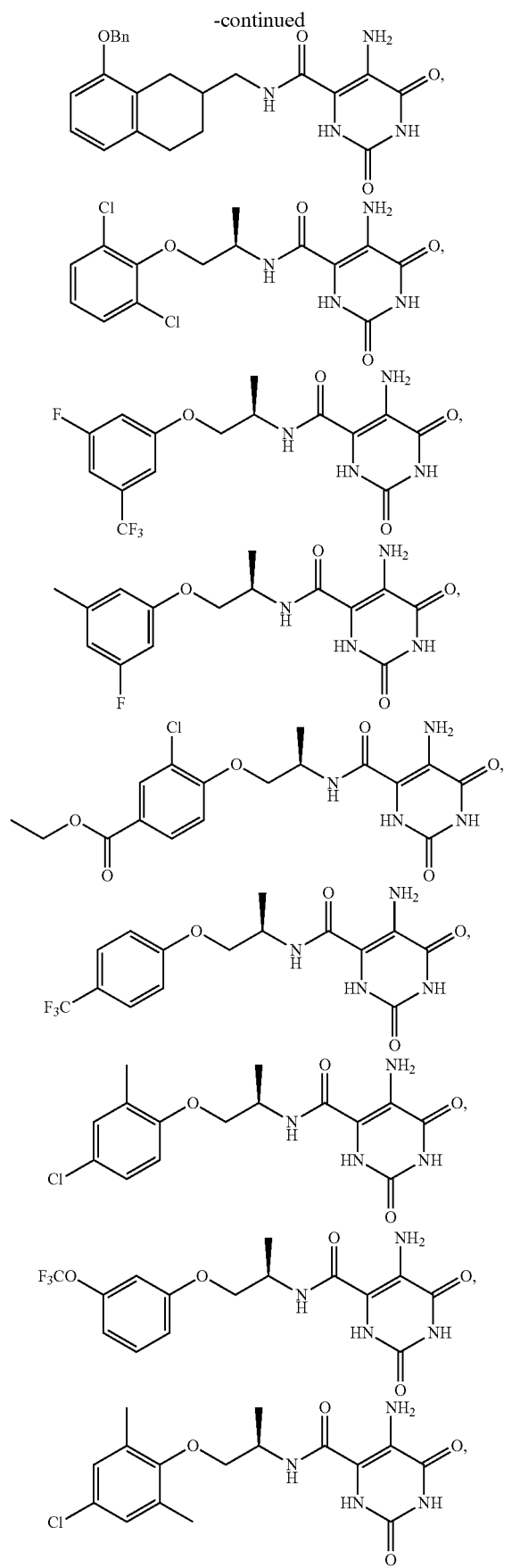
166
-continued
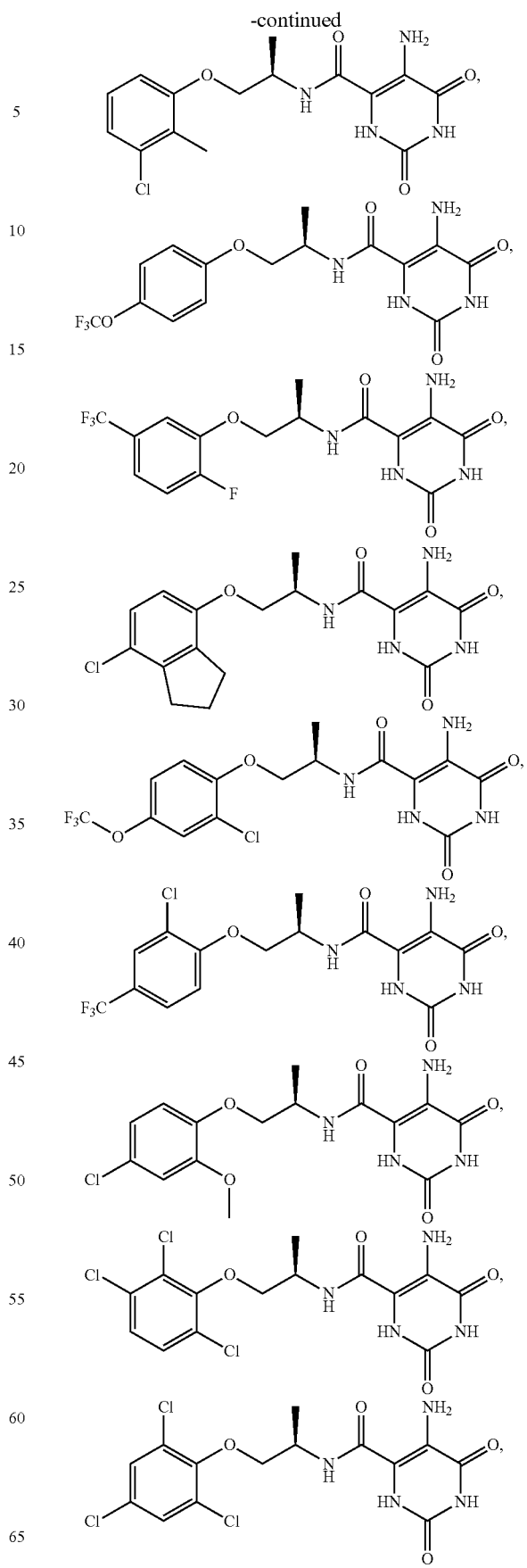

167
-continued
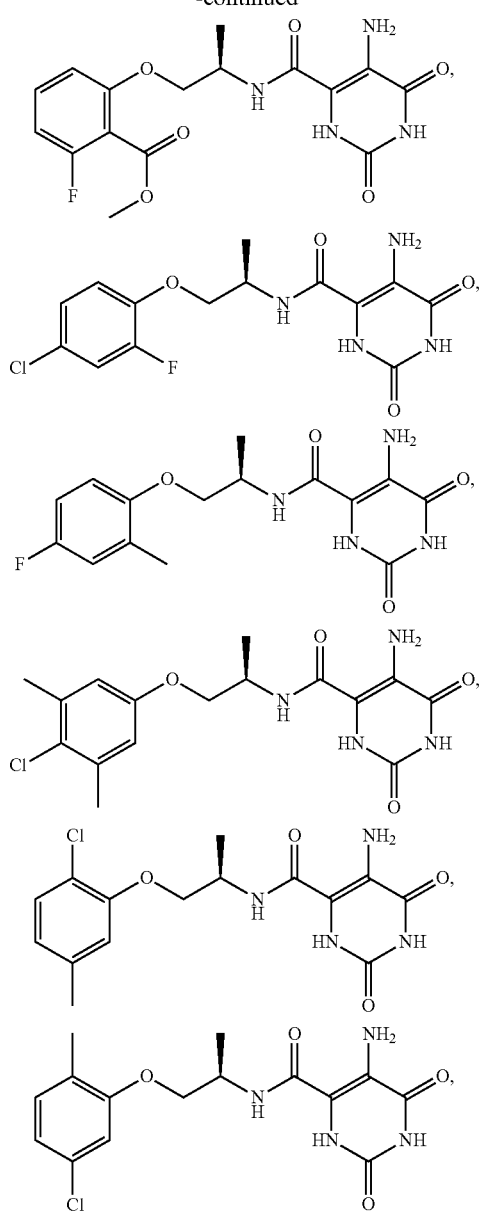
168
-continued
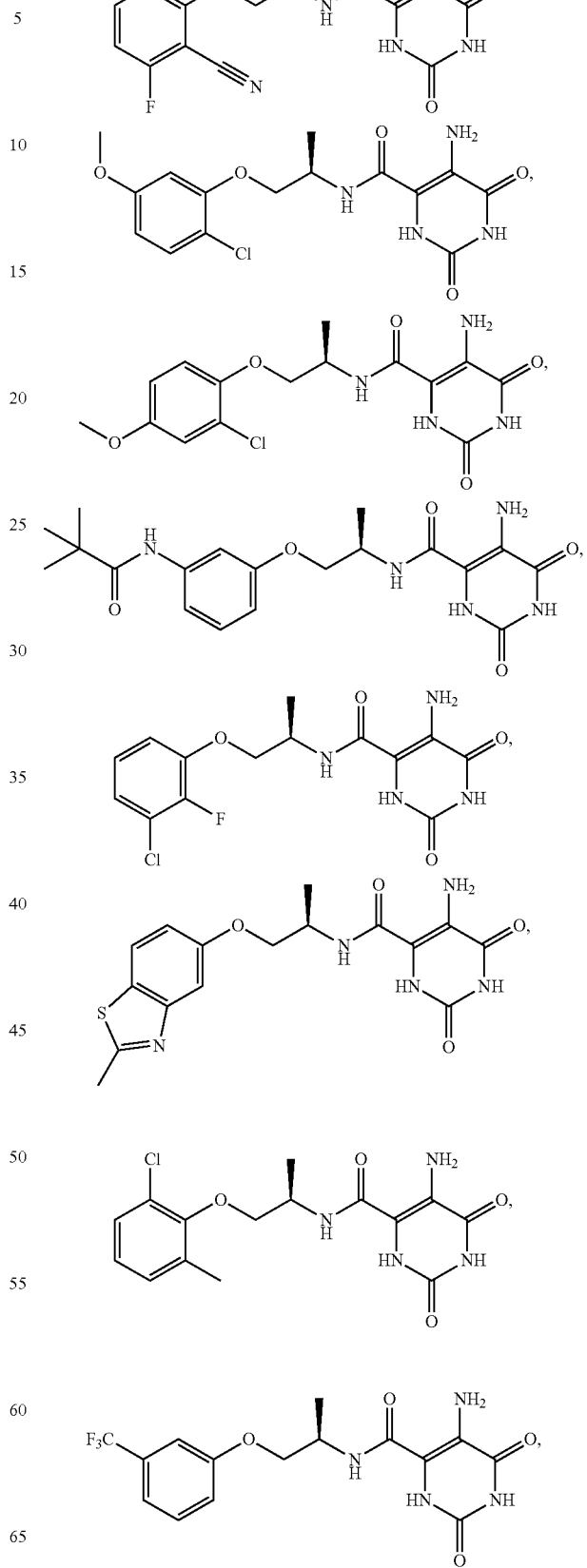

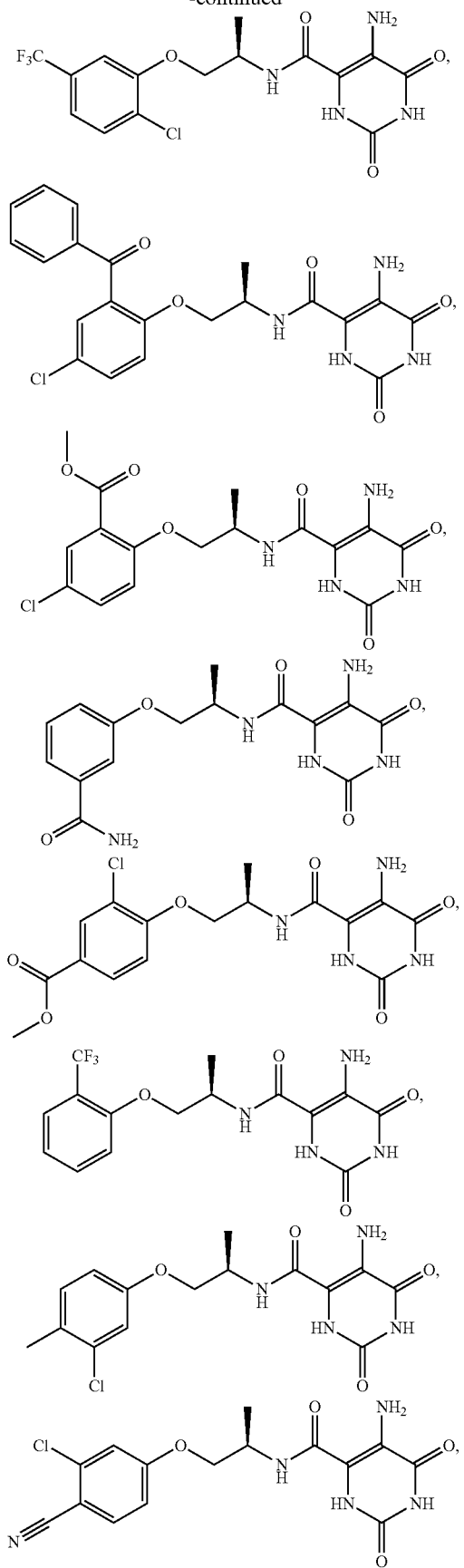
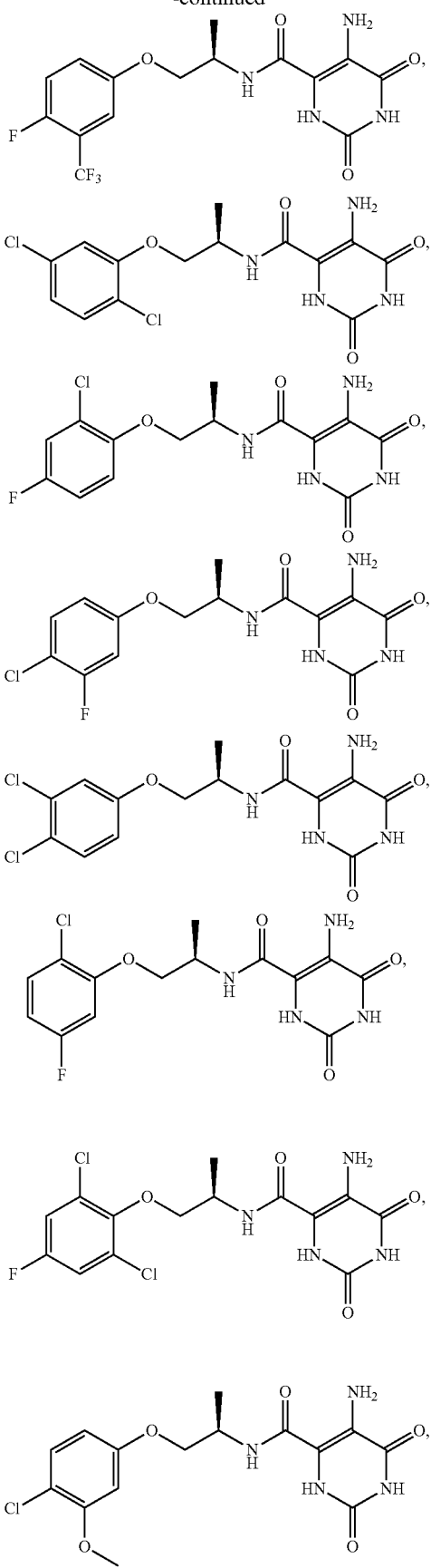

| 171 | 172 |
|---|---|
| -continued | -continued |
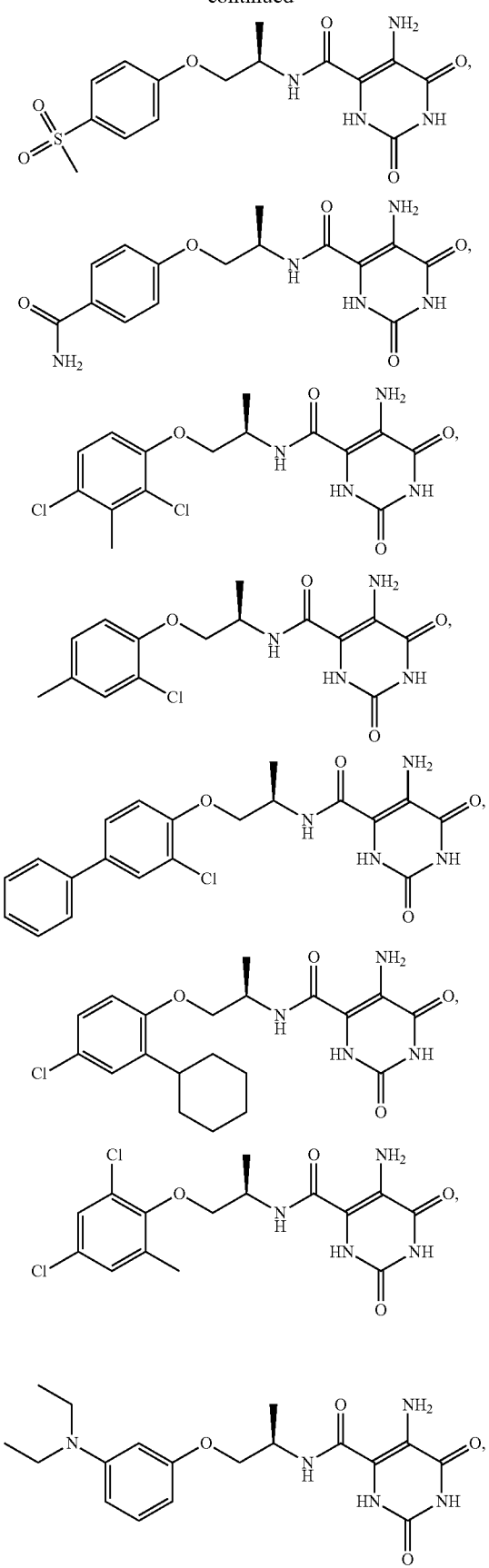
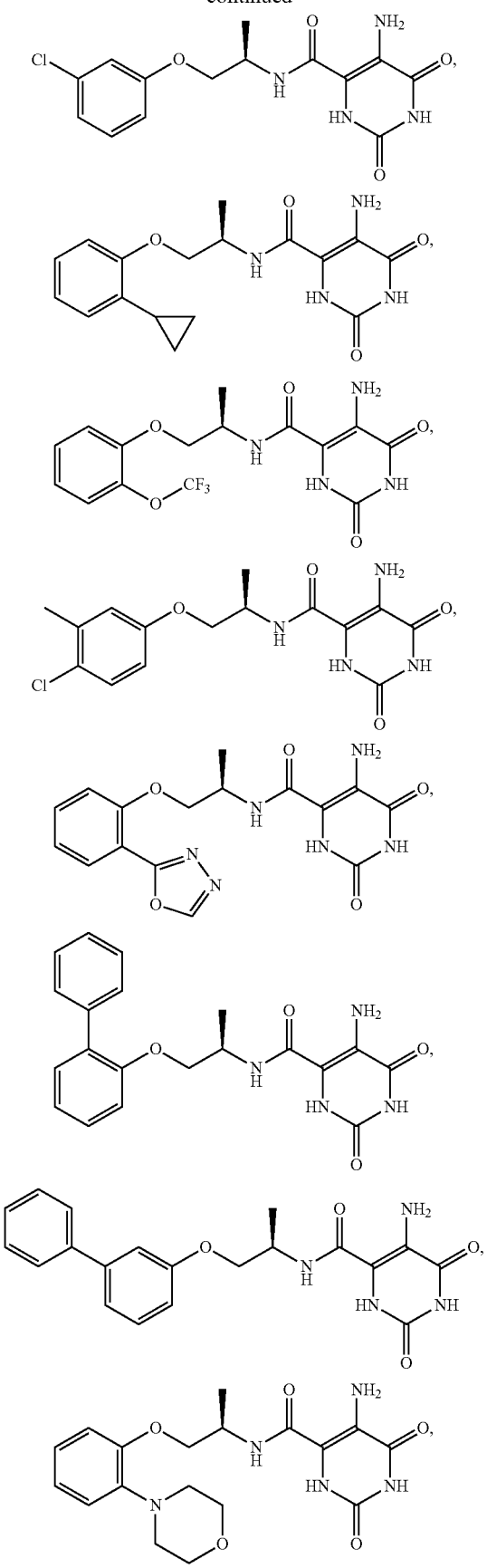

173
-continued
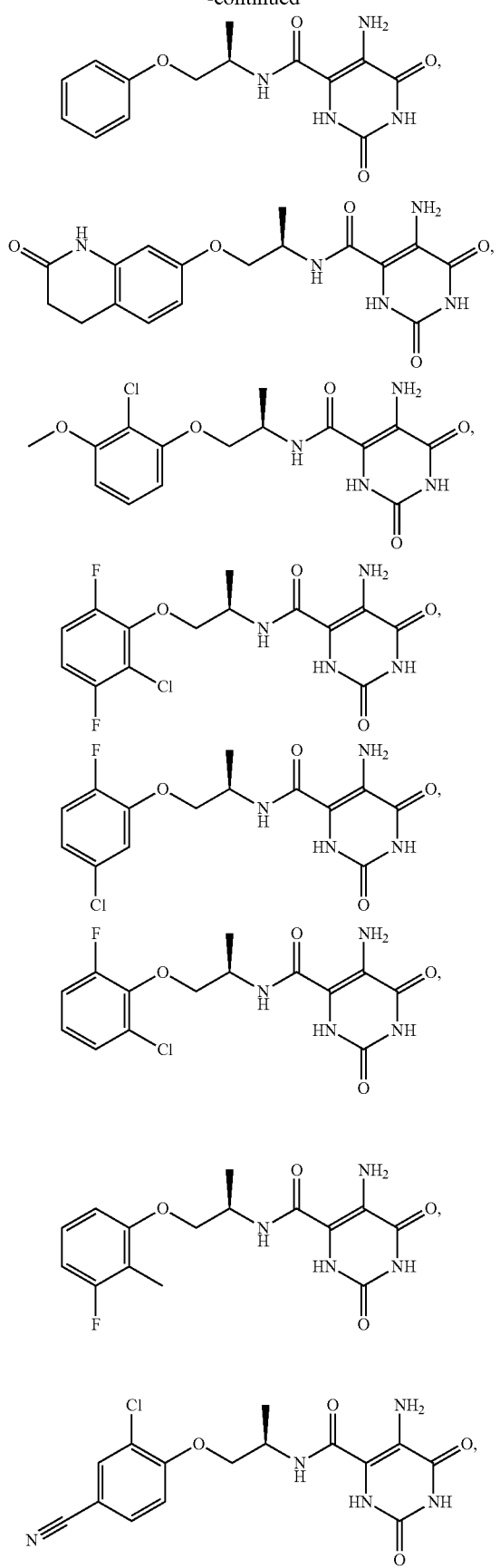
174
-continued
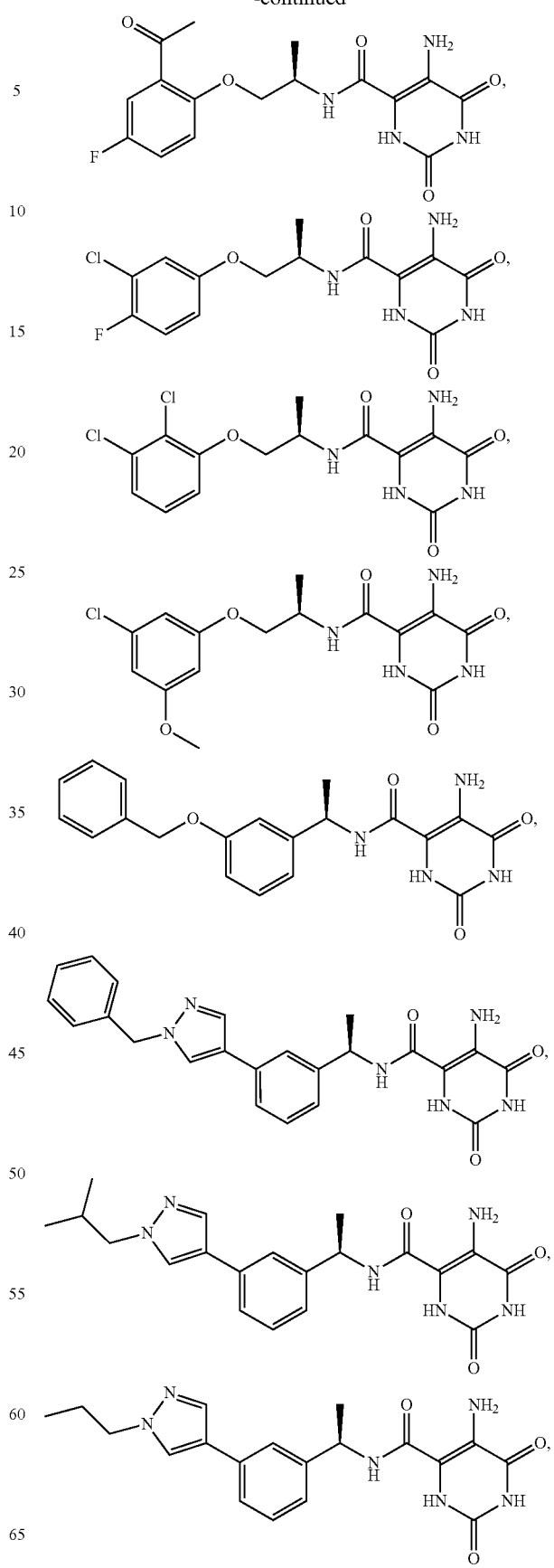

175
-continued
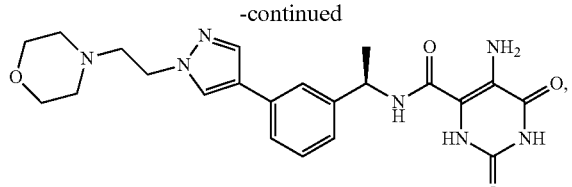
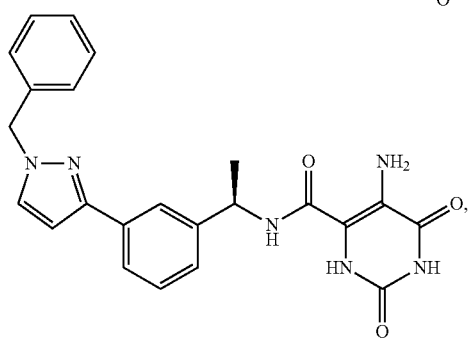
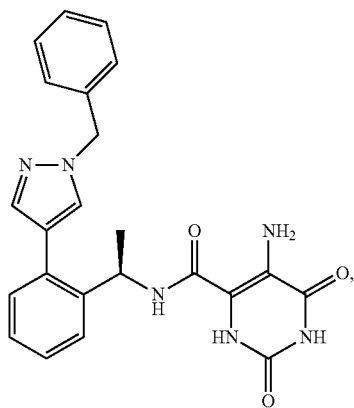
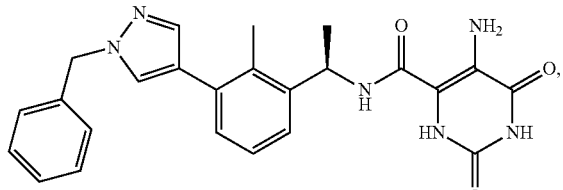
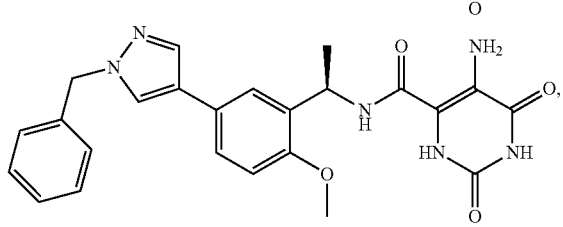
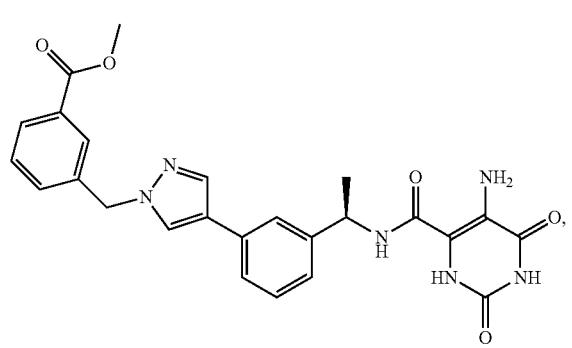
176
-continued
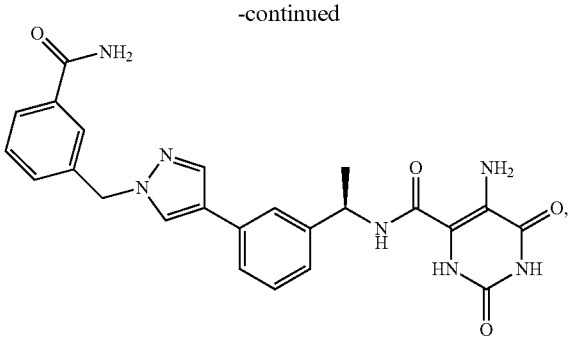
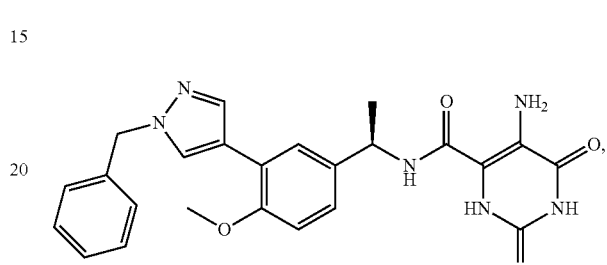
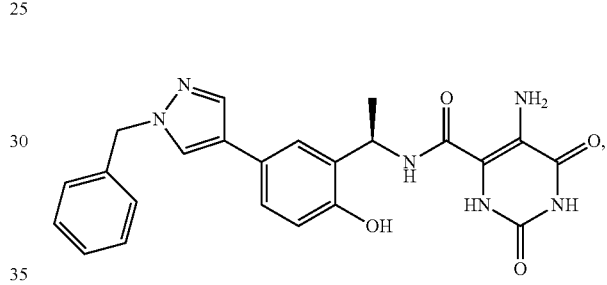
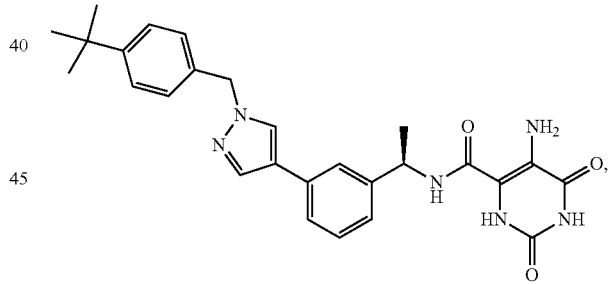
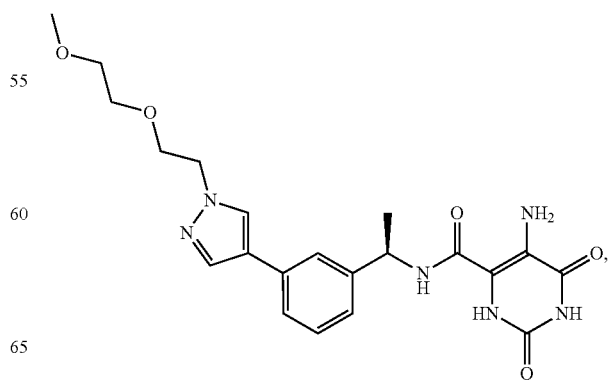

177
-continued
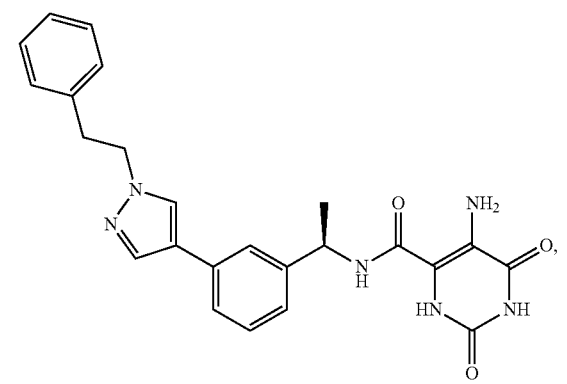
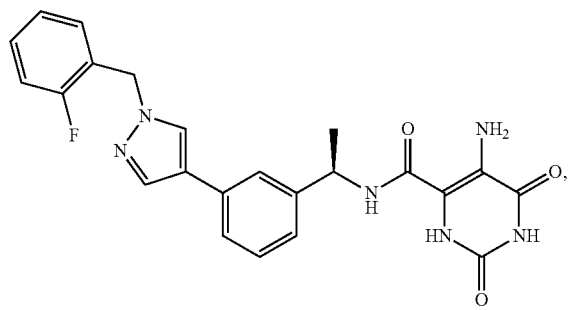
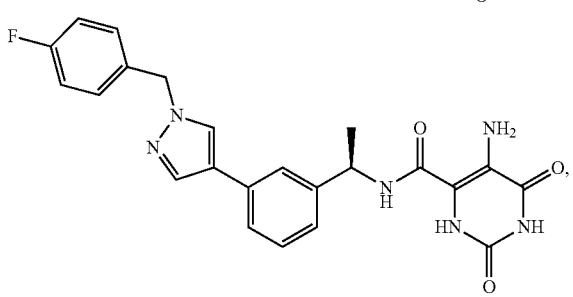
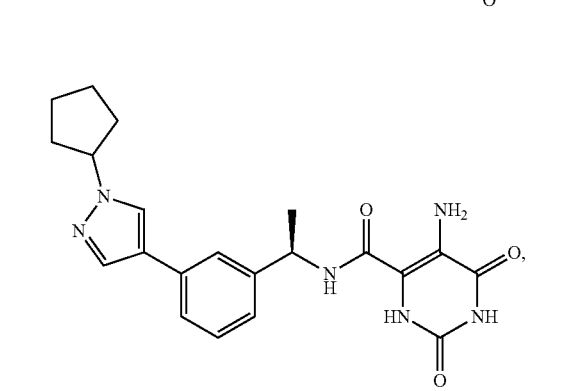
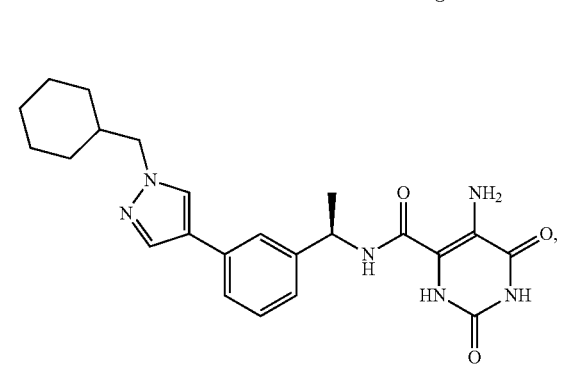
178
-continued
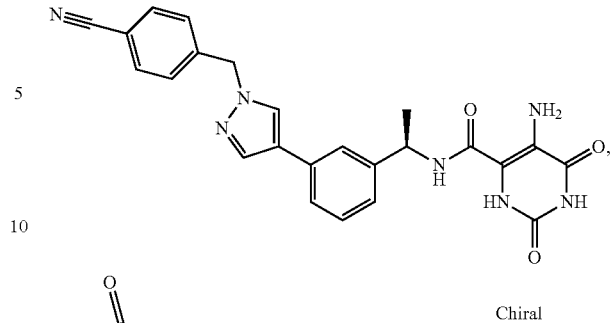
Chiral
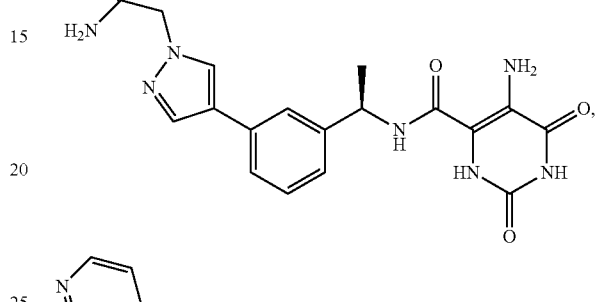
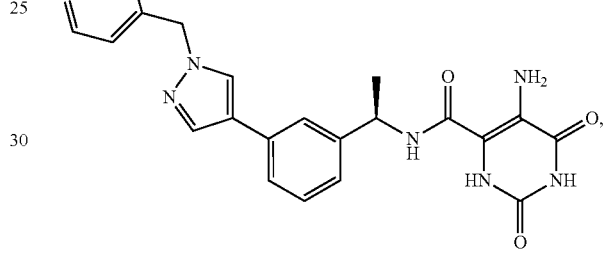
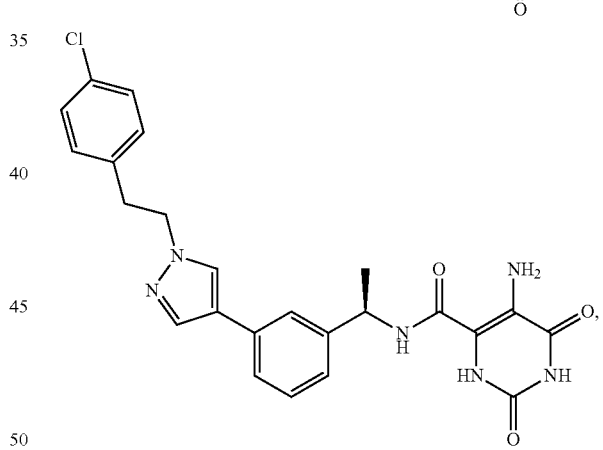
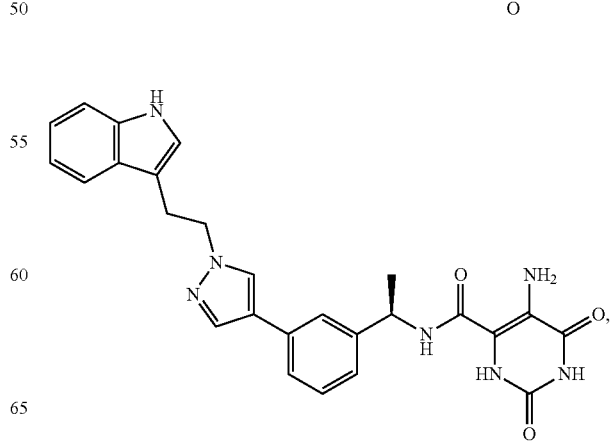

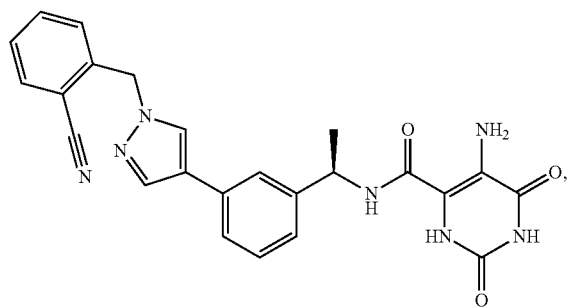
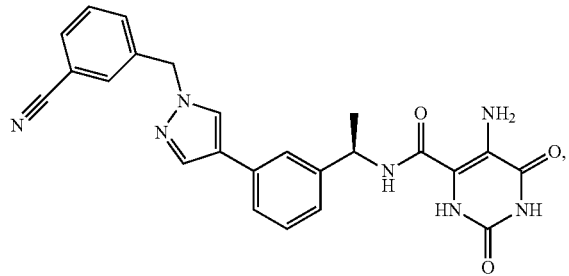
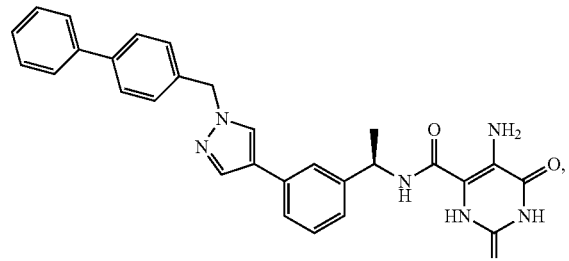
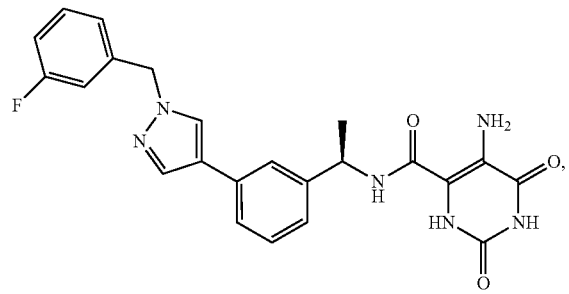
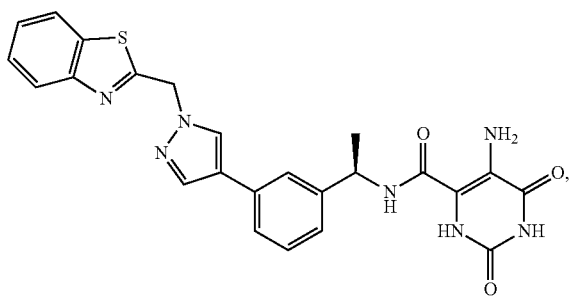
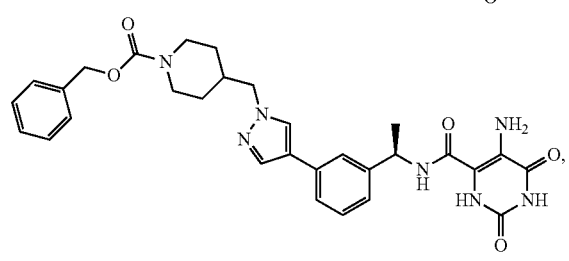
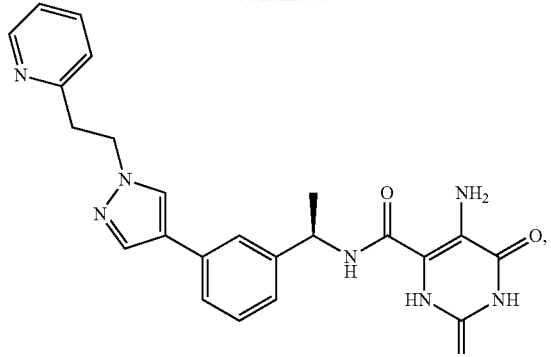
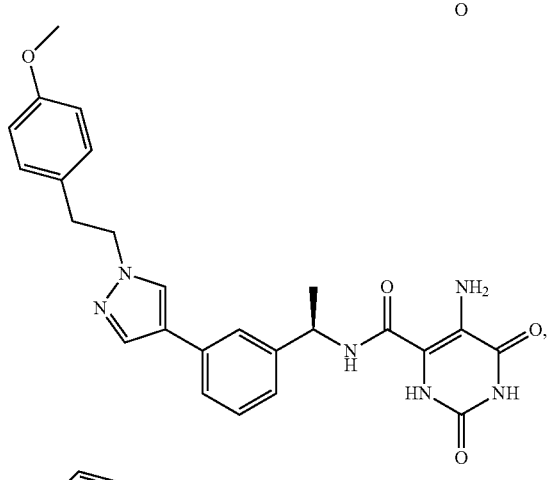
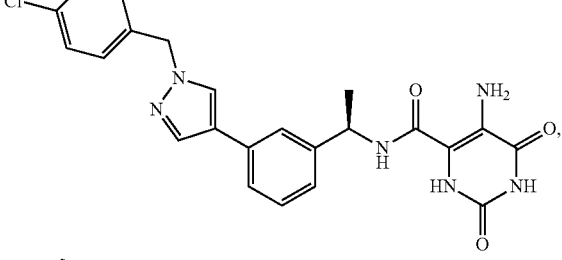
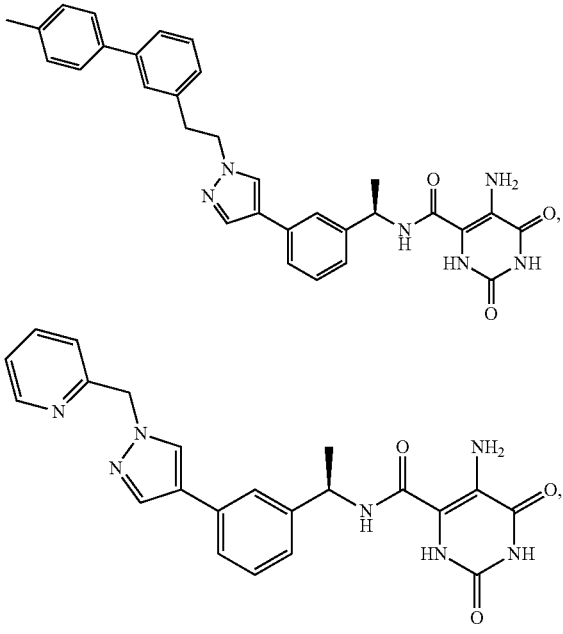

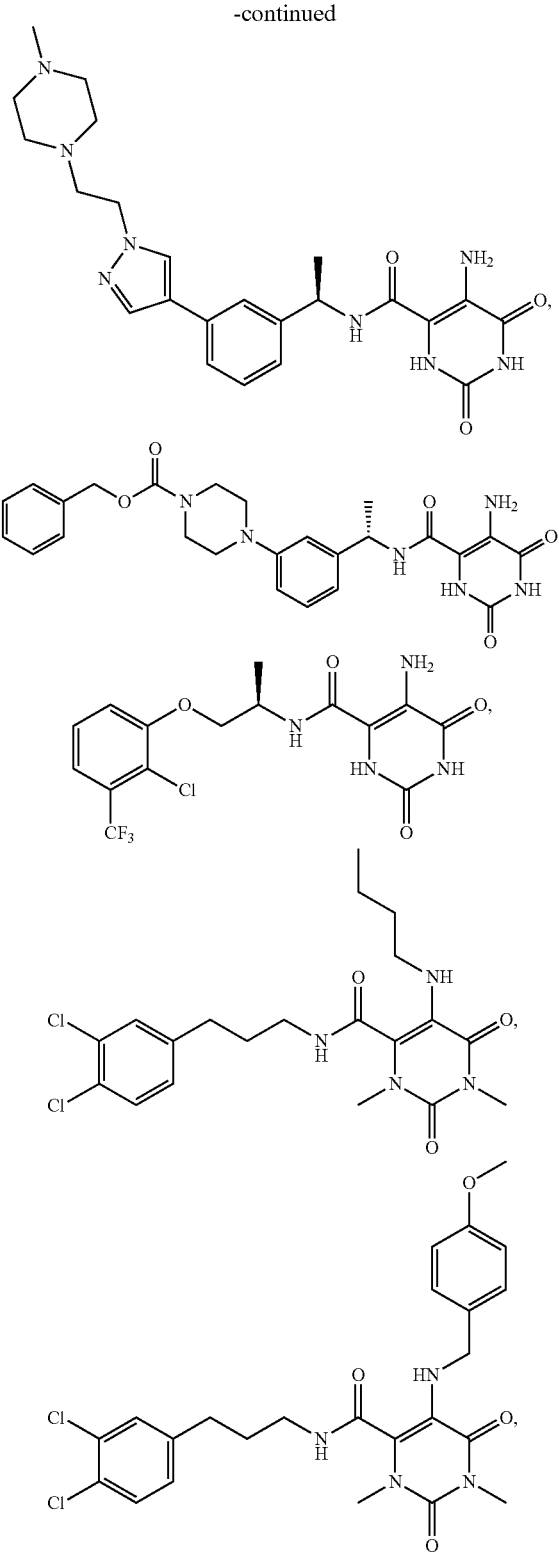
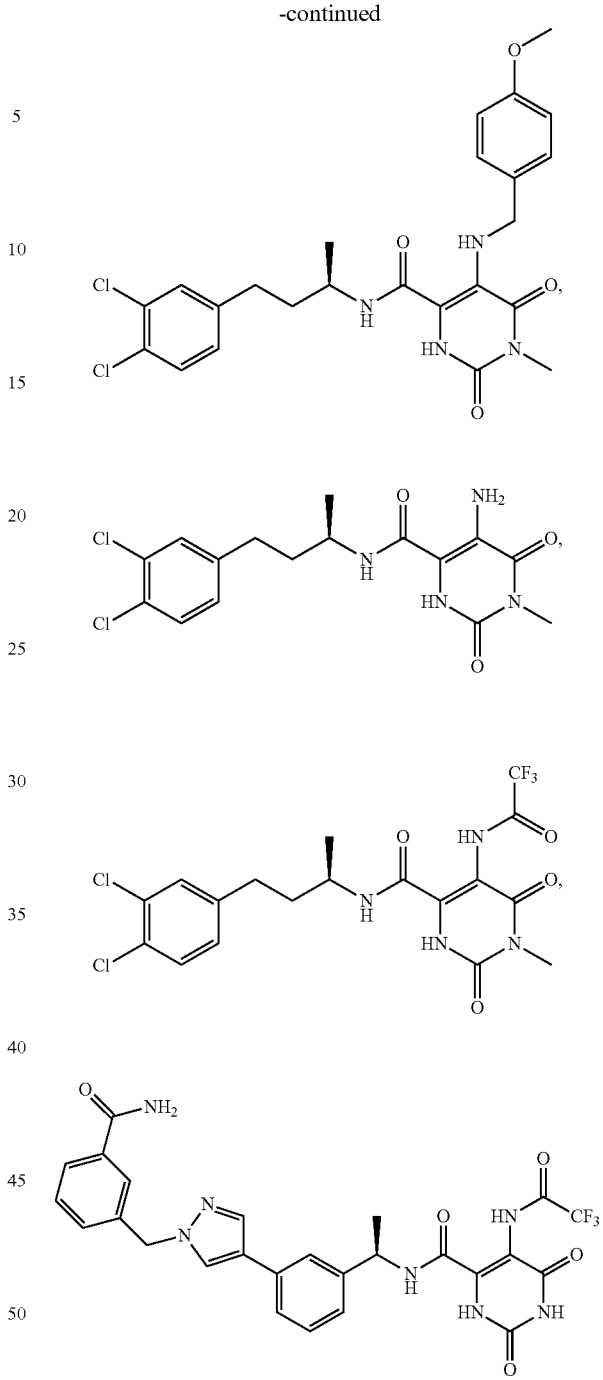
or a stereoisomer, a tautomer, or a pharmaceutically acceptable salt thereof.
11. A pharmaceutical composition, comprising: a pharmaceutically acceptable carrier and a compound of claim 1.
* * * * *